United States Patent
Gillies et al.

(10) Patent No.: US 11,230,568 B2
(45) Date of Patent: Jan. 25, 2022

(54) MELANOCORTIN 1 RECEPTOR LIGANDS AND METHODS OF USE

(71) Applicants: H. LEE MOFFITT CANCER CENTER AND RESEARCH INSTITUTE, INC., Tampa, FL (US); INTEZYNE TECHNOLOGIES INC., Tampa, FL (US); ARIZONA BOARD OF REGENTS ON BEHALF OF THE UNIVERSITY OF ARIZONA, Tucson, AZ (US); BOARD OF REGENTS, UNIVERSITY OF TEXAS SYSTEM, Austin, TX (US)

(72) Inventors: Robert J. Gillies, Tampa, FL (US); David L. Morse, Tampa, FL (US); Natalie M. Barkey, Tampa, FL (US); Kevin N. Sill, Tampa, FL (US); Josef Vagner, Tucson, AZ (US); Narges K. Tafreshi, Tampa, FL (US); Jonathan L. Sessler, Austin, TX (US); Christian Preihs, Austin, TX (US); Victor J. Hruby, Tucson, AZ (US)

(73) Assignees: H. LEE MOFFITT CANCER CENTER AND RESEARCH INSTITUTE, INC., Tampa, FL (US); INTEZYNE TECHNOLOGIES INC., Tampa, FL (US); ARIZONA BOARD OF REGENTS ON BEHALF OF THE UNIVERSITY OF ARIZONA, Tucson, AZ (US); BOARD OF REGENTS, UNTVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 16/450,382

(22) Filed: Jun. 24, 2019

(65) Prior Publication Data
US 2020/0002376 A1 Jan. 2, 2020

Related U.S. Application Data

(63) Continuation of application No. 15/263,028, filed on Sep. 12, 2016, now Pat. No. 10,329,326, which is a
(Continued)

(51) Int. Cl.
| | |
|---|---|
| A61K 38/00 | (2006.01) |
| C07K 5/117 | (2006.01) |
| A61K 49/10 | (2006.01) |
| C07K 14/72 | (2006.01) |
| A61K 47/64 | (2017.01) |
| A61K 47/69 | (2017.01) |
| C07K 14/68 | (2006.01) |
| A61K 49/00 | (2006.01) |
| A61K 49/18 | (2006.01) |
| C07K 7/08 | (2006.01) |
| A61K 38/34 | (2006.01) |

(52) U.S. Cl.
CPC ............ *C07K 5/1024* (2013.01); *A61K 47/64* (2017.08); *A61K 47/6907* (2017.08); *A61K 49/0056* (2013.01); *A61K 49/101* (2013.01); *A61K 49/1809* (2013.01); *C07K 7/08* (2013.01); *C07K 14/68* (2013.01); *C07K 14/723* (2013.01); *A61K 38/34* (2013.01)

(58) Field of Classification Search
None
See application file for complete search history.

(56) References Cited

U.S. PATENT DOCUMENTS

| | | |
|---|---|---|
| 5,714,576 A | 2/1998 | Hruby et al. |
| 5,830,994 A | 11/1998 | D'Hinterland et al. |

(Continued)

FOREIGN PATENT DOCUMENTS

| | | |
|---|---|---|
| WO | WO 2005-120588 | 12/2005 |
| WO | WO 2011-063367 | 5/2011 |

OTHER PUBLICATIONS

Raposinho et al. Melanocortin-1 Receptor-Targeting with Radiolabeled a-Melanocyte Stimulating Hormone Analogs for Melanoma, Peptide Science vol. 94 / No. 6, p. 820-829, 2010.*

(Continued)

*Primary Examiner* — Jeanette M Lieb
(74) *Attorney, Agent, or Firm* — Saliwanchik, Lloyd & Eisenschenk

(57) ABSTRACT

The subject invention pertains to a modified MC1R peptide ligand comprising a peptide that is a melanocortin 1 receptor (MC1R) ligand and a functionality or linker, such as a click functionality, for conjugation to a surface or agent. The modified MC1R peptide ligand can be coupled, e.g., via a click reaction with a complementary click functionality attached, to a moiety to form an MC1R-targeted agent. Drugs, contrast agents, polymers, particles, micelles, surfaces of larger structures, or other moieties can be targeted to the MC1R. The subject invention also pertains to a MC1R peptide ligand-micelle complex comprising a peptide that is a melanocortin 1 receptor ligand connected via a click reaction product to a micelle. The micelle is stable in vivo and can target melanoma tumor cells by association of the peptide ligand with the MC1R or the tumor and selectively provide a detectable and/or therapeutic agent (such as an imageable contrast agent and/or anti-cancer agent) selectively to the tumor cell.

18 Claims, 55 Drawing Sheets
Specification includes a Sequence Listing.

Related U.S. Application Data continuation of application No. 14/117,949, filed as application No. PCT/US2012/038425 on May 17, 2012, now Pat. No. 9,441,013.

(60) Provisional application No. 61/487,239, filed on May 17, 2011, provisional application No. 61/487,245, filed on May 17, 2011, provisional application No. 61/531,357, filed on Sep. 6, 2011, provisional application No. 61/618,144, filed on Mar. 30, 2012.

(56) References Cited

U.S. PATENT DOCUMENTS

| | | | |
|---|---|---|---|
| 6,228,840 | B1 | 5/2001 | Wei et al. |
| 6,350,430 | B1 | 2/2002 | Dooley et al. |
| 7,045,503 | B1 | 5/2006 | McBride et al. |
| 7,160,873 | B2 | 1/2007 | Magda et al. |
| 7,582,610 | B2 | 9/2009 | Haskell-Luevano |
| 9,290,539 | B2 | 3/2016 | Cai et al. |
| 9,539,301 | B2 | 1/2017 | Cai et al. |
| 9,814,755 | B2 | 11/2017 | Hruby et al. |
| 9,821,023 | B2 | 11/2017 | Hruby et al. |
| 2002/0197269 | A1 | 12/2002 | Lingnau |
| 2005/0038230 | A1 | 2/2005 | Sharma et al. |
| 2005/0187164 | A1 | 8/2005 | Pinel |
| 2007/0270411 | A1 | 11/2007 | Szewczyk et al. |
| 2009/0232838 | A1 | 9/2009 | Dong et al. |
| 2009/0297444 | A1 | 12/2009 | Perricone et al. |
| 2010/0209420 | A1* | 8/2010 | Lamb ............ A61P 35/04 424/133.1 |
| 2017/0022252 | A1 | 1/2017 | Hruby et al. |

OTHER PUBLICATIONS

Barkey N.M. et al., "Development of melanoma-targeted polymer micelles by conjugation of a Melanocortin 1 Receptor (MC1R) specific ligand" *Journal of Medicinal Chemistry*, 2011, 54(23):8078-8084.

Cai M. et al., "Novel 3D Pharmacophore of α-MSH/γ-MSH Hybrids Leads to Selective Human MC1R and MC3R Analogues" *Journal of Medicinal Chemistry*, 2005, 48(6):1839-1848.

Cai M. et al., "Cell Signaling and Trafficking of Human Melanocortin Receptors in Real Time Using Two-photon Fluorescence and Confocal Laser Microscopy: Differentiation of Agonists and Antagonists" *Chemical Biology & Drug Design*, 2006, 68(4):183-193.

Cannan R.K. and Kibrick A., "Complex Formation between Carboxylic Acids and Divalent Metal Cations" *Journal of the American Chemical Society*, 1938, 60:2314-2320.

Chen J. et al., "Melanoma-targeting Properties of $^{99m}$Technetium-labeled Cyclic α-Melanocyte-stimulating Hormone Peptide Analogues" *Cancer Research*, 2000, 60(20):5649-5658.

Chen J. et al., "In vivo Evaluation of $^{99m}$Tc/$^{188}$Re-Labeled Linear Alpha-Melanocyte Stimulating Hormone Analogs for Specific Melanoma Targeting" *Nuclear Medicine and Biology*, 1999, 26(6):687-693.

Chrastina A. et al., "Overcoming in vivo barriers to targeted nanodelivery" *Interdisciplinary Reviews: Nanomedicine and Nanobiotechnology*, 2011, 3(4):421-437.

Ehrlich J. and Bogert M.T., "Experiments in the Veratrole and Quinoxaline Groups" *Journal of Organic Chemistry*, 1947, 12:522-534.

Hall J.E. et al., "Obesity-induced Hypertension: Role of Sympathetic Nervous System, Leptin, and Melanocortins" *Journal of Biological Chemistry*, 2010, 285(23):17271-17276.

Handl H.L. et al., "Lanthanide-based time-resolved fluorescence of in cyto ligand-receptor interactions" *Analytical Biochemistry*, 2004, 330(2):242-250.

Hu J. et al., "Drug-Loaded and Superparamagnetic Iron Oxide Nanoparticle Surface-Embedded Amphiphilic Block Copolymer Micelles for Integrated Chemotherapeutic Drug Delivery and MR Imaging" *Langmuir*, 2012, 28(4):2073-2082. Epub ahead of print(DOI:10.1021/1 a203992q).

Jia Z. et al., "One-Pot Conversion of RAFT-Generated Multifunctional Block Copolymers of HPMA to Doxorubicin Conjugated Acid- and Reductant-Sensitive Crosslinked Micelles" *Biomacromolecules*, 2008, 9(11):3106-3113.

Jun D.-J. et al., "Melanocortins induce interleukin 6 gene expression and secretion through melanocortin receptors 2 and 5 in 3T3-LI adipocytes" *Journal of Molecular Endocrinology*, 2010, 44:225-236.

Kedar U. et al., "Advances in polymeric micelles for drug delivery and tumor targeting" *Nanomedicine: Nanotechnology, Biology and Medicine*, 2010, 6:714-729.

Kelly J.M. et al., "Immobilized α-melanocyte stimulating hormone 10-13 (GKPV) inhibits tumor necrosis factor-α stimulated NF-κB activity" *Peptides*, 2006, 27(2):431-437.

Kessinger C. et al., "In vivo angiogenesis imaging of solid tumors by $α_vβ_3$-targeted, dual-modality micellar nanoprobes" *Experimental Biology and Medicine*, 2010, 235:957-965.

Kim S. et al., "Overcoming the barriers in micellar drug delivery: loading efficiency, in vivo stability, and micelle-cell interaction" *Expert Opinion on Drug Delivery*, 2010, 7(1):49-62.

Kim T.H. et al., "Evaluation of Temperture-Sensitive, Indocyanine Green-Encapsulating Micelles for Noninvasive Near-Infrared Tumor Imaging" *Pharma-ceutical Research*, 2010, 27:1900-1913.

Koikov L.N. et al., "Sub-Nanomolar hMC1R Agonists by End-Capping of the Melanocortin Tetrapeptide His-D-Phe-Arg-Trp-NH$_2$" *Bioorganic & Medicinal Chemistry Letters*, 2003, 13(16):2647-2650.

Koikov L.N. et al., "Analogs of sub-nanomolar hMC1R agonist LK-184 [Ph(CH$_2$)$_3$CO-His-D-Phe-Arg-Trp-NH$_2$]. An additional binding site within the human melanocortin receptor 1?" *Bioorganic & Medicinal Chemistry Letters*, 2004, 14:3997-4000.

Koo H. et al., "In Vivo Targeted Delivery of Nanoparticles for Theranosis" *Accounts of Chemical Research*, 2011, 44(10):1018-1028.

Lee H. et al., "The Effects of Particle Size and Molecular Targeting on the Intratumoral and Suncellular Distribution of Polymeric Nanoparticles" *Molecular Pharmaceutics*, 2010, 7(4):1195-1208.

Lee H. et al., "In Vivo Distribution of Polymeric Nanoparticles at the Whole Body, Tumor and Cellular Levels" *Pharmaceutical Research*, 2010, 27(11):2343-2355.

Li J. et al., "Redox-sensitive micelles self-assembled from amphiphilic hyaluronic acid-deoxycholic acid conjugates for targeted intracellular delivery of paclitaxel" *Biomaterials*, 2012, 33:2310-2320.

Li Y. et al., "Well-Defined, Reversible Boronate Crosslinked Nanocarriers for Targeted Drug Delivery in Response to Acidic pH values and cis-Diols" *Angewandte Chemie* (International ed. in English), 2012, 51:1-7.

Liu T. et al., "Multifunctional pH-Disintegrable micellar nanoparticles of asymmetrically functionalized β-cyclodextrin-Based star copolymer covalently conjugated with doxorubicin and DOTA-Gd moieties" *Biomaterials*, 2012, 33:2521-2531.

Mayorov A.V. et al., "Effects of Macrocycle Size and Rigidity on Melanocortin Receptor-1 and -5 Selectivity in Cyclic Lactam α-Melanocyte-Stimulating Hormone Analogs" *Chemical Biology & Drug Design*, 2006, 67(5):329-335.

Oerlemans C. et al., "Polymeric Micelles in Anticancer Therapy: Targeting, Imaging, and Triggered Release" *Pharmaceutical Research*, 2010, 27:2569-2589.

Poon Z. et al., "Highly stable, ligand-clustered "patchy" micelle nanocarriers for systemic tumor targeting" *Nanomedicine: Nanotechnology, Biology and Medicine*, 2010, 7(2):201-209.

Rios-Doria J. et al., "A Versatile Polymer Micelle Drug Delivery System for Encapsulation and In Vivo Stabilization of Hydrophobic Anticancer Drugs" *Journal of Drug Delivery*, 2012, 2012:951741, in press: Oct. 15, 2011.

Rodrigues A.R. et al., "Melanocortin 5 receptor activates ERK1/2 through a PI3K-regulated signaling mechanism" *Molecular and Cellular Endocrinology*, 2009, 303:74-81.

(56) References Cited

OTHER PUBLICATIONS

Sawyer T. et al., "4-Norleucine, 7-D-phenylalanine-α-melanocyte-stimuiating hormone: A highly potent α-melanotropin with ultralong biological activity" *Proceedings of the National Academy of Sciences*, 1980, 77(10):5754-5758.

Sessler J.L. et al., "Texaphyrins: Synthesis and Applications" *Accounts of Chemical Research*, 1994, 27:43-50.

Sessler J.L. et al., "New texaphyrin-type expanded porphyrins" *Pure and Applied Chemistry*, 1996, 68(6):1291-1295.

Sessler J.L. and Miller R.A., "Texaphyrins. New Drugs with Diverse Clinical Applications in Radiation and Photodynamic Therapy" *Biochemical Pharmacology*, 2000, 59:733-739.

Sessler J.L. et al., "Gadolinium(III) Texaphyrin: A Novel MRI Contrast Agent" *Journal of the American Chemical Society*, 1993, 115(22):10368-10369.

Sessler J.L. et al., "Synthesis and Structural Characterization of Lanthanide(III) Texaphyrins" *Inorganic Chemistry*, 1993, 32:3175-3187.

Sessler J.L. et al., "An Expanded Porphyrin: The Synthesis and Structure of a New Aromatic Pentadentate Ligand" *Journal of the American Chemical Society*, 1988, 110(16):5586-5588.

Shiraishi K. et al., "Polyion complex micelle MRI contrast agents from Poly(ethylene glycol)-b-poly(L-lysine) block copolymers having Gd-DOTA; preparations and their control of $T_1$-relaxivities and blood circulation characteristics" *Journal of Controlled Release*, 2010, 148:160-167.

Siegrist W. et al., "Characterization of Receptors for α-Melanocyte-stimulating Hormone on Human Melanoma Cells" *Cancer Research*, 1989, 49(22):6352-6358.

Sun T.-M. et al., "Simultaneous Delivery of siRNA and Pacilitaxel via a "Two-in-One" Micelleplex Promotes Synergistic Tumor Supression" *ACS Nano*, 2011, 5(2):1483-1494.

Tang N. et al., "Improving Penetration in Tumors with Nanoassemblies of Phospholipids and Doxorubicin" *Journal of the National Cancer Institute*, 2007, 99(13):1004-1015.

Todorovic A. et al., "N-Terminal Fatty Acylated His-DPhe-Arg-Trp-$NH_2$ Tetrapeptides: Influence of Fatty Acid Chain Length on Potency and Selectivity at the Mouse Melanocortin Receptors and Human Melanocytes" *Journal of Medicinal Chemistry*, 2005, 48:3328-3336.

Van Der Ploeg L.H.T. et al., "A role for the melanocortin 4 receptor in sexual function" *Proceedings of the National Academy of Sciences*, 2002, 99(17):11381-11386.

Viala J. et al., "Phases IB and II Multidose Trial of Gadolinium Texaphyrin, a Radiation Sensitizer Detectable at MR Imaging: Preliminary Results in Brain Metastases" *Radiology*, 1999, 212(3):755-759.

Webb T.R. and Clark A.J.L., "Minireview: The Melanocortin 2 Receptor Accessory Proteins" *Molecular Endocrinology*, 2010, 24(3):475-484.

Xiong X.-B. and Lavasanifar A., "Traceable Multifunctional Micellar Nanocarriers for Cancer-Targeted Co-delivery of MDR-1 siRNA and Doxorubicin" *ACS Nano*, 2011,5(6):5202-5213.

Yang R. et al., "Galactose-Decorated Cross-Linked Biodegradable Poly(ethylene glycol)-b-poly(ε-caprolactone) Block Copolymer Micelles for Enhanced Hepatoma-Targeting Delivery of Paclitaxel" *Biomacromolecules*, 2011, 12:3047-3055.

Yang X. et al., "Tumor-Targeting, pH-Responsive, and Stable Unimolecular Micelles as Drug Nanocarriers for Targeted Cancer Therapy" *Bioconjugate Chemistry*, 2010, 21(3):496-504.

Yang Y. et al., "Novel Binding Motif of ACTH Analogues at the Melanocortin Receptors" *Biochemistry*, 2009, 48:9775-9784.

Yokoyama M., "Clinical Applications of Polymeric Micelle Carrier Systems in Chemotherapy and Image Diagnosis of Solid Tumors" *Journal of Experimental and Clinical Medicine*, 2011, 3(4):151-158.

Young S.W. et al., "Gadolinium(III) texaphyrin: A tumor selective radiation sensitizer that is detectable by MRI" *Proceedings of the National Academy of Sciences*, 1996, 93:6610-6615.

Plitas G. and Ariyan C.E., "Controversies in the Management of Regional Nodes in Melanoma" *Journal of the National Comprehensive Cancer Network*, 2012, 10:414-421.

Raposinho, P. D. et al. "Melanocortin-1 Receptor-Targeting With Radiolabeled Cyclic α-Melanocyte-Stimulating Hormone Analogs for Melanoma Imaging" *Peptide Science*, 2010, pp. 820-829, vol. 94, No. 6.

* cited by examiner

4-Phenylbutyryl-HfRWGK(hex-5-ynoyl)-NH₂

| well | formulation (% Gd-Tx w/w) | [micelle] (mg/mL) | [Gd-Tx] (mg/mL) | T1 (average) (s) |
|---|---|---|---|---|
| 1 | 5 | 20 | 1 | 0.135 |
| 2 | 0.5 | 20 | 0.1 | 0.907 |
| 3 | 0.05 | 20 | 0.01 | 1.348 |
| 4 | 5 | 0.2 | 0.01 | 2.086 |
| 5 | 0.5 | 0.2 | 0.001 | 2.440 |
| 6 | 0.05 | 0.2 | 0.0001 | 2.671 |

FIG. 8

| Statistical Analysis for Significance – unpaired two-tailed t-test | |
|---|---|
| Groups | p-value |
| * | 5% vs. 10% XL | 0.0002 |
| ** | 10% vs. 15% XL | 0.032 |
| Δ | 5% vs. 10% UXL | 0.018 |
| ΔΔ | 10% vs. 15% UXL | 0.084 |
| ‡ | XL vs. UXL | <0.002 |

FIG. 14

| Ligand | Ki (nM) | | |
|---|---|---|---|
| | MC1R | MC4R | MC5R |
| NDP-a-MSH | 1.8 | 19 | 10 |
| ML21-1 | 0.24 | 254 | 46 |
| ML-21-1 triblock polymer | 26 | NB | NB |
| ML21-1 micelle UXL | 11 | NB | NB |
| ML21-1 micelle XL | 2.9 | NB | NB |

FIG. 15

| Sample # | Micelle | % Gd-Tx Encap. (calculated) | % Gd-Tx Encap. (actual) | Charge (mV) | DLS Size (nm) | NTS Mean (nm) | NTS 90 percentile (nm) |
|---|---|---|---|---|---|---|---|
| 1 | UT, UXL | 5.4 | 5.3 | -26.61 | 208.20 | 170 | 270 |
| 2 | T, UXL | 5.4 | 5.2 | -29.23 | 113.60 | 70 | 130 |
| 3 | UT, XL | 5.3 | 5.1 | -11.12 | 174.70 | 110 | 250 |
| 4 | T, XL | 5.2 | 5.0 | -13.73 | 179.40 | 70 | 170 |
| 5 | UT, UXL | 0.54 | 0.51 | -17.70 | 88.90 | 30 | 110 |
| 6 | T, UXL | 0.53 | 0.50 | -17.74 | 88.80 | 70 | 120 |
| 7 | UT, XL | 0.52 | 0.52 | -10.73 | 87.50 | 30 | 100 |
| 8 | T, XL | 0.51 | 0.51 | -9.49 | 82.50 | 70 | 130 |
| 9 | UT, UXL | 0.054 | 0.049 | -20.33 | 104.80 | 130 | 180 |
| 10 | T, UXL | 0.053 | 0.05 | -17.28 | 49.40 | 130 | 190 |
| 11 | UT, XL | 0.052 | 0.052 | -2.62 | 87.30 | 90 | 210 |
| 12 | T, XL | 0.051 | 0.051 | -0.33 | 93.50 | 30 | 150 |

FIG. 16

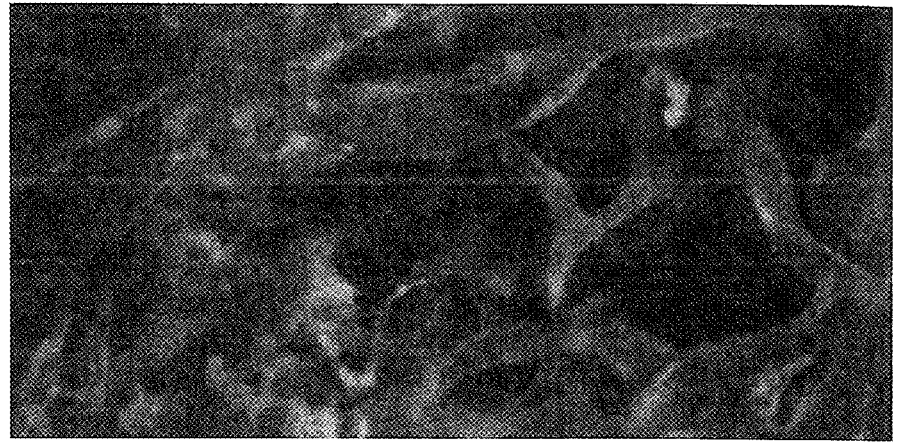
FIG. 31A
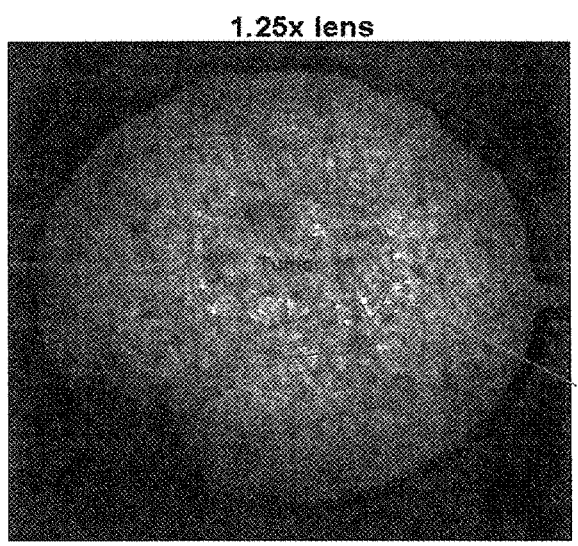 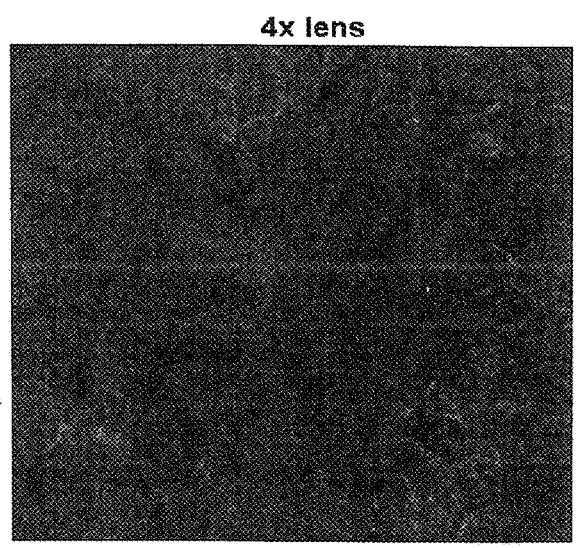
FIG. 31B-1                FIG. 31B-2

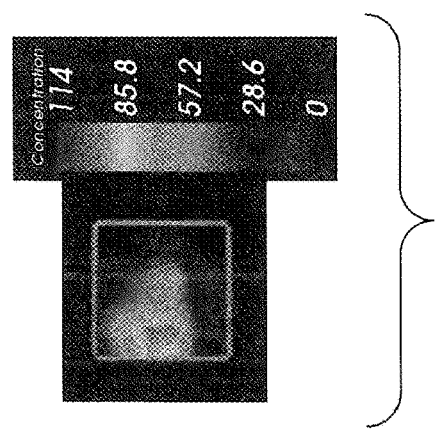
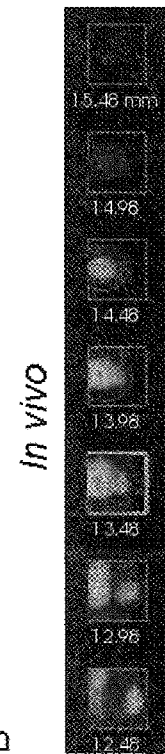
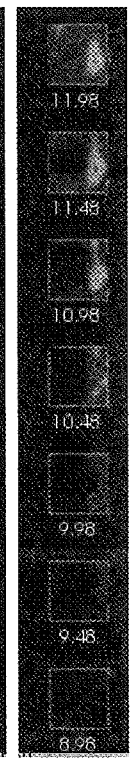
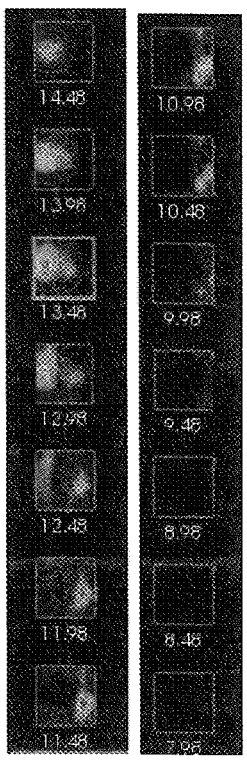
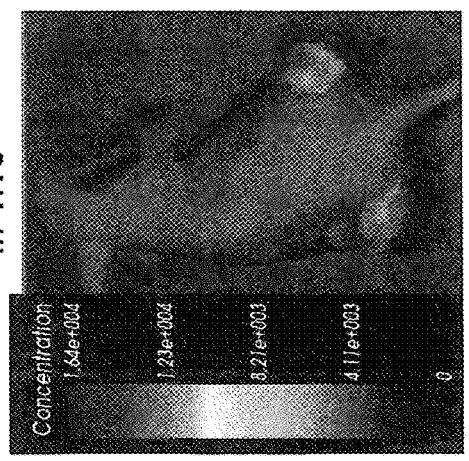
FIG. 32A
FIG. 32B
FIG. 32C

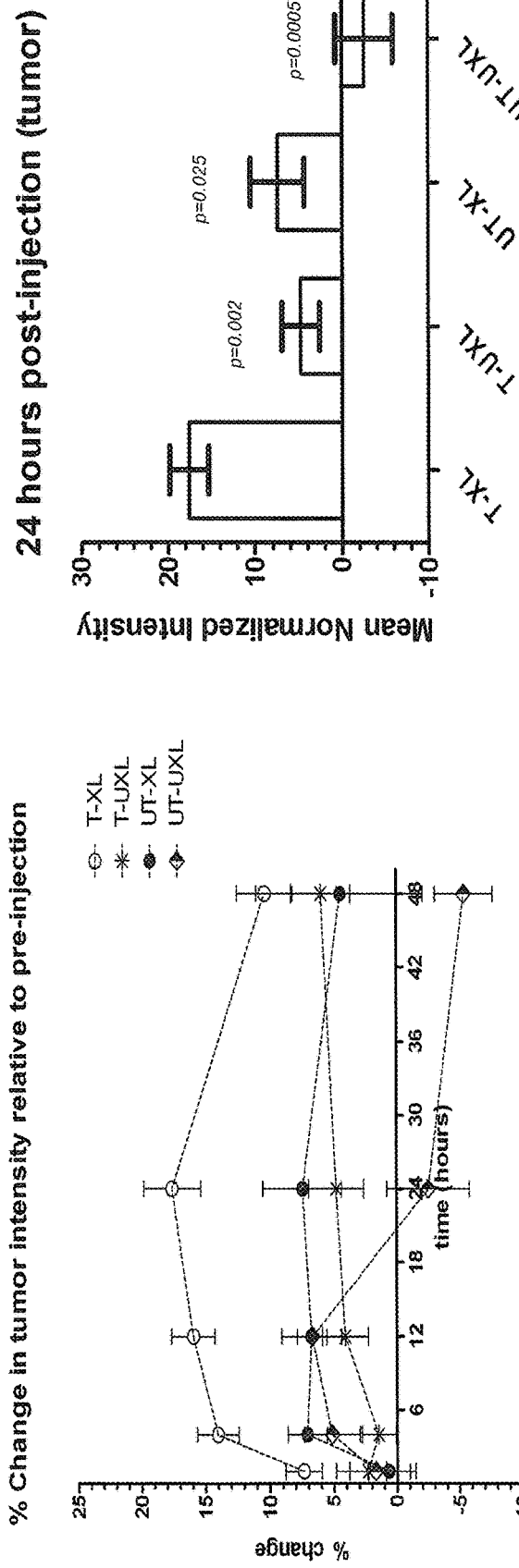
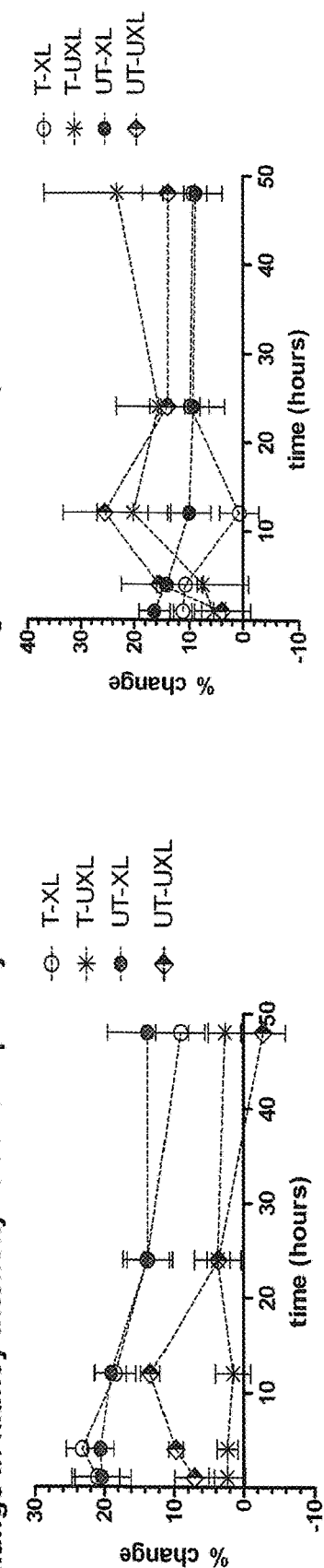
FIG. 38A
FIG. 38B
FIG. 38C
FIG. 38D

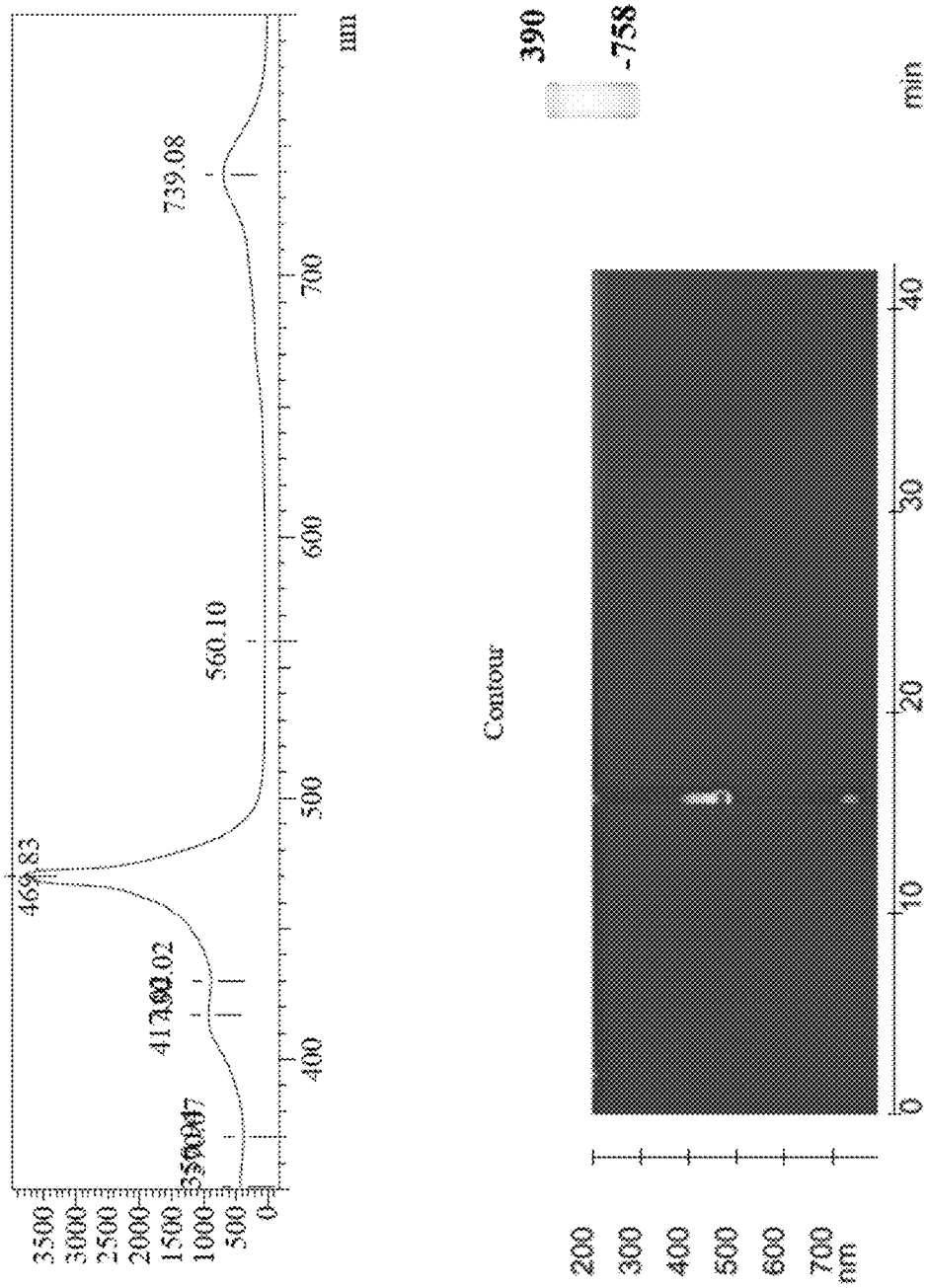
FIG. 42C
FIG. 42D

MELANOCORTIN 1 RECEPTOR LIGANDS AND METHODS OF USE

CROSS-REFERENCE TO RELATED APPLICATIONS

The present application is a continuation of U.S. application Ser. No. 15/263,028, filed Sep. 12, 2016, which is a continuation of U.S. application Ser. No. 14/117,949, filed Nov. 15, 2013, now U.S. Pat. No. 9,441,013, which is the National Stage of International Application Number PCT/US2012/038425, filed May 17, 2012, which claims the benefit of U.S. Provisional Application Ser. No. 61/487,239, filed May 17, 2011, U.S. Provisional Application Ser. No. 61/487,245, filed May 17, 2011, U.S. Provisional Application Ser. No. 61/531,357, filed Sep. 6, 2011, and U.S. Provisional Application Ser. No. 61/618,144, filed Mar. 30, 2012, which are hereby incorporated by reference herein in their entirety, including any figures, tables, nucleic acid sequences, amino acid sequences, and drawings.

GOVERNMENT SUPPORT

This invention was made with Government support under Grant No. CA097360 awarded by the National Institute of Health (NIH). The Government has certain rights in the invention.

The Sequence Listing for this application is labeled "2OB9114.TXT" which was created on Jun. 24, 2019 and is 6 KB. The entire contents of the sequence listing is incorporated herein by reference in its entirety.

BACKGROUND OF THE INVENTION

The incidence of malignant melanoma is rising faster than that of any other cancer in the United States; reportedly, melanoma diagnoses doubled from 1986 to 2001 [1]. Melanoma progression is associated with altered expression of cell surface proteins, including adhesion proteins and receptors [2-7]. It has been estimated that over 80% of malignant melanomas express high levels of the melanocyte stimulating hormone (αMSH) receptor, melanocortin 1 receptor (MC1R)[8]; thus, MC1R has been investigated as a target for selective imaging and therapeutic agents. MC1R belongs to a family of five G protein-coupled receptors (MC1R-MC5R) known as the "melanocortins." The melanocortins have been discovered in a wide range of tissues and organs throughout the body, ranging from the hair/skin (MC1R)[9] and kidneys (MC5R)[10] to the adrenal gland (MC2R)[11] and hypothalamus (MC3R/MC4R)[12, 13] and are known to play a role in skin pigmentation, hair coloration, obesity, metabolism, diabetes, sexual behavior, erectile dysfunction, stress response and mood.[9-16] Endogenously, the agonists for the melanocortins are the α-, β-, γ-melanocyte stimulating hormones (MSH) and adrenocorticotropic hormone (ACTH, MC2R specific), all of which contain the same central sequence of His-Phe-Arg-Trp (SEQ ID NO:1)[17]. This high degree of pharmacophore homology makes it difficult to design a selective ligand which is highly specific for receptor subtype.

Due to its high expression on the surface of melanomas, MC1R has been investigated as a target for selective imaging and therapeutic agents, and a number of selective ligands have been developed[18-20]. The most well known of these, [Nle$^4$,D-Phe$^7$]-α-MSH, has been investigated extensively by Chen who showed that $^{99}$mTc-CGCG labeled NDP-α-MSH bound to melanomas with very high avidity (6.5% ID/g)[21]. Unfortunately, NDP-α-MSH has also been shown to possess relatively strong nanomolar binding affinities with MC3R, MC4R and MC5R as well[22-24]. Such off-target binding is highly undesirable given the presence of these receptors in sensitive organs such as the kidney and brain. A co-injection of lysine has been reported to diminish off-target binding in the kidneys[21, 25, 26], and presumably most agents will not be able to cross the blood-brain barrier; nonetheless, the need for the development of highly specific and selective ligands against MC1R is one of importance.

The development of ligands that can be attached to micelles and/or liposomes and designed to selectively target cancer cells relative to healthy organs represents a major hurdle in current research. Many such attempts fail either from (1) a loss of affinity resulting from the attachment of small peptides to large micelles or liposomes; (2) an inherent instability that results in collapse before entering the vicinity of the tumor; or (3) a nanoparticle size that is too large to escape the vasculature. In order to effectively design targeted particles, each of these issues must be addressed.

BRIEF SUMMARY OF THE INVENTION

It has been estimated that over 80% of malignant melanomas express high levels of the melanocyte stimulating hormone (αMSH) receptor, melanocortin 1 receptor (MC1R). Although there have been ligands designed to attach to micelles and selectivity target cancer cells relative to healthy organs, many fail either from (1) a loss of affinity resulting from the attachment of small peptides to large micelles (2) an inherent instability of the system in vivo; or (3) a nanoparticle size that is too large. According to embodiments of the invention, a series of hMC1R ligands known to be selective against hMC1R are modified for attachment to a polymer, gel, or surface of a particle, micelle, or other structure. The most selective ligand was appended to a triblock polymer micelle via click chemistry to a 100 nm polymer micelle comprises a targeted micelle with a nanomolar binding affinity to hMC1R.

One aspect of the invention concerns a modified melanocortin 1 receptor (MC1R) peptide ligand, comprising an MC1R peptide ligand coupled to a click functionality at the C-terminus or N-terminus of the MC1R peptide ligand. In some embodiments, the click functionality is an alkyne. The modified MC1R peptide ligand may comprise, for example, the amino acid motif His-Phe-Arg-Trp (HFRW) (SEQ ID NO:1) or His-DPhe-Arg-Trp (HfRW) (SEQ ID NO:2). In some embodiments, MC1R peptide ligand is selected from:

```
                                          (SEQ ID NO: 3)
4-phenylbutyryl-His-DPhe-Arg-Trp-Gly-Lys (hex-5-ynoyl)-NH₂;

(SEQ ID NO: 4)
H-Lys(hex-5-ynoyl)-Tyr-Val-Nle-Gly-His-DNal(2')-

Arg-DTrp-Asp-Arg-Phe-Gly-NH₂;
or (SEQ ID NO: 5)
H-Lys(hex-5-ynoyl)Tyr-Val-Nle-Gly-His-DNal(2')-

Arg-DPhe-Asp-Arg-Phe-Gly-NH₂.
```

Throughout the various aspects of the invention described herein, in addition to click reactions, it should be understood that other methods for conjugating the MC1R peptide ligand to micelles or to other structures may be utilized. The attachment of peptide moieties to hydrophilic polymers are known in the art, as multiple bio-conjugation approaches exist. As described herein, a preferred approach utilizes the copper catalyzed click chemistry reaction between an alkyne and an azide to form a 1,2,3-triazole linkage. In some embodiments, a metal-free click reaction can be utilized to form a triazole linkage between the azide and alkyne moieties (Jewett J C and C R Bertozzi, "Cu-free click cycloaddition reactions in chemical biology," *Chem Soc Rev.*, 2010 April; 39(4): 1272-1279, which is incorporated herein by reference in its entirety). Other bio-conjugation approaches include, but are not limited to, the reaction between an amine and aldehyde to form an imine linkage; the oxidation of two thiol moieties to form a disulfide; the thiolene click reaction between an alkene and a thiol to form a thioether (Killops K L et al., "Robust, Efficient, and Orthogonal Synthesis of Dendrimers via Thiol-ene "Click Chemistry", *JACS,* 2008, which is incorporated herein by reference in its entirety); reaction between an amine an ester to form an amide; the Michael addition conjugation between an amine and a maleimide to form a secondary amine linkage; and the reaction between an amine and an activated ester to form an amide.

Another aspect of the invention is a method of preparing a MC1R peptide ligand of the invention, comprising: providing an MC1R peptide ligand; and covalently bonding a moiety comprising a click functionality to the C-terminus or N-terminus of the MC1R peptide ligand, wherein a MC1R peptide ligand comprising a click functionality is formed.

In some embodiments, the C-terminus or N-terminus of the MC1R peptide ligand comprises a lysine (Lys) residue or other nitrogen-bearing, thiol-bearing, or —OH bearing residue, and wherein the moiety comprising the click functionality is covalently bound to the residue. In some embodiments, the residue at the C-terminus or N-terminus comprises the Lys residue. Preferably, the moiety having the click functionality comprises a terminal alkynyl acid of 5 to 12 carbons.

Another aspect of the invention concerns a melanocortin 1-targeted agent comprising: a MC1R peptide ligand; and a moiety (a "payload"), wherein the MC1R peptide ligand and the moiety are covalently linked by a click reaction product (a reaction product of a first click functionality and a complementary second click functionality). The moiety is one to be directed to MC1R expressing cells, such as a drug, contrast agent, polymer, gel, particle, surface, or any combination thereof.

Another aspect of the invention concerns a method of delivering a moiety to cells expressing the melanocortin 1 receptor (MC1R), comprising administering an MC1R-targeted agent of the invention to the cells in vitro or in vivo. In in vivo embodiments, MC1R-targeted agent may be administered to a human or non-human animal subject systemically, or locally at the site of the cells. In some embodiments, the MC1R-targeted agent is administered to the subject intravascularly (e.g., intravenously or intra-arterially). In some embodiments, the moiety ("payload") carried by the MC1R-targeted agent is an anti-cancer agent (such as a chemotherapeutic agent). Preferably, the anti-cancer agent is one having efficacy against MC1R-expressing cells (melanoma cells). In some embodiments, the moiety carried by the MC1R-targeted agent is a contrast agent, such as imaging contrast agents. Examples of imaging contrast agents include, but are not limited to, near infrared fluorescent dyes (e.g., ICG derivatives); gold for CT contrast; Gd, Tc99m or $^{111}$In chelate for MRI or SPECT imaging; Yttrium for radiotherapy, 18-F, 11-C, 18-O, Gallium 64, Copper-64 for PET imaging. Examples of anti-cancer agents include, but are not limited to, alkylating chemotherapy agents such as melphalan or ifosfamide; and other systemic melanoma chemotherapies such as Dacarbazine, paclitaxel, and vincristine.

In some embodiments, the subject is one diagnosed with melanoma. In some embodiments, the subject is one diagnosed with melanoma, and the moiety of the MC1R-targeted agent comprises an anti-cancer agent having efficacy for the treatment of melanoma (e.g., an agent that kills melanoma cells or inhibits the growth of melanoma cells). In some embodiments, the subject has not been diagnosed with melanoma.

In some embodiments, the moiety carried by the MC1R-targeted agent comprises an imaging contrast agent, and the delivery method further comprises imaging the subject using an imaging modality (e.g., with an imaging device) appropriate for the administered contrast agent, thereby determining the localization of the contrast agent within the subject (for example, to determine the location of MC1R expressing cells).

Another aspect of the invention concerns a pharmaceutical composition comprising an MC1R targeted agent of the invention, and a pharmaceutically acceptable carrier.

Another aspect of the invention concerns a modified melanocortin 1 receptor (MC1R) peptide ligand-micelle complex, comprising: an MC1R peptide ligand; and a micelle comprising an inner core, outer core and hydrophilic shell, wherein the MC1R peptide ligand is linked to the shell of the micelle by a click reaction product. In some embodiments, the inner core of the micelle comprises a hydrophobic polypeptide, the outer core comprises a crosslinked peptide comprising a multiplicity of crosslinked amino acid residues and the hydrophilic shell comprises a water soluble polymer, and the inner core is covalently attached to the outer core and the outer core is covalently attached to the hydrophilic shell. In some embodiments, the water soluble polymer comprises polyethylene glycol. In some embodiments, the click reaction product comprises a 1,2,3-triazole from the addition of an azide and an alkyne. In some embodiments, the click reaction product is coupled to the C-terminus of the MC1R ligand. In some embodiments, the click reaction product is coupled to the N-terminus of the MC1R ligand. In some embodiments, the MC1R peptide ligand and a first click functionality of the click reaction product are selected from:

```
                                              (SEQ ID NO: 3)
4-phenylbutyryl-His-DPhe-Arg-Trp-Gly-Lys (hex-5-ynoyl)-NH₂;

(SEQ ID NO: 4)
H-Lys(hex-5-ynoyl)-Tyr-Val-Nle-Gly-His-DNal(2')-

Arg-DTrp-Asp-Arg-Phe-Gly-NH₂;
or
                                              (SEQ ID NO: 5)
H-Lys(hex-5-ynoyl)Tyr-Val-Nle-Gly-His-DNal(2')-

Arg-DPhe-Asp-Arg-Phe-Gly-NH₂.
```

In some embodiments, the MC1R peptide ligand comprises the amino acid motif His-Phe-Arg-Trp (HFRW) (SEQ ID NO:1) or His-DPhe-Arg-Trp (HfRW) (SEQ ID NO:2).

In some embodiments, the MC1R peptide ligand-micelle complex further comprises an agent residing in the inner core of the micelle. The agent may be an anti-cancer agent, contrast agent, or some other agent to be administered.

Another aspect of the invention concerns a pharmaceutical composition comprising an MC1R peptide ligand-micelle complex, and a pharmaceutically acceptable carrier.

Another aspect of the invention concerns a method of imaging a melanoma tumor of a subject, comprising: administering the MC1R peptide ligand-micelle complex of the invention to the subject, wherein a contrast agent is present within the inner core of the micelle, and wherein the MC1R peptide ligand-micelle complex concentrates in the tumor; and observing a signal from the contrast agent by an imaging device. In some embodiments, method of imaging comprises:

providing a MC1R peptide ligand-micelle complex of the invention;
incorporating a contrast agent into the inner core of the MC1R peptide ligand micelle complex;
administering the MC1R peptide ligand-micelle complex with the contrast agent to a human or non-human animal subject, wherein the MC1R peptide ligand-micelle complex concentrates in the tumor; and
observing a signal from the contrast agent by an imaging device.

In some embodiments, the contrast agent comprises a near infrared (NIR) fluorescent dye, such as an ICG derivative. In some embodiments, the contrast agent comprises a CT contrast agent, such as gold. In some embodiments, the contrast agent is a MRI or SPECT contrast agent, such as Gd, Tc99m, or an $^{111}$In chelate. In some embodiments, the contrast agent comprises a PET imaging agent, such as 18-F, 11-C, 18-O, or Gallium 64.

Another aspect of the invention concerns a method of treating melanoma tumor cells in a subject, comprising: administering the MC1R peptide ligand-micelle complex of the invention to the subject, wherein an anti-cancer agent is present within the inner core of the micelle, and wherein the MC1R peptide ligand-micelle complex releases the anti-cancer agent at the site of the tumor. Preferably, the anti-cancer agent is one that demonstrates efficacy in the treatment of melanoma (for example, kills melanoma cells or inhibits the growth of melanoma cells). In some embodiments, the method comprises:

providing a MC1R peptide ligand-micelle complex of the invention;
incorporating an anti-cancer agent into the inner core of the MC1R peptide ligand-micelle complex; and
administering the MC1R peptide ligand-micelle complex with the anti-cancer agent to the subject, wherein the MC1R peptide ligand-micelle complex releases the anti-cancer agent at the site of the tumor.

In some embodiments, the anti-cancer agent is a radiotherapy agent, such as Yttrium. In some embodiments, the anti-cancer agent comprises an alkylating chemotherapy agent, such as melphalan or ifosfamide. In some embodiments, the agent comprises a systemic melanoma chemotherapy agent, such as dacarbazine, paclitaxel, and/or vincristine.

Another aspect of the invention concerns a method of preparing a MC1R peptide ligand-micelle complex, comprising:

providing multiplicity of triblock polymer chains comprising a hydrophobic polypeptide block attached to a central crosslinkable peptide block comprising a multiplicity of crosslinkable amino acid residues attached to a water soluble polymer block, wherein a portion of the triblock polymer chains further comprise a first click functionality covalently attached to the water soluble polymer block distal to the central crosslinkable peptide block and wherein the triblock polymer chains self assemble into a micelle;
providing a MC1R peptide ligand comprising a complementary second click functionality covalently attached to a MCIR targeting peptide; and
combining the triblock polymer chains with the MC1R peptide ligand, wherein the first click functionality and the complementary second click functionality react to form a reaction product that covalently joins the triblock polymer to the MC1R peptide ligand to form a MC1R peptide ligand-micelle complex.

In some embodiments, the MC1R peptide ligand is 4-phenylbutyryl-His-DPhe-Arg-Trp-Gly-Lys(hex-5-ynoyl)-NH$_2$ (SEQ ID NO:3); H-Lys(hex-5-ynoyl)-Tyr-Val-Nle-Gly-His-DNal(2')-Arg-DTrp-Asp-Arg-Phe-Gly-NH$_2$ (SEQ ID NO:4); or H-Lys(hex-5-ynoyl)Tyr-Val-Nle-Gly-His-DNal(2')-Arg-DPhe-Asp-Arg-Phe-Gly-NH$_2$ (SEQ ID NO:5).

In some embodiments, the method for preparing a MC1R peptide ligand-micelle complex further comprises crosslinking the multiplicity of crosslinkable amino acid residues. In some embodiments, the method further comprises the incorporation of an agent. In some embodiments, the agent comprises a contrast agent, anti-cancer agent, or both. In some embodiments, the anti-cancer agent is a chemotherapeutic agent, such as a taxane.

Fluorescent and MRI targeted molecular imaging probes have been designed that bind strongly and specifically to the melanocortin 1 receptor (MC1R) that is found expressed on the surface of over 80% of melanoma cells. In some embodiments, the binding portion of the probes is the MC1R ligand with the structure 4-phenylbutyryl-His-DPhe-Arg-Trp-Gly-Lys (hex-5-ynoyl)-NH$_2$ (SEQ ID NO:3) that shows high (0.2 nM) binding affinity for MC1R. Functionalization of the ligand at the C-terminus with an alkyne for use in Cu-catalyzed click chemistry was used to attach a fluorescent dye or a micelle. Fluorescent targeted molecular imaging probes were developed by binding the MC1R ligand to a near infrared fluorescent dye, and cellular uptake of the probe by receptor-mediated endocytosis was shown in engineered A375/MC1R cells in vitro as well as in vivo by intravital fluorescence imaging with higher uptake values in tumors with high expression of MC1R compared to low (P<0.05). MRI targeted molecular imaging probes were developed by binding the MC1R ligand to a micelle containing a gadolinium texaphyrin (Gd-Tx) chelate. These Gd-Tx micelles, stabilized by crosslinking with Fe(III), are able to actively target MC1R expressing xenograft tumors in vitro and in vivo suggesting that appropriately designed micelles may eventually be able to deliver therapeutic payloads. The incidence of malignant melanoma is rising faster than that of any other cancer in the United States, with diagnoses having doubled from 1986 to 2001. Nodal metastases are frequently the initial manifestation of metastatic spread in patients with melanoma and accurate determination of nodal status is important for treatment planning. Currently, sentinel lymph node biopsies are performed to determine if the cancer has metastasized; however, one study showed only 24.3% (288/1184) of melanoma patients who had a sentinel lymph node biopsy had metastases. The diagnostic probes of the invention can be used to determine if a biopsy is avoidable. For example, the probes can be administered to subjects with melanoma before and/or after treatment and the detectable signal from the probe is observed to check nodal status and ascertain whether the cancer has metastasized. If a positive signal is detected, further diagnostic methods may be utilized, such as sentinel nodal biopsy, and/or therapy may be undertaken.

BRIEF DESCRIPTION OF THE DRAWINGS

(FIG. 4B) untargeted micelles; and (FIG. 4C) 4-targeted micelles against HCT116/hMC1R cells. X-axis concentrations for (FIG. 4A) and (FIG. 4C) were normalized to the targeting group.

FIG. 8: Tabulated averaged data of quantified MR T1 weighted signals from the data displayed in FIG. 7.

FIGS. 12-15: Results of europium-time resolved fluorescence (Eu-TRF) binding assays.

FIG. 16: Micelle characterization data from twelve samples.

FIG. 26A shows uptake of the MC1RL-800 probe on A375/MC1R cells. The probe is detected on the cell membrane as early as 15 seconds after incubation and internalized into the cells by 5 min after incubation. No binding or uptake of the probe was observed when high concentrations of NDP-α-MSH was used as a blocking agent before adding the probe to the cells. FIG. 26B shows in vivo uptake studies of the MC1R-635 probe using the dorsal skin-fold window chamber xenograft tumor for intravital confocal imaging. The fluorescent signal from the probe was detected on the cell surface (yellow arrow) by 5 min after i.v. injection of the probe, and was detected inside the cells 24 h after injection.

FIGS. 27A-1, 27A-2, and 27B: In vivo and ex vivo targeting of MC1RL-800. FIG. 27A-1 shows a representative image of normalized fluorescence intensity maps of a mouse bearing xenograft tumors, 2 hours post intravenous injection of the probe (left mouse): A375 cells that constitutively express low levels of MC1R were used to form the low-expressing tumor (left flank) and A375/MC1R cells were used to form the high expressing tumor (right flank). A blocking experiment was performed using co-injection of 0.25 μg unlabeled NDP-α-MSH and 5 nmol/kg of the MC1RL-800 probe to determine target specificity (right mouse). Inset (FIG. 27A-2) is showing quantification of MC1RL-800 normalized fluorescent count of low and high expressing tumors in control and blocking animals. Data represent mean±s.d. NC: Normalized Count (FIG. 27B) are ex vivo images of low- and high-expressing tumors with corresponding IHC staining of MC1R.

FIGS. 28A, 28B-1, and 28B-2: FIG. 28A shows ex vivo bio-distribution of MC1RL-800 in the tumors, kidneys and liver at different time-points post-injection. No signal was detected in the heart, lung, brain and other organs (not shown). The values were normalized as percentage of the highest signal. FIGS. 28B-1 and 28B-2 show mathematical modeling of ex vivo and in vivo bio-distribution of the probe, respectively. Sim: simulation, T: Tumor, K: kidneys.

FIGS. 29A-1, 29A-2, and 29B: Reduction of MC1RL-800 kidney uptake. FIGS. 29A-1 and 29A-2 show pharmacokinetics of different concentrations of injected probe in MC1R low expressing and high expressing tumors and kidneys. Note that the lower concentration (1 nmol/kg) has the lowest kidney accumulation. Insets show representative images of normalized fluorescence intensity maps of a mouse bearing xenograft tumors, 2 hours post intravenous injection of the probe for each concentration. FIG. 29B shows co-injection of 1 nmol/kg of MC4R/5R compound and 5 nmol/kg of MC1RL-800 (right image) to reduce kidney uptake of the probe. Inset shows representative images of mice bearing xenograft tumors, 30 min post intravenous injection of the probe (control, left image) and probe plus MC4R/5R compound (co-injection, right image). Data represent mean±s.d. NC: Normalized Counts.

FIGS. 31A, 31B-1, and 31B-2: FIG. 31A shows verification of rat microvessel patency using Multiphoton Laser Scanning Microscope. Mice were intravenously injected with Blue Dextran to verify GFP rat microvessel (green) patency. Note the flowing of the Dextran in green microvessels. FIGS. 31B-1 and 31B-2 show in vivo uptake studies of the MC1RL-800 probe using the dorsal skin-fold window chamber xenograft tumor for intravital confocal imaging. The probe (red) has been taken into the tumor surrounded by GFP microvessels (green) at 24 hr after injection.

FIGS. 32A-C: MC1RL-800 concentration and location combined with the 3D probe profile in the tumors using Optix-MX3 imaging system in vivo and ex vivo. FIG. 32A shows 3D topography of a representative mouse bearing A375 xenograft tumor (left leg) and A375/MC1R tumor (right leg) 2 hours post intravenous injection of the probe and ex vivo image of the same tumor. FIG. 32B shows A357/MC1R slices from top to bottom through the tumor volume. The distance from the surface of the scanning stage underneath the mouse is indicated in mm underneath each slice. FIG. 32C shows an enlarged image of the currently selected slice (green squared labeled image, 13.48 in the ex vivo panel of FIG. 32B). The color bar in FIG. 32C indicates the corresponding concentration of probe. Note that the ex vivo image and IHC staining of the center slice from the same tumor is shown in FIG. 27B.

FIG. 38A-D: Buildup and clearance data of Gd-Tx contrast enhancement in (a-b) tumor, (c) liver and (d) kidney. p-values are in comparison to T-XL group. All groups contained 3 mice except where noted. $^{\perp}$One mouse expired between 24 h and 48 h time point. $^{+}$One mouse expired upon injection of micelle agent.

FIG. 42A-D: HPLC spectrum for 6.

DETAILED DISCLOSURE OF THE INVENTION

Figure 1:
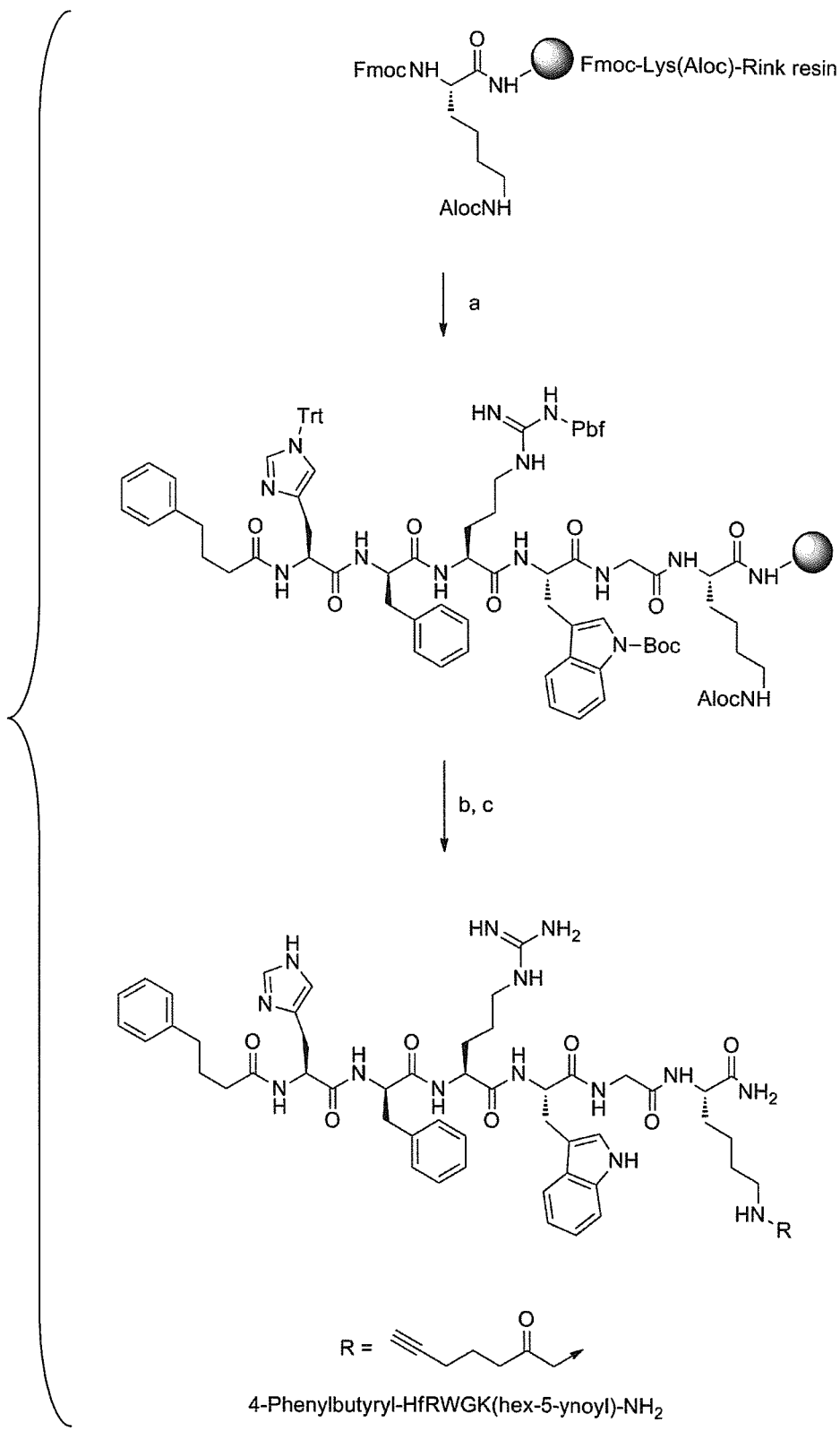
FIG. 1: A synthetic route that was used for compound 4, in which a) (i) Fmoc-AA-OH (3 eq), HOCt or HOBt (3 eq), and DIC (3 eq) in DMF/DCM (10 mL/1 g of resin) for amino acid couplings; b) Piperidine/DMF (1:10, 2+20 minutes); (ii) 4-phenylbutyric acid (6 eq), and DIC (3 eq) in DMF/DCM; b) (i) Pd(0)tetrakistriphenylphosphine (0.01 eq), N,N'-dimethylbarbituric acid (5 eq) in degassed DCM (2×30 minutes) (ii) 5-hexynoic acid (5 eq) and DIC (3 eq) in DMF/DCM c) (i) TFA-scavengers cocktail (91% trifluoroacetic acid, 3% water, 3% thioanisole, 3% ethanedithiol); (ii) ether extraction; (iii) HLPC purification.

According to an embodiment of the invention, MC1R-ligands are selected from those disclosed in the literature [22, 27, 28] for their selectivity to MC1R over other G protein-coupled receptors and modified for attachment to a surface, for example the surface of a polymer-based micelle. For example, one ligand that displays a high affinity for MC1R, with little-to-no interaction with MC4R and MC5R, is functionalization and attached to a 100 nm micelle where attachment does not significantly alter its binding affinity to MC1R. In one embodiment of the invention the attachment of the ligand comprises a functionality that can react with a complementary functionality on a polymer, such as a polymer-based micelle, via click chemistry. Some ligands with MC1R binding affinity are given in Table 1, below.

TABLE 1

Structures of ligands screened for MC1R selectivity.

| Compound | Structure |
|---|---|
| 1 | 4-phenylbutyryl-His-DPhe-Arg-Trp-NH$_2$ (SEQ ID NO: 6) |
| 2 | Ac-Homophenylalanine-His-DPhe-Arg-Trp-NH$_2$ (SEQ ID NO: 7) |
| 3 | 4-hydroxycinnamoyl-His-DPhe-Arg-Trp-NH$_2$ (SEQ ID NO: 8) |
| 4 | 4-phenylbutyryl-His-DPhe-Arg-Trp-Gly-Lys (hex-5-ynoyl)-NH$_2$ (SEQ ID NO: 3) |
| 5 | H-Tyr-Val-Nle-Gly-His-DNal(2')-Arg-DTrp-Asp-Arg-Phe-Gly-NH$_2$ (SEQ ID NO: 9) | ticles structures; compound 3 where the flexible —(CH$_2$)$_3$— of compound 1 is replace with a more rigid double bond (—CH═CH—) and with a 4-hydroxy function incorporated with the phenyl ring as an alternative N-terminal attachment point; and peptides known from a prior study (compounds 5 and 7) [22]. The 4-phenylbutyroyl of compound 1 was substituted with an Ac-homophenylalaninyl (HPE) moiety of compound 2, wherein the amino group is an alternative attachment point to the C-terminal attachment via a lysine ξ-amino as in compound 4. Compounds 4, 6, and 8, are ligands comprising a click functionality, an alkyne, for attachment to a moiety comprising a complementary functionality.

In general, unless otherwise specified, the abbreviations used for the designation of amino acids and the protective groups used therefore are based on recommendations of the IUPAC-IUB Commission of Biochemical Nomenclature (Biochemistry, 11:1726-1732 (1972)). The nomenclature used to define compounds of the invention is that specified by IUPAC, published in European Journal of Biochemistry, 138:9-37 (1984). With regard to certain amino acids disclosed herein, their structures and abbreviations are apparent from the peptide structure below.

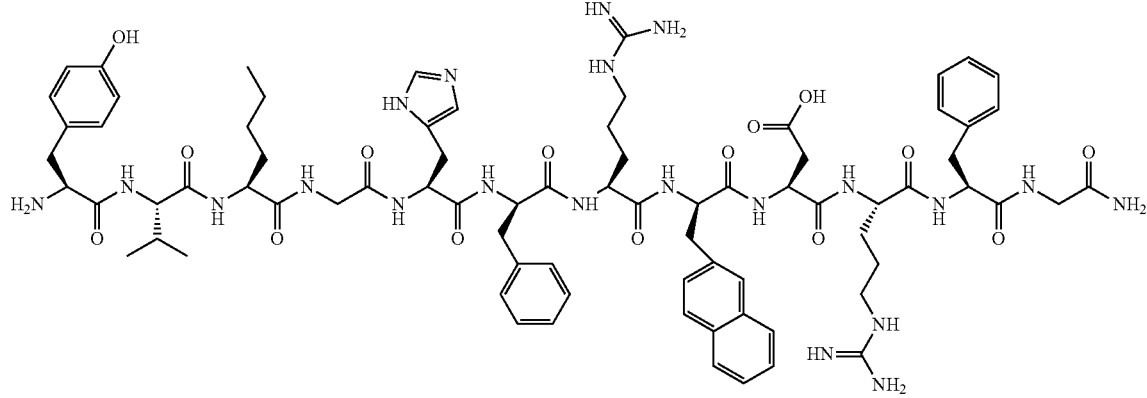

H-Tyr-Val-Nle-Gly-His-DPhe-Arg-DNal(2')-Asp-Arg-Phe-Gly-NH$_2$ (SEQ ID NO:11)

TABLE 1 -continued

Structures of ligands screened for MC1R selectivity.

| Compound | Structure |
|---|---|
| 6 | H-Lys(hex-5-ynoyl)-Tyr-Val-Nle-Gly-His-DNal(2')-Arg-DTrp-Asp-Arg-Phe-Gly-NH$_2$ (SEQ ID NO: 4) |
| 7 | H-Tyr-Val-Nle-Gly-His-DNal(2')-Arg-DPhe-Asp-Arg-Phe-Gly-NH$_2$ (SEQ ID NO: 10) |
| 8 | H-Lys(hex-5-ynoyl)Tyr-Val-Nle-Gly-His-DNal(2')-Arg-DPhe-Asp-Arg-Phe-Gly-NH$_2$ (SEQ ID NO: 5) |

MC1R-selective ligands evaluated include: one based on LK-184 (compound 1); [20, 29] compound 2, an N-terminal amino analog compound to facilitate attachment to nanopar- The letter "D" preceding any three-letter abbreviation for an amino acid, e.g. as in "D-Nal" or "D-Phe," denotes the D-form of the amino acid. The letter "L" preceding an amino acid three-letter abbreviation denotes the natural L-form of the amino acid. For purposes of this disclosure, unless otherwise indicated, absence of a "D" or "L" designation indicates that the abbreviation refers to both the D- and L-forms. Where the common single-letter abbreviation is used, capitalization refers to the L-form and small letter designation refers to the D-form, unless otherwise indicated. For each amino acid, an additional conservative substitution includes the "homolog" of that amino acid, where the "homolog" is an amino acid with a methylene group (CH$_2$) inserted into the side chain at the beta position of that side chain. Examples of such homologs include, without limitation, homophenylalanine, homoarginine, homoserine, and the like. As used herein, the term "peptide," is defined as an amino acid sequence from three amino acids to about 700 amino acids in length.

As used herein, "MC1R ligand" and "ligand" refer to a compound with affinity for melanocortin receptors, particularly melanocortin 1 receptors, that can result in measurable biological activity in cells, tissues, or organisms that contain the MC receptor or blocks stimulation by a known MC agonist. Assays that demonstrate melanocortin receptor agonistic or antagonist activity of compounds are well known in the art.

Related peptides includes allelic variants; fragments; derivatives; substitution, deletion, and insertion variants; fusion polypeptides; and orthologs; and each amino acid of each such related peptide may be either natural or unnatural of the "D" or "L" configuration which corresponds to the stereochemical designation "S" and "R," respectively, as defined in the RS system of Cahn et al., (*Pure Applied Chemistry*, 45:11-30 (1974), and references cited therein). Such related peptides may be mature peptides, i.e., lacking a signal peptide.

Embodiments of the invention are directed to a MC1R-ligand comprising a reactive functionality towards a complementary functionality on a moiety such as a small molecule, a polymer or a functionalized surface, for example a functionality on the polymer shell of an in vivo stable micelle wherein the MC1R comprises a functionality that allows attachment via a Huisgen 1,3-dipolar cycloaddition, Diels-Alder reaction, or any other reaction that has the features of "click" chemistry to a complementary functionality on the moiety. Click chemistry involves a reaction that displays selectivity and high conversion, generally although not necessarily, without driving the reaction by removal of a side product. In addition to use with a polymer shell of a micelle, the MC1R-ligand can be attached as end groups or side groups of a water soluble or water suspendable homopolymer or copolymer. The homopolymer or copolymer can be linear, branched, hyperbranched, dendritic, or a network. The copolymer can be a random copolymer, block copolymer, or graft copolymer. Surfaces can be that of a particle, including polymeric, ceramic, glass, or metal where the surface is flat or irregular including within the pores of a solid porous material. The dimensions of particles can be in the nanometer, micrometer or of larger dimensions.

Some embodiments of the invention provide a stabilized, targeted micelle system capable of delivering systemic diagnostic agents and/or therapeutic agents ("theragnostics") specifically to a tumor site. Gadolinium-texaphyrin (Gd-Tx) has been investigated as a radiation sensitizing agent, and is used for exemplification herein. In some embodiments, the therapeutic agent is a chemotherapeutic agent, such as a taxane.

The MC1R-ligand can be coupled via a linking group to a small molecule, polymer or functionalized surface that includes a contrast agent (e.g., imaging contrast agent) or a therapeutic agent by a stable or biodegradable linker. The contrast agents can include: near infrared (NIR) fluorescent dyes, such as ICG derivatives; CT contrast agents, such as gold; MRI or SPECT contrast agents, such as Gd, Tc99m, and $^{111}$In chelates; radiotherapy agents, such as Yttrium; PET imaging agents comprising, for example, 18-F, 11-C, 18-O, or Gallium 64; alkylating chemotherapy agents, such as melphalan or ifosfamide; and compounds for systemic melanoma chemotherapies, such as dacarbazine, paclitaxel, and vincristine.

In some embodiments of the invention, the MC1R-ligand is attached to a stable micelle (an MC1R peptide ligand-micelle complex) comprising a diblock, triblock or tetrablock copolymer that self organizes into: an inner core comprising a hydrophobic block that provides an environment where a drug or other agent can reside within the micelle; an outer core comprising a intermediate unit or block comprising at least one group that crosslinks, hence stabilizing the micelle; and a hydrophilic shell comprising a water soluble polymer with a functionality distal to the core wherein the functionality is used to attach the targeting MC1R-ligand. Micelles of this type are disclosed in Breitenkamp, et al., U.S. Pat. No. 7,638,558, and incorporated herein by reference. The crosslink of the outer shell can be a chemical crosslink which comprise one or more covalent bonds or a physical crosslink that involve associated functional groups or ions, which bind by ligation of ions, dipolar interactions, or any other intermolecular forces. The crosslink can be a disulfide, ester, hydrazone, Schiff base, zinc complexation, Iron (III) complexation, or other crosslinking that can be reversible. In embodiments of the invention, the crosslink is stable in vivo at a normal pH exhibited in most normal cells but uncrosslinks at the lower pH of a malignant cell that is targeted, permitting delivery of a payload to a desired anatomical site, such as a tumor site, through a pH-triggered mechanism. Barkey N M et al., "Development of Melanoma Targeted Polymer Micelles by Conjugation of a Melanocortin 1 Receptor (MC1R) Specific Ligand," *J. Med. Chem.*, October 2011, 54:8078-8084, which describes the formation of embodiments of MC1R peptide ligand-micelle complexes of the invention, is incorporated herein by reference in its entirety (see, for example, compound #4 in Table 1 of Barkey N M et al.).

Water soluble, hydrophilic, polymers that can be used include polyethyleneoxide (also referred to as polyethylene glycol or PEG), poly(N-vinyl-2-pyrolidone), poly(N-isopropylacrylamide), poly(hydroxyethyl acrylate), poly(hydroxylethyl methacrylate), poly(N-(2-hydroxypropoyl)methacrylamide) (HMPA), or any derivatives thereof. Such water soluble polymers are prepared in a manner such that the distal end to the core has a reactive functionalized that is complementary to a reactive functionality on the targeting MC1R-ligand. In an embodiment of the invention, the reactive functionality on the hydrophilic polymer can be a triazine and the complementary functionality on the MC1R-ligand can be a terminal alkyne. In another embodiment of the invention the reactive functionality on the hydrophilic polymer can be a terminal alkyne and the complementary functionality on the MC1R-ligand can be a triazine.

In an embodiment of the invention, the micelle has an inner core that comprises a poly(amino acid) block where a sufficient proportion of the amino acid repeating units have a hydrophobic side group to render the block hydrophobic. The amino acids can be natural or unnatural. The amino acids can include phenylalanine, alanine benzyl glutamate, alkyl glutamate, benzyl aspartate, alkyl aspartate, leucine, tyrosine, serine, threonine, glutamic acid, aspartic acid, or a combination thereof.

In some embodiments of the invention, the micelle has an outer core comprising a reaction functionality that can be combined with a like reaction functionality to form a cross-link. For example, a pair of thiol functionality can be combined to form a disulfide. The combined functionality can be with the inclusion of a disubstituted coupling reagent. For example, a carboxylic acid functionality can be combined with a divalent or polyvalent salt to form an ionic crosslink, or condensed with a diol, diamine, or other symmetrically or asymmetrically disubstituted reagent to form a covalent crosslink.

Some embodiments of the invention are directed to a method for the preparation of the MC1R-ligands comprising a functional group that can undergo a click reaction, as shown in FIG. 1. The method involves preparation of a peptide sequence comprising a 4-propynyl amide at either the C terminal or, alternately, the N terminal end of the peptide. The peptide can be prepared using a Rink Amide Tentagel resin (0.23 mmol/g) using a Fmoc/tBu synthetic strategy and standard activations. The protected peptide is selectively deprotected with cleavage of the Aloc group, and subsequently condensed with a click reagent containing compound, for example a 5-hexynoic acid, to form the 5-hexynyl amide group, as the site for surface attachment of the MC1R-ligand. The remainder of the protection groups and the cleavage from the resin can be carried out by addition of a TFA scavenger cocktail.

Figure 2:
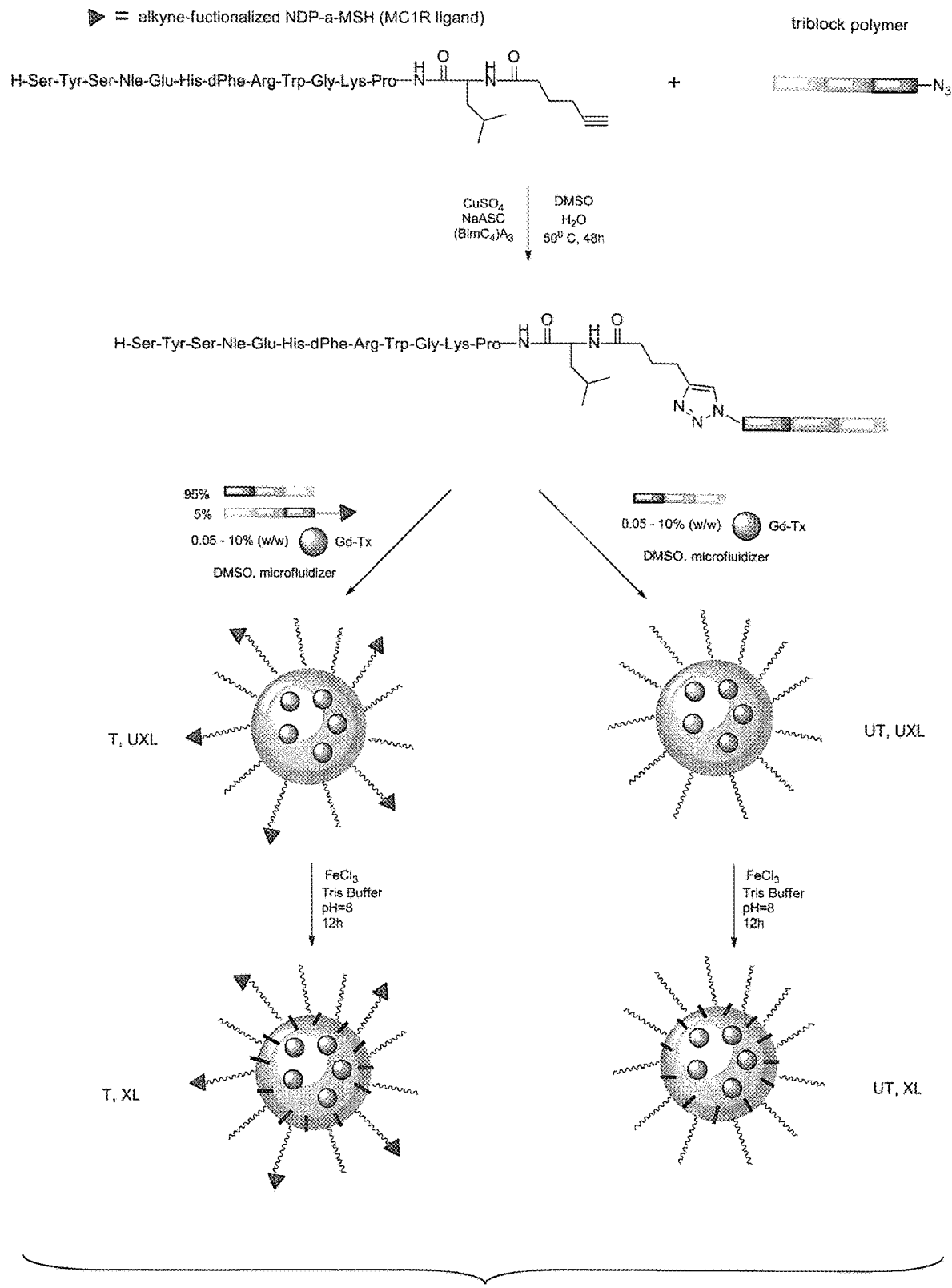
FIG. 2: A reaction scheme for preparation of the MC1R peptide ligand micelle complex according to an embodiment of the invention (SEQ ID NO:15).

Some embodiments of the invention are directed to the functionalization of a surface with a MC1R-ligand comprising a functional group for a click reaction and a surface comprising the complementary functionality. In an embodiment of the invention, an MC1R-ligand comprises an alkyne functionality at an amino acid residue at the C terminal end, or alternately at the N terminal end, is added to an azide functionalized surface of an in vivo stable micelle. In cases in which the surface is the surface of a micelle, a MC1R peptide ligand micelle complex can be formed as shown in FIG. 2.

Some embodiments of the invention are directed to the delivery of drugs, contrast agents, or other agents attached to the MC1R-ligand or contained within a particle or micelle that is attached to the MC1R-ligand, to a patient. The micelle can be an in vivo stable micelle that can de-crosslink at a low pH. The terms "subject", "individual", or "patient" as used herein refer to any human or non-human animal, including mammals, to whom treatment with a composition according to the present invention is provided. Mammalian species that benefit from the disclosed methods of treatment include, and are not limited to, apes, chimpanzees, orangutans, humans, monkeys; domesticated animals (e.g., pets) such as dogs, cats, guinea pigs, hamsters, rabbits, rats, mice, and ferrets; and domesticated farm animals such as cows, horses, swine, and sheep.

The methods of the present invention can be advantageously combined with at least one additional diagnostic and/or treatment method, including but not limited to, chemotherapy, radiation therapy, surgery, immunotherapy or any other therapy known to those of skill in the art for the treatment and management of a cancer.

While MC1R peptide ligands of the invention can be administered to cells in vitro and in vivo as isolated agents, it is preferred to administer these MC1R peptide ligands as part of a pharmaceutical composition. The subject invention thus further provides compositions comprising a peptide of the invention in association with at least one pharmaceutically acceptable carrier. The pharmaceutical composition can be adapted for various routes of administration, such as enteral, parenteral, intravenous, intramuscular, topical, subcutaneous, intratumoral, and so forth. Administration can be continuous or at distinct intervals, as can be determined by a person of ordinary skill in the art.

The MC1R peptide ligands of the invention can be formulated according to known methods for preparing pharmaceutically useful compositions. Formulations are described in a number of sources which are well known and readily available to those skilled in the art. For example, *Remington's Pharmaceutical Science* (Martin, E. W., 1995, Easton Pa., Mack Publishing Company, 19$^{th}$ ed.) describes formulations which can be used in connection with the subject invention. Formulations suitable for administration include, for example, aqueous sterile injection solutions, which may contain antioxidants, buffers, bacteriostats, and solutes that render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the compositions of the subject invention can include other agents conventional in the art having regard to the type of formulation in question.

Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, alpha-ketoglutarate, and alpha-glycerophosphate. Suitable inorganic salts may also be formed, including hydrochloride, sulfate, nitrate, bicarbonate, and carbonate salts.

Pharmaceutically acceptable salts of compounds may be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The active agent (MC1R peptide ligands/complexes) may also be administered intravenously or intraperitoneally by infusion or injection. Solutions of the active agent can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the compounds of the invention which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

MC1R peptide ligands/complexes of the invention may be administered locally at the desired anatomical site, such as a tumor site, or remote from the desired state, or systemically. Sterile injectable solutions are prepared by incorporating the MC1R peptide ligands of the invention in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the agents may be applied in pure-form, i.e., when they are liquids. However, it will generally be desirable to administer them topically to the skin as compositions, in combination with a dermatologically acceptable carrier, which may be a solid or a liquid.

The agents of the subject invention can be applied topically to a subject's skin to reduce the size (and may include complete removal) of malignant or benign growths. The MC1R peptide ligands of the invention can be applied directly to the growth. For example, the MC1R peptide ligand may be applied to the growth in a formulation such as an ointment, cream, lotion, solution, tincture, or the like. Drug delivery systems for delivery of pharmacological substances to dermal lesions can also be used, such as that described in U.S. Pat. No. 5,167,649 (Zook).

Useful solid carriers include finely divided solids such as talc, clay, microcrystalline cellulose, silica, alumina and the like. Useful liquid carriers include water, alcohols or glycols or water-alcohol/glycol blends, in which the peptide can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver the peptides to the skin are disclosed in Jacquet et al. (U.S. Pat. No. 4,608,392), Geria (U.S. Pat. No. 4,992,478), Smith et al. (U.S. Pat. No. 4,559,157) and Woltzman (U.S. Pat. No. 4,820,508).

Useful dosages of the pharmaceutical compositions of the present invention can be determined by comparing their in vitro activity, and in vivo activity in animal models. Methods for the extrapolation of effective dosages in mice, and other animals, to humans are known in the art; for example, see U.S. Pat. No. 4,938,949.

Patients in need of treatment and/or diagnosis using the compositions and methods of the present invention can be identified using standard techniques known to those in the medical or veterinary professions, as appropriate.

As used herein, the terms "cancer" and "malignancy" are used inclusively. As used herein, the terms "cancer" and "malignancy" refer to or describe the physiological condition in mammals that is typically characterized by unregulated cell growth. The cancer may be drug-resistant or drug-sensitive. Examples of cancer include but are not limited to, carcinoma, lymphoma, blastoma, sarcoma, and leukemia. More particular examples of such cancers include melanoma breast cancer, prostate cancer, colon cancer, squamous cell cancer, small-cell lung cancer, non-small cell lung cancer, gastrointestinal cancer, pancreatic cancer, cervical cancer, ovarian cancer, peritoneal cancer, liver cancer, e.g., hepatic carcinoma, bladder cancer, colorectal cancer, endometrial carcinoma, kidney cancer, and thyroid cancer. The cancer may be primary or metastatic. In some embodiments, the cancer is metastatic melanoma.

Other non-limiting examples of cancers are basal cell carcinoma, biliary tract cancer; bone cancer; brain and CNS cancer; choriocarcinoma; connective tissue cancer; esophageal cancer; eye cancer; cancer of the head and neck; gastric cancer; intra-epithelial neoplasm; larynx cancer; lymphoma including Hodgkin's and Non-Hodgkin's lymphoma; myeloma; neuroblastoma; oral cavity cancer (e.g., lip, tongue, mouth, and pharynx); retinoblastoma; rhabdomyosarcoma; rectal cancer; cancer of the respiratory system; sarcoma; skin cancer; stomach cancer; testicular cancer; uterine cancer; cancer of the urinary system, as well as other carcinomas and sarcomas. Examples of cancer are listed in Table 15 below.

As used herein, the terms "administering" or "administer" is defined as the introduction of a substance (MC1R peptide ligand or complex) into cells in vitro or into the body of an individual in vivo and includes oral, nasal, ocular, rectal, vaginal and parenteral routes. The MC1R peptide ligand or complex may be administered individually or in combination with other agents via any route of administration, including but not limited to subcutaneous (SQ), intramuscular (IM), intravenous (IV), intraperitoneal (IP), intradermal (ID), via the nasal, ocular or oral mucosa (IN), or orally. For example, the MC1R peptide ligand or complex can be administered by direct injection into a tumor or at a site remote from the tumor.

The MC1R peptide ligand or complex can be administered to treat a disorder, such as cancer. As used herein, the terms "treat" or "treatment" refer to both therapeutic treatment and prophylactic or preventative measures, wherein the object is to prevent or slow down (lessen) an undesired physiological change or disorder, such as the development or spread of cancer or other proliferation disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. For example, treatment with a peptide of the invention may include reduction of undesirable cell proliferation, and/or induction of apoptosis and cytotoxicity. "Treatment" can also mean prolonging survival as compared to expected survival if not receiving treatment. Those in need of treatment include those already with the condition or disorder as well as those prone to have the condition or disorder or those in which the condition or disorder is to be prevented or onset delayed. Optionally, the patient may be identified (e.g., diagnosed) as one suffering from the disease or condition (e.g., cancer) prior to administration of the peptide of the invention.

As used herein, the term "(therapeutically) effective amount" refers to an amount of the MC1R peptide ligand or complex of the invention or other agent (e.g., a drug) effective to treat a disease or disorder in a mammal. In the case of cancer or other proliferation disorder, the therapeutically effective amount of the agent may reduce (i.e., slow to some extent and preferably stop) unwanted cellular proliferation; reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve, to some extent, one or more of the symptoms associated with the cancer. To the extent the administered MC1R peptide ligand or complex prevents growth of and/or kills existing cancer cells, it may be cytostatic and/or cytotoxic. For cancer therapy, efficacy can, for example, be measured by assessing the time to disease progression (TTP) and/or determining the response rate (RR).

As used herein, the term "growth inhibitory amount" of the MC1R peptide ligand or complex of the invention refers to an amount which inhibits growth or proliferation of a target cell, such as a tumor cell, either in vitro or in vivo, irrespective of the mechanism by which cell growth is inhibited (e.g., by cytostatic properties, cytotoxic properties, etc.). In a preferred embodiment, the growth inhibitory amount inhibits (i.e., slows to some extent and preferably stops) proliferation or growth of the target cell in vivo or in cell culture by greater than about 20%, preferably greater than about 50%, most preferably greater than about 75% (e.g., from about 75% to about 100%).

The terms "cell" and "cells" are used interchangeably herein and are intended to include either a single cell or a plurality of cells, in vitro or in vivo, unless otherwise specified.

In some embodiments, an agent is coupled to the MC1R peptide ligand or incorporated within the micelle of the complex. In some embodiments, the agent is an anti-cancer agent, such as a chemotherapeutic agent, biologic, etc. having anti-cancer activity.

As used herein, the term "anti-cancer agent" refers to a substance or treatment (e.g., radiation therapy) that inhibits the function of cancer cells, inhibits their formation, and/or causes their destruction in vitro or in vivo. Examples include, but are not limited to, cytotoxic agents (e.g., 5-fluorouracil, TAXOL), chemotherapeutic agents, and anti-signaling agents (e.g., the PI3K inhibitor LY). In addition to being coupled to the MC1R peptide ligand or incorporated within the micelle, additional anti-cancer agents may be administered before, during, after administration of the MC1R peptide ligand or complex. Anti-cancer agents include but are not limited to the chemotherapeutic agents listed Table 14.

As used herein, the term "cytotoxic agent" refers to a substance that inhibits or prevents the function of cells and/or causes destruction of cells in vitro and/or in vivo. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, and radioactive isotopes of Lu), chemotherapeutic agents, toxins such as small molecule toxins or enzymatically active toxins of bacterial, fungal, plant or animal origin, and antibodies, including fragments and/or variants thereof.

As used herein, the term "chemotherapeutic agent" is a chemical compound useful in the treatment of cancer, such as, for example, taxanes, e.g., paclitaxel (TAXOL, BRISTOL-MYERS SQUIBB Oncology, Princeton, N.J.) and doxetaxel (TAXOTERE, Rhone-Poulenc Rorer, Antony, France), chlorambucil, vincristine, vinblastine, anti-estrogens including for example tamoxifen, raloxifene, aromatase inhibiting 4(5)-imidazoles, 4-hydroxytamoxifen, trioxifene, keoxifene, LY117018, onapristone, and toremifene (FARESTON, GTx, Memphis, Tenn.), and anti-androgens such as flutamide, nilutamide, bicalutamide, leuprolide, and goserelin, etc. Examples of chemotherapeutic agents that may be used in conjunction with the compounds of the invention are listed in Table 14. In some embodiments, the chemotherapeutic agent is one or more anthracyclines. Anthracyclines are a family of chemotherapy drugs that are also antibiotics. The anthracyclines act to prevent cell division by disrupting the structure of the DNA and terminate its function by: (1) intercalating into the base pairs in the DNA minor grooves; and (2) causing free radical damage of the ribose in the DNA. The anthracyclines are frequently used in leukemia therapy. Examples of anthracyclines include daunorubicin (CERUBIDINE), doxorubicin (ADRIAMYCIN, RUBEX), epirubicin (ELLENCE, PHARMORUBICIN), and idarubicin (IDAMYCIN).

TABLE 14

Examples of Chemotherapeutic Agents

| | |
|---|---|
| 13-cis-Retinoic Acid | Mylocel |
| 2-Amino-6-Mercaptopurine | Letrozole |
| | Neosar |
| 2-CdA | Neulasta |
| 2-Chlorodeoxyadenosine | Neumega |
| 5-fluorouracil | Neupogen |
| 5-FU | Nilandron |
| 6-TG | Nilutamide |
| 6-Thioguanine | Nitrogen Mustard |
| 6-Mercaptopurine | Novaldex |
| 6-MP | Novantrone |
| Accutane | Octreotide |
| Actinomycin-D | Octreotide acetate |
| Adriamycin | Oncospar |
| Adrucil | Oncovin |
| Agrylin | Ontak |
| Ala-Cort | Onxal |
| Aldesleukin | Oprevelkin |
| Alemtuzumab | Orapred |
| Alitretinoin | Orasone |
| Alkaban-AQ | Oxaliplatin |
| Alkeran | Paclitaxel |
| All-transretinoic acid | Pamidronate |
| Alpha interferon | Panretin |
| Altretamine | Paraplatin |
| Amethopterin | Pediapred |
| Amifostine | PEG Interferon |
| Aminoglutethimide | Pegaspargase |
| Anagrelide | Pegfilgrastim |
| Anandron | PEG-INTRON |
| Anastrozole | PEG-L-asparaginase |
| Arabinosylcytosine | Phenylalanine Mustard |
| Ara-C | Platinol |
| Aranesp | Platinol-AQ |
| Aredia | Prednisolone |
| Arimidex | Prednisone |
| Aromasin | Prelone |
| Arsenic trioxide | Procarbazine |
| Asparaginase | PROCRIT |
| ATRA | Proleukin |
| Avastin | Prolifeprospan 20 with Carmustine implant |
| BCG | Purinethol |
| BCNU | Raloxifene |
| Bevacizumab | Rheumatrex |
| Bexarotene | Rituxan |
| Bicalutamide | Rituximab |
| BiCNU | Roveron-A (interferon alfa-2a) |
| Blenoxane | Rubex |
| Bleomycin | Rubidomycin hydrochloride |
| Bortezomib | Sandostatin |
| Busulfan | Sandostatin LAR |
| Busulfex | Sargramostim |
| C225 | Solu-Cortef |
| Calcium Leucovorin | Solu-Medrol |
| Campath | STI-571 |
| Camptosar | Streptozocin |
| Camptothecin-11 | Tamoxifen |
| Capecitabine | Targretin |
| Carac | Taxol |
| Carboplatin | Taxotere |
| Carmustine | Temodar |
| Carmustine wafer | Temozolomide |
| Casodex | Teniposide |
| CCNU | TESPA |
| CDDP | Thalidomide |

TABLE 14-continued

Examples of Chemotherapeutic Agents

| | |
|---|---|
| CeeNU | Thalomid |
| Cerubidine | TheraCys |
| cetuximab | Thioguanine |
| Chlorambucil | Thioguanine Tabloid |
| Cisplatin | Thiophosphoamide |
| Citrovorum Factor | Thioplex |
| Cladribine | Thiotepa |
| Cortisone | TICE |
| Cosmegen | Toposar |
| CPT-11 | Topotecan |
| Cyclophosphamide | Toremifene |
| Cytadren | Trastuzumab |
| Cytarabine | Tretinoin |
| Cytarabine liposomal | Trexall |
| Cytosar-U | Trisenox |
| Cytoxan | TSPA |
| Dacarbazine | VCR |
| Dactinomycin | Velban |
| Darbepoetin alfa | Velcade |
| Daunomycin | VePesid |
| Daunorubicin | Vesanoid |
| Daunorubicin hydrochloride | Viadur |
| | Vinblastine |
| Daunorubicin liposomal | Vinblastine Sulfate |
| DaunoXome | Vincasar Pfs |
| Decadron | Vincristine |
| Delta-Cortef | Vinorelbine |
| Deltasone | Vinorelbine tartrate |
| Denileukin diftitox | VLB |
| DepoCyt | VP-16 |
| Dexamethasone | Vumon |
| Dexamethasone acetate | Xeloda |
| dexamethasone sodium phosphate | Zanosar |
| | Zevalin |
| Dexasone | Zinecard |
| Dexrazoxane | Zoladex |
| DHAD | Zoledronic acid |
| DIC | Zometa |
| Diodex | Gliadel wafer |
| Docetaxel | Glivec |
| Doxil | GM-CSF |
| Doxorubicin | Goserelin |
| Doxorubicin liposomal | granulocyte-colony stimulating factor |
| Droxia | Granulocyte macrophage colony stimulating factor |
| DTIC | |
| DTIC-Dome | Halotestin |
| Duralone | Herceptin |
| Efudex | Hexadrol |
| Eligard | Hexalen |
| Ellence | Hexamethylmelamine |
| Eloxatin | HMM |
| Elspar | Hycamtin |
| Emcyt | Hydrea |
| Epirubicin | Hydrocort Acetate |
| Epoetin alfa | Hydrocortisone |
| Erbitux | Hydrocortisone sodium phosphate |
| Erwinia L-asparaginase | Hydrocortisone sodium succinate |
| Estramustine | Hydrocortone phosphate |
| Ethyol | Hydroxyurea |
| Etopophos | Ibritumomab |
| Etoposide | Ibritumomab Tiuxetan |
| Etoposide phosphate | Idamycin |
| Eulexin | Idarubicin |
| Evista | Ifex |
| Exemestane | IFN-alpha |
| Fareston | Ifosfamide |
| Faslodex | IL-2 |
| Femara | IL-11 |
| Filgrastim | Imatinib mesylate |
| Floxuridine | Imidazole Carboxamide |
| Fludara | Interferon alfa |
| Fludarabine | Interferon Alfa-2b (PEG conjugate) |
| Fluoroplex | Interleukin-2 |
| Fluorouracil | Interleukin-11 |
| Fluorouracil (cream) | Intron A (interferon alfa-2b) |
| Fluoxymesterone | Leucovorin |
| Flutamide | Leukeran |
| Folinic Acid | Leukine |
| FUDR | Leuprolide |
| Fulvestrant | Leurocristine |
| G-CSF | Leustatin |
| Gefitinib | Liposomal Ara-C |
| Gemcitabine | Liquid Pred |
| Gemtuzumab ozogamicin | Lomustine |
| Gemzar | L-PAM |
| Gleevec | L-Sarcolysin |
| Lupron | Meticorten |
| Lupron Depot | Mitomycin |
| Matulane | Mitomycin-C |
| Maxidex | Mitoxantrone |
| Mechlorethamine | M-Prednisol |
| Mechlorethamine Hydrochlorine | MTC |
| | MTX |
| Medralone | Mustargen |
| Medrol | Mustine |
| Megace | Mutamycin |
| Megestrol | Myleran |
| Megestrol Acetate | Iressa |
| Melphalan | Irinotecan |
| Mercaptopurine | Isotretinoin |
| Mesna | Kidrolase |
| Mesnex | Lanacort |
| Methotrexate | L-asparaginase |
| Methotrexate Sodium | LCR |
| Methylprednisolone | |

TABLE 15

Examples of Cancer Types

| | |
|---|---|
| Acute Lymphoblastic Leukemia, Adult | Hairy Cell Leukemia |
| Acute Lymphoblastic Leukemia, Childhood | Head and Neck Cancer |
| | Hepatocellular (Liver) Cancer, Adult (Primary) |
| Acute Myeloid Leukemia, Adult | Hepatocellular (Liver) Cancer, Childhood (Primary) |
| Acute Myeloid Leukemia, Childhood | |
| Adrenocortical Carcinoma | Hodgkin's Lymphoma, Adult |
| Adrenocortical Carcinoma, Childhood | Hodgkin's Lymphoma, Childhood |
| AIDS-Related Cancers | Hodgkin's Lymphoma During Pregnancy |
| AIDS-Related Lymphoma | Hypopharyngeal Cancer |
| Anal Cancer | Hypothalamic and Visual Pathway Glioma, Childhood |
| Astrocytoma, Childhood Cerebellar | |
| Astrocytoma, Childhood Cerebral | Intraocular Melanoma |
| Basal Cell Carcinoma | Islet Cell Carcinoma (Endocrine Pancreas) |
| Bile Duct Cancer, Extrahepatic | Kaposi's Sarcoma |
| Bladder Cancer | Kidney (Renal Cell) Cancer |

TABLE 15-continued

Examples of Cancer Types

Bladder Cancer, Childhood
Bone Cancer, Osteosarcoma/Malignant Fibrous Histiocytoma
Brain Stem Glioma, Childhood
Brain Tumor, Adult
Brain Tumor, Brain Stem Glioma, Childhood
Brain Tumor, Cerebellar Astrocytoma, Childhood
Brain Tumor, Cerebral Astrocytoma/Malignant Glioma, Childhood
Brain Tumor, Ependymoma Childhood
Brain Tumor, Medulloblastoma, Childhood
Brain Tumor, Supratentorial Primitive Neuroectodermal Tumors, Childhood
Brain Tumor, Visual Pathway and Hypothalamic Glioma, Childhood
Brain Tumor, Childhood
Breast Cancer
Breast Cancer, Childhood
Breast Cancer, Male
Bronchial Adenomas/Carcinoids, Childhood
Burkitt's Lymphoma
Carcinoid Tumor, Childhood
Carcinoid Tumor, Gastrointestinal
Carcinoma of Unknown Primary
Central Nervous System Lymphoma, Primary
Cerebellar Astrocytoma, Childhood
Cerebral Astrocytoma/Malignant Glioma, Childhood
Cervical Cancer
Childhood Cancers
Chronic Lymphocytic Leukemia
Chronic Myelogenous Leukemia
Chronic Myeloproliferative Disorders
Colon Cancer
Colorectal Cancer, Childhood
Cutaneous T-Cell Lymphoma, see Mycosis Fungoides and Sézary Syndrome
Endometrial Cancer
Ependymoma, Childhood
Esophageal Cancer
Esophageal Cancer, Childhood
Ewing's Family of Tumors
Extracranial Germ Cell Tumor, Childhood
Extragonadal Germ Cell Tumor
Extrahepatic Bile Duct Cancer
Eye Cancer, Intraocular Melanoma
Eye Cancer, Retinoblastoma
Gallbladder Cancer
Gastric (Stomach) Cancer
Gastric (Stomach) Cancer, Childhood
Gastrointestinal Carcinoid Tumor
Germ Cell Tumor, Extracranial, Childhood
Germ Cell Tumor, Extragonadal
Germ Cell Tumor, Ovarian
Gestational Trophoblastic Tumor
Glioma, Adult
Glioma, Childhood Brain Stem
Glioma, Childhood Cerebral Astrocytoma
Glioma, Childhood Visual Pathway and Hypothalamic
Skin Cancer (Melanoma)
Skin Carcinoma, Merkel Cell
Small Cell Lung Cancer
Small Intestine Cancer
Soft Tissue Sarcoma, Adult
Soft Tissue Sarcoma, Childhood
Squamous Cell Carcinoma, see Skin Cancer (non-Melanoma)
Kidney Cancer, Childhood
Laryngeal Cancer
Laryngeal Cancer, Childhood
Leukemia, Acute Lymphoblastic, Adult
Leukemia, Acute Lymphoblastic, Childhood
Leukemia, Acute Myeloid, Adult
Leukemia, Acute Myeloid, Childhood
Leukemia, Chronic Lymphocytic
Leukemia, Chronic Myelogenous
Leukemia, Hairy Cell
Lip and Oral Cavity Cancer
Liver Cancer, Adult (Primary)
Liver Cancer, Childhood (Primary)
Lung Cancer, Non-Small Cell
Lung Cancer, Small Cell
Lymphoma, AIDS-Related
Lymphoma, Burkitt's
Lymphoma, Cutaneous T-Cell, see Mycosis Fungoides and Sézary Syndrome
Lymphoma, Hodgkin's, Adult
Lymphoma, Hodgkin's, Childhood
Lymphoma, Hodgkin's During Pregnancy
Lymphoma, Non-Hodgkin's, Adult
Lymphoma, Non-Hodgkin's, Childhood
Lymphoma, Non-Hodgkin's During Pregnancy
Lymphoma, Primary Central Nervous System
Macroglobulinemia, Waldenström's
Malignant Fibrous Histiocytoma of Bone/Osteosarcoma
Medulloblastoma, Childhood
Melanoma
Melanoma, Intraocular (Eye)
Merkel Cell Carcinoma
Mesothelioma, Adult Malignant
Mesothelioma, Childhood
Metastatic Squamous Neck Cancer with Occult Primary
Multiple Endocrine Neoplasia Syndrome, Childhood
Multiple Myeloma/Plasma Cell Neoplasm
Mycosis Fungoides
Myelodysplastic Syndromes
Myelodysplastic/Myeloproliferative Diseases
Myelogenous Leukemia, Chronic
Myeloid Leukemia, Adult Acute
Myeloid Leukemia, Childhood Acute
Myeloma, Multiple
Myeloproliferative Disorders, Chronic
Nasal Cavity and Paranasal Sinus Cancer
Nasopharyngeal Cancer
Nasopharyngeal Cancer, Childhood
Neuroblastoma
Non-Hodgkin's Lymphoma, Adult
Non-Hodgkin's Lymphoma, Childhood
Non-Hodgkin's Lymphoma During Pregnancy
Non-Small Cell Lung Cancer
Oral Cancer, Childhood
Oral Cavity Cancer, Lip and
Oropharyngeal Cancer
Osteosarcoma/Malignant Fibrous Histiocytoma of Bone
Ovarian Cancer, Childhood
Ovarian Epithelial Cancer
Ovarian Germ Cell Tumor
Ovarian Low Malignant Potential Tumor
Pancreatic Cancer
Pancreatic Cancer, Childhood
Pancreatic Cancer, Islet Cell
Paranasal Sinus and Nasal Cavity Cancer
Parathyroid Cancer
Penile Cancer
Pheochromocytoma
Pineoblastoma and Supratentorial Primitive Neuroectodermal Tumors, Childhood
Pituitary Tumor
Plasma Cell Neoplasm/Multiple Myeloma
Pleuropulmonary Blastoma
Pregnancy and Breast Cancer

TABLE 15-continued

Examples of Cancer Types

| | |
|---|---|
| Squamous Neck Cancer with Occult Primary, Metastatic | Pregnancy and Hodgkin's Lymphoma |
| Stomach (Gastric) Cancer | Pregnancy and Non-Hodgkin's Lymphoma |
| Stomach (Gastric) Cancer, Childhood | Primary Central Nervous System Lymphoma |
| Supratentorial Primitive Neuroectodermal Tumors, Childhood | Prostate Cancer |
| | Rectal Cancer |
| | Renal Cell (Kidney) Cancer |
| T-Cell Lymphoma, Cutaneous, see Mycosis Fungoides and Sézary Syndrome | Renal Cell (Kidney) Cancer, Childhood |
| | Renal Pelvis and Ureter, Transitional Cell Cancer |
| Testicular Cancer | Retinoblastoma |
| Thymoma, Childhood | Rhabdomyosarcoma, Childhood |
| Thymoma and Thymic Carcinoma | Salivary Gland Cancer |
| Thyroid Cancer | Salivary Gland Cancer, Childhood |
| Thyroid Cancer, Childhood | Sarcoma, Ewing's Family of Tumors |
| Transitional Cell Cancer of the Renal Pelvis and Ureter | Sarcoma, Kaposi's |
| | Sarcoma, Soft Tissue, Adult |
| Trophoblastic Tumor, Gestational | Sarcoma, Soft Tissue, Childhood |
| Unknown Primary Site, Carcinoma of, Adult | Sarcoma, Uterine |
| | Sezary Syndrome |
| Unknown Primary Site, Cancer of, Childhood | Skin Cancer (non-Melanoma) |
| | Skin Cancer, Childhood |
| Unusual Cancers of Childhood | |
| Ureter and Renal Pelvis, Transitional Cell Cancer | |
| Urethral Cancer | |
| Uterine Cancer, Endometrial | |
| Uterine Sarcoma | |
| Vaginal Cancer | |
| Visual Pathway and Hypothalamic Glioma, Childhood | |
| Vulvar Cancer | |
| Waldenström's Macroglobulinemia | |
| Wilms' Tumor | |

As used herein, the term "tumor" refers to all neoplastic cell growth and proliferation, whether malignant or benign, and all pre-cancerous and cancerous cells and tissues. For example, a particular cancer may be characterized by a solid tumor mass or a non-solid tumor. A primary tumor mass refers to a growth of cancer cells in a tissue resulting from the transformation of a normal cell of that tissue. In most cases, the primary tumor mass is identified by the presence of a cyst, which can be found through visual or palpation methods, or by irregularity in shape, texture, or weight of the tissue. However, some primary tumors are not palpable and can be detected only through medical imaging techniques such as X-rays (e.g., mammography), or by needle aspirations. The use of these latter techniques is more common in early detection. Molecular and phenotypic analysis of cancer cells within a tissue will usually confirm if the cancer is endogenous to the tissue or if the lesion is due to metastasis from another site. Depending upon the type of agent (payload) utilized, the compositions of the invention may be capable of inducing apoptosis in tumor cells and reducing tumor cell growth. The compositions of the invention can be administered locally at the site of a tumor (e.g., by direct injection) or remotely. Depending upon the payload, the compositions of the invention can induce cell death in circulating tumor cells (CTC) in a subject, e.g., by administering the compositions intravenously. Furthermore, depending upon payload, the compositions of the invention can prevent or reduce onset of metastasis to other tissues. Furthermore, in cases in which the payload is a detectable moiety, such as a contrast agent, the compositions of the invention can be used to detect metastasis to other tissues and potentially avoid the need for nodal biopsy.

As used herein, the term "payload" refers to agents and moieties linked to the MC1R peptide ligand or residing within the inner core of the MC1R peptide ligand-micelle complex. The payload may be any desired agent or moiety that is capable of being directly or indirectly linked to the MC1R peptide ligand or incorporated within the micelle. Examples of payloads include, but are not limited to, molecules such as contrast agents (e.g., detectable substances such as dyes), biologically active agents, such as biologics, anti-cancer agents such as chemotherapeutic agents (see, for example, Table 14), or other drugs. The terms "payload", "agent", and "moiety" are used interchangeably herein.

As used in this specification, the singular forms "a", "an", and "the" include plural reference unless the context clearly dictates otherwise. Thus, for example, a reference to "a cell" includes one or more cells. A reference to "a peptide" includes one or more such peptide, and so forth.

The practice of the present invention can employ, unless otherwise indicated, conventional techniques of molecular biology, microbiology, recombinant DNA technology, electrophysiology, and pharmacology that are within the skill of the art. Such techniques are explained fully in the literature (see, e.g., Sambrook, Fritsch & Maniatis, Molecular Cloning: A Laboratory Manual, Second Edition (1989); DNA Cloning, Vols. I and II (D. N. Glover Ed. 1985); Perbal, B., A Practical Guide to Molecular Cloning (1984); the series, Methods In Enzymology (S. Colowick and N. Kaplan Eds., Academic Press, Inc.); Transcription and Translation (Hames et al. Eds. 1984); Gene Transfer Vectors For Mammalian Cells (J. H. Miller et al. Eds. (1987) Cold Spring Harbor Laboratory, Cold Spring Harbor, N.Y.); Scopes, Protein Purification: Principles and Practice (2nd ed., Springer-Verlag); and PCR: A Practical Approach (McPherson et al. Eds. (1991) IRL Press)), each of which are incorporated herein by reference in their entirety.

EXEMPLIFIED EMBODIMENTS

Embodiment 1

A modified melanocortin 1 receptor (MC1R) peptide ligand, comprising an MC1R peptide ligand coupled to a functionality.

Embodiment 2

The modified MC1R peptide ligand of embodiment 1, wherein the functionality is an alkyne, azide, amine, aldehyde, thiol, alkene, ester, or maleimide.

Embodiment 3

The modified MC1R peptide ligand of embodiment 1, wherein the functionality is coupled to the C-terminus of said MC1R ligand.

Embodiment 4

The modified MC1R peptide ligand of embodiment 1, wherein the functionality is coupled to the N-terminus of said MC1R ligand.

Embodiment 5

The modified MC1R peptide ligand of embodiment 1, wherein the MC1R peptide ligand is selected from:

```
                                           (SEQ ID NO: 3)
4-phenylbutyryl-His-DPhe-Arg-Trp-Gly-Lys (hex-5-ynoyl)-NH2;

(SEQ ID NO: 4)
H-Lys(hex-5-ynoyl)-Tyr-Val-Nle-Gly-His-DNal(2')-

Arg-DTrp-Asp-Arg-Phe-Gly-NH2;
or
                                           (SEQ ID NO: 5)
H-Lys(hex-5-ynoyl)Tyr-Val-Nle-Gly-His-DNal(2')-

Arg-DPhe-Asp-Arg-Phe-Gly-NH2.
```

Embodiment 6

The modified MC1R peptide ligand of embodiment 1, wherein the MC1R peptide ligand comprises the amino acid motif His-Phe-Arg-Trp (HFRW) (SEQ ID NO:1).

Embodiment 7

The modified MC1R peptide ligand of embodiment 1, wherein the MC1R peptide ligand comprises the amino acid motif His-DPhe-Arg-Trp (HfRW) (SEQ ID NO:2).

Embodiment 8

A method of preparing a MC1R peptide ligand according to embodiment 1, comprising:
providing an MC1R peptide ligand; and
covalently bonding a moiety comprising a functionality to the C-terminus or N-terminus of the MC1R peptide ligand, wherein a MC1R peptide ligand comprising a functionality is formed.

Embodiment 9

The method of embodiment 8, wherein the MC1R peptide ligand comprises a Lys residue or other nitrogen-bearing, thiol-bearing, or —OH bearing residue at the C-terminus or N-terminus, and wherein the moiety comprising the functionality is covalently bound to the residue.

Embodiment 10

The method of embodiment 9, wherein the residue at the C-terminus or N-terminus comprises the Lys residue.

Embodiment 11

The method of embodiment 8, wherein the moiety comprises a terminal alkynyl acid of 5 to 12 carbons.

Embodiment 12

A melanocortin 1 receptor (MC1R)-targeted agent comprising:
a MC1R peptide ligand; and
a moiety, wherein the MC1R peptide ligand and the moiety are covalently linked by a reaction product of a first functionality coupled to the peptide ligand and a complementary second functionality coupled to the moiety.

Embodiment 13

The melanocortin 1-targeted agent of embodiment 12, wherein the moiety comprises an anti-cancer agent, drug (e.g., chemotherapeutic agent, immunotherapeutic agent, etc.), contrast agent, polymer, gel, particle, surface, or any combination of one or more of the foregoing.

Embodiment 14

The melanocortin 1-targeted agent of embodiment 13, wherein the moiety comprises a contrast agent comprising a fluorescent dye.

Embodiment 15

The melanocortin 1-targeted agent of embodiment 14, wherein the fluorescent dye comprises RDye800CW.

Embodiment 16

The melanocortin 1-targeted agent of any one of embodiment 13-15, wherein the contrast agent is covalently linked to the N terminus of the MC1R peptide ligand.

Embodiment 17

The melanocortin 1-targeted agent of embodiment 13 or 14, wherein the contrast agent is covalently linked to the C terminus of the MC1R peptide ligand.

Embodiment 18

The melanocortin 1-targeted agent of embodiment 12, wherein the first functionality comprises an alkyne, azide, amine, aldehyde, thiol, alkene, ester, or maleimide and the reaction product is a 1,2,3-triazole, imine, disulfide, thioether, primary amide, or secondary amide.

Embodiment 19

A method of delivering a moiety to cells expressing the melanocortin 1 receptor (MC1R), comprising administering an MC1R-targeted agent of embodiment 12 or 13 to the cells in vitro or in vivo.

Embodiment 20

The method of embodiment 19, wherein the MC1R-targeted agent is administered to the cells in vivo.

Embodiment 21

The method of embodiment 20, wherein the MC1R-targeted agent is administered systemically to a human or non-human animal subject.

Embodiment 22

The method of embodiment 21, wherein the MC1R-targeted agent is administered to the subject intravascularly (e.g., intravenously).

Embodiment 23

The method of embodiment 20, wherein the MC1R-targeted agent is administered locally to the cells.

Embodiment 24

The method of embodiment 19, wherein the MC1R-targeted agent is administered to a human or non-human animal subject, and wherein the moiety comprises a contrast agent.

Embodiment 25

The method of embodiment 20, further comprising imaging the subject using an imaging modality.

Embodiment 26

The method of embodiment 19, wherein the MC1R-targeted agent is administered locally or systemically to a human or non-human animal subject having melanoma, and wherein the moiety comprises an anti-cancer agent.

Embodiment 27

The method of embodiment 26, wherein the anti-cancer agent kills or inhibits the growth of melanoma cells.

Embodiment 28

A pharmaceutical composition comprising the MC1-R targeted agent of embodiment 12 or 13, and a pharmaceutically acceptable carrier.

Embodiment 29

A method of treating melanoma in a human or non-human animal subject, comprising administering an MC1R-targeted agent of embodiment 12 or 13 to the subject, wherein the moiety comprises an anti-cancer agent.

Embodiment 30

The method of embodiment 29, wherein the anti-cancer agent kills or inhibits the growth of melanoma cells.

Embodiment 31

A modified melanocortin 1 receptor (MC1R) peptide ligand-micelle complex, comprising:
an MC1R peptide ligand; and
a micelle comprising an inner core, outer core and hydrophilic shell, wherein the MC1R peptide ligand is linked to the shell of the micelle by a linker.

Embodiment 32

The MC1R peptide ligand-micelle complex of embodiment 31, further comprising an agent residing in the inner core of the micelle.

Embodiment 33

The MC1R peptide ligand-micelle complex of embodiment 31 or 32, wherein the linker comprises a 1,2,3-triazole, imine, disulfide, thioether, primary amide, or secondary amide.

Embodiment 34

The MC1R peptide ligand-micelle complex of embodiment 31 or 32, wherein the inner core of the micelle comprises a hydrophobic polypeptide, the outer core comprises a crosslinked peptide comprising a multiplicity of crosslinked amino acid residues and the hydrophilic shell comprises a water soluble polymer, and wherein the inner core is covalently attached to the outer core and the outer core is covalently attached to the hydrophilic shell.

Embodiment 35

The MC1R peptide ligand-micelle complex of embodiment 34, wherein the water soluble polymer comprises polyethylene glycol.

Embodiment 36

The MC1R peptide ligand-micelle complex of embodiment 31 or 32, wherein the linker is a 1,2,3-triazole from the addition of an azide and an alkyne.

Embodiment 37

The MC1R peptide ligand-micelle complex of embodiment 31 or 32, wherein the linker is coupled to the C-terminus of said MC1R ligand.

Embodiment 38

The MC1R peptide ligand-micelle complex of embodiment 31 or 32, wherein the linker is coupled to the N-terminus of said MC1R ligand.

Embodiment 39

The MC1R peptide ligand-micelle complex of embodiment 31 or 32, wherein the linker comprises a reaction product, and wherein the MC1R peptide ligand is selected from:

```
                                              (SEQ ID NO: 3)
4-phenylbutyryl-His-DPhe-Arg-Trp-Gly-Lys
(hex-5-ynoyl)-NH2;
                                              (SEQ ID NO: 4)
H-Lys(hex-5-ynoyl)-Tyr-Val-Nle-Gly-His-DNal(2')-
Arg-DTrp-Asp-Arg-Phe-Gly-NH2;
or
                                              (SEQ ID NO: 5)
H-Lys(hex-5-ynoyl)Tyr-Val-Nle-Gly-His-DNal(2')-
Arg-DPhe-Asp-Arg-Phe-Gly-NH2.
```

Embodiment 40

The MC1R peptide ligand-micelle complex of embodiment 31 or 32, wherein the MC1R peptide ligand comprises the amino acid motif His-Phe-Arg-Trp (HFRW) (SEQ ID NO:1).

Embodiment 41

The MC1R peptide ligand-micelle complex of embodiment 31 or 32, wherein the MC1R peptide ligand comprises the amino acid motif His-DPhe-Arg-Trp (HfRW) (SEQ ID NO:2).

Embodiment 42

The MC1R peptide ligand-micelle complex of embodiment 32, wherein the agent comprises an anti-cancer drug.

Embodiment 43

The MC1R peptide ligand-micelle complex of embodiment 32, wherein the agent comprises a contrast agent.

Embodiment 44

A method of imaging a melanoma tumor of a subject, comprising:
  administering the MC1R peptide ligand-micelle complex of embodiment 31 or 32 to the subject, wherein a contrast agent is present within the inner core of the micelle, and wherein the MC1R peptide ligand-micelle complex concentrates in the tumor; and
  observing a signal from the contrast agent, e.g., using an imaging device also referred to herein as an imaging modality).

Embodiment 45

A method of imaging a melanoma tumor, comprising:
  providing a MC1R peptide ligand-micelle complex of embodiment 31 or 32;
  incorporating a contrast agent into the inner core of said MC1R peptide ligand micelle complex;
  administering the MC1R peptide ligand-micelle complex with the contrast agent to a human or non-human animal subject, wherein the MC1R peptide ligand-micelle complex concentrates in the tumor; and
  observing a signal from the contrast agent, e.g., using an imaging device (also referred to herein as an imaging modality).

Embodiment 46

The method of embodiment 45, wherein the contrast agent is a near infrared (NIR) fluorescent dye.

Embodiment 47

The method of embodiment 46, wherein the NIR fluorescent dye comprises a ICG derivative.

Embodiment 48

The method of embodiment 45, wherein the contrast agent is a CT contrast agent.

Embodiment 49

The method of embodiment 48, wherein the CT contrast agent comprises gold.

Embodiment 50

The method of embodiment 45, wherein the contrast agent is a MRI or SPECT contrast agent.

Embodiment 51

The method of embodiment 50, wherein the MRI or SPECT contrast agent comprises Gd, Tc99m, or an $^{111}$In chelate.

Embodiment 52

The method of embodiment 45, wherein the contrast agent is a PET imaging agent.

Embodiment 53

The method of embodiment 52, wherein the PET imaging agent comprises 18-F, 11-C, 18-O, or Gallium 64.

Embodiment 54

A method of treating melanoma tumor cells in a subject, comprising:
  administering the MC1R peptide ligand-micelle complex of embodiment 31 or 32, to the subject, wherein an anti-cancer agent is present within the inner core of the micelle, and wherein the MC1R peptide ligand-micelle complex releases the anti-cancer agent at the site of the tumor.

Embodiment 55

A method of treating melanoma tumor cells in a subject, comprising:
  providing a MC1R peptide ligand-micelle complex of embodiment 31 or 32;
  incorporating an anti-cancer agent into the inner core of said MC1R peptide ligand-micelle complex;
  administering the MC1R peptide ligand-micelle complex with the anti-cancer agent to the subject, wherein the MC1R peptide ligand-micelle complex releases the anti-cancer agent at the site of the tumor.

Embodiment 56

The method of embodiment 55, wherein the anti-cancer agent is a radiotherapy agent.

Embodiment 57

The method of embodiment 56, wherein the radiotherapy agent comprises Yttrium.

Embodiment 58

The method of embodiment 55, wherein the anti-cancer agent comprises an alkylating chemotherapy agent.

Embodiment 59

The method of embodiment 58, wherein the alkylating chemotherapy agent comprises melphalan or ifosfamide.

Embodiment 60

The method of embodiment 55, wherein the anti-cancer agent is a systemic melanoma chemotherapy agent.

Embodiment 61

The method of embodiment 60, wherein the systemic melanoma chemotherapy agent comprises dacarbazine, paclitaxel, and/or vincristine.

Embodiment 62

A method of preparing a MC1R peptide ligand-micelle complex, comprising:
providing a MC1R peptide ligand comprising a first functionality covalently attached to a MC1R targeting peptide;
providing a multiplicity of triblock polymer chains comprising a hydrophobic polypeptide block attached to a central crosslinkable peptide block comprising a multiplicity of crosslinkable amino acid residues attached to a water soluble polymer block, wherein a portion of the triblock polymer chains further comprise a second functionality covalently attached to the water soluble polymer block distal to the central crosslinkable peptide block, wherein the second functionality is complementary to the first functionality and wherein the triblock polymer chains self-assemble into a micelle; and
combining the triblock polymer chains with the MC1R peptide ligand, wherein the first functionality and the complementary second click functionality react to form a reaction product that covalently joins the triblock polymer to the MC1R peptide ligand to form a MC1R peptide ligand-micelle complex.

Embodiment 63

The method of embodiment 62, wherein the MC1R peptide ligand is 4-phenylbutyryl-His-DPhe-Arg-Trp-Gly-Lys(hex-5-ynoyl)-NH$_2$ (SEQ ID NO:3); H-Lys(hex-5-ynoyl)-Tyr-Val-Nle-Gly-His-DNal(2')-Arg-DTrp-Asp-Arg-Phe-Gly-NH$_2$ (SEQ ID NO:4); or H-Lys(hex-5-ynoyl)Tyr-Val-Nle-Gly-His-DNal(2')-Arg-DPhe-Asp-Arg-Phe-Gly-NH$_2$ (SEQ ID NO:5).

Embodiment 64

The method of embodiment 62 or 63, further comprising crosslinking the multiplicity of crosslinkable amino acid residues.

Embodiment 65

The method of embodiment 62 or 63, further comprising the incorporation of an agent.

Embodiment 66

The method of embodiment 65, wherein the agent comprises a contrast agent, anti-cancer agent, or both.

Embodiment 67

A pharmaceutical composition comprising the MC1R peptide ligand-micelle complex of embodiment 31 or 32; and a pharmaceutically acceptable carrier.

Embodiment 68

The MC1R peptide ligand, method, composition, or MC1R peptide ligand-micelle complex of any one of embodiments 1-67, wherein the agent is a biologically active agent or contrast agent.

Embodiment 69

The MC1R peptide ligand, method, composition, or MC1R peptide ligand-micelle complex of embodiment 68, wherein the biologically active agent is a drug or biologic.

Embodiment 70

The MC1R peptide ligand, method, composition, or MC1R peptide ligand-micelle complex of embodiment 68, wherein the biologically active agent is an anti-cancer agent.

Embodiment 71

The MC1R peptide ligand, method, composition, or MC1R peptide ligand-micelle complex of embodiment 70, wherein the anti-cancer agent is an immunotherapeutic agent, a chemotherapeutic agent listed in Table 14, or another chemotherapeutic agent.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

All patents, patent applications, provisional applications, and publications referred to or cited herein, supra or infra, are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Materials and Methods for Example 1

Abbreviations used for amino acids and designation of peptides follow the rules of the IUPAC-IUB Commission of Biochemical Nomenclature in *J. Biol. Chem.* 1972, 247:977-983. The following additional abbreviations are used: Aloc, allyloxycarbonyl; Boc, tert-butyloxycarbonyl; $^t$Bu, tert-butyl; DMSO, dimethylsulfoxide; DVB, divinylbenzene; Fmoc, (9H-fluoren-9-ylmethoxy)carbonyl; HBTU, 2-(1H-benzotriazol-1-yl)-1,1,3,3-tetramethyluronium hexafluorophosphate; HOBt, N-hydroxybenzotriazole; HOCt, 6-chloro-1H-hydroxybenzotriazole; NMI, N-methylimidazole; Pbf, 2,2,4,6,7-pentamethyl-dihydrobenzofuran-5-sulfonyl; PS, polystyrene; RP-HPLC, reverse-phase high performance liquid chromatography; TFA, trifluoroacetic acid; and Trt, triphenylmethyl (trityl).

Materials.

N-α-Fmoc-protected amino acids, HBTU, HCTU, HOCt and HOBt were purchased from Anaspec (San Jose, Calif.) or from Novabiochem (San Diego, Calif.). Rink amide Tentagel S and R resins were acquired from Rapp Polymere (Tubingen, Germany). Rink amide 1%-DVB PS resin was acquired from Novabiochem (San Diego, Calif.). For the N-α-Fmoc-protected amino acids, the following side chain protecting groups were used: Arg($N^g$-Pbf); Asp(O-tBu); His($N^{im}$-Trt); Trp($N^i$-Boc); Tyr($^t$Bu), and Lys($N^\varepsilon$-Aloc). IRDye 800CW maleimide was acquired from Li-Cor (Lincoln, Nebr.). Reagent grade solvents, reagents, and acetonitrile (ACN) for HPLC were acquired from VWR (West Chester, Pa.) or Aldrich-Sigma (Milwaukee, Wis.), and were used without further purification unless otherwise noted. N-terminal heterocyclic acids, NMI, and scavengers were obtained from Sigma-Aldrich or TCI. The solid-phase synthesis was performed in fitted syringes using a Domino manual synthesizer obtained from Torviq (Niles, Mich.). The C-18 Sep-Pak™ Vac RC cartridges for solid phase extraction were purchased from Waters (Milford, Mass.).

Ligand Synthesis.

Ligands 1-8 were prepared as previously published by solid-phase synthesis as summarized in Scheme 1 on Rink Amide Tentagel resin (0.23 mmol/g) using a Fmoc/$^t$Bu synthetic strategy and standard activations.[30, 31] After final deprotection of the Fmoc group, the resin was coupled with HOBt ester of 4-phenylbutyric acid (compounds 1, 4), acetylated with acetic anhydride/pyridine (compound 2) or left unreacted as a free amino group (compounds 5-8). The 4-hydroxycinnamoyl-His-DPhe-Arg-Trp-NH (SEQ ID NO:8) NH-resin was treated with 50% piperidine in DMF to remove 4-hydroxycinnamoyl oligomers. The ligands were cleaved off the resins with TFA-scavenger cocktail (91% TFA, 3% water, 3% thioanisole, 3% ethanedithiol), extracted with cold diethylether, then dissolved in 1.0 m aqueous acetic acid. The crude ligands were purified by SEC and HPLC. The pure compounds were dissolved in DI water or DMSO at approximately 1.0 mM concentrations and concentration was determined by Trp-HPLC measurement[32, 33].

Ligand Purification and Characterization.

Peptides were purified using solid-phase extraction. Briefly, C-18 Sep-Pak™ cartridges (100 mg or 500 mg) were used and pre-conditioned initially with acetonitrile, methanol, and water. After loading the compound, the column was washed with DI water, and then gradually with 5, 10, 20, 30, 50 and 70% of aqueous ACN. Fractions containing product were collected, concentrated to remove organic solvent and lyophilized. Product purity was verified by analytical RP-HPLC using a Waters Alliance 2695 Separation Model with a Waters 2487 dual wavelength detector (220 and 280 nm) on a reverse phase column (Waters XBridge C18, 3.0×75 mm, 3.5 mm). Peptides were eluted with a linear gradient of aqueous ACN/0.1% TFA at a flow rate of 0.3 mL/min. Purification of ligands was achieved on a Waters 600 HPLC using a reverse phase column (Waters) (Bridge C18, 19.0×250 mm, 10 mm). Peptides were eluted with a linear gradient of ACN/0.1% TFA at a flow rate of 5.0-10.0 mL/min. Separation was monitored at 230 and 280 nm. Size exclusion chromatography was performed on a borosilicate glass column (2.6×250 mm, Sigma, St. Louis, Mo.) filled with medium sized Sephadex G-25 or G-10. The compounds were eluted with an isocratic flow of 1.0 M aqueous acetic acid. Mass spectra and HPLC characterization is given in Table 2, below.

QC and Purification:

The purity of products was checked by analytical PR-HPLC using a Waters Alliance 2695 Separation Model with a Waters 2487 dual wavelength detector (220 and 280 nm) on a reverse phase column (Waters)(Bridge C18, 3.0×75 mm, 3.5 μm). Peptides were eluted with a linear gradient of aqueous ACN/0.1% TFA at a flow rate of 0.3 mL/min. Purification of ligands was achieved on a Waters 600 HPLC using a reverse phase column (Waters)(Bridge C18, 19.0× 250 mm, 10 μm). Peptides were eluted with a linear gradient of ACN/0.1% TFA at a flow rate of 5.0-10.0 mL/min. Separation was monitored at 230 and 280 nm. Size exclusion chromatography was performed on a borosilicate glass column (2.6×250 mm, Sigma, St. Louis, Mo.) filled with medium sized Sephadex G-25 or G-10. The compounds were eluted with an isocratic flow of 1.0 M aqueous acetic acid.

Solid-Phase Extraction (SPE): C-18 Sep-Pak™ cartridges (100 mg or 500 mg) were used and pre-conditioned initially with 5 column volumes (5 times the volume of packed column bed) each of acetonitrile, methanol, and water. After loading the compound, the column was washed with DI water, and then gradually with 5, 10, 20, 30, 50, and 70% of aqueous ACN. Fraction containing product were collected, concentrated to remove organic solvent, and lyophilized.

Quantitative HPLC: The peptide concentrations were determined by monitoring absorbance of peptides against 0.5 mM solution of Tryptophan in DMSO at 280 nm. The peptides were initially dissolved in DMSO at approximately 1-5 mM concentration. Co-injections of peptide and Trp were made on analytical HPLC with a number of different volumes and peptide concentration calculated from area under the peaks using the formula given here:

$$\text{Peptide Conc.} = \frac{[\text{Abs. of Comp.}]}{[\text{Abs. of } Trp]} \times \frac{0.5}{\frac{\sum \varepsilon_{280}(Trp + Tyr + Cys + Cy5 + \ldots)}{\varepsilon_{280}}} \times \frac{\text{Vol. of } Trp}{\text{Vol. of Comp.}}$$

$\varepsilon_{280}$ of compounds were determined by summation of tryptophans ($\varepsilon_{280}$=5500), tyrosine ($\varepsilon_{280}$=1490), thiol ($\varepsilon_{280}$=63), and Cy5 dye ($\varepsilon_{280}$=5800), and normalized to extinction coefficient of one tryptophan. Other amino acids in these peptides do not absorb significantly at this wavelength. For Cy5 dye, $\varepsilon_{280}$ was determined in a similar manner by comparing the absorbances of 0.5 mM of both Trp and Cy5-maleimide ester in DMSO at 280 nm wavelength. Mass spectra and HPLC characterization data are provided in Table 2, below.

Mass Spectrometry:

Mass spectra of positive ions were recorded either with a single stage reflectron MALDI-TOF mass spectrometer (Bruker Rexlex III, Bruker Daltonics, Billerica, Mass.; α-cyanocinnamic acid as a matrix) in reflectron mode or with a low resolution ESI mass spectrometer (Finnigan, Thermoquest LCQ ion trap instrument, Lake Forrest, Calif.) and/or using high resolution Fourier transform mass spectrometer (FT-ICR MS, Bruker Apex Qh, Bremen, Germany) equipped with an ESI source. For internal calibration, an appropriate mixture of standard peptides was used with an average resolution of ca. 10,000 on the Reflex III and 60,000 on the FT-ICR instrument.

TABLE 2

High resolution mass spectral data and HPLC[a]

| Compound | $R_t$ (k') | Calc. [MH$^+$] | Exp. [MH$^+$] |
|---|---|---|---|
| 1 | 4.14 | 790.4147 | 790.5 |
| 2 | 3.89 | 746.4362 | 746.5 |
| 3 | 2.54 | 790.3783 | 790.4 |
| 4 | 4.32 | 1069.5730 | 1069.5726 |
| 5 | 3.61 | 1601.8124 | 1601.8 |
| 6 | 3.90 | 1823.9493 | 1824.0 |
| 7 | 3.41 | 1562.8015 | 1562.5 |
| 8 | 3.79 | 1784.9384 | 1784.3 |

[a]Peptide was eluted with a linear ACN/0.1% CF$_3$CO$_2$H aqueous gradient (10% to 90% in 30 min) at a flow rate of 0.3 mL/min);
Waters XBridge C-18 column (3.0 × 150 mm, 3.5 μm);
HPLC k' = (peptide retention time-solvent retention time)/solvent retention time.
All the obtained purified peptides showed >95% purity.
[b] The major molecular peak corresponds to [M + 3Na]$^+$, formula C$_{105}$H$_{127}$O$_{24}$S$_5$N$_{18}$Na$_3$.

Cell Culture.

HCT116 cells overexpressing hMC1R and HEK293 cells overexpressing hMC4R[23] or hMC5R were used in all studies. The parental human colorectal carcinoma cell line, HCT116 (American Type Culture Collection, CCL 247) was also used. Cells were maintained under standard conditions (37° C. and 5% CO$_2$) and were grown in Dulbecco's modified Eagle medium (DMEM) supplemented with 10% FBS and 5% penicillin/streptomycin. For HCT116/hMC1R cells, geneticin (G418S, 0.4 mg/mL) was added to the media to ensure proper selection.

Europium Binding Assays.

Competitive binding assays were performed using HCT116/hMC1R cells and HEK293/hMC4R or hMC5R as previously described, with slight modifications[23]. HCT116/hMC1R cells were plated in black PerkinElmer 96-well plates and HEK293/hMC4R and HEK293/hMC5R cells were plated on SigmaScreen Poly-D-Lysine Coated Plates (SigmaAldrich), all at a density of 10,000-30,000 cells/well. Poly-D-Lysine Coated Plates contain a PDL polymer coating that creates a uniform positive charge at the surface of the plastic, thereby facilitating cell attachment, growth and differentiation. Cells were grown in the 96-well plates for 2-3 days. On the day of the experiment, the media was aspirated and 50 μL of non-labeled competing ligand was added to each well in a series of decreasing concentrations (ranging from ~1 μM to 0.1 nM), followed by 50 μL of Eu-NDP-α-MSH at 10 nM. Both labeled and non-labeled ligands were diluted in binding media (DMEM, 1 mM 1,10-phenanthroline, 200 mg/L bacitracin, 0.5 mg/L leupeptin, 0.3% BSA). In the case of the triblock polymer micelle solutions, micelles were allowed to equilibrate in solution for a period of 30 min prior to cell addition. Cells were incubated with labeled and non-labeled ligands for 1 hour at 37° C. Following incubation, cells were washed three times with wash buffer (50 mM Tris-HCl, 0.2% BSA, 30 mM NaCl) and 50 μL of enhancement solution (PerkinElmer) was added to each well. Cells were incubated for an additional 30 min at 37° C. prior to reading. The plates were read on a PerkinElmer VICTORx4 2030 multilabel reader using the standard Eu TRF measurement (340 nm excitation, 400 s delay, and emission collection for 400 s at 615 nm). Competition curves were analyzed with GraphPad Prism software using the sigmoidal dose-response (variable slope) classical equation for nonlinear regression analysis.

Synthesis of Targeted Triblock Polymers.

Triblock polymer with a terminal azide incorporated into the polyethylene glycol (PEG) block were obtained from Intezyne Technologies, LLC (Tampa, Fla.). The triblock polymer comprised a shell hydrophilic block of PEG, a outer core block of comprising Asp, and a core block comprising a hydrophobic block of Leu and Tyr. To a solution of 1:1 DMSO:H2O (10 mL) was added 4 (16 mmol, 1.2 equiv), triblock polymer (13.3 mmol, 1 equiv), sodium ascorbate (334.15 mmol, 25 equiv), (BimC$_4$A)$_3$ catalyst[34] (13.42 mmol, 1 equiv). The solution was heated to 50° C. and stirred for 2 days. The mixture was then cooled and placed in a 3500 MW dialysis bag and dialyzed against EDTA/H2O (×3) and H2O (×3). Following purification by dialysis, the solution was lyophilized. Successful click coupling was verified through visualization of the triazole-H in 1H NMR (8.02 ppm).

Micelle Formulation.

Triblock polymers were dissolved at 20 mg/mL in 30% tert-butanol/water at room temperature, stirred for 4 hours and then lyophilized. For the targeted micelle system, 10% targeted polymer and 90% untargeted polymer were used in the formulation mixture. Micelle size was determined by dynamic light scattering (DLS) and surface charge was determined by zeta measurement.

Competitive Binding Assays.

Figure 3A:
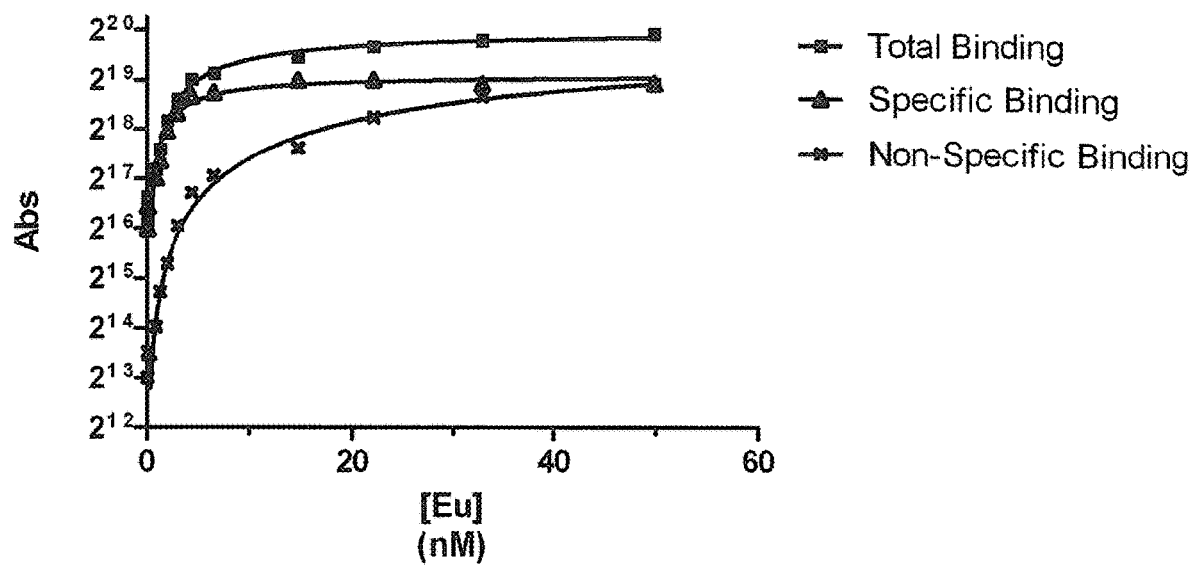
FIGS. 3A-B: Representative competitive binding assays for targeted and untargeted micelles on HCT116/MC1R cells.
Figure 3B:
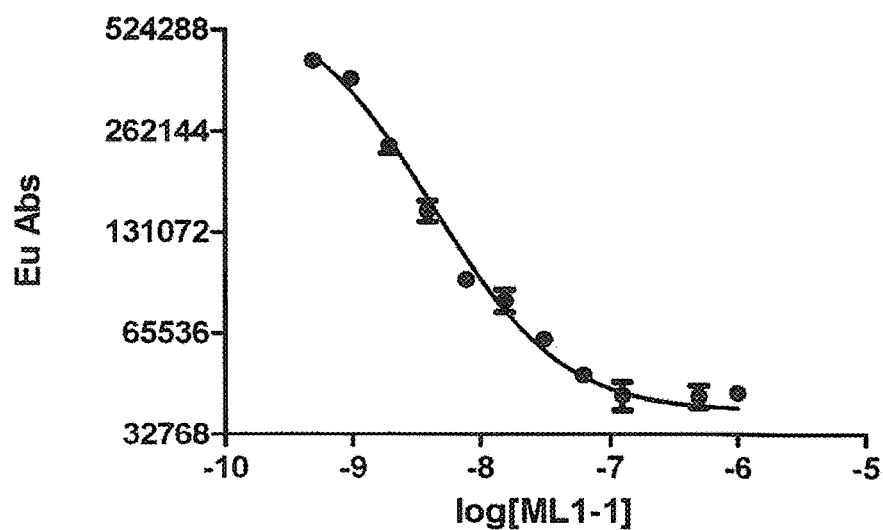

Competitive binding assays were performed using HCT116/hMC1R, HEK293/hMC4R and HEK293/hMC5R cells with ligands 1-8. 1, 2 and 4 were found to both strongly and selectively bind to the hMC1R receptor (FIG. 3, Table 2), with 1 and 4 showing slightly higher affinities for hMC1R as compared to 2 ($K_i$ is 0.17 nM, 0.24 nM and 1.77 nM for 1, 4 and 2, respectively, against hMC1R), and the selectivity of 1 is slightly higher than that of 2. Ligands 5-8 demonstrated a high affinity for hMC1R as well; however, they were also shown to have an even stronger affinity for hMC4R and hMC5R. Ligand 3 demonstrated no affinity to hMC1R.

TABLE 3

Affinity and selectivity of ligands assayed in this publication.

| | Ki (nM)[+] | | | | | | | | | |
|---|---|---|---|---|---|---|---|---|---|---|
| | Values determined | | | | | Values derived from literature | | | | |
| Ligand | MC1R | MC4R | MC5R | 1R/4R | 1R/5R | MC1R | MC4R | MC5R | 1R/4R | 1R/5R |
| 1 | 0.17 | 160.00 | 27.00 | 946.75 | 159.76 | 0.01 | 7.30 | NA | 1216.67 | NA |
| 2 | 1.77 | 988.20 | 58.19 | 558.31 | 32.88 | NA | NA | NA | NA | NA |
| 3 | NB[¬] | NB | NB | NA | NA | NA | NA | NA | NA | NA |
| 4 | 0.24 | NA[∥] | NA | NA | NA | NA | NA | NA | NA | NA |
| 5 | 1.98 | 0.75 | 0.76 | 0.38 | 0.38 | 0.30[⊥] | 6.00[⊥] | 3.50[⊥] | 20.00 | 11.67 |
| 6 | 2.59 | 1.74 | 1.48 | 0.67 | 0.57 | NA | NA | NA | NA | NA |
| 7 | 5.64 | 0.77 | 0.71 | 0.13 | 0.13 | 1.60[⊥] | 20.00[⊥] | 3.30[⊥] | 12.50 | 2.06 |
| 8 | 4.19 | 4.40 | 3.90 | 1.05 | 0.93 | NA | NA | NA | NA | NA |
| 4-targeted polymer | 25.65 | NA | NA | NA | NA | NA | NA | NA | NA | NA |
| 4-targeted micelles | 11.47 | NA | NA | NA | NA | NA | NA | NA | NA | NA |
| NDP-a-MSH | 1.80 | 18.80 | 9.90 | 10.44 | 5.50 | 0.40 | 3.50 | NA | 8.75 | NA |

[+]All values represent Ki values except where denoted.
[¬]NB = Non-binding;
[∥]NA = Not available;
[⊥]Value denotes an EC50 (nM) value.

Figure 4A:
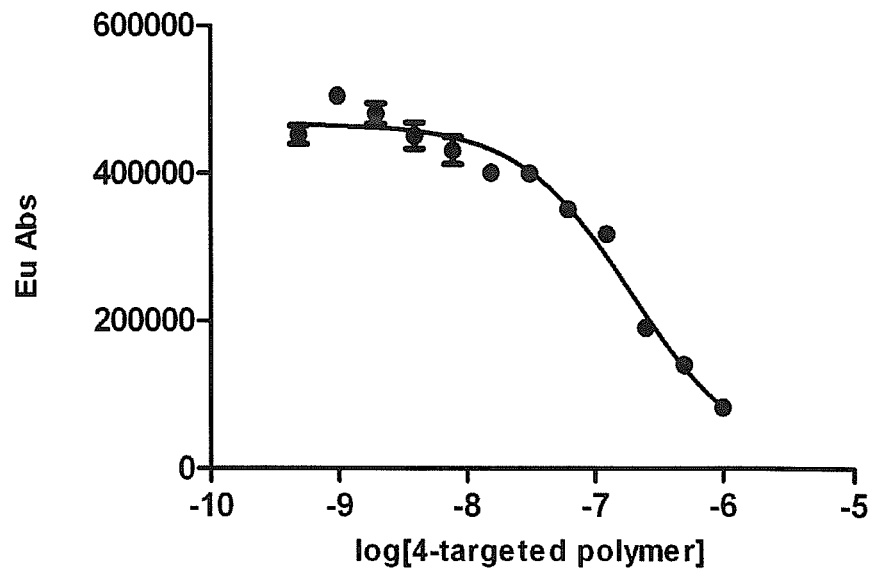
FIGS. 4A-C: Representative competitive binding assays for (FIG. 4A) 4-targeted polymer.
Figure 4B:
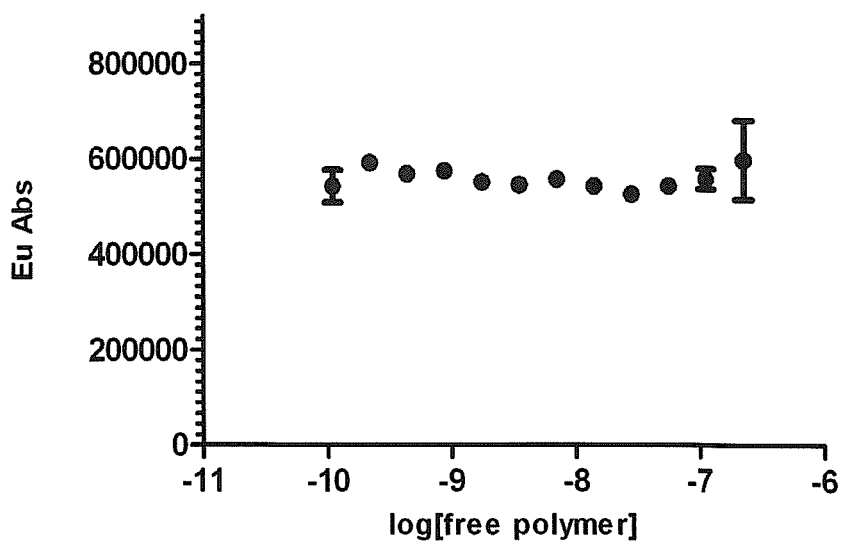
Figure 4C:
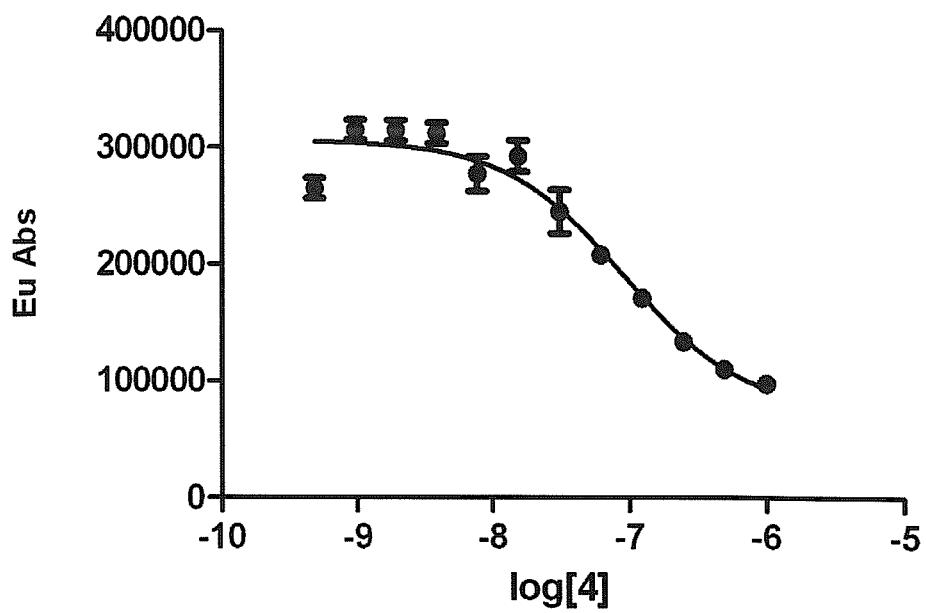

Competitive binding assays were also performed using 4-targeted triblock polymers, triblock polymer micelles, as well as untargeted micelles as a control (FIG. 4A-C). The 4-targeted micelle exhibits an increased binding avidity to the hMC1R receptor compared to the free polymer ($K_i$ is 11.47 nM versus 25.65 nM for the micelle and polymer respectively), and a slightly weaker avidity than the native ligand ($K_i$ is 11.47 nM versus 1.17 nM for the micelle and ligand respectively). Not surprisingly, no binding is observed with the untargeted micelles, indicating that the triblock polymer does not interact non-specifically with the cell surface. DLS and zeta potential measurements showed the size and surface charge of the 4-targeted micelles to be 91 nm and 0.93 mV, respectively.

Example 1—Preparation of MC1R-Targeted Tri-Block Polymer Micelle

Historically, ligands which are known to interact with the hMC1R receptor also demonstrate cross-reactivity with other melanocortin receptors, namely hMC4R and hMC5R. While MC1R is known to be expressed almost exclusively in melanoma cells and melanocytes, hMC4R and hMC5R have high expression levels in normal tissues including kidney and brain, thus non-specific ligand binding is not ideal. To combat this problem and minimize off-target effects, several ligands from the literature were examined that have been reported to possess nanomolar binding affinities for hMC1R (Table 3). Ligand 1 was reported to have a high affinity and selectivity for MC1R (1R/4R selectivity ratio of 1200)[20, 28] and was consequently chosen as a template for the design of the novel ligands 2, 3 and 4. Additionally, ligands 5 and 7 were reported to have moderate hMC1R selectivities over hMC4R and hMC5R[22]; thus, each was functionalized with a terminal alkyne for attachment to a nanoparticle scaffold.

Literature reported dissociation constants for all ligands tested are listed in Table 3 for comparison. The most specific of these ligands, 1, was determined to have an hMC1R/hMC4R selectivity of 950, which is in good agreement with the literature reported selectivity of 1200. Likewise, ligand 2, based on the same parent amino acid sequence as 1, was found to have high 1R/4R selectivity; however, its 1R/5R selectivity was substantially lower. Unfortunately, ligands 3 and 5-8 were found to be not at all selective for MC1R, with ligand 3 showing no affinity for any of the receptors tested. Results for ligands 5 and 7 deviate from that which has been previously reported; this discrepancy may be due to differences in the binding assays used to derive the affinity constants. The $K_i$ values are based on europium time-resolved fluorescence assays; however, previously determined EC50 values for these ligands were derived via $^{125}$I-labeled competitive binding assays.

As 1 was determined to be the ligand with the highest hMC1R affinity and selectivity, it was chosen for modification with a terminal alkyne for attachment of a triblock polymer micelle. Compound 4 did not demonstrate a loss of affinity of MC1R following alkyne functionalization. This is in good agreement with the literature data for MC1R specific ligands, which argues that functionalization at the N-terminus of the peptide does not negatively impact binding due to the location of this region in a large hydrophobic cavity or open extracellular part of the receptor, rather than in a confined pocket[20, 28, 29].

As predicted, 1 and 2 have similar binding profiles given the similarity in their structures; however, it was surprising to see a complete loss of affinity in 3. The differences in affinity among these three ligands arise from the structural differences at the N-terminal end of the peptide, given that they all share the same R—HfRW—$NH_2$ parent scaffold. However, whereas 1 and 2 contain Ph-$(CH_2)_3$—CO— and Ac-Hpe groups, both of which are non-polar, at the N-terminus, 3 contains a 4-hydroxyPh-CH=CH—CO—, which is more polar due the incorporation of the hydroxyl. Conversely, several analogues of 3 possess low nanomolar affinities against MC1R with varying selectivities (Table 3). Thus, it seems reasonable to conclude that the loss in affinity experienced by 3 results from the incorporation of the alkene, rather than the increased polarity from the addition of the hydroxyl group. While the exact reasons behind the affinity of 3, or lack thereof, remain unclear, it is plausible that incorporation of the alkene in this ligand causes the peptide to adopt too rigid a structure, thereby reducing its ability to conform to the receptor binding pocket.

Ligands 5-8 are about twice as large and display binding affinities one-to-two orders of magnitude higher with hMC1R as compared to ligands 1-4. Ligands 6 and 8 were synthesized as analogues of ligands 5 and 7, respectively, to be used for potential attachment to nanoparticles. The similarity in binding affinities of 5 versus 6 and 7 versus 8 further demonstrates that the H-terminal end of these peptides is a suitable location for the placement of an attachment of a scaffold, as it does not seem to impact the binding ability of the ligand.

A targeted triblock polymer micelle was prepared by combining 10% 4-targeted polymer with 90% untargeted polymer. As a control, competitive binding assays were performed with targeted free polymer and untargeted micelles. As previously stated, the 4-targeted micelle exhibits an increased binding avidity to the hMC1R receptor as compared to the free polymer and a slightly weaker avidity than the native ligand. The increase in binding avidity for the targeted micelles as compared to the targeted free polymer is noteworthy in that it (1) demonstrates the in vitro stability of the micelle; and (2) it indicates that the binding avidity of the 4-targeted micelles may be benefiting from multivalent interactions.

While it may be tempting to expect the presence of multivalent interactions to have a more profound effect on the binding affinity of the micelle system, it is important to remember that multivalency is a complex thermodynamic issue that is influenced by a number of variables, including the enthalpies for each ligand upon individual binding events and the entropic consequences experienced by the micelle polymer upon binding. Additionally, ligand proximity and steric repulsions between ligands and polymer chains have been shown to be important factors that influence the degree, if any, to which multivalency is experienced in micellar systems[35]. It is also important to note that improved avidity observed through multivalent interactions are most typically seen while using ligands with relatively low affinity. In the case of 4, it is unlikely that multivalent interactions would greatly enhance binding avidity given the high affinity of the targeting ligand for binding the MC1R receptor[35, 36]. Finally, the experimental set-up also is a factor. For example, each polymer is composed of roughly 100 polymer chains, meaning that at 10% targeting, roughly 10 targeting groups are present per micelle. While this may initially seem like a high number, it is essential to consider the accessibility of these ligands to cell surface, as the experimental set-up of the time-resolved fluorescence binding assay does not necessarily lend itself conducive to multivalent interactions in three dimensions. As a consequence of the assay design, cells are adhered to plates in a monolayer and are only exposed to the targeted particles on one surface. This limited exposure, combined with the inflexible nature of the micelle, arguably can explain the slight decrease in binding affinity experienced in these supramolecular systems.

What is surprising and counter-intuitive is the slight decrease in binding affinity experienced between the targeted polymer, targeted micelles and the native ligand. However, this decrease in affinity may be the result of the conjugation of a large, flexible PEG group to a rather small ligand. In addition to adding to the entropy of the ligand system through increased flexibility and size, PEG chains are known to have at least moderate interaction with non-polar hydrophobic groups[37]. Consequently, it is possible that the PEG moiety on the end of the triblock polymer is weakly interacting with the hydrophobic amino acids of the targeting group, thereby decreasing its affinity for MC1R.

An hMC1R ligand was identified in literature and modified by the inventors for attachment to a triblock polymer micelle. Functionalization and subsequent attachment of the ligand to a 100 nm polymer micelle resulted in a slight decrease in affinity to MC1R. Presumably, this decrease results from the thermodynamic hurdles encountered in appending a small peptide to a large nanoparticle, as well as an inherent handicap in the assay design. As mentioned in the introduction, three hurdles must be overcome in the design of an effective targeted nanoparticle delivery system: (1) it must be insured that there is no loss of ligand affinity resulting from the attachment of a small peptide to a large nanoparticles, or any such loss in affinity must be compensated by multivalent binding interactions; (2) nanoparticles must be inherently stable; and (3) nanoparticles must be sufficiently small to escape the vasculature and enter the tumor. The inventors believe that the invention addresses the first two of these concerns. The ligand remains selective after attachment and the increased binding affinity observed between the free 4-targeted polymer and 4-targeted micelle have demonstrated the in vitro stability of the system. Additionally, based on DLS data, the inventors are confident that the micelles are of sufficient size to escape the vasculature and in vivo studies to evaluate the selectivity and stability of this targeted micellar system in mice are currently underway.

Figure 5A:
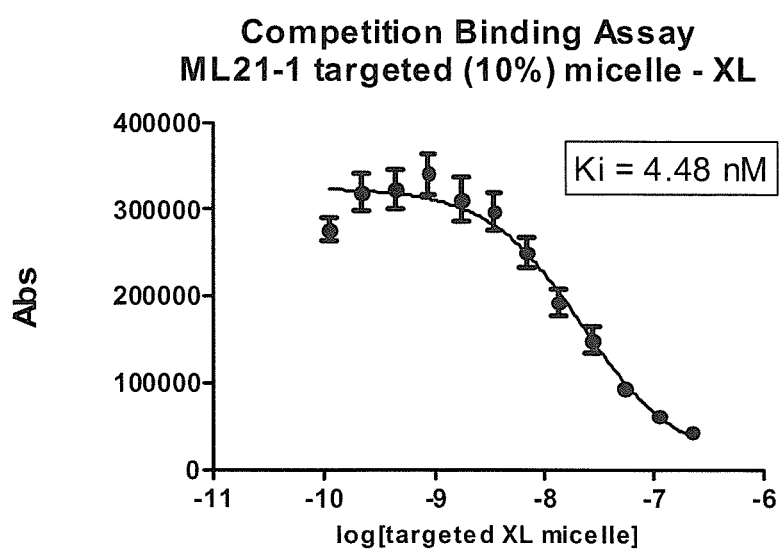
FIGS. 5A-B: Plot of absorbance of a Gd-Tx agent in a (FIG. 5A) 4-targeted (ML21-1 targeted) crosslinked (XL) micelle and a (FIG. 5B) 4-targeted (ML21-1 targeted) uncrosslinked (UXL) micelle for in vitro binding of the 4-targeted micelles at nanomolar concentrations.
Figure 5B:
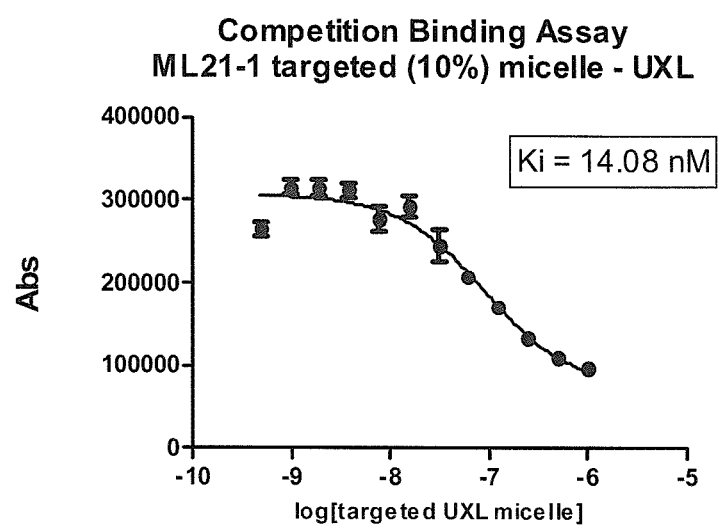
Figure 6:
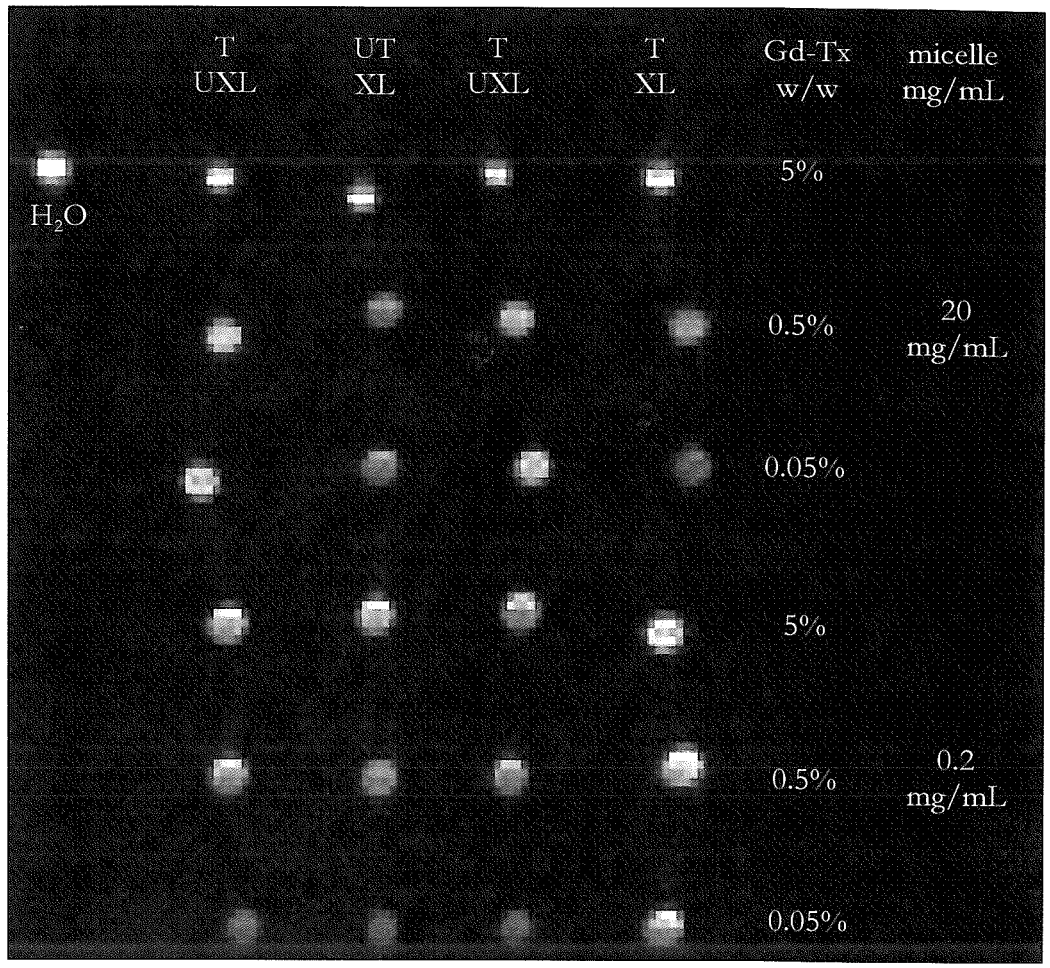
FIG. 6: Grid of in vitro MR T1 weighted signals from Gd-Tx containing 4-targeted (T) and 4-free (UT) micelles that are crosslinked (XL) or crosslink free (UXL) for various loadings of Gd-Tx in the micelles and two different concentrations of the micelles.
Figure 7:
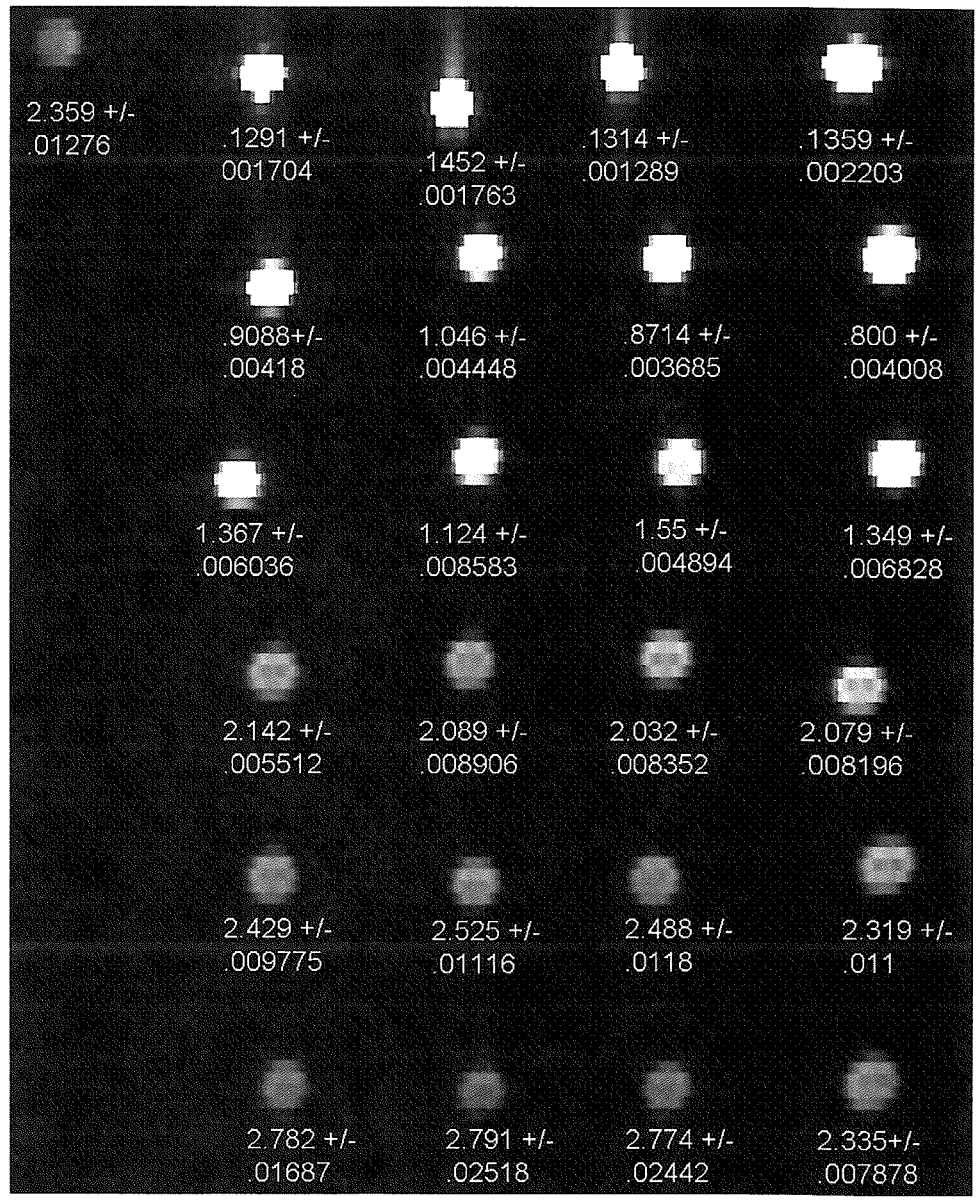
FIG. 7: Grid of in vitro MR T1 weighted signals from Gd-Tx containing 4-targeted (T) and 4-free (UT) micelles that are crosslinked (XL) or crosslink free (UXL), where the columns are of the same order as FIG. 6, for various loadings of Gd-Tx in the micelles showing an optimal signal at loadings of Gd-Tx at a concentration of about 1.3% Gd-Tx in the micelle.

MC1R-ligand 1 is known to have stronger affinity and higher selectivity to hMC1R than NDP-α-MSH. MC1R-ligand 4 conjugated with the triblock polymer to form a stable micelle upon crosslinking or to form uncrosslinked micelles of 70-100 nm loaded with Gd-Texaphyrin, a T1-weighted MR radiation enhancer shown below, at 0.05 to 10% weight. FIGS. 5A and B are plots of competitive binding of the MC1R-ligand 4 conjugated with the triblock polymer, referred to in the Figure as ML21-1, which shows that nanomolar binding affinity the micelle retained nanomolar binding affinity and a significantly higher affinity is observed for the crosslinked micelle over uncrosslinked micelles. In vitro studies displayed measurable contrast for Gd-Tx at low concentrations as indicated in FIG. 6. As can be seen in FIG. 7, micelles in row 3 show higher T1 values than those in row 4, even though both contain 0.01 mg/mL Gd-Tx. This indicates that micelles with higher percentages of encapsulated Gd-Tx within a single micelle, as tabulated in FIG. 8, are experiencing a T2 weighting as a result of the tightly packed gadolinium. Micelles with Gd-Tx encapsulated at 5%, 0.5% and 0.05% were prepared at 0.1 mg/mL Gd-Tx and measurements were made where T1 values indicate that micelles with lower Gd-Tx encapsulated produce lower T1 values as indicated in Table 4, below.

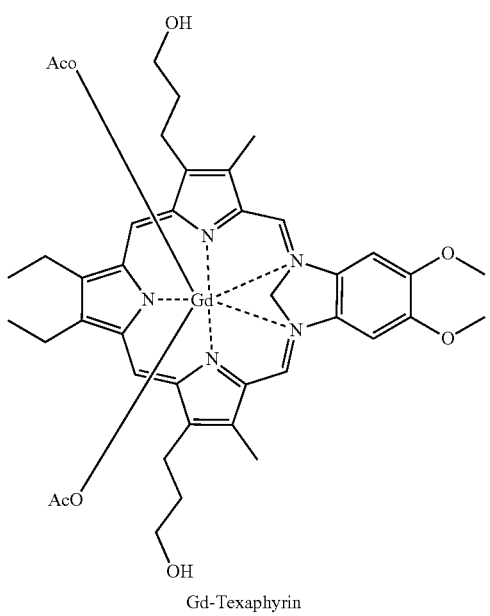
Gd-Texaphyrin

TABLE 4

T1 Values for Gd-Texaphyrin Containing Capsules

| (% Gd-Tx w/w) | [micelle] (mg/mL) | [Gd-Tx] (mg/mL) | T1 (s) |
|---|---|---|---|
| 5 | 0.2 | 0.01 | 2.40 |
| 0.5 | 2 | 0.01 | 2.35 |
| 0.05 | 20 | 0.01 | 1.64 |
| H20 | | | 2.89 |

Figure 9:
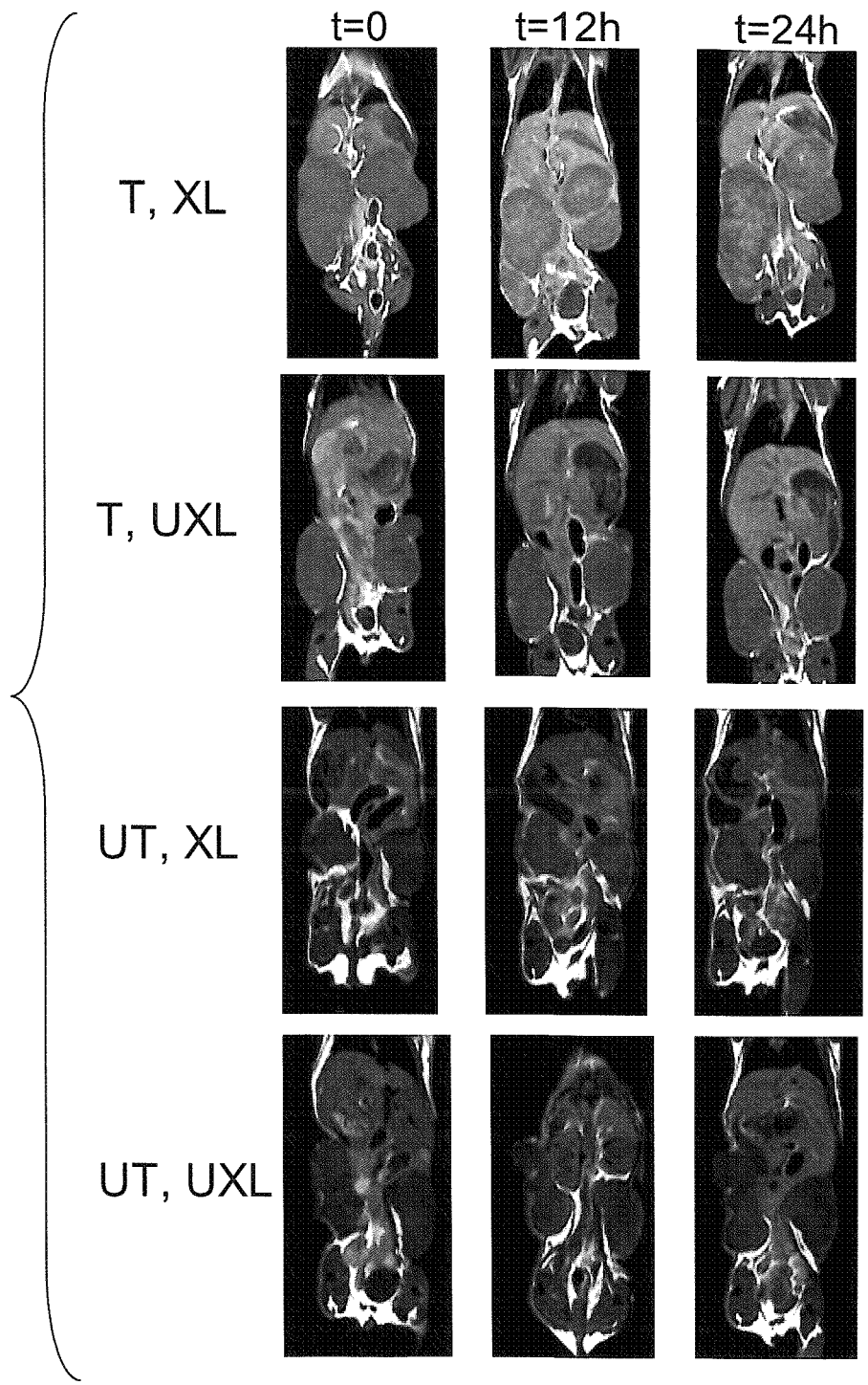
FIG. 9: In vivo MR T1 weighted images of mice that were injected with micelles to produce a 12 mg/mL Gd-Tx concentration with targeted or untagged micelles that are crosslinked or uncrosslinked.
Figure 10:
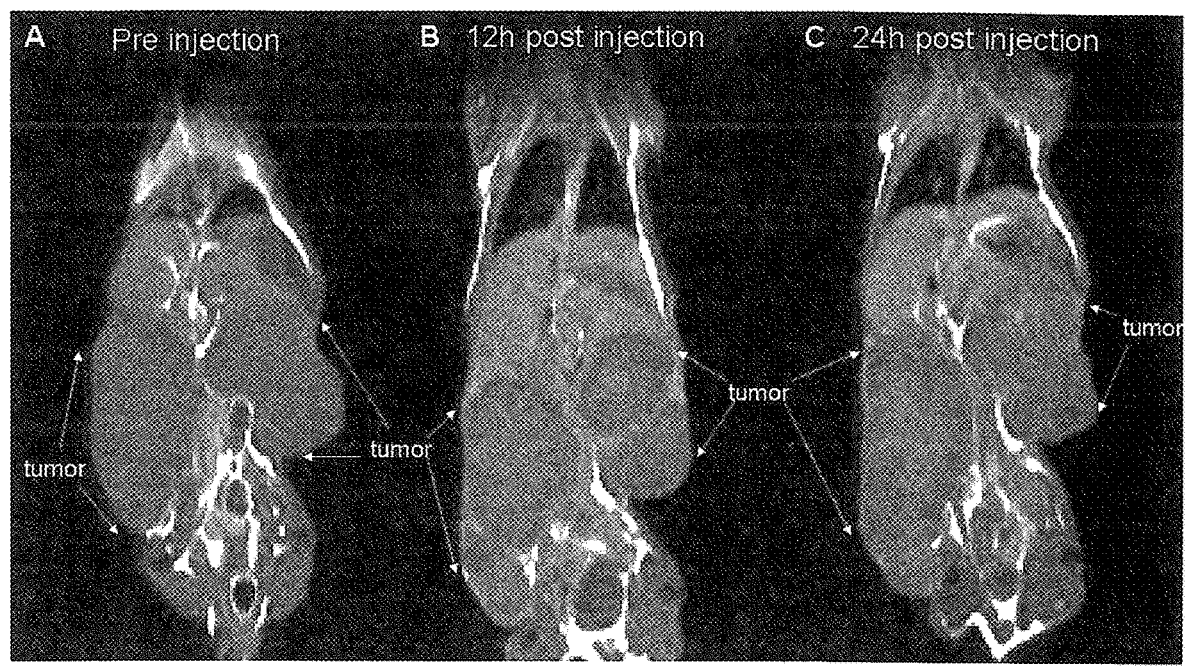
FIG. 10: A closer view of the in vivo MR T1 weighted images of Mice of FIG. 9 for micelles with the 4-targeted crosslinked micelles, where the tumor images are indicated.
Figure 11:
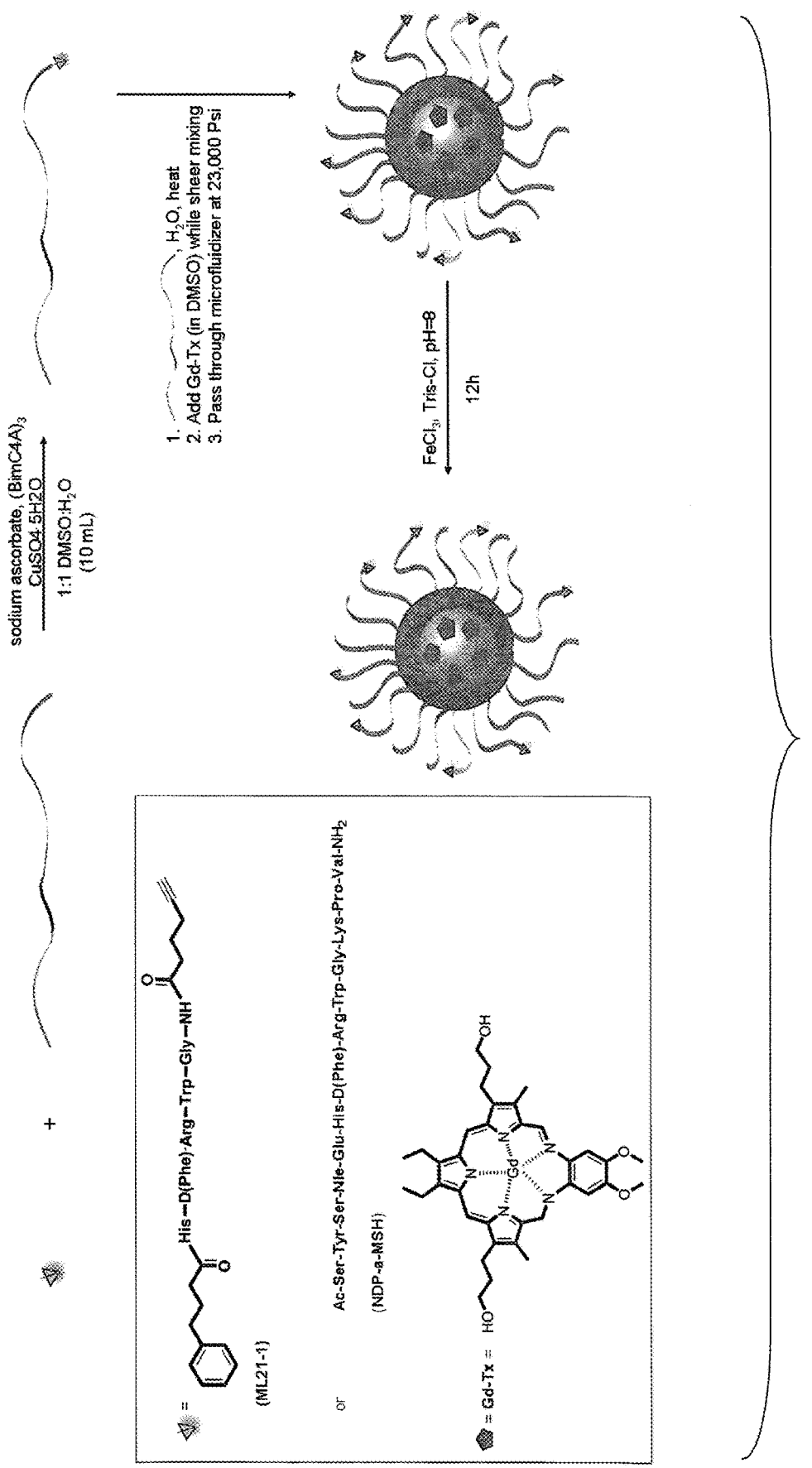
FIG. 11: A reaction scheme for preparation of the MC1R peptide ligand micelle complex according to an embodiment of the invention (a gadolinium-texaphyrin (Gd-Tx) micelle formulation) (SEQ ID NOs:16-17).
Figure 12:
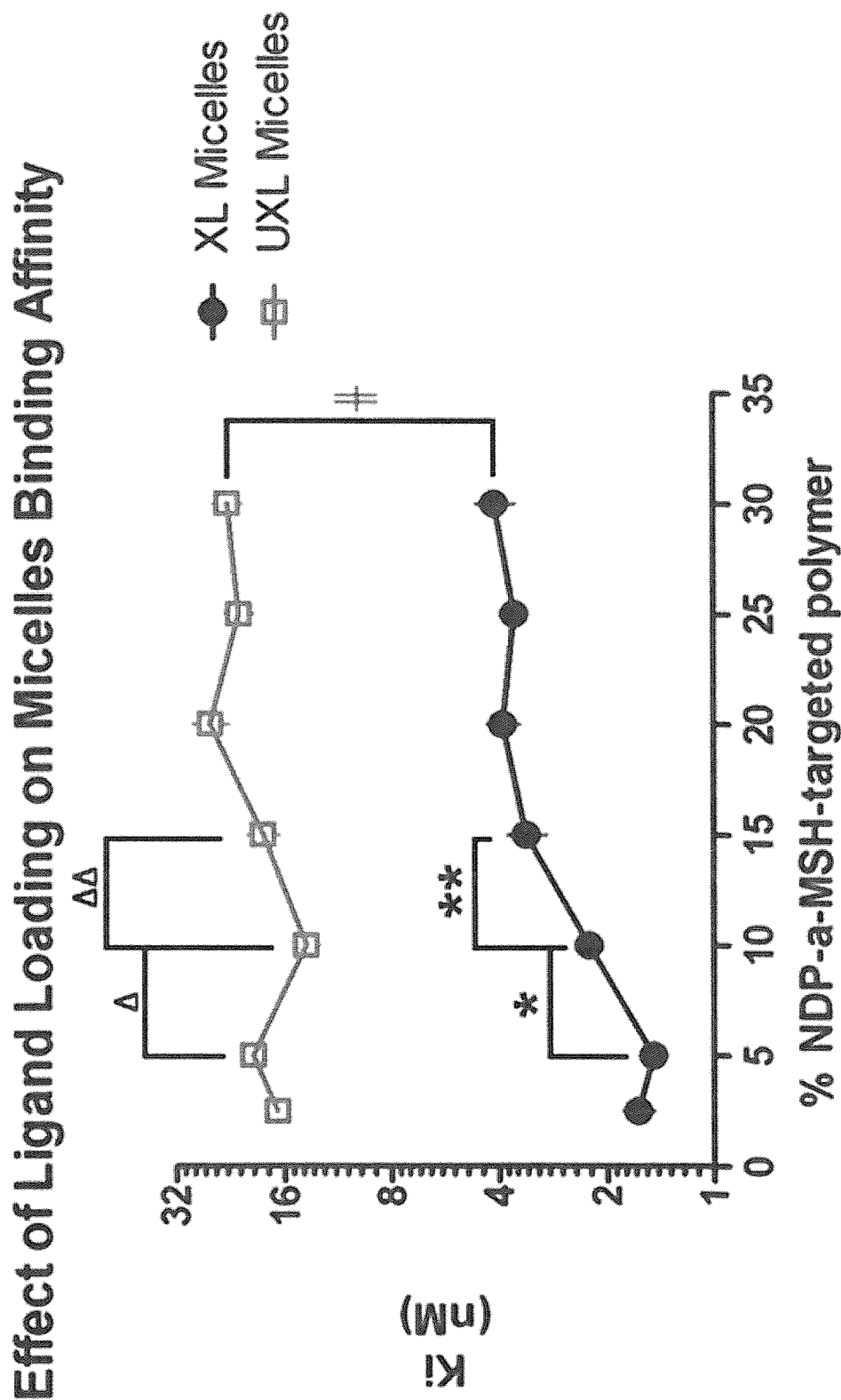
Figure 13:
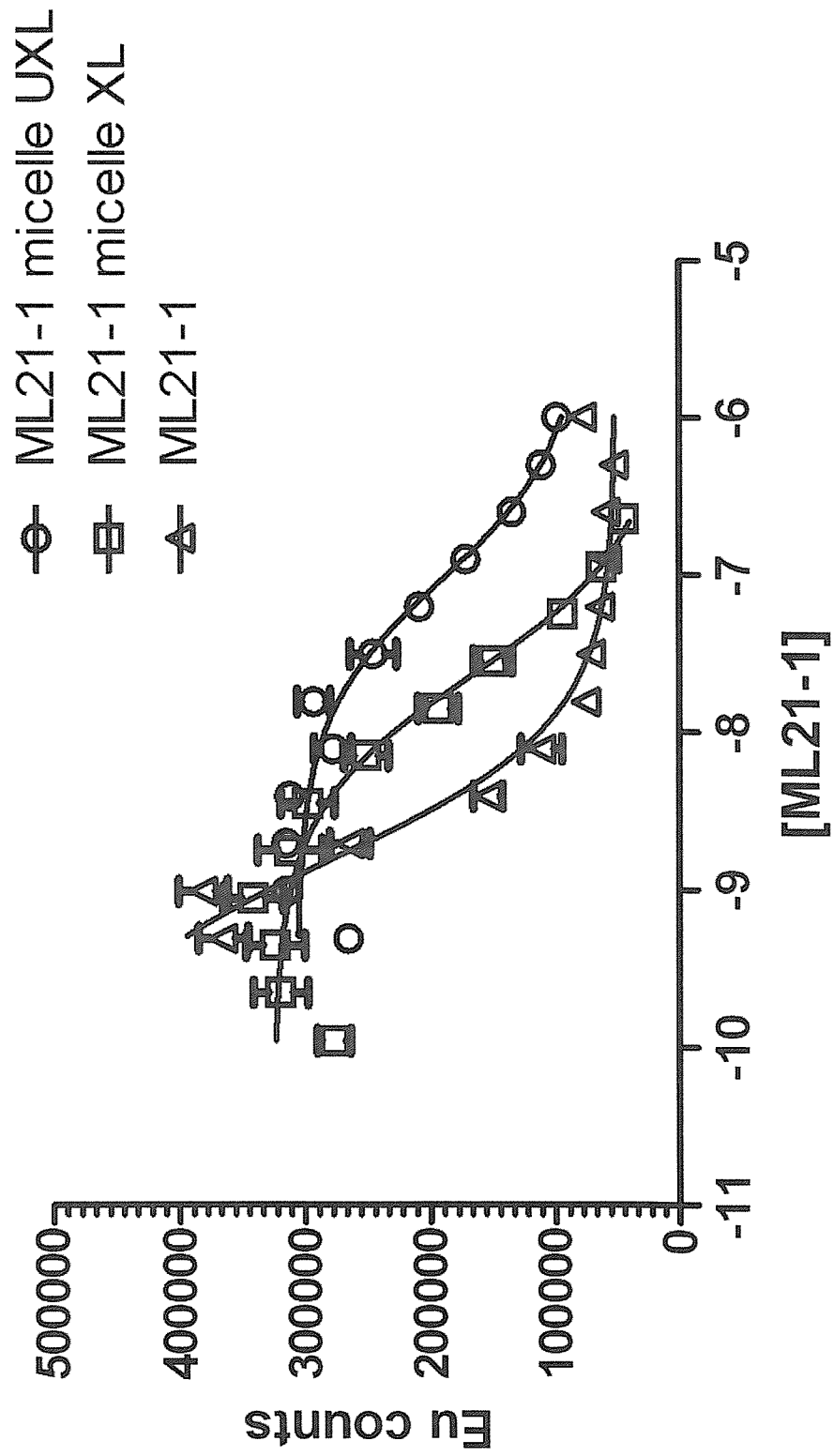
Figure 17:
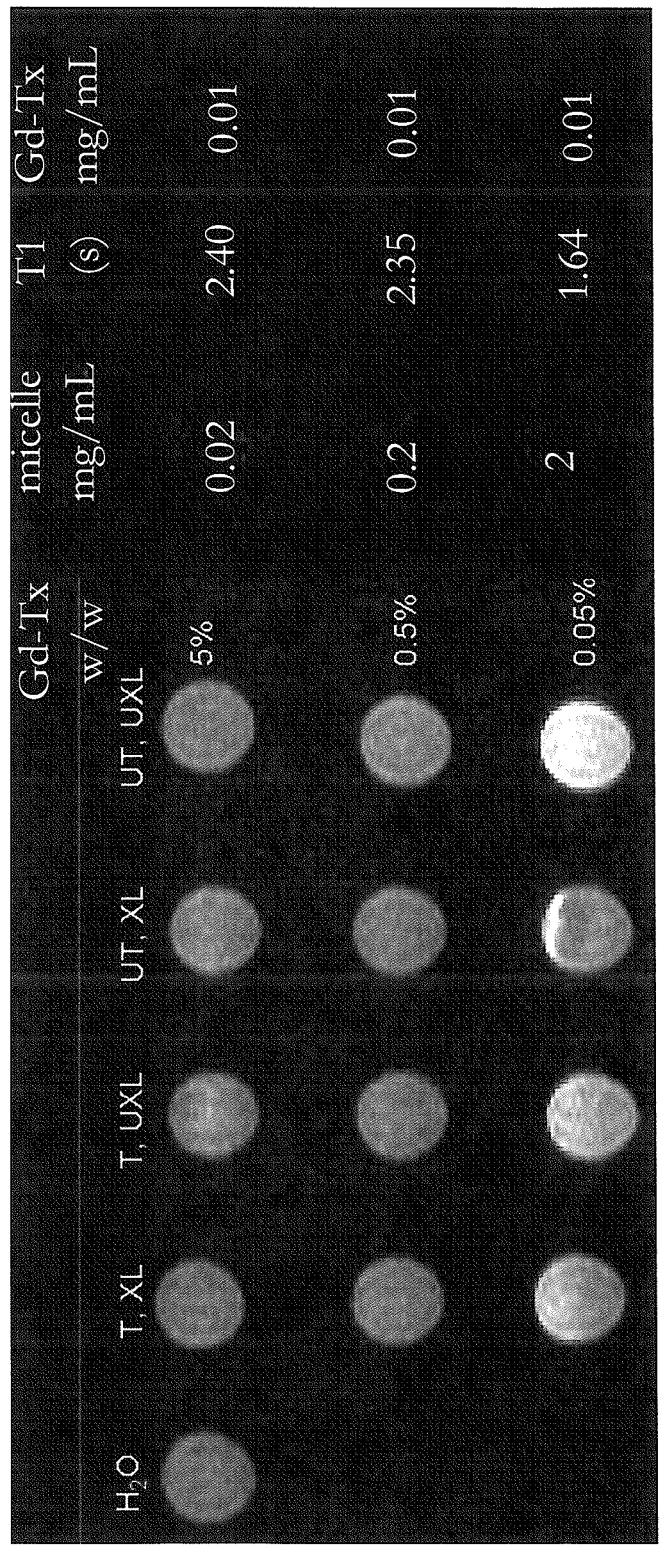
FIG. 17: In vitro SCOUT phantoms of Gd-Tx micelle with a multiple TR SEMS. The TR calculation sequence consisted of TR values of 20, 10.99, 6.03, 3.31, 1.82, 1.00, 0.55, 0.30, 0.17, 0.09 and 0.05 s; TE=8.62 ms; data matrix=128×128, 4 averages, 2 dummy scans, FOV=80 mm×40 mm or 40 mm×90 mm and the slice thickness=1-2 mm. T1 values were calculated using the vnmrj software (Agilent Life Sciences Technologies, Santa Clara, Calif.), and values were verified using MATLAB (Mathworks, Natick, Mass.).
Figure 18:
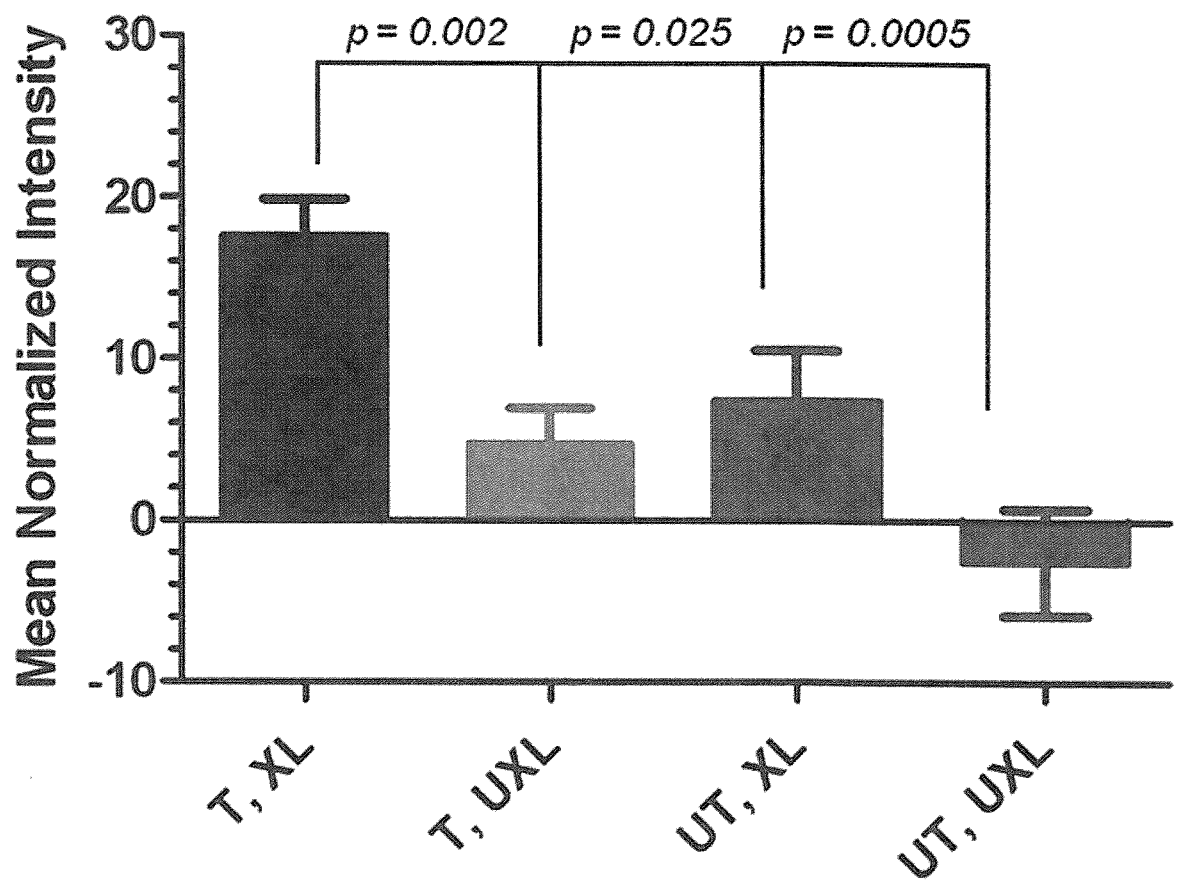
FIGS. 18-21: In vivo MRI results.
Figure 19:
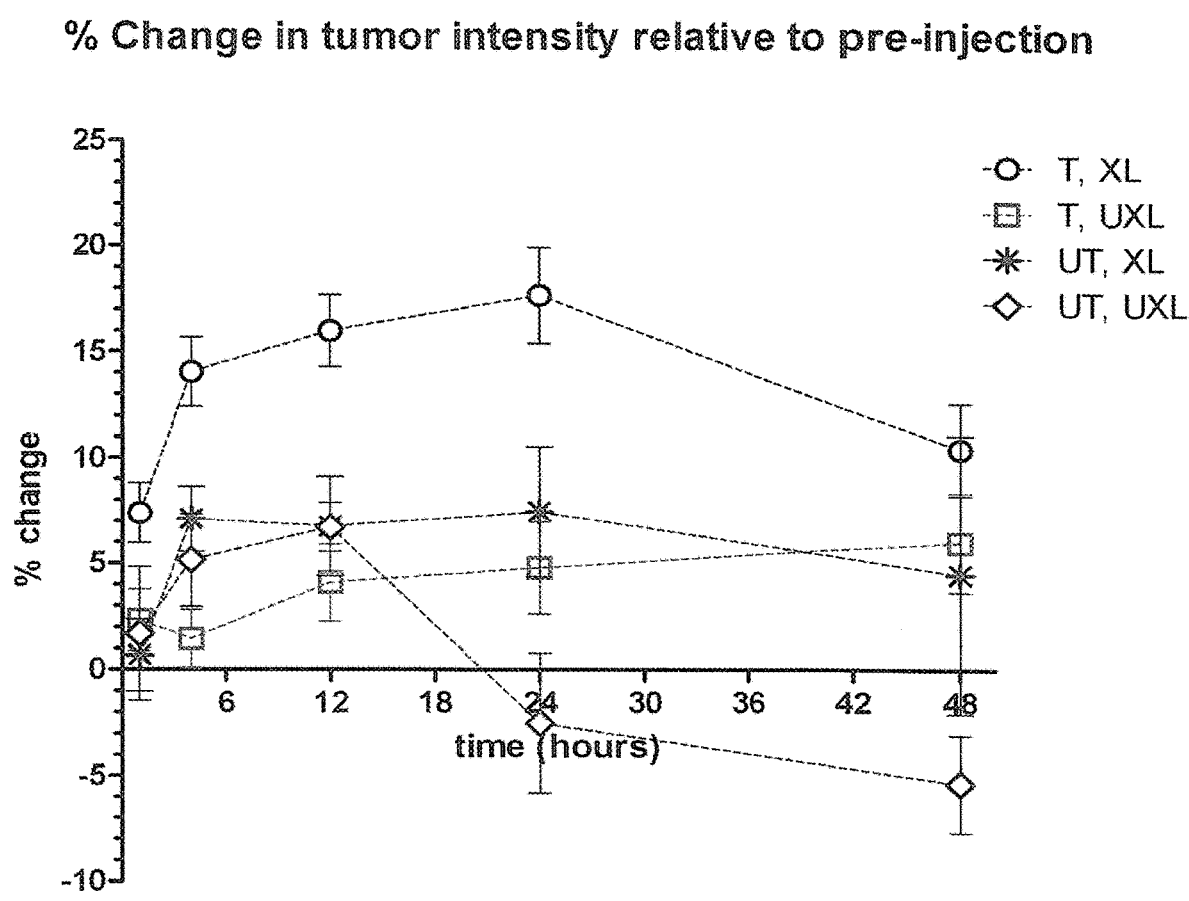
Figure 20:
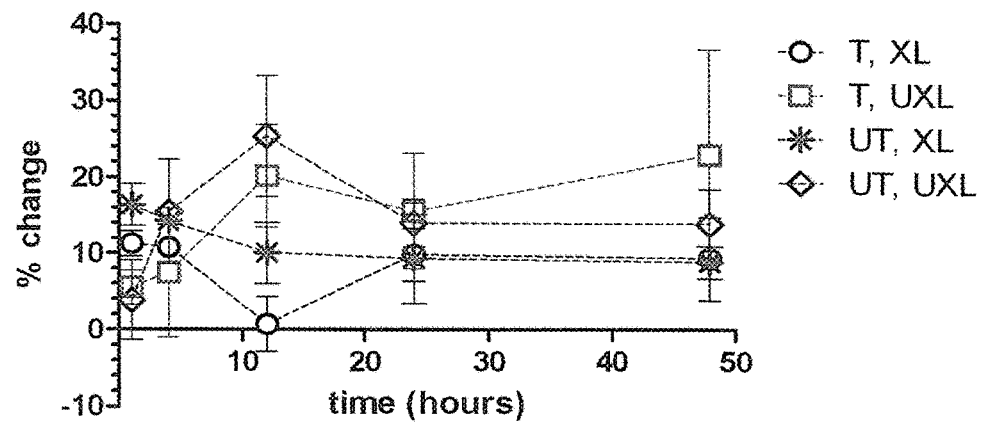
Figure 21:
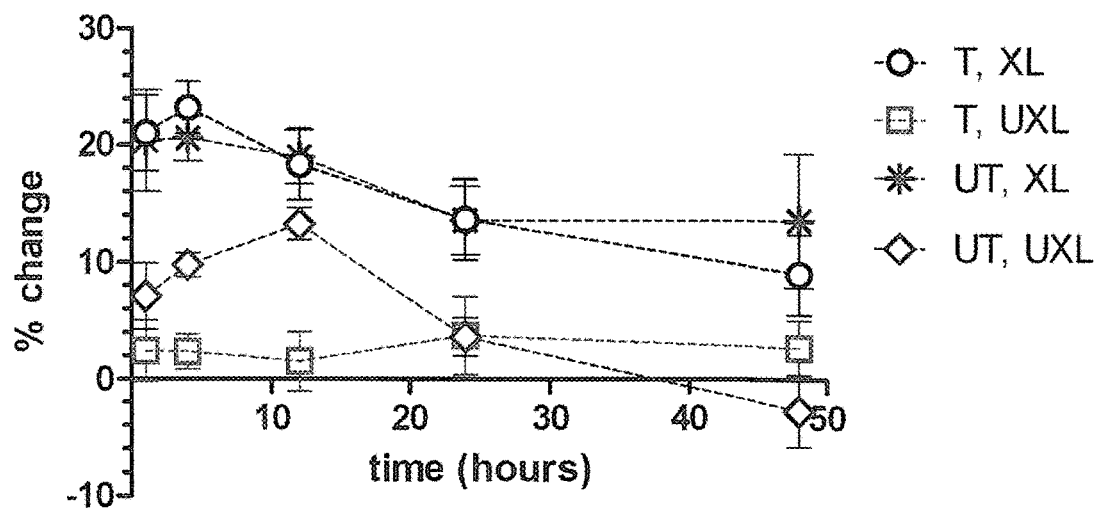
Figure 22:
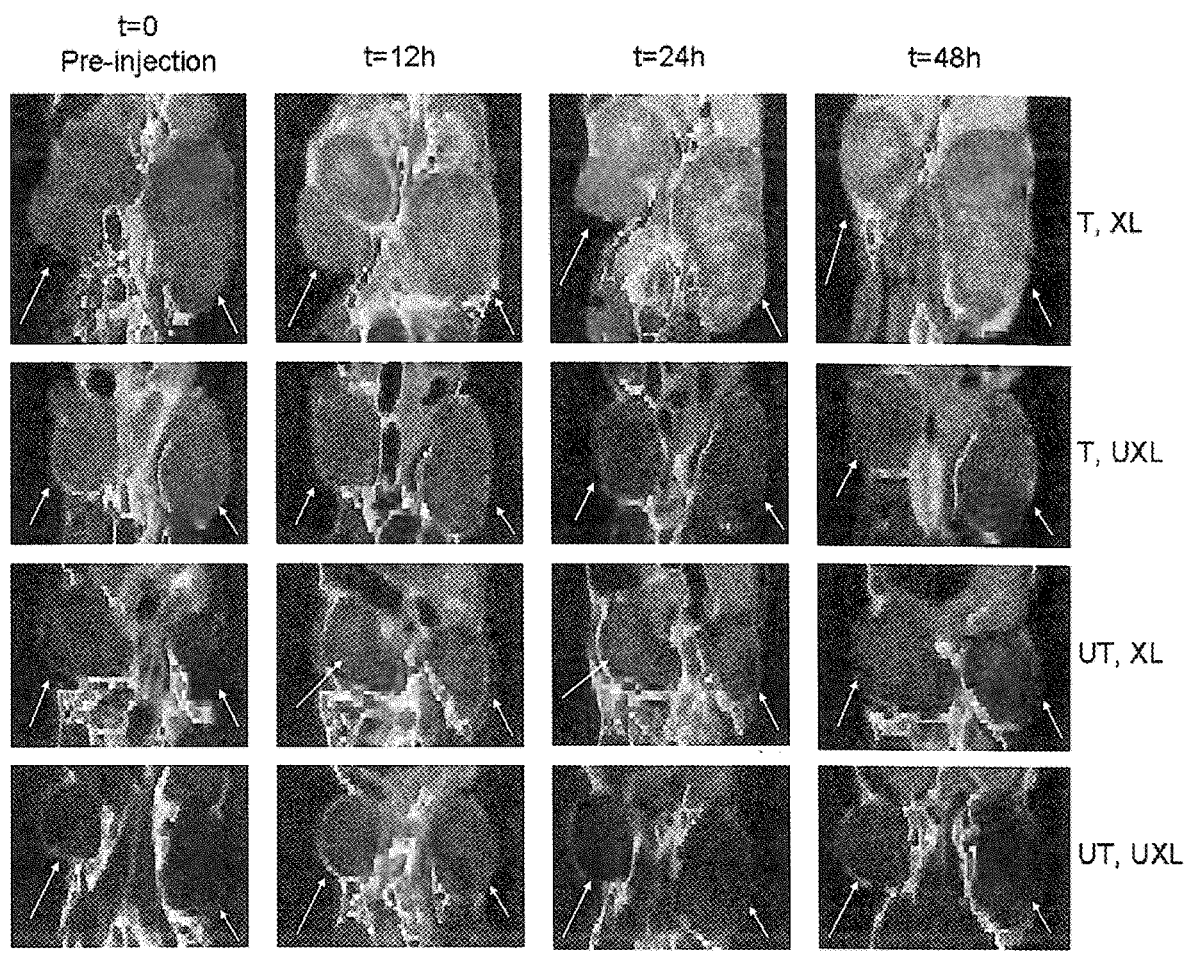
FIG. 22: Coronal-90, T1-weighted contrast-enhanced SEM images through the center slice of subcutaneous MC1R-expressing tumors. Arrows indicated the location of the tumors. Data matrix=128×128; FOV of 40 mm (read)× 90 mm (phase); 15 one-mm thick slices were taken with a 0.5 mm gap between slices; TR=180 ms; TE=8.62 ms; and 8 averages for total scan time of about 3 minutes per SEMS image. Images were processed using MATLAB (Mathworks, Matick, Mass.).
Figure 23:
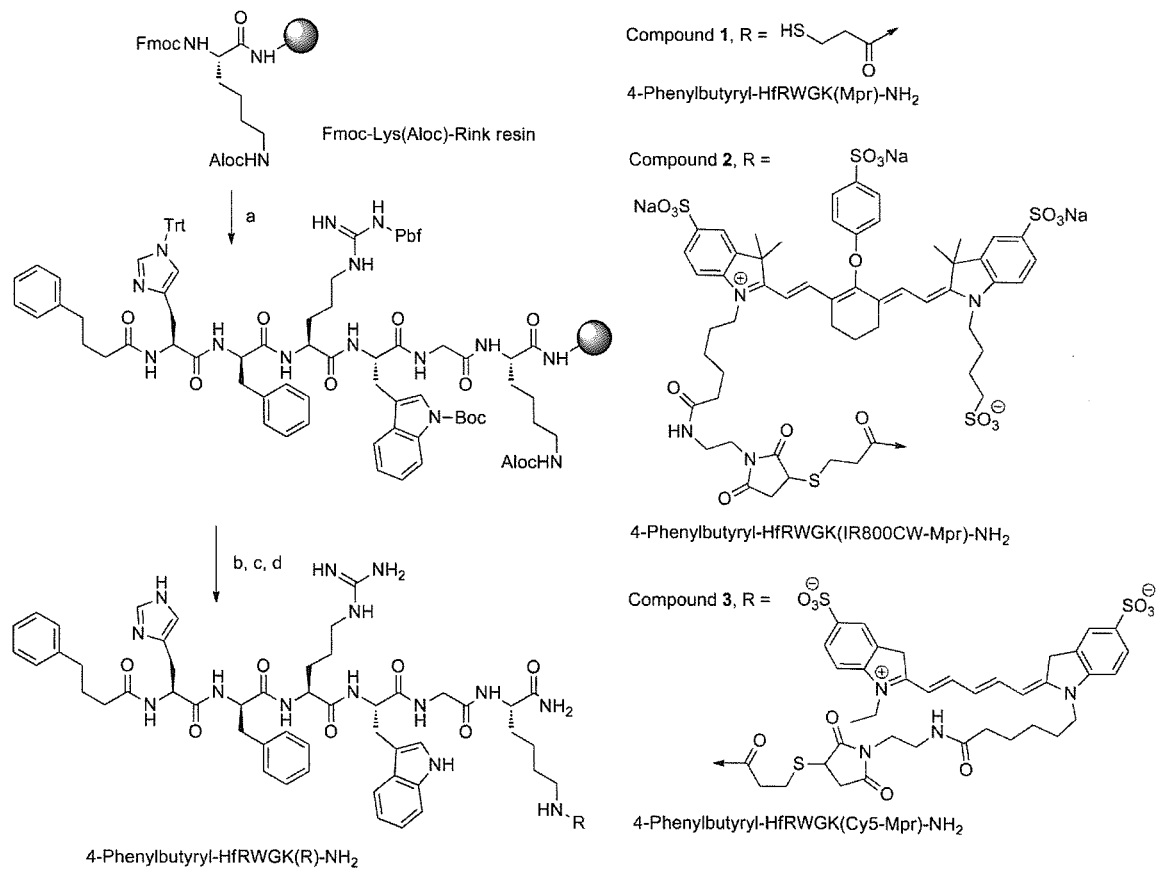
FIG. 23: A synthetic route for Cy5 and IR800CW ligands (Scheme Si). a. Fmoc/tBu synthesis continued as follows: i) Fmoc-aa-OH (3 eq), HOBt (3 eq), DIEA (6 eq), and HBTU (3 eq) in DMF for amino acid couplings; ii) Piperidine/DMF (1:4) for Fmoc deprotection; b. Aloc deprotection: i) Pd(0) TPP$_4$ (0.2 eq), dimethylbarbituric acid (5.0 eq) in DCM (0.5 M) for 30 min' ii) Trt-OH (3 eq), DIEA (6 eq), and HBTU (3 eq) in DMF; c. TFA-scavengers cocktail (91% trifluoroacetic acid, 3% water, 3% triisopropylsilane, and 1,2-ethylenedithiol (3%) for 4 hrs; d. IR800CW maleimide or Cy5 maleimide (1 eq) in DMF.

In vivo studies were carried out where mice were injected with micelles at 12 mg/mL Gd-Tx concentration. T1-weighted images were obtained pre-injection and at 4 hours, 12 hours, 24 hours and 48 hours after injection, for Gd-Tx containing micelles that contained the MC1R-ligand for targeting (T) or lacked the ligand (UT) and were either crosslinked (XL) of not (UXL), as shown in FIG. 9. No contrast was visible at 4 hours and the contrast begins to clear at 48 hours. Only mice injected with MC1R-ligand comprising crosslinked micelles (T, XL) exhibited appreciable contrast, indicating that only these MC1R-ligand comprising crosslinked micelles were sufficiently stable to enter and persist in the tumor. FIG. 10 shows the enhancement of the tumor image by the presence of the MC1R-ligand comprising crosslinked micelles. Further in vivo MRI results are shown in FIGS. 18-22.

The MT-XL micelles are successful at specifically delivering a theragnostic agent to the site of the tumor. Previous systems have fallen short of this goal in that they have encountered wide-spread toxicity, especially in the liver, kidneys and spleen. The inventors have successfully demonstrated that MT-XL micelles: (1) are specific for their target; (2) are able to deeply permeate the tumor; and (3) show a long tumor half-life, making them ideal for therapy. While this example focuses mainly on tumor imaging, similar constructs can be used to specifically deliver high doses of chemotherapeutic agents, such as taxanes, or other agents, to MC1R-expressing tumors or other MC1R-expressing cells or tissues, with low systemic toxicity.

REFERENCES

Welch, H. G., S. Woloshin, and L. M. Schwartz, *Skin biopsy rates and incidence of melanoma: population based ecological study*. BMJ, 2005. 331: p. 481.
2. Lehmann, J. M., et al., *Discrimination between benign and malignant cells of melanocytic lineage by two novel antigens, a glycoprotein with a molecular weight of 113,000 and a protein with a molecular weight of 76,000*. Cancer Res, 1987. 47(3): p. 841-5.
3. Wang, R., R. Kobayashi, and J. M. Bishop, *Cellular adherence elicits ligand-independent activation of the Met cell-surface receptor*. Proc Natl Acad Sci USA, 1996. 93(16): p. 8425-30.
4. Wang, Y., et al., *Molecular analysis of melanoma precursor lesions*. Cell Growth Differ, 1996. 7(12): p. 1733-40.
5. Wang, Z., et al., *Molecular and functional phenotypes of melanoma cells with abnormalities in HLA class I antigen expression*. Tissue Antigens, 1996. 47(5): p. 382-90.
6. Yang, P., et al., *Macroscopic spectral imaging and gene expression analysis of the early stages of melanoma*. Mol Med, 1999. 5(12): p. 785-94.
7. Hsu, M., et al., *Cadherin repertoire determines partner-specific gap junctional communication during melanoma progression*. J Cell Sci, 2000. 113 (Pt 9): p. 1535-42.
8. Siegrist, W., et al., *Characterization of receptors for alpha-melanocyte-stimulating hormone on human melanoma cells*. Cancer Res, 1989. 49(22): p. 6352-8.
9. Garcia-Borron, J. C., B. L. Sanchez-Laorden, and C. Jimenez-Cervantes, *Melanocortin-1 receptor structure and functional regulation*. Pigment Cell Res, 2005. 18: p. 393-410.
10. Rodrigues, A. R., et al., *Melanocortin 5 receptor activates ERK1/2 through a PI3K-regulated signaling mechanism*. Molecular and Cellular Endocrinology, 2009. 303: p. 74-81.
11. Webb, T. R. and A. J. L. Clark, *Minireview: The Melanocortin 2 Receptor Accessory Proteins*. Molecular Endocrinology, 2009. 24(3): p. 475-484.
12. Ploeg, L. H. T. V. d., et al., *A role for the melanocortin 4 receptor in sexual function*. PNAS, 2002. 99(17): p. 11381-11386.
13. Begriche, K., et al., *The role of melanocortin neuronal pathways in circadian biology: a new homeostatic output involving melanocortin-3 receptors?* obesity reviews, 2009. 10 ((Suppl. 2)): p. 14-24.
14. Hall, J. E., et al., *Obesity-induced Hypertension: Role of Sympathetic Nervous System, Leptin, and Melanocortins*. J. Bio. Chem, 2010. 28(23): p. 17271-17276.
15. Jun, D.-J., et al., *Melanocortins induce interleukin 6 gene expression and secretion through melanocortin receptors 2 and 5 in 3T3-L1 adipocytes*. Journal of Molecular Endocrinology, 2010. 44(225-236): p. 225.
16. Fridmanis, D., et al., *Identification of domains responsible for specific membrane transport and ligand specificity of the ACTH receptor (MC2R)*. Molecular and Cellular Endocrinology, 2010. 321: p. 175-183.
17. Corander, M. P., M. Fenech, and A. P. Coll, *The science of self preservation: how melanocortin action in the brain modulates body weight, blood pressure and ischaemic damage*. Circulation, 2010. 120(22): p. 2260-2268.
18. Cai, M., et al., *Cell signaling and trafficking of human melanocortin receptors in real time using two photon fluorescence and confocal laser microscopy: differentiation of agonists and antagonists*. Chem Biol Drug Des, 2006. 68(4): p. 183-93.

19. Mayorov, A. V., et al., *Effects of macrocycle size and rigidity on melanocortin receptor-1 and-5 selectivity in cyclic lactam alpha-melanocyte-stimulating hormone analogs.* Chem Biol Drug Des, 2006. 67(5): p. 329-35.
20. Koikov, L. N., et al., *Sub-nanomolar hMC1R agonists by end-capping of the melanocortin tetrapeptide His-D-Phe-Arg-Trp-NH(2).* Bioorg Med Chem Lett, 2003. 13(16): p. 2647-50.
21. Chen, J., et al., *In vivo evaluation of 99mTc/188Re-labeled linear alpha-melanocyte stimulating hormone analogs for specific melanoma targeting.* Nucl Med Biol, 1999. 26(6): p. 687-93.
22. Cai, M., et al., *Novel 3D Pharmacophore of r-MSH/ç-MSH Hybrids Leads to Selective Human MC1R and MC3R Analogues.* J. Med. Chem., 2005. 48(6): p. 1839-1848.
23. Handl, H. L., et al., *Lanthanide-based time-resolved fluorescence of in cyto ligand-receptor interactions.* Anal Biochem, 2004. 330(2): p. 242-50.
24. Yang, Y., et al., *Novel Binding Motif of ACTH Analogues at the Melanocortin Receptors.* Biochemistry, 2009. 48: p. 9775-9784.
25. Wei, L., et al., *Synthesis and Biologic Evaluation of 64Cu-Labeled Rhenium-Cyclized α-MSH Peptide Analog Using a Cross-Bridged Cyclam Chelator.* THE JOURNAL OF NUCLEAR MEDICINE, 2007. 48(1): p. 64-72.
26. Chen, J., et al., *Melanoma-targeting properties of (99m) technetium-labeled cyclic alpha-melanocyte-stimulating hormone peptide analogues.* Cancer Res, 2000. 60(20): p. 5649-58.
27. Koikov, L. N., et al., *Sub-Nanomolar hMC1R Agonists by End-Capping of the Melanocortin Tetrapeptide His-D-Phe-Arg-Trp-NH2.* Bioorganic& Medicinal Chemistry Letters, 2003. 13: p. 2647-2650.
28. Koikov, L. N., et al., *Analogs of sub-nanomolar hMC1R agonist LK-184 [Ph(CH2)3CO-His-D-Phe-Arg-Trp-NH2]. An additional binding site within the human melanocortin receptor I?* Bioorganic& Medicinal Chemistry Letters, 2004. 14(3997-4000): p. 3997.
29. Koikov, L. N., et al., *End-capping of the modified melanocortin tetrapeptide (p-Cl)Phe-D-Phe-Arg-Trp-NH2 as a route to hMC1R agonists.* Bioorg Med Chem Lett, 2004. 14: p. 4389-4842.
30. Vagner, J., et al., Bioorg. Med. Chem. Lett, 2004. 14(211-215): p. 211.
31. Handl, H. L., et al., Bioconj Chem, 2007. 18: p. 1101-1109.
32. Vagner, J., et al., Angew. Chem. Int. Ed, 2008. 47: p. 1685-1688.
33. Josan, J. S., et al., Int. J. Pept. Res. Ther., 2008. 14: p. 93-300.
34. Rodionov, V. O., et al., *Benzimidazole and Related Ligands for Cu-Catalyzed Azide-Alkyne Cycloaddition.* J. Am. Chem. Soc., 2007. 129: p. 12696-12704.
35. Martin, A. L., B. Li, and E. R. Gillies, *Surface Functionalization of Nanomaterials with Dendritic Groups: Toward Enhanced Binding to Biological Targets.* J. Am. Chem. Soc., 2008. 131: p. 734-741.
36. Carlson, C. B., et al., *Selective Tumor Cell Targeting Using Low-Affinity, Multivalent Interactions.* ACS Chem. Bio., 2007. 2(2): p. 119-127.
37. Sheth, S. R., N. Efremova, and D. E. Leckband, *Interactions of poly(ethylene oxide) brushes with chemically selective surfaces.* J. Phys. Chem. B., 2000. 104: p. 7652-7662.

Materials and Methods for Example 2

Cell Culture.

A375 human malignant melanoma cells were grown in Dulbecco's Modified Eagle's Medium (DMEM) containing 10% fetal bovine serum (Life Technologies, Gaithersburg, Md.), 100 units/mL penicillin and 100 µg/mL streptomycin in 5% $CO_2$ at 37° C. The cell line was obtained from American Type Culture Collection (ATCC), expanded for two passages, and cryopreserved. All experiments were performed with cells of passage number less than 25. Cells were authenticated a negative for *mycoplasma* by testing at the ATCC and were monitored by microscopy and confirmed to maintain morphological traits over subsequent passages.

DNA Microarray Analysis of Melanoma Cell Lines.

RNA extracts of melanoma cell lines were analyzed using the Affymetrix U133A array platform (33). Cell lines represented on the array are: 5 melanocyte lines—FOM101.1, FOM103.1, FOM104.1, FOM113.1, FOM99.1; 10 primary tumor lines—SbC12, WM1366, WM1361A, WM793, WM1819, WM278, WM3248, WM35, WM75, WM983A; 11 metastatic lines—WM1321, WM1346, WM1361B, WM858, WM1617, WM164, WM1727A, WM239A, WM46, WM51, 1205Lu; and 2 lines of unknown stage-origin/phenotype—WM3451 and WM1799. Data generated from these arrays have been published previously (33, 34) and have been deposited in the NCBIs Gene Expression Omnibus (GEO, http://www.ncbi.nlm.nih.gov/geo/). Data are accessible using GEO Series accession GSE4845.

DNA Microarray Analysis of Patient Samples.

Affymetrix expression data for MC1R in patient tissue samples were compiled from publicly available datasets. The CEL files for four of the normal skin samples and the skin tumor samples were downloaded from the GEO database (http://www.ncbi.nlm.nih.gov/projects/geo/index.cgi), data series GSE7553. Normal tissue data, including additional normal skin samples were from the GEO data series GSE7307, Human Body Index. The CEL files were processed using the MAS 5.0 algorithm (Affymetrix, Santa Clara, Calif.) and screened through a rigorous quality control panel to remove samples with a low percentage of probesets called present by the MAS 5 algorithm, indicating problems with the amplification process or poor sample quality; high scaling factors, indicating poor transcript abundance during hybridization; and poor 3'/5' ratios, indicating RNA degradation either prior to or during processing. The remaining samples were normalized to the trimmed average of 500 in the MAS 5 algorithm before comparison of the expression values across tumors and normal samples.

Immunohistochemistry (IHC) of Melanoma Tissue Microarray (TMA).

A TMA was constructed at the Moffitt Tissue Core containing human tissue samples of formalin-fixed and paraffin-embedded (FFPE) specimens. The TMA contains the following samples 11 normal skin tissue, 11 normal skin from melanoma, 10 compound nevi, 10 junctional nevi, 10 intradermal nevi, 40 Clark's atypical dysplastic nevi, 15 primary cutaneous melanoma in situ, 15 primary cutaneous melanoma (0.1-0.75 mm), 15 primary cutaneous melanoma (0.75-1 mm), 15 primary cutaneous melanoma (1-2 mm), 15 primary cutaneous melanoma (2-4 mm), 15 primary cutaneous melanoma (>4 mm), 10 melanoma distant metastasis-M1, 10 melanoma distant metastasis-M2, 10 melanoma distant metastasis-M3, 40 melanoma in regional lymph nodes, 15 primary mucosal melanoma. The TMA consists of cylindrical punches of the FFPE blocks using a Manual Tissue Arrayer (Beecher Instruments, Sun Prairie, Wis.). The same method was previously reported for construction of a Ewing sarcoma TMA at the Moffitt Tissue Core Facility (35), except the melanoma TMA has only one sample per case (duplicate samples in Ewing) due to the large number of cases. No identifiable human subject information was associated with the melanoma TMA.

Rabbit MC1R polyclonal antibody, 1:200 dilution, (GTX70735, GeneTex) was used for staining with diaminobenzidine (DAB). The slides were scanned in the Moffitt Analytical Microscopy Core Facility (AMC) using an Aperio ScanScope XT digital slide scanner (Aperio, Calif.). The digital image of each sample was evaluated by the study pathologist (TWM). Scoring ranged from 0 to 9 and was derived from the product of staining intensity (0-3+)×the percentage of positive tumor (on a scale of 0-3). Scores ≥4 are considered moderate to strong positive.

Generation of Stably Transfected A375 Cells Bearing the MC1R Gene.

pCMV6 containing *Homo sapiens* MC1R and neomycin as a selection marker was purchased (Origene, Rockville, Md.). To identify the optimal concentration for selection, a range (100-1000 µg/ml) of G418 (Invitrogen) was tested on cells. A375 cells were transfected with 5 ug of the vector. In response to G418, massive cell death was observed after ~5 days. After 2 weeks, resistant colonies appeared. Large colonies were selected and transferred to individual plates. The clone with the highest expression of MC1R was determined using qRT-PCR as previously described (36). MC1R specific primer sets were designed using Gene Runner Software for Windows version 3.05: forward, 5'-AATGT-CATTGACGTGATCACCTG-3' (SEQ ID NO:12) and reverse, 5'-GCAGTGCGTAGAAGATGGAGAT-3' (SEQ ID NO:13). β-actin was used for normalization (36). A clone with the highest expression was selected and maintained in medium containing 300 m/ml of G418.

Characterization of hMC1R Expression on A375 Cells by Immunocytochemistry (ICC).

To verify the cell surface expression of hMC1R, two sets of A375 (parental) and A375/hMC1R cells were plated at a cell density of 1×10$^4$ cells/well on glass coverslips placed at the bottom of culture wells and incubated for 16 hours. Cells were then treated with 30 µg/ml MC1R antibody (Almone Labs) and 5.0 µg/mL of WGA (Invitrogen) at 4° C. for 10 minutes, washed 3 times with PBS, fixed with cold methanol:acetone (1:1) and air dried for 20 minutes. Plates were washed 3 times with warm PBS and incubated with 1:2000 secondary antibody (Alexa-Fluor 680 goat anti-mouse IgG, Invitrogen). After three washes with PBS, coverslips were mounted with mounting medium and DAPI (Vector Laboratories, Inc., Burlingame, Calif.). Samples were viewed in the Moffitt Analytical Microscopy Core Facility using an automated Zeiss Observer Z.1 inverted microscope using 40×/1.3NA oil immersion objectives through narrow bandpass DAPI and FITC/A488 Chroma filter cubes and Nomarski Differential Interference Contrast polarizing and analyzing prisms. Images were produced using the AxioCam MRm CCD camera and Axiovision version 4.6 software suite (Carl Zeiss Inc., Germany).

Synthesis, Purification and Characterization

Materials.

N$^\alpha$-Fmoc protected amino acids, HBTU, and HOBt were purchased from SynPep (Dublin, Calif.) or from Novabiochem (San Diego, Calif.). Rink amide Tentagel S resin was acquired from Rapp Polymere (Tubingen, Germany). The following side chain protecting groups were used for the amino acids: Arg(N$^g$-Pbf); His(N$^{im}$-Trt); Trp(N$^{in}$-Trt); Lys (N$^\epsilon$-Aloc).

IR800CW maleimide dye was purchase from Licor (Lincoln, Nebr.). Cy5 maleimide dye was purchase from Licor (Lincoln, Nebr.). Peptide synthesis solvents, dry solvents, and solvents for HPLC (reagent grade), and 4-phenylbutyric acid, were acquired from VWR (West Chester, Pa.) or Sigma-Aldrich (Milwaukee, Wis.), and were used without further purification unless otherwise noted. Compounds were manually assembled using 5 to 50 mL plastic syringe reactors equipped with a frit, and Domino manual synthesizer obtained from Torviq (Niles, Mich.). The C-18 Sep-Pak™ Vac RC cartdridges for solid phase extraction were purchased from Waters (Milford, Mass.).

Peptide Synthesis.

Ligands were synthesized on Tentagel Rink amide resin (initial loading: 0.2 mmol/g) using N$^\alpha$-Fmoc protecting groups and a standard DIC/HOBt or HBTU/HOBt activation strategy. The resin was swollen in THF for an hour, washed with DMF, and Fmoc protecting group removed with 20% piperidine in DMF (2 min+20 min). The resin was washed with DMF, DCM, 0.2 M HOBt in DMF, and finally with DMF and the first amino acid coupled using pre-activated 0.3 M HOBt ester in DMF (3 eq. of N$^\alpha$-Fmoc amino acid, 3 eq. of HOBt and 6 eq. of DIC). An on-resin test using Bromophenol Blue was used for qualitative and continuous monitoring of reaction progress. To avoid deletion sequences and slower coupling rate in longer sequences, the double coupling was performed at all steps with 3 eq. of amino acid, 3 eq. of HBTU and 6 eq. of DIEA in DMF. Any unreacted NH$_2$ groups on the resin thereafter were capped using an excess of 50% acetic anhydride in pyridine for 5 min. When the coupling reaction was finished, the resin was washed with DMF, and the same procedure was repeated for the next amino acid until all residues were coupled.

Aloc Cleavage.

The orthogonal protecting Aloc group of C-terminal Lys was cleaved as follows. The resin was washed with DCM then flushed with argon for 10 min. A cleavage mixture of dimethylbarbituric acid (5 equiv.), Pd(TPP)$_4$ (0.2 equiv.) in DCM (0.5 M solution) was flushed with argon and injected into the syringe. The reaction mixture was stirred for 30 min then repeated. The resin was washed with DMF, 10% DIEA in DMF, DMF, 2% sodium diethyldithiocarbamate trihydride, 10% DIEA in DMF, DCM and DMF. The Trt-Mpr was attached to the free amine via HBTU coupling as described above.

Cleavage of Ligand from the Resin.

A cleavage cocktail (10 mL per 1 g of resin) of TFA (91%), water (3%), triisopropylsilane (3%), and 1,2-ethylenedithiol (3%) was injected into the resin and stirred for 4 h at room temperature. The crude ligand was isolated from the resin by filtration, the filtrate was reduced to low volume by evaporation using a stream of nitrogen, and the ligand was precipitated in ice-cold diethyl ether, washed several times with ether, dried, dissolved in water and lyophilized to give off-white solid powders that were stored at −20° C. until purified. The crude compound was purified by size-exclusion chromatography.

Labeling Procedure.

The purified thiol compound (1 mmol) was dissolved in 1 mL DMF and reacted with 1 equiv. of IR800CW or Cy5 maleimide under argon atmosphere. The reaction was monitored by HPLC and additional aliquotes (0.1 equiv.) of dye were added until the reaction complete. The compound was purified by HPLC.

Purification and Analysis.

Purity of the peptides was ensured using analytical HPLC (Waters Alliance 2695 separation model with a dual wavelength detector Waters 2487) with a reverse-phase column (Waters Symmetry, 3.0 75 mm, 3.5 μm; flow rate=0.3 mL/min). (Conditions: HPLC, linear gradient from 10 to 90% B over 30 min, where A is 0.1% TFA and B is acetonitrile). Size exclusion chromatography was performed on a borosilicate glass column (2.6×250 mm, Sigma, St. Louis, Mo.) filled with medium sized Sephadex G-25 or G-10. The compounds were eluted with an isocratic flow of 1.0 M aqueous acetic acid. Solid-Phase Extraction (SPE) was employed where simple isolation of final compound was needed from excess salts and buffers for e.g., lanthaligand synthesis. For this purpose, C-18 Sep-Pak™ cartridges (100 mg or 500 mg) were used and pre-conditioned initially with 5 column volumes (5 times the volume of packed column bed) each of acetonitrile, methanol, and water, in that order. After loading the compound, the column was washed several times with water, and then gradually with 5, 10, 20, 30, 50, and 70% of aqueous acetonitrile to elute the peptide. Structures were characterized by ESI (Finnigan, Thermoquest LCQ ion trap instrument), MALDI-TOF or FT-ICR mass spectrometry. An appropriate mixture of standard peptides was used for internal calibrations.

Binding Assays.

A375 melanoma cells engineered to express MC1R were used to assess ligand binding in a competitive binding assay as described before (32).

The receptor number of A375/MC1R (engineered cells to express MC1R), was determined using saturation binding assay following a previously described method (37), except that Eu-DTPA labeled NDP-α-MSH was used as a test ligand and 5 μM of NDP-α-MSH was used as a blocking ligand. These cells were used as a MC1R high expressing line, while the parental (A375) cells were used as a low expressing line with 400±93 sites/cell (38).

In Vitro MC1R Probe Uptake Study.

To study the uptake of the MC1R probe in vitro, two sets of A375 (parental) and A375/hMC1R cells were plated at a cell density of $1\times10^4$ cells/well on glass coverslips placed at the bottom of culture wells and incubated for 16 hours. Cells were incubated in media containing 15 nM probe and uptake evaluated by fluorescence microscopy at different time points from 40 seconds to 15 minutes. To determine specificity, MC1R receptors were blocked by a 10 minute pre-incubation with 2 μM of NDP-α-MSH prior to addition of MC1R probe and images acquired 1 minute after addition of labeled probe. Samples were viewed using an Axio Observer Z1 inverted fluorescence microscope (Carl Zeiss, Inc, Germany) using 40×/1.3NA oil immersion objectives through a narrow band Cy5 filter. Cy5 fluorescence images were prepared with a DIC overlay image using Axiovision 4.6 software (Carl Zeiss, Inc, Germany).

In Vivo Uptake Study: Intravital Imaging of the Dorsal Skin-Fold Window Chamber Tumor Xenograft Model.

All procedures were carried out in compliance with the Guide for the Care and Use of Laboratory Animal Resources (1996), National Research Council, and approved by the Institutional Animal Care and Use Committee, University of South Florida. A dorsal skin-fold window chamber was used to study the pharmacokinetics of imaging agent uptake immediately after i.v. injection of the probe. Starting 3 days prior to the surgery, mice were daily administered 1 ml of sterile saline subcutaneously at the planned site of the window in order to loosen connective tissue and create a receiving "pocket". SCID mice were prepared immediately before surgery; the surgical site was shaved, and then a combination of oxygen and isoflurane was used for anesthesia (animals underwent induction with 3.5% isoflurane and were maintained at 1.5-2.0%). The window chamber method utilizes a titanium steel or plexiglass "saddle" that is sutured to the back of the mouse and holds a flap of dorsal skin vertically away from the mouse's body. A small "window" of skin (approximately 5 mm in diameter) was surgically excised from the retained skin flap of the anesthetized SCID mouse. Tumor constructs were engineered using the tumor droplet method. A375/MC1R or A375 parental melanoma cells were suspended in 2.5 mg/ml of type I collagen (BD Biosciences #354249) and 1×DMEM at a final concentration of $2.5\times10^6$ cells/ml. Using a 48-well non-tissue culture plate, a 15 μl drop of the tumor cell suspension was polymerized in the center of the well. After brief polymerization (10-15 minutes) at 37° C., a microvessel outer layer was added that completely surrounded the droplet. The microvessel outer layer consisted of 3 mg/ml of type I collagen, 1×DMEM and, 12,000 to 15,000 GFP expressing rat microvessel fragments/ml. After 4-6 days of culture at 37 C, the constructs were then implanted into the "window chamber" by placing them directly onto the exposed subcutaneous fascia. A glass cover was then attached to the center of the "saddle" to cover the fascia and implanted tumor cells. Post-operatively, tumor growth and microcirculation can be visualized in this model for approximately a month.

GFP expressing microvessel fragments were prepared from the epidydimal fat of transgenic GFP SpragueDawley rats. A rat was anesthetized, and the abdomen sprayed with 70% ethanol. Skin was clamped just below penis with a hemostat and an incision made with large scissors starting in the center and cutting laterally. A small incision was made into the scrotum using small scissors exposing the epidydimal fat. The epidydimal fat pads were carefully removed using forceps and the animal euthanized by extending the incision and performing a thoracotomy while remaining under deep anesthesia. Microvessels were then prepared as follows: Epididymal fat pads were removed and digested with collagenase (2 mg/ml). Following digestion, large tissue debris was removed using a 500 μm filter and subsequent filtration step done with a 30 μm filter to collect the microvessel fragments. Microvessel fragments were then added to a solution of type I rat tail collagen at a final concentration of 3 mg/ml (BD Bioscience, San Jose, Calif.) with 1×DMEM, and kept on ice to keep collagen from polymerizing. This preparation was added to the cancer cell droplet and placed under the glass cover of a dorsal skin-fold window chamber on a SCID mouse following a 3 to 4 day in vitro incubation. As the tumor xenograft is established, rat microvessels become patent with the mouse vasculature (39).

Seven days after implantation of microvessels and tumor cells, mice were intravenously injected with 100 μl of 5% 10,000 MW Cascade Blue Dextran (Invitrogen, CA) in sterile H2O to verify microvessel patency. Then, 5 nmol/kg of the MC1R-Cy5 probe was injected into the tail vein. Confocal images of probe uptake into the melanoma tumor cells were continuously acquired prior to, during and after injection of probe using the Olympus FV1000 (MPE) Multiphoton Laser Scanning Microscope (Lisa Muma Weitz Advanced Microscopy and Cell Imaging facility at USF) using a 1.25× and 25× lens and acquisition rate of 3570 Pixels/minute. The Cy5 conjugated ligand was measured by exciting the ligand with an IR laser at 635 nm and the emitted light was detected using a 655-755 nm filter.

Tumor Xenograft Studies and Fluorescence Imaging.

Female nu/nu mice 6-8 weeks old (Harlan Sprague Dawley, Inc., Indianapolis, Ind.) were injected subcutaneously (s.c.) with $1\times10^6$ MC1R expressing A375 cells in the right and the parental one in the left flank. Tumor volume was determined with calipers using the formula: volume= (length×width$^2$)/2. Once tumors reached 500-800 mm$^3$, 1 nmol/kg-30 nmol/kg of MC1R imaging probe in 100 µL sterile saline was injected into the tail vein. In vivo fluorescence images were acquired using the Optix-MX3 (Advance Research Technologies, Inc. a subsidiary of SoftScan Healthcare Group, Montreal, Canada). Animals were positioned on a heating pad and anesthetized using isoflurane (flow 2-2.5 l/min). Fluorescence images were acquired using a scan resolution of 1.5 mm and a 790-nm pulsed laser diode with 40 MHz frequency and 12-ns time window. Images were analyzed using Optix-MX3 Optiview Software (version 3.01). Autofluorescence background was subtracted by determining the mean tumor fluorescence signal prior to injection, then mean normalized intensity values were obtained within a ROI on these images.

Ex Vivo Studies.

Tumors were excised and center slice of each tumor was imaged using both Optix-MX3 (as described above) and IVIS 200 imaging system (Caliper LifeSciences, MA). For IVIS 200 acquisitions, the standard ICG excitation and emission filter set was used for imaging. After imaging, the slices were fixed in formalin and embedded in paraffin for histology. Formalin fixed sections (5 µm) were stained with hematoxylin and eosin (H&E). Sections were also IHC stained with MC1R primary antibody as described above for TMAs.

Biodistribution Studies.

Mice were imaged and euthanized at 2-72 hr post-injection. Tumors, kidneys and liver were excised, rinsed with PBS, blotted dry, and then imaged ex vivo with Optix-MX3 as described above. Images were analyzed as described above.

Log D.

The log of the octanol-water partition coefficient at pH 7.4 (log $D_{7.4}$) was determined by miniaturised shake flask assay. Briefly, (200 µL to 1 mL) n-octanol (Sigam) was added to a solution of the test compound prepared in PBS (25 mM $NaH_2PO_4/Na_2HPO_4$ buffer, pH 7.4, Sigma, HPLC grade). Then, three different ratios of octanol to PBS buffer were prepared. The mixture was stirred in a vortex mixer at room temperature for 1 min and then two layers were separated by centrifuge. The concentration of compound in each layer was determined by HPLC (Poroshell 120 EC-C18 column) using (26% acetonitrile in water, 0.1% TFA) in 280 nm channel. All sample injections were performed 3 times, and the results were averaged to yield the final values.

Statistics.

Data are represented as mean±s.d. All statistical analyses were performed with GraphPad Prism version 5.01. Unpaired Student's t-test was used to determine the statistical significance of differences between two independent groups of variables. For all tests, a p≤0.05 was considered significant.

Example 2—Development of a Melanoma Targeted Probe for Imaging of Melanocortin Receptor 1 (MC1R)

Nodal metastases are frequently the initial manifestation of metastatic spread in patients with melanoma and accurate determination of nodal status is important for both prognostic evaluation and treatment planning. The melanocortin 1 receptor (MC1R) is overexpressed in most human melanoma metastases, thus making it a promising target for imaging and therapy of melanomas. In this study, using DNA and tissue microarray, MC1R expression was analyzed in different normal tissues and melanoma samples, confirming the expression of MC1R in a large fraction of patients with melanoma. The inventors had developed a peptidomimetic ligand with high specificity and affinity for MC1R. Here, the inventors have conjugated this ligand to a near-infrared fluorescent dye to generate a MC1R specific optical probe (MC1RL-800, 0.4±0.1 nM $K_i$). The uptake of the probe was studied in engineered A375/MC1R cells in vitro as well as in vivo by intravital fluorescence imaging, showing internalization of the probe. The in vivo tumor targeting of MC1RL-800 was evaluated by intravenous injection of probe into nude mice bearing bilateral subcutaneous tumors of A375 cells with low MC1R receptor numbers and engineered A375/MC1R cells. Fluorescence imaging showed that the agent has higher uptake values in tumors with high expression compared to low (P<0.05), demonstrating the effect of expression levels on image contrast-to-noise. In addition, the tumor uptake was significantly blocked by co-injection with excess NDP-α-MSH peptide (P<0.05), indicating specificity of the probe in vivo. The biodistribution of MC1RL-800 was investigated in xenograft bearing mice, showing high kidney uptake as early as 30 min post-injection. As kidney is known to express the melanocortin receptor family member (MC4R and MC5R), kidney uptake of the probe was reduced significantly (P<0.05) by co-injection of a ligand the inventors have previously identified to have higher MC5R affinity compared to MC1R. The pharmacokinetics of probe uptake and clearance was also characterized using a three-compartment mathematical model. The MC1R-specific imaging probe developed in this study displays excellent potential for in vivo detection of melanoma metastases.

Malignant melanoma is the most common cause of death from cutaneous malignancies and the fastest increasing cancer in the U.S. (1, 2). Assessment of metastatic spread to lymph nodes draining the tumor site is very important not only for staging and prognosis but also for adjuvant therapy in melanoma (3-5). Sentinel lymph node biopsy (SLNB) is the current gold standard for evaluating regional lymph node involvement (6). The sentinel lymph node (SLN) receives lymph draining directly from the tumor site. In this method, a radio colloid is injected intradermally around the tumor and SLNs are determined, removed and examined by histological methods for detection of intranodal metastasis (7). If cancerous, the patient is then offered a completion lymphadenectomy to remove the remainder of the lymph nodes in that anatomic area. This method has limitations, as it is a surgical intervention with all the ensuing complications from infection to lymphedema (8), and 80% of patients are negative for lymph node metastasis and therefore have undergone an unnecessary procedure (9).

Standard imaging techniques have been used for assessment of regional nodal status, including CT, ultrasound, MRI, and $^{18}$F-FDG PET (10, 11). However, each of these techniques have limitations as tools for detection of metastatic melanoma. For example, ultrasound is limited to detection of superficial nodes. $^{18}$F-FDG PET lacks sufficient sensitivity to detect micrometastasis in regional nodes, especially for the initial assessment of early-stage melanoma metastasis where tumor volume is small or metabolically inactive (12-14). In addition, this tracer can not discriminate between malignancy and inflammatory lymphadenopathy (15, 16). None of these imaging modalities are specific for enhancement of melanoma metastases. Therefore, melanoma-specific molecular imaging probes are needed for the non-invasive detection of metastasis with high sensitivity for staging of regional lymph node involvement, and for detection of distal metastases for diagnosis and to follow therapy response. There is also increasing interest in the use of novel targeted therapies in malignant melanomas that are resistant to most systemic therapies (17).

Melanoma progression is associated with altered expression of cell surface proteins, including adhesion proteins and receptors (18-20). It has been estimated that over 80% of malignant melanomas express high levels of the MC1R (21). MC1R is a member of a family of five G protein-coupled receptors (MC1R-MC5R) for melanocortins (22-24), such as melanocyte stimulating hormones (MSH). Because of the high expression of MC1R in melanoma, it has been investigated as a target for selective imaging and therapeutic agents and a number of selective ligands have been developed (25-27). One of these ligands, [Nle$^4$,D-Phe$^7$]-α-MSH (NDP-α-MSH) has a high affinity against MCR, except MC2R, and has been investigated extensively (28-31).

In this study, the inventors evaluated the expression of MC1R through immunohistochemistry (IHC) and DNA microarray analysis in both melanoma patient samples and cell lines. While MC1R is not a novel target, this represents the most extensive study on its distribution in melanoma to date. In addition, the inventors recently described a high affinity selective ligand against MC1R with lower affinity for MC4R or MC5R (32). By conjugating a near-infrared fluorescent dye to this ligand, we have developed a MC1R specific molecular imaging probe (MC1RL-800). The inventors have used this probe to image the expression of MC1R in vivo following intravenous injection into nude mice bearing bilateral high- and low-MC1R expressing tumors. In vivo tumor cell uptake of this probe was studied by intravital imaging of a dorsal skin-fold window-chamber mouse xenograft tumor model. The in vivo biodistribution and pharmacokinetics of the probe was also studied. The molecular imaging probe designed in this study has potential for the detection and staging of melanoma metastases that overexpress the MC1R, and could be used for the targeted delivery of therapy.

Figure 24A:
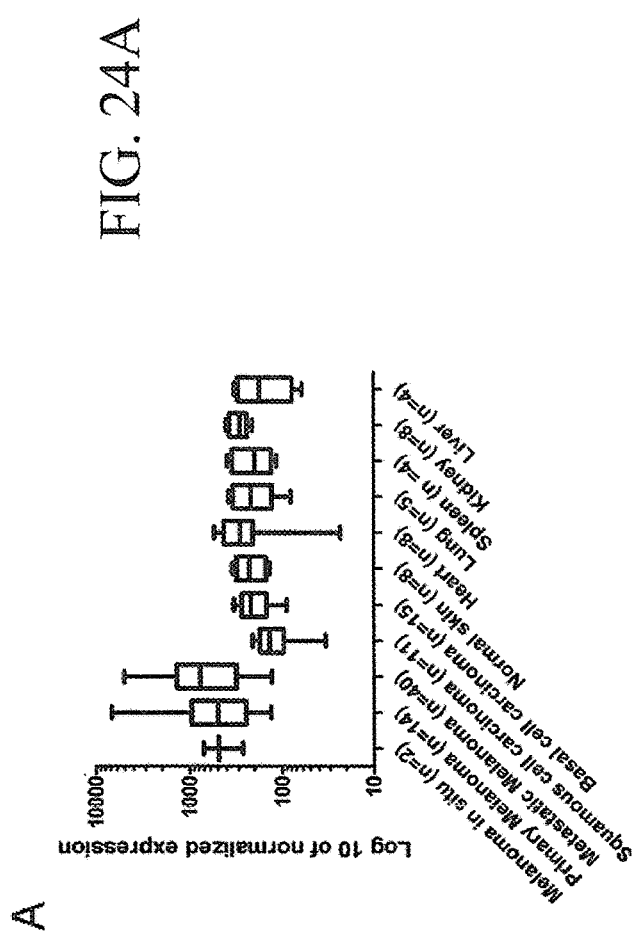
FIGS. 24A-C: DNA microarray expression profile of MC1R in melanoma, other skin cancers and normal tissues (FIG. 24A). Data are represented as mean±SD. Note the $\log_{10}$ scale. DNA microarray of primary human melanocytes (white), melanoma cell lines with the NRAS mutation (gray) and melanoma cell lines with the BRAF mutation (black) (FIG. 24B). Representative IHC staining of MC1R in normal skin with a pathology score of 3 and different types of melanoma with pathology score of equal to or greater than 4 (FIG. 24C).

Results
A. MC1R Expression in Patient Tissue Samples
It has been estimated that 80% of malignant melanomas express high levels of MC1R (21). For further confirmation and to characterize mRNA expression in patient tissue samples, the inventors analyzed publicly available DNA microarray data sets, which showed that MC1R mRNA expression was highly and generally expressed in a large fraction of melanomas (FIG. 24A, note log scale). In contrast, MC1R expression was not elevated in other skin cancers, normal skin and organs involved in toxicity and drug clearance, i.e, heart, lung, spleen, liver and kidney.

Figure 24C:
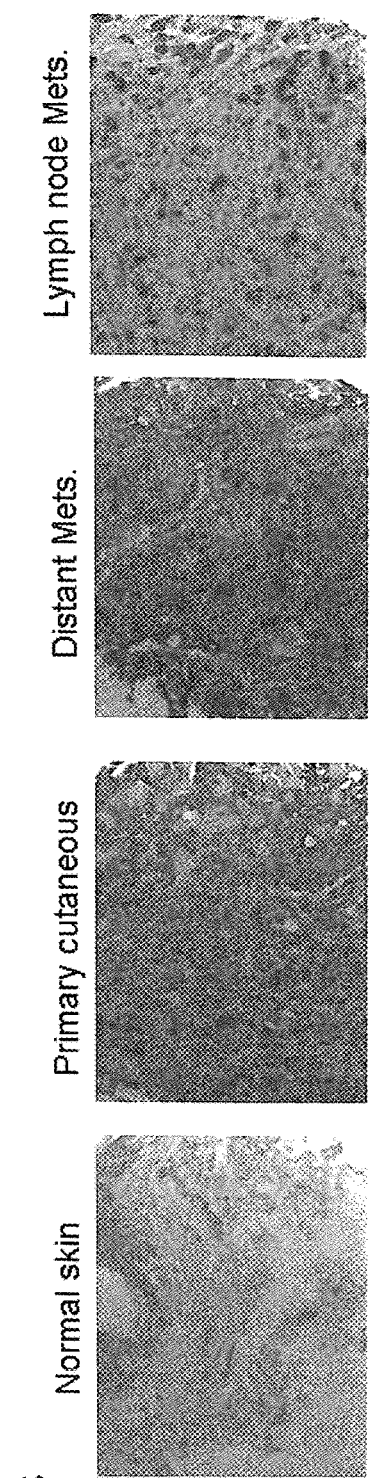

To determine MC1R protein expression in patient samples, immunohistochemistry (IHC) was performed on a melanoma tissue microarray containing 267 samples. FIG. 24C shows representative staining in normal skin relative to staining in a primary cutaneous melanoma, distant metastasis and lymph node metastasis. None of the normal skin samples (n=19) had staining with a pathology score of ≥4, i.e. homogeneous moderate to high staining (Table 5). Benign lesions (n=65) and samples of local invasion to regional lymph nodes (n=35) had percentages of ≥4 staining ranging from 15 to 33%. A relationship between primary cutaneous melanoma lesion size and pathology score was observed, with smaller lesions ranging from melanoma in situ to lesions 1 mm in diameter scoring 18% to 33%≥4, and lesions from 1 mm to ≥4 mm in diameter scoring 46 to 79%≥4. Primary mucosal melanomas (n=11) and melanoma from distant metastasis had scores ranging from 40% to 67%≥4.

TABLE 5

IHC Scoring of MC1R Expression in Patient Tissue Samples

| Tissue type | n | Pathology score | | | | | | | % = 4 |
| --- | --- | --- | --- | --- | --- | --- | --- | --- | --- |
| | | 0 | 1 | 2 | 3 | 4 | 6 | 9 | |
| normal skin | 19 | 0 | 1 | 5 | 13 | 0 | 0 | 0 | 0 |
| compound nevi | 9 | 0 | 0 | 0 | 6 | 0 | 3 | 0 | 33 |
| junctional nevi | 5 | 0 | 0 | 0 | 4 | 0 | 1 | 0 | 20 |
| intradermal nevi | 7 | 0 | 0 | 0 | 5 | 0 | 2 | 0 | 29 |
| Clark's, atypical, dysplastic nevi | 33 | 0 | 1 | 5 | 22 | 0 | 5 | 0 | 15 |
| Primary cutaneous melanoma (in situ) | 11 | 0 | 0 | 0 | 9 | 0 | 2 | 0 | 18 |
| Primary cutaneous melanoma (0.1-0.75 mm) | 12 | 0 | 2 | 1 | 5 | 0 | 4 | 0 | 33 |
| Primary cutaneous melanoma (0.75-1 mm) | 13 | 0 | 0 | 3 | 7 | 0 | 3 | 0 | 23 |
| Primary cutaneous melanoma (1-2 mm) | 13 | 0 | 0 | 3 | 4 | 0 | 6 | 0 | 46 |
| Primary cutaneous melanoma (2-4 mm) | 12 | 0 | 0 | 1 | 3 | 1 | 6 | 1 | 67 |
| Primary cutaneous melanoma (>4 mm) | 14 | 0 | 1 | 1 | 1 | 0 | 8 | 3 | 79 |
| Primary mucosal melanoma | 11 | 0 | 1 | 1 | 3 | 0 | 4 | 2 | 55 |
| Melanoma in regional lymph nodes | 35 | 1 | 3 | 10 | 12 | 0 | 9 | 0 | 26 |
| Melanoma distant metastasis, M1 | 9 | 0 | 1 | 0 | 4 | 0 | 3 | 1 | 44 |
| Melanoma distant metastasis, M2 | 9 | 0 | 0 | 1 | 2 | 0 | 5 | 1 | 67 |
| Melanoma distant metastasis, M3 | 10 | 0 | 1 | 0 | 5 | 0 | 4 | 0 | 40 |

B. MC1R Expression in Melanoma Cell Lines

Figure 24B:
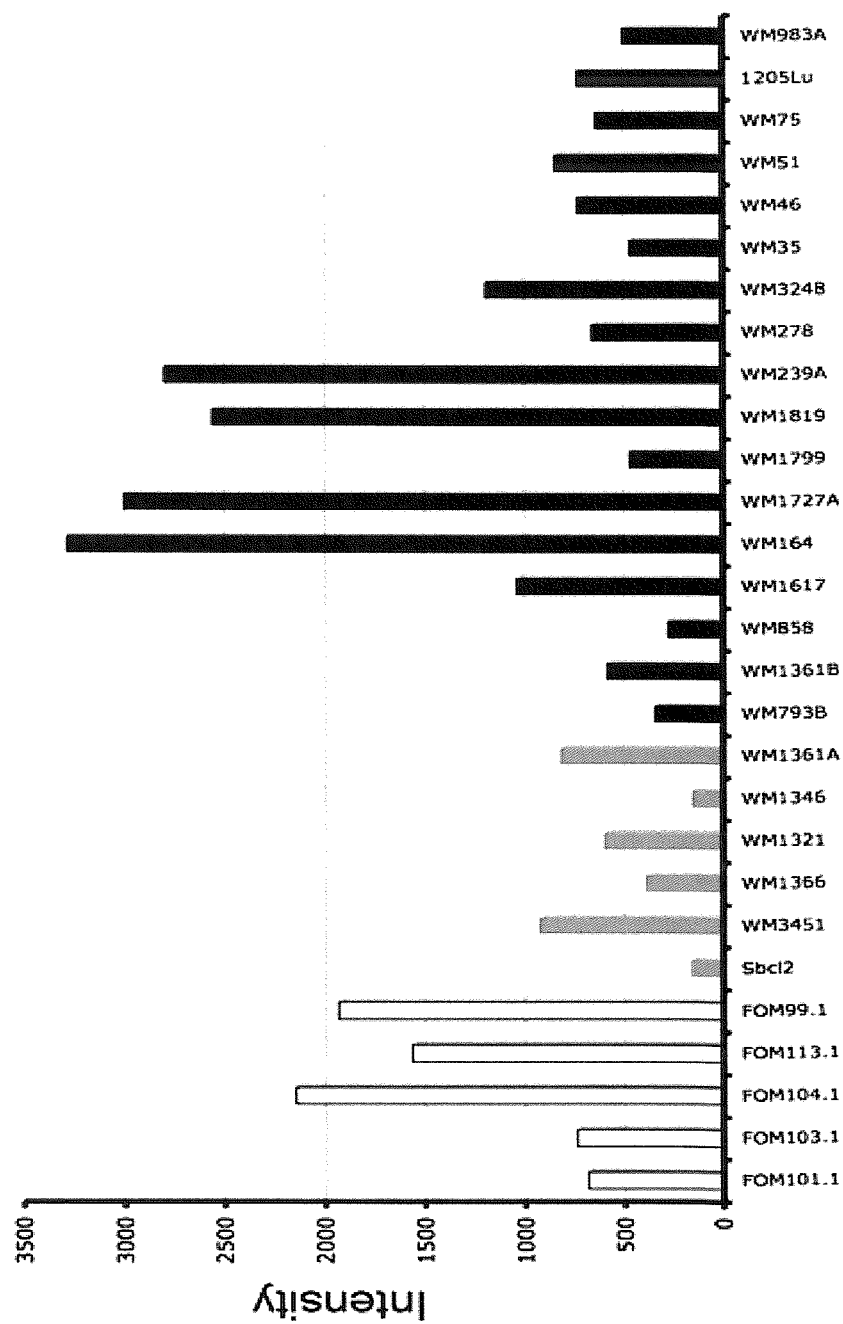

MC1R expression was examined on a previously published DNA microarray of a panel of melanoma cell lines (33, 34) (FIG. 24B). Moderate to high expression was observed in all primary melanocytes and NRAS-positive melanoma cells had low to moderate expression. In contrast, expression in BRAF-positive melanoma cells was highly heterogeneous, with some lines exhibiting very low expression (WM 858, 7938, 1799, 35) and some with extremely high expression (WM 164, 1727A, 1819, 239A). Notably, 3 of the 4 high expressing lines were metastatic: WM164, WM239A and WM1727A.

C. Characterization of MC1R Expression in A375/MC1R Cells

Figure 25A:
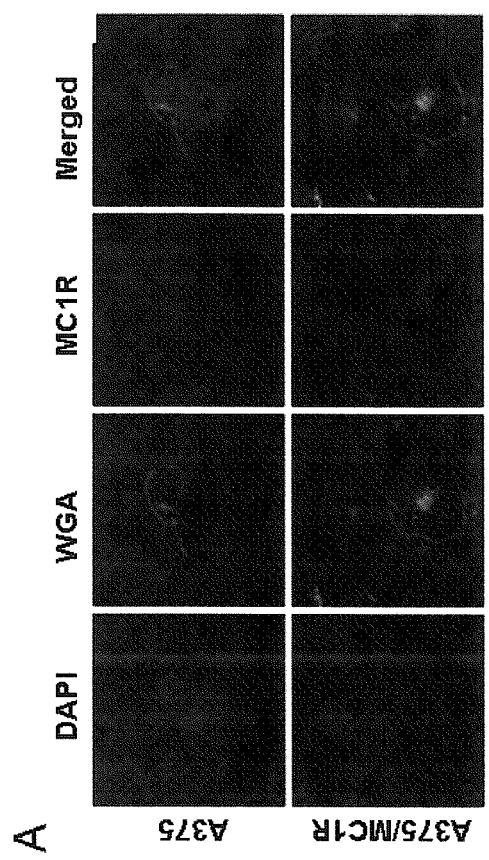
FIGS. 25A-C: ICC of MC1R expression on the surface of A375 parental and engineered cells (FIG. 25A). Confocal micrographs of cells incubated with the nuclear marker DAPI (blue), the plasma- and plasma-membrane marker, WGA (green) and MC1R antibody-Alexa 555 (red). To inhibit cellular uptake, cells were incubated with antibodies and dyes at 4° C. for 10 min. The merged image shows colocalization of MC1R (red) with membrane marker (green) indicating accumulation of the receptor on the cell-surface (yellow). Representative saturation binding assays for A375/hMC1R cells (FIG. 25B). A representative competition binding plot of MC1RL-800 imaging probe to A375/hMC1R cells (FIG. 25C).

A375 malignant melanoma cells were transfected to stably overexpress MC1R for evaluation of the MC1RL-800 imaging probe both in vitro and in vivo. The A375 malignant melanoma cell line was chosen due to their very low endogenous expression of MC1R (38, 40), providing both low- and high-expressing cells for the in vitro as well as in vivo selectivity studies. qRT-PCR of A375 and A375/MC1R cells revealed the mRNA gene expression level in the engineered cells to be 457, compared to a gene expression level of 4.5 in the parental cells. For further confirmation, hMC1R expression on the cell surface of the cells was characterized through ICC (FIG. 25A). Both engineered A375/hMC1R and parental A375 cells were incubated with the nuclear marker DAPI, the plasma membrane marker WGA and an MC1R antibody conjugated to a fluorescent dye (Alexa 555). The merged images illustrate colocalization of MC1R (red) with membrane marker (WGA, green) indicating accumulation of the receptor on the cell-surface (yellow). Notably, the parental A375 line does appear to have a detectable amount of MC1R antibody binding to the cells surface.

Figures 25B, 25C:
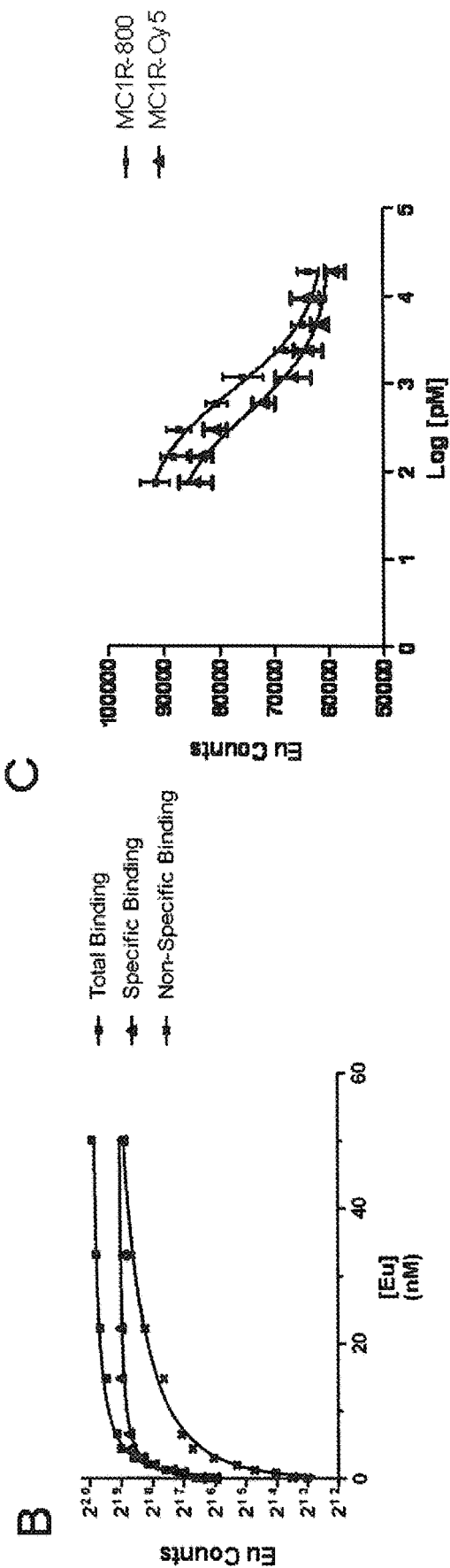

To determine MC1R receptor number on the cell surface, saturation binding assays were performed using Eu-NDP-α-MSH. Increasing amounts of Eu-NDP-α-MSH were added to A375/MC1R cells. Non-specific binding was determined in the presence of 5 μm unlabeled NDP-α-MSH (FIG. 25B). Results indicate that the Kd, Bmax and receptor number were 1.8 nM, 668,046±67,108 and 75,000 respectively.

D. Synthesis and Characterization of MC1R Targeted Probes

The inventors recently described a high affinity and selective MC1R ligand; 4-phenylbutyryl-His-DPhe-Arg-Trp-Gly-Lys(hex-5-ynoyl)-NH$_2$ (SEQ ID NO:3). $K_i$ values for this ligand against MC1R, MC4R and MC5R were 0.24 nM, 254 nM and 46 nM, respectively (32). Here, the inventors further describe the attachment of this ligand to a near-infrared (NIR) dye with an excitation at 800 nm (4-phenylbutyryl-His-DPhe-Arg-Trp-Gly-Lys(Mpr-IR800CW)-NH$_2$ (SEQ ID NO:14), LiCor IR800CW Maleimide) as well as Cy5.

To evaluate the binding affinity of the MC1RL-800 and MC1R-Cy5 probes, competition binding assays were preformed on A375/hMC1R cells with Eu-NDP-a-MSH as the competed ligand (FIG. 25C). The MC1RL-800 and MC1R-Cy5 probes retained high affinity against MC1R, with an $K_i$ of 0.4±0.1 nM and 0.3±0.05 nM, respectively, compared to the $K_i$ for unlabeled ligand of 0.24 nM Ki (32).

E. Cellular and Tumor Uptake Studies

Figure 26A:
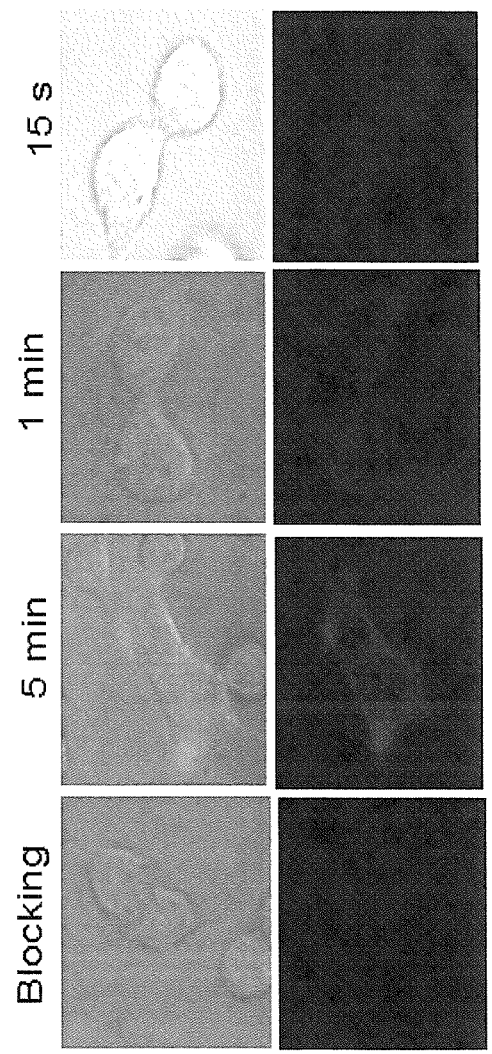
FIGS. 26A-B: Uptake studies of MC1R targeted imaging probes in vitro and in vivo.

To study uptake of the MC1R probe onto and into cells, MC1RL-800 probe was incubated with live cells and images were acquired at different time-points after incubation using an inverted microscope. The binding of dye to the surface of A375/MC1R cells was observed as early as 15 seconds after incubation and intracellular accumulation was observed within 5 minutes (FIG. 26A). No attachment of the probe was observed when 2 μM of NDP-α-MSH was used as a blocking agent before adding the probe to the cells (FIG. 26A).

Figure 26B:
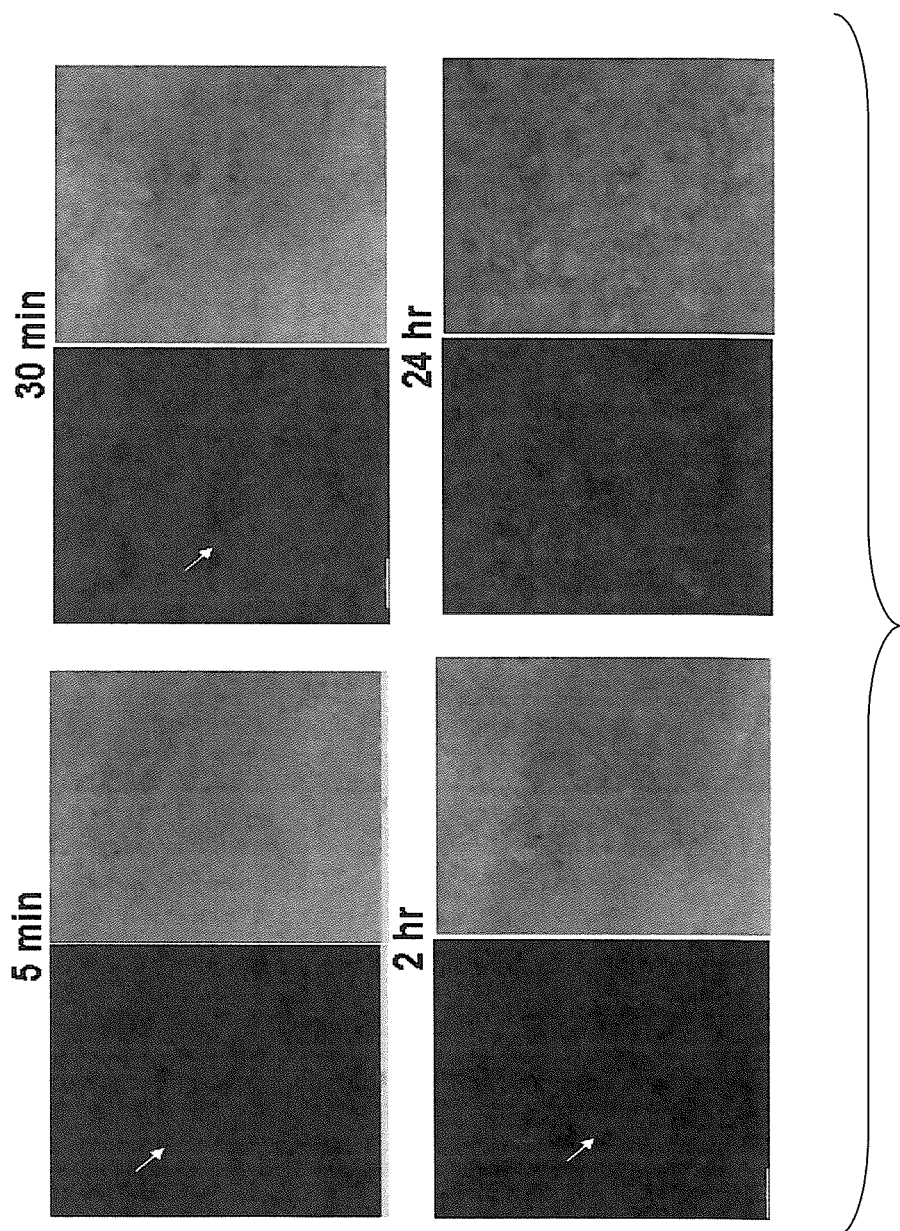

To study distribution of the probe into tumors and tumor cells, intravital imaging of a dorsal skin-fold window chamber xenograft tumor model was employed (see Methods). Briefly, the dorsal skin of a mouse is folded up into a saddle frame, and one side of the skin is removed in a circular region of ~1 cm in diameter and a round cover slip is placed over the opening, enabling high-resolution microscopic studies (41). For this experiment, A375/MC1R cells were mixed with matrigel and GFP expressing rat microvessels which were xenografted into the window chamber under the glass cover. Following a 5-7 day period of tumor growth, microvessel patency was verified by i.v. injection of blue Dextran and regions of the tumor with patent GFP vessels were chosen for study (see FIG. 31A). Then, 5 nmol/kg of the MC1R-Cy5 probe was intravenously injected. Extravasation, tumor cell binding and uptake of the probe was observed by continuous confocal microscope acquisitions. FIGS. 31B-1 and 31B-2 show the whole tumor surrounded by GFP microvessels at 24 hr after injection of probe using low magnification (1.25 and 4×), while uptake of the probe at different time points post-injection are shown in FIG. 26B using higher magnification (25×). The probe was observed to extravasate, penetrate into the tumor and bind to cells as early as 5 min after injection. At five minutes to two hours after injection, most of the MC1R probe was observed on the surface of the tumor cells, with lesser amounts taken into the cells. At 24 hours post-injection, the tumor cells had fully internalized the probe.

F. In Vivo Tumor Targeting

Figures 1, 2, 27A:
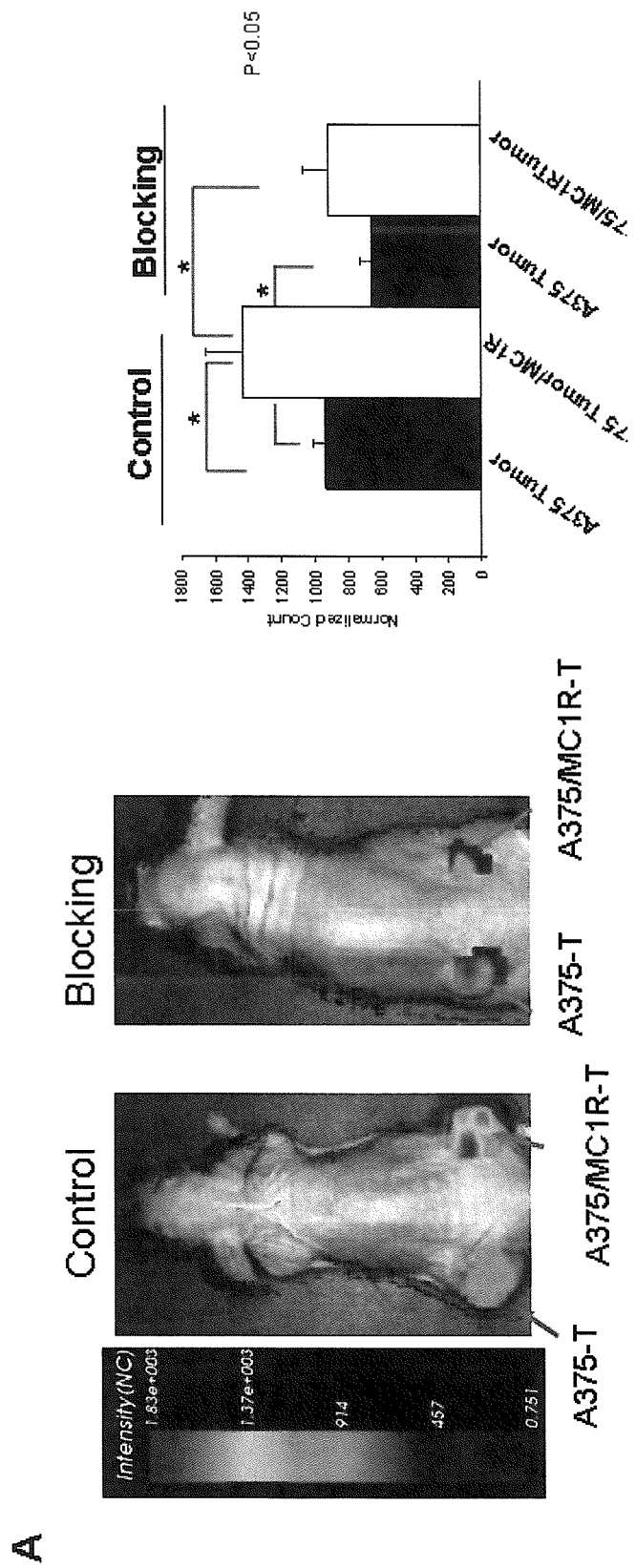
Figure 27B:
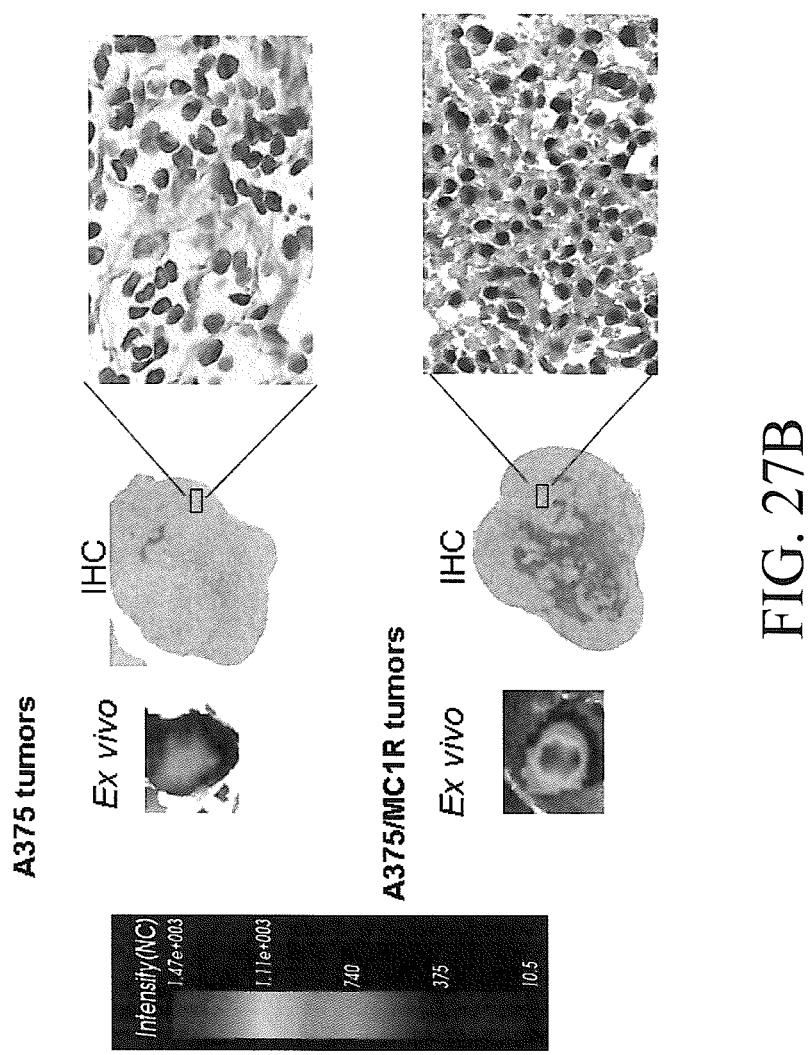

To investigate tumor targeting of the probe in vivo, bilateral subcutaneous xenograft tumors were established with A375/MC1R engineered cells in the right flank, and A375 parental cells with relatively low MC1R expression in the left flank. After tumor growth to approximately 500-800 mm$^3$, MC1RL-800 was injected intravenously and fluorescence accumulation was monitored over time. At 2 h post-injection, the A375 tumors with low MC1R expression had significantly lower normalized fluorescence signal compared to A375/MC1R tumors (P≤0.05, n=3) (FIG. 27A-1, left mouse, and FIG. 32A). Representative A357/MC1R tumor slices in the volume in vivo as well as ex vivo are shown in FIGS. 32B and 32C, indicating heterogeneity of probe labeling within the tumor. The in vivo specificity of the probe was confirmed by co-injection of 0.25 μg of NDP-α-MSH with 5 nmol/kg of the MC1RL-800 probe. After blocking, the probe-related fluorescence signal decreased 1.54 fold in the A375/MC1R tumors (P≤0.05, n=3) and 1.4 fold in A375 tumor (P≤0.05, n=3) relative to the unblocked tumor at 2 hr after injection (FIG. 27A-1, right mouse). Ex vivo images of the corresponding center sections of the high- and low-expressing tumors confirmed the in vivo results. IHC staining confirmed the high and low MC1R expression in the two tumor types, and areas with the highest IHC staining corresponded to areas with the highest fluorescence signal (FIG. 27B).

G. Biodistribution and Mathematical Modeling

Figure 28A:
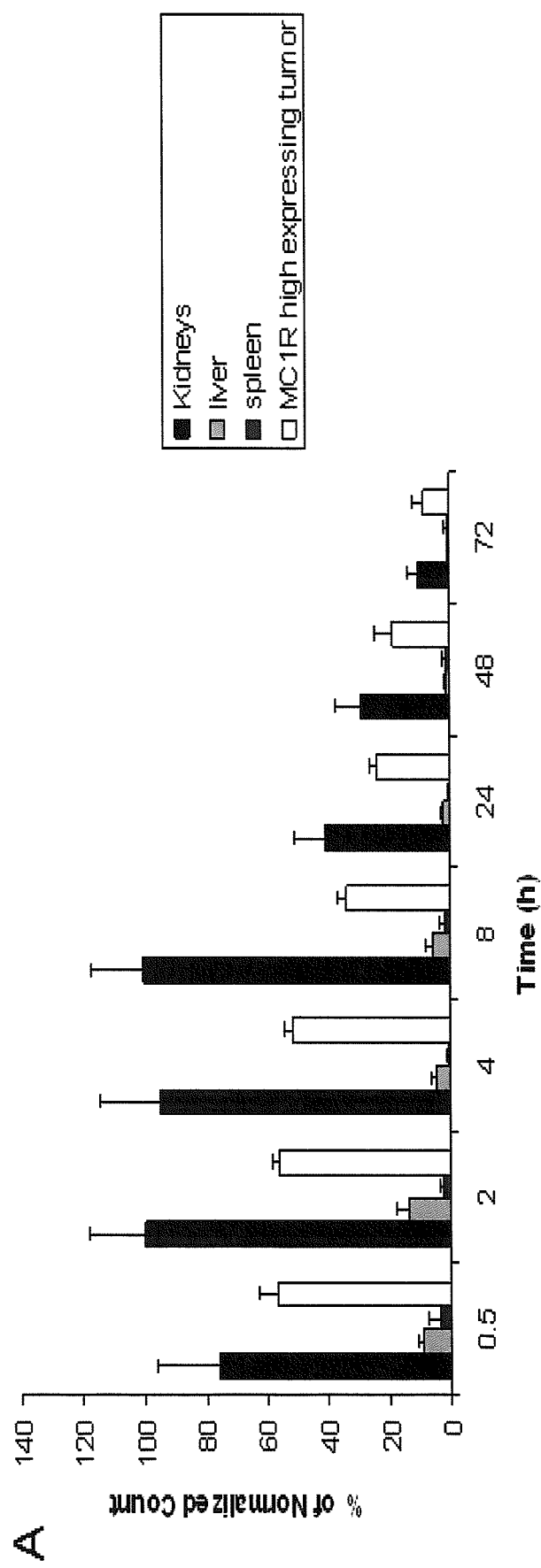

For biodistribution studies, mice bearing high expressing (A375/MC1R) tumors were injected with probe (n=3), and tissue distribution of fluorescence signal determined after removing tumors and organs from 30 min to 72 hr post-administration (FIG. 28A). At 30 minutes post-injection, probe was retained at relatively high levels in the MC1R high expressing tumor. At early time points, probe accumulation in the kidneys was significantly higher than in the tumors, e.g at 2 hr after injection, kidney signal was 2 fold higher, P<0.001. However, the accumulation was no longer significant by 72 hr after injection and the probe was cleared from both tumors and kidneys by 96 hr after injection. MC1RL-800 did not accumulate in the liver and no signal was detected in the other organs, such as spleen, heart, brain, etc.

The pharmacokinetics of probe uptake and clearance was also characterized using a three-compartment mathematical model, which includes tumor, kidney and mouse volumes, and assumes mass conservation of the ligand. This model was used to account for the interference of the tumor ligand release in the uptake and clearance dynamics of blood and kidneys. The results showed, while this effect is negligible in humans, it is significant in mouse models.

Figures 1, 2, 28B:
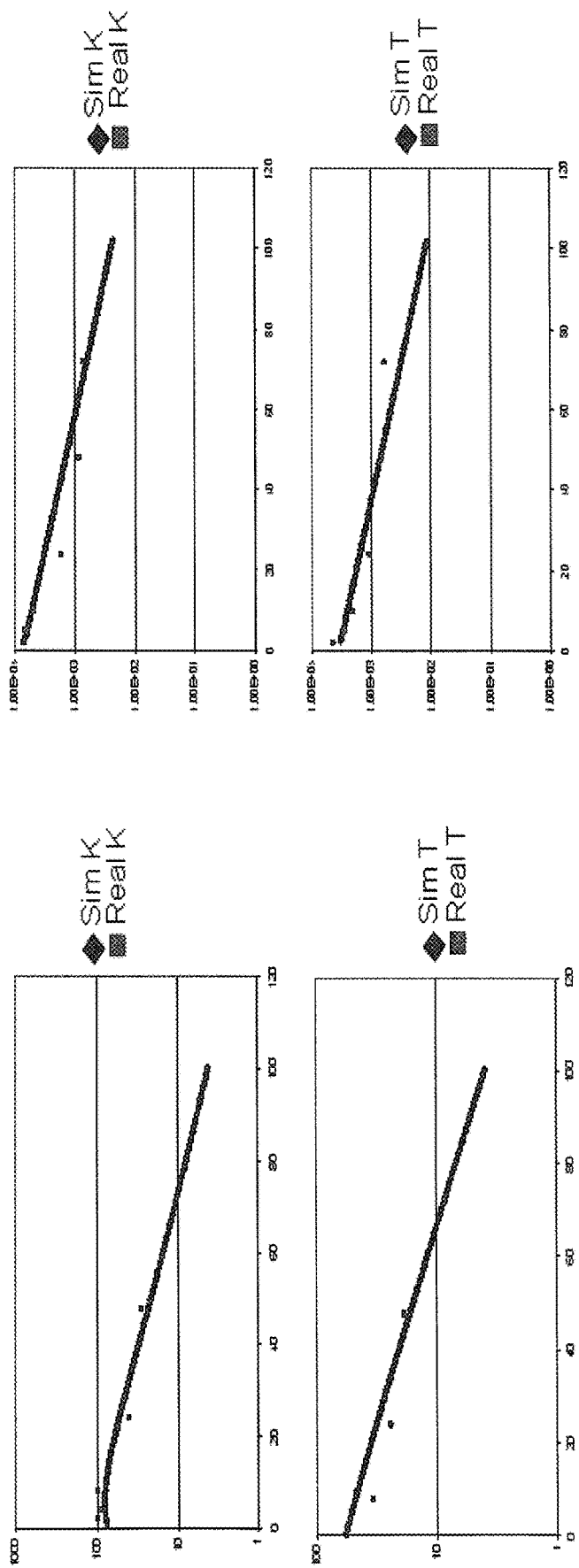

Both ex vivo and in vivo biodistribution studies fit in the model (FIG. 28B), suggesting using in vivo fluorescent imaging which provides high sensitivity for biodistribution study instead of sacrificing multiples animals at multiple time points. In addition, the probe is cleared at the same rate from both kidneys and tumor according to the inventors' model.

H. Determination of Log D of MC1RL-800

To measure lipophilicity of the probe, log D (distribution co-efficient) was determined. Lipophilicity is a key determinant of the pharmacokinetic behavior of drugs and can influence distribution into tissues, absorption and the binding characteristics of a drug, as well as determination of the solubility of a compound (reviewed by (42). The log D of MC1RL-800 probe was calculated −2.96, demonstrating high solubility of the probe but low permeability across the gastrointestinal tract or blood brain barrier.

I. Reduction of Kidney Uptake

Figures 1, 2, 29A:
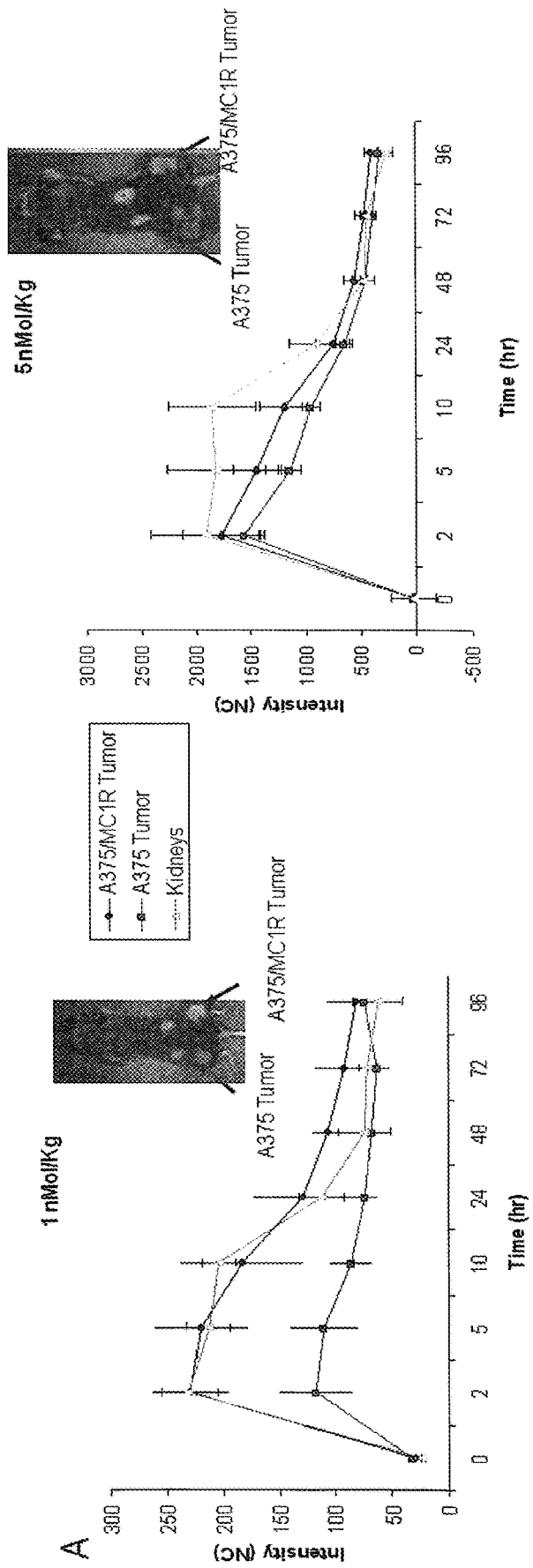

Significant renal accumulation was observed as early as 15 min after intravenous injection of the probe. To determine whether the amount of the MC1RL-800 probe injected had an effect on kidney uptake and retention, different amounts of the probe were injected intravenously (i.v.) and the pharmacokinetics of uptake and clearance monitored (FIGS. 30A-D). As expected, the lower dose (1 nmol/kg) provided greater discrimination and more rapid renal clearance, compared to the higher dose (5 nmol/kg) (FIGS. 29A-1 and 29A-2). Furthermore, with either dose, the measureable tumor and kidney half-lives were approximately 10 hr. Compared to previous studies, it is possible that this represents the time for dye to be acid quenched following internalization, and this will be characterized more fully in the future using Eu-labeled ligands.

Figure 29B:
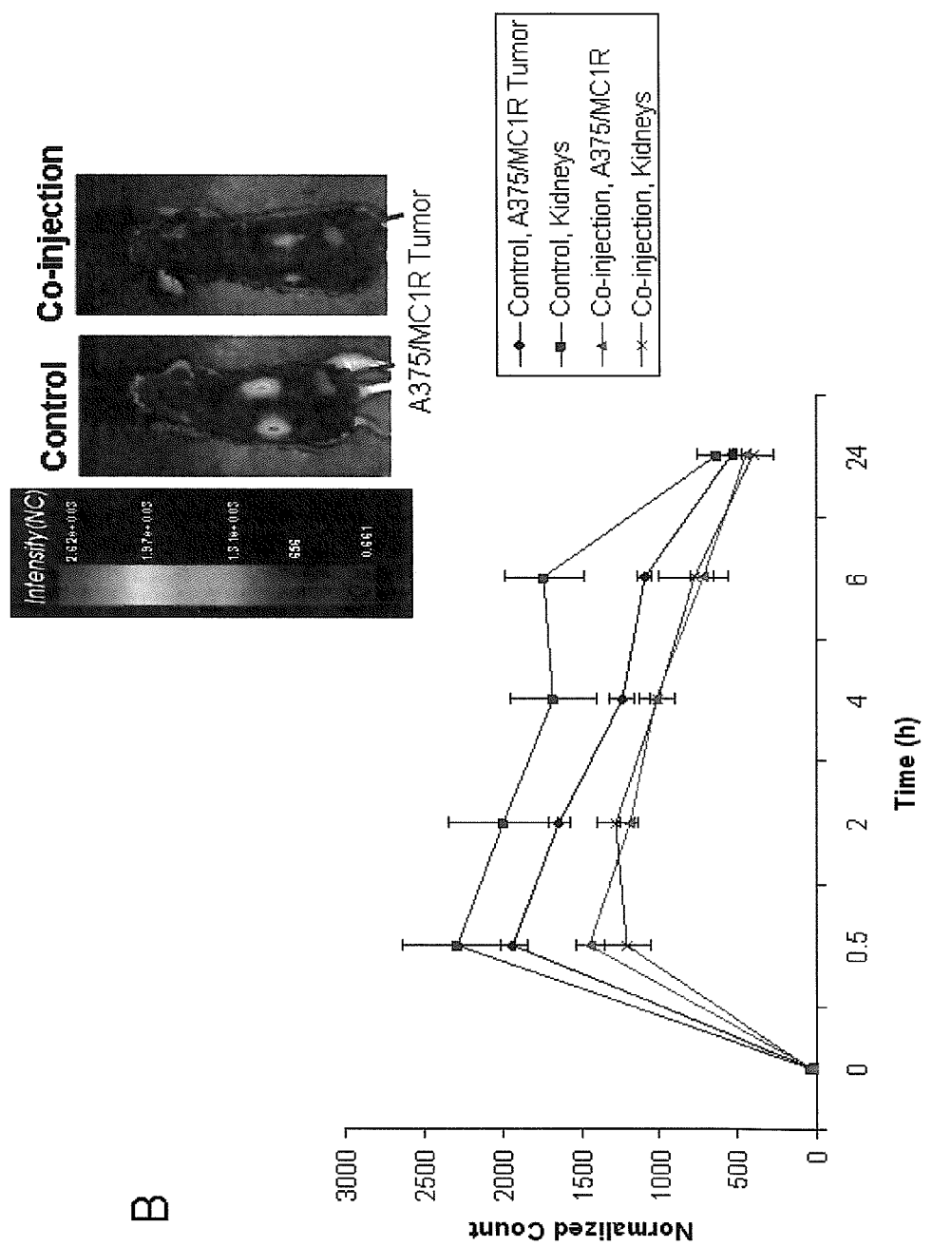
Figures 30A, 30B:
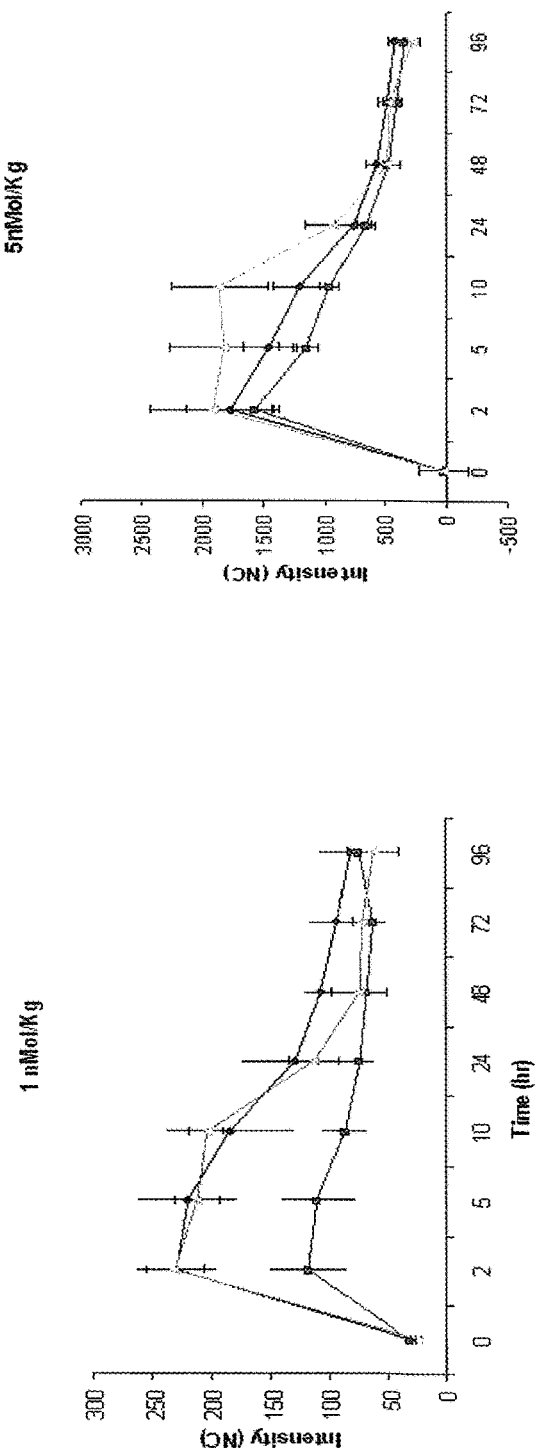
FIGS. 30A-D: Pharmacokinetics of different MC1RL-800 probe concentrations injected into mice bearing low- and high-MC1R expressing tumors and kidneys (1 nMol/Kg, 5 nMol/Kg, 10 nMol/Kg, and 30 nMol/Kg, respectively). Note that the peak signal in the tumors and kidneys occurs 2-hours post-injection and the lowest probe concentration injected had the lowest kidney accumulation. Data represent mean±s.d.
Figure 30D:
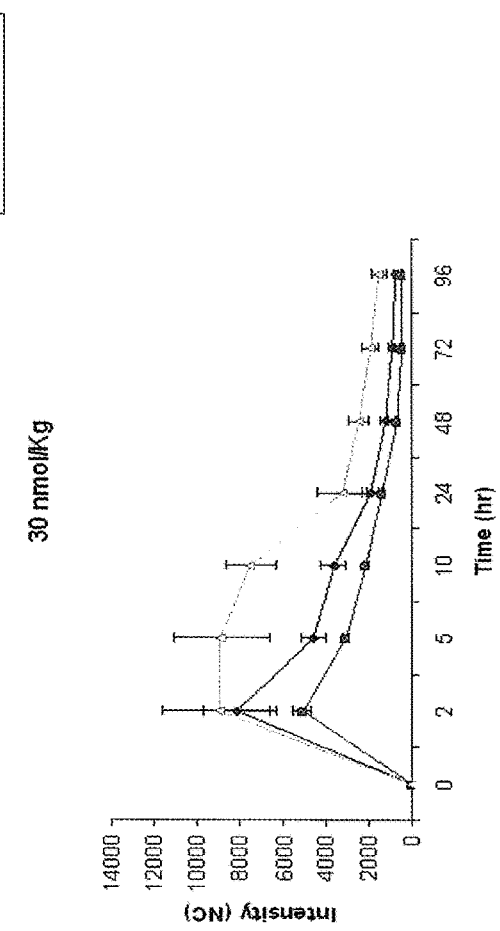
Figure 30C:
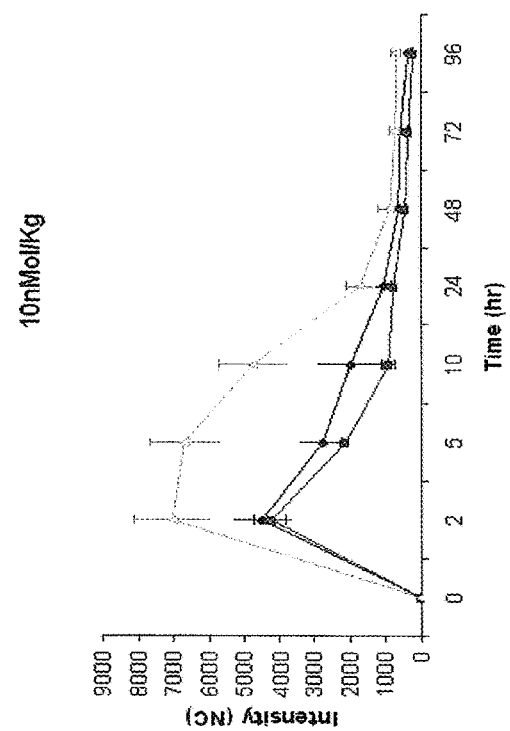
Figure 33:
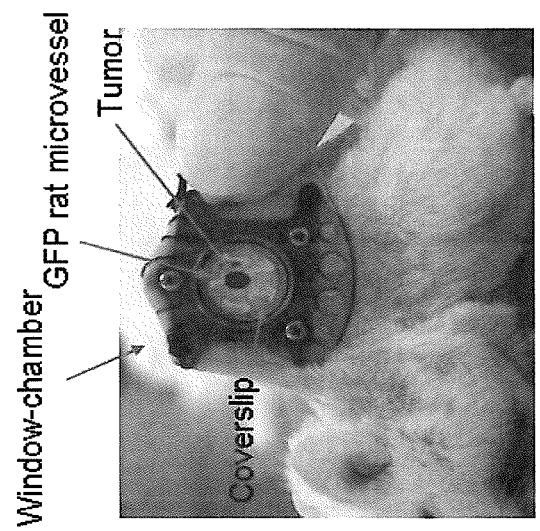
FIG. 33: Dorsal skin-fold window-chamber xenograft tumor model in SCID mouse. Intravital confocal imaging of MC1R-800CW probe tumor cell uptake in vivo using the dorsal skin-fold window chamber xenograft tumor model is shown in FIG. 26B.

In addition, as the kidneys express MC5R (43, 44) and have little or no expression of MC1R (vide supra), the inventors hypothesized that renal accumulation is occurring via off-target binding of the probe to MC5R. To test this, 1 nmol/kg of an MC4R/5R-selective ligand, H-Tyr-Val-Nle-Gly-His-DNal(2')-Arg-DPhe-Asp-Arg-Phe-Gly-NH$_2$ (SEQ ID NO:10), (32) was injected. This agent has Ki values of 5.6, 0.77 and 0.71 nM for MC1R, MC4R and MC5R, respectively. Co-injection of MC4R/5R compound along with 5 nmol/kg of MC1RL-800 significantly reduced renal uptake, e.g 1.56 fold lower at 2 hr after injection, P<0.05, compared to control animals (FIG. 29B). Whereas the A375/MC1R tumors had a significantly lower 1.54 fold decrease following blocking. Thus, it appears that the renal uptake of MC1RL-800 is due to off-target binding, which can be pharmacologically blocked.

Early detection of primary melanoma tumors is essential because there is no effective treatment for metastatic melanoma. MC1R is known to be over-expressed in the majority of melanoma patients (21, 45-47), representing one of the few specific targets potentially useful for diagnosis and therapy of metastatic melanoma. MC1R, has been intensively studied as a target for melanoma therapies; however, to the best of the inventors' knowledge, this represents the first publication in which it has been so extensively evaluated in terms of expression levels in patient samples and cell lines. In addition, the inventors have developed MC1R specific imaging probes and characterized their tumor cell specificity, binding and uptake both in vitro and in vivo.

It has been previously reported that up to 80% of melanoma cells express high levels of MC1R (21); however, those data were obtained through the use of radioassays using human cell lines, rather than patient tissue samples. It is not uncommon for protein expression in cultured cell lines to differ from that of primary tumors; in fact, such discrepancies are common throughout literature and undoubtedly play a role in the increased sensitivity of cancer lines to chemotherapy relative to solid tumors (48). Previous reports of MC1R expression in human melanoma and human uveal melanoma tissues have been as high as 95% (49, 50); however, these studies have taken a "present/not present" binary approach to data scoring. The inventors have rigorously sought to quantify MC1R expression in patient samples with the assistance of a dermatopathologist. The data that the inventors have collected from human tissues samples suggests that MC1R is moderately to highly expressed (with a score of ≥4) on only 40% to 60% of melanoma patient tumors, leading us to believe that earlier reports, citing high expression of MC1R in 80-95% of melanoma cells (21, 49, 50), may have been an overestimate.

Based on the inventors' analysis of publically available DNA microarray data from non-affected human tissues, MC1R mRNA expression is not elevated in non-melanoma skin cancer, normal skin cells, or organs which are typically involved in pharmaceutical clearance, such as the heart, liver, spleen or kidney. These findings are in good agreement with recent literature (49, 50). Additionally, Salazar-Onfray et.al (50) conducted an analysis of a broad panel of normal tissues through IHC and found that MC1R was detected only in low levels in adrenal grand, cerebellum and liver, and very weakly in normal appendix, myocardium, kidney and myometrium. Their data indicated that while MC1R is not expressed at detectable levels on fresh monocytes, in vitro stimulation with several cytokines such as IL-4, GM-CSF, and IL-10 can induce a strong expression of MC1R. Herein, the inventors report high expression of MC1R mRNA in melanocytes, and high protein expression in the basal layer of normal skin samples. Melanocytes are known to be present in the basal layer. The inventors' results indicate that MC1R is heterogeneously expressed in normal skin relative to the ubiquitous and high expression observed in a large fraction of melanomas. The inventors' findings, combined with previous reports from the literature, suggest that MC1R may be useful as a marker for a large subset of patients with melanoma for specific targeting.

It has been known that MC1R ligands also show cross-reactivity with other melanocortin receptors, mainly MC4R and MC5R. Since MC4R and MC5R have high expression levels in normal tissues including kidney and brain, MC1R ligands with non-specific binding to MC4R and MC5R are not ideal for targeting of melanoma in patients. Recently, the inventors described a high affinity peptidomimetic ligand against MC1R and demonstrated very low interaction against MC4R and MC5R, 1000 and 200 times lower affinity compared with MC1R, respectively (32). As this ligand had the highest hMC1R affinity and selectivity in the inventors' earlier study, it was chosen for more study here. The use of small peptidomimetics as carriers for the delivery of imaging or therapeutic moieties to diseased tissues offers several advantages such as high biostability, easy synthesis and modification, faster blood clearance, high-affinity and high-specificity and a low toxicity and immunogenicity (51-55).

In this research, the inventors further developed a molecular imaging probe by attachment of a near-infrared fluorescent dye IRDye800CW to the C-terminus of the MC1R specific ligand via lysine-mercaptopropionic acid linker (named MC1RL-800). As determined by the europium time-resolved fluorescence competition binding assay using Eu-NDP-α-MSH, the MC1RL-800 probe displays high in vitro binding affinity to MC1R in A375/MC1R cells (Ki 0.4±0.1 nM), a slightly weaker avidity than unmodified peptide (0.17 nM). The in vitro microscopic results showed binding of the probe on the cell membrane as early as 15 seconds after adding the probe.

To determine the uptake profile of the probe to the tumor cells immediately after injection, in vivo, intravital confocal imaging of a dorsal skin-fold window chamber tumor model was used. The window chamber model has been used for high-resolution imaging using wide-field fluorescence, transmission or reflectance imaging, as well as epifluorescence, confocal and multiphoton/nonlinear microscopy (41). The inventors' results showed internalization of the probes at 24 h after injection, which makes the ligand a good candidate for radionuclide labeling and radiotherapy.

MC1R expression ranges from several hundred to around 10,000 receptors per cell in different human cell lines (21). Therefore, development of a non-invasive imaging method for visualizing and quantifying MC1R expression will be useful for monitoring alteration in MC1R expression as an indicator of treatment response (56). The inventors' in vivo results indicate that MC1RL-800 imaging probe is able to differentiate different levels of MC1R expression in A375 melanoma tumors with low levels of MC1R (400±93 sites/cell, (38) and A375/MC1R tumors with high levels of expression (75,000 sites/cell). In addition, co-injection of NDP-a-MSH and MC1RL-800 probe significantly decreased the probe-related fluorescence signal (P<0.05) in both A375 and A375/MC1R tumor, showing the specific recognition of MC1R by the probe in the tumors.

Here, the inventors used whole animal imaging and ex vivo imaging of tumors and organs to study MC1RL-800 probe biodistribution and both were in agreement and fit in the inventors' mathematical model. Therefore, near infrared fluorescent imaging provides high sensitivity for detection, visualization, and quantification of fluorescence distributed throughout the body of living mice and consequently, there is no need to sacrifice multiple animals at multiple time points for this type of study.

The in vivo biodistribution of MC1RL-800 indicates high tumor and kidney uptake as early as 15 min after injection. While the inventors show higher accumulation of the probe in kidneys compared to MC1R high expressing tumor at early time points, the probe was completely cleared from both kidneys and tumor at the same rate by 72 hr after injection based on the inventors' experimental as well as simulation data. Co-injection of MC4R/5R-selective ligand is shown to significantly decrease the nonspecific accumulation of the probe in the kidneys. MC4R/5R-selective ligand has high affinity against MC5R which is expressed in the kidneys (43). The results here confirmed high specificity of this compound against MC5R. Thus, it appears that the renal uptake of MC1RL-800 is due to off-target binding and can be pharmacologically blocked. In addition, the inventors' study showed that the lower dose of 1 nmol/kg provides greater discrimination and faster renal clearance compared to the higher dose at 5 nmol/Kg, re-demonstrating its high affinity to MC1R compared to MC5R. Therefore, kidney accumulation of the probe can be reduced either by co-injection of MC4R/5R-selective ligand or by using lower doses of the MC1RL-800 probe. Although, kidney accumulation should not be a serious problem in use of the probe for detection of regional lymph node metastases, since it will be administered peritumorally and clear through the lymphatics where macrophages will likely ingest the probe decreasing systemic circulation. Also, since the probe clears within days after administration, toxicity to the kidneys should be minimal when delivered systemically for detection of distal metastases.

In summary, to the best of the inventors' knowledge, this represents the first account in which MC1R has been validated as a potential target in both melanoma cell lines (through DNA microarray) and patient samples (through DNA microarray and IHC). The inventors' results have indicated that, while MC1R is highly expressed in 40%-67% of melanomas, previous reports suggesting high expression in 80% of melanomas may have been an over-estimate. In addition, the specific MC1R fluorescent imaging probe with high affinity to the MC1R was successfully synthesized and characterized. The uptake study of the probe was carried out in vitro as well as in vivo. The inventors' study demonstrates that the probe can differentiate high- from low-MC1R expressing tumors. Therefore, MC1RL-800 is a promising molecular probe for imaging of MC1R-positive melanoma and MC1R expression. Despite the promising tumor-targeting properties of the probe, its biodistribution profile could still be improved. Lower kidney uptake could be obtained by decreasing affinity for MC5R by modifying the physicochemical properties or peptidomimetic structure of the ligand.

Since the boundaries of lesions often cannot be reliably determined in patients with melanoma, repeated surgical excisions are frequently required to achieve tumor-free margins (57). Invisible NIR fluorescent light with high resolution and sensitivity is used for real-time intraoperative image-guidance during surgery (58). The targeted agents of the invention (e.g., fluorescent targeted agents) can also offer an opportunity for image guided surgery for assessment of tumor margins in melanoma patients.

In conclusion, the imaging probe developed in this study is useful for translation as a clinical PET tracer for noninvasive identification of regional lymph node metastasis when injected locally at the primary lesion site as well as detection of distal metastases in malignant melanomas. In addition, it could have particular benefit for the evaluation of therapeutic efficacy. In the future, this ligand could also be used in clinic as a MC1R targeted delivery vehicle for radionuclides, toxins, and chemotherapeutic molecules.

REFERENCES (FOR EXAMPLE 2)

1. Jemal A, Murray T, Ward E, et al. Cancer statistics, 2005. CA Cancer J Clin 2005; 55: 10-30.
2. Thompson J F, Uren R F. Lymphatic mapping in management of patients with primary cutaneous melanoma. Lancet Oncol 2005; 6: 877-85.
3. Balch C M. [Diagnosis and prognosis of malignant melanoma]. Dtsch Med Wochenschr 1985; 110: 1783-6.
4. Phan G Q, Messina J L, Sondak V K, Zager J S. Sentinel lymph node biopsy for melanoma: indications and rationale. Cancer Control 2009; 16: 234-9.
5. Scott J D, McKinley B P, Bishop A, Trocha S D. Treatment and outcomes of melanoma with a Breslow's depth greater than or equal to one millimeter in a regional teaching hospital. Am Surg 2005; 71: 198-201.
6. Balch C M, Buzaid A C, Soong S J, et al. Final version of the American Joint Committee on Cancer staging system for cutaneous melanoma. J Clin Oncol 2001; 19: 3635-48.
7. Uren R F, Howman-Giles R, Chung D, Thompson J F. Nuclear medicine aspects of melanoma and breast lymphatic mapping. Semin Oncol 2004; 31: 338-48.

8. Hettiaratchy S P, Kang N, O'Toole G, Allan R, Cook M G, Powell B W. Sentinel lymph node biopsy in malignant melanoma: a series of 100 consecutive patients. Br J Plast Surg 2000; 53: 559-62.
9. Essner R, Scheri R, Kavanagh M, Torisu-Itakura H, Wanek L A, Morton D L. Surgical management of the groin lymph nodes in melanoma in the era of sentinel lymph node dissection. Arch Surg 2006; 141: 877-82; discussion 82-4.
10. Ho Shon I A, Chung D K, Saw R P, Thompson J F. Imaging in cutaneous melanoma. Nucl Med Commun 2008; 29: 847-76.
11. Mohr P, Eggermont A M, Hauschild A, Buzaid A. Staging of cutaneous melanoma. Ann Oncol 2009; 20 Suppl 6: vi14-21.
12. Krug B, Crott R, Lonneux M, Baurain J F, Pirson A S, Vander Borght T. Role of PET in the initial staging of cutaneous malignant melanoma: systematic review. Radiology 2008; 249: 836-44.
13. Singh B, Ezziddin S, Palmedo H, et al. Preoperative 18F-FDG-PET/C T imaging and sentinel node biopsy in the detection of regional lymph node metastases in malignant melanoma. Melanoma Res 2008; 18: 346-52.
14. Veit-Haibach P, Vogt F M, Jablonka R, et al. Diagnostic accuracy of contrast-enhanced FDG-PET/C T in primary staging of cutaneous malignant melanoma. Eur J Nucl Med Mol Imaging 2009; 36: 910-8.
15. Harland C C, Kale S G, Jackson P, Mortimer P S, Bamber J C. Differentiation of common benign pigmented skin lesions from melanoma by high-resolution ultrasound. Br J Dermatol 2000; 143: 281-9.
16. Hofmann U, Szedlak M, Rittgen W, Jung E G, Schadendorf D. Primary staging and follow-up in melanoma patients—monocenter evaluation of methods, costs and patient survival. Br J Cancer 2002; 87: 151-7.
17. Wagner J D. A role for FDG-PET in the surgical management of stage IV melanoma. Ann Surg Oncol 2004; 11: 721-2.
18. Hsu M, Andl T, Li G, Meinkoth J L, Herlyn M. Cadherin repertoire determines partner-specific gap junctional communication during melanoma progression. J Cell Sci 2000; 113 (Pt 9): 1535-42.
19. Wang R, Kobayashi R, Bishop J M. Cellular adherence elicits ligand-independent activation of the Met cell-surface receptor. Proc Natl Acad Sci USA 1996; 93: 8425-30.
20. Yang P, Farkas D L, Kirkwood J M, Abernethy J L, Edington H D, Becker D. Macroscopic spectral imaging and gene expression analysis of the early stages of melanoma. Mol Med 1999; 5: 785-94.
21. Siegrist W, Solca F, Stutz S, et al. Characterization of receptors for alpha-melanocyte-stimulating hormone on human melanoma cells. Cancer Res 1989; 49: 6352-8.
22. Geschwind, I I, Huseby R A, Nishioka R. The effect of melanocyte-stimulating hormone on coat color in the mouse. Recent Prog Horm Res 1972; 28: 91-130.
23. Hunt G, Kyne S, Wakamatsu K, Ito S, Thody A J. Nle4DPhe7 alpha-melanocyte-stimulating hormone increases the eumelanin:phaeomelanin ratio in cultured human melanocytes. J Invest Dermatol 1995; 104: 83-5.
24. Tamate H B, Takeuchi T. Action of the e locus of mice in the response of phaeomelanic hair follicles to alpha-melanocyte-stimulating hormone in vitro. Science 1984; 224: 1241-2.
25. Cai M, Varga E V, Stankova M, et al. Cell signaling and trafficking of human melanocortin receptors in real time using two-photon fluorescence and confocal laser microscopy: differentiation of agonists and antagonists. Chem Biol Drug Des 2006; 68: 183-26. Koikov L N, Ebetino F H, Solinsky M G, Cross-Doersen D, Knittel J J. Sub-nanomolar hMC1R agonists by end-capping of the melanocortin tetrapeptide His-D-Phe-Arg-Trp-NH(2). Bioorg Med Chem Lett 2003; 13: 2647-50.
27. Mayorov A V, Han S Y, Cai M, Hammer M R, Trivedi D, Hruby V J. Effects of macrocycle size and rigidity on melanocortin receptor-1 and -5 selectivity in cyclic lactam alpha-melanocyte-stimulating hormone analogs. Chem Biol Drug Des 2006; 67: 329-35.
28. Chen J, Giblin M F, Wang N, Jurisson S S, Quinn T P. In vivo evaluation of 99mTc/188Re-labeled linear alpha-melanocyte stimulating hormone analogs for specific melanoma targeting. Nucl Med Biol 1999; 26: 687-93.
29. Cai M, Mayorov A V, Cabello C, Stankova M, Trivedi D, Hruby V J. Novel 3D pharmacophore of alpha-MSH/gamma-MSH hybrids leads to selective human MC1R and MC3R analogues. J Med Chem 2005; 48: 1839-48.
30. Handl H L, Vagner J, Yamamura H I, Hruby V J, Gillies R J. Lanthanide-based time-resolved fluorescence of in cyto ligand-receptor interactions. Anal Biochem 2004; 330: 242-50.
31. Yang Y, Hruby V J, Chen M, Crasto C, Cai M, Harmon C M. Novel binding motif of ACTH analogues at the melanocortin receptors. Biochemistry 2009; 48: 9775-84.
32. Barkey N M, Tafreshi N K, Josan J S, et al. Development of melanoma-targeted polymer micelles by conjugation of a melanocortin 1 receptor (MC1R) specific ligand. J Med Chem 2011; 54: 8078-84.
33. Hoek K S, Schlegel N C, Brafford P, et al. Metastatic potential of melanomas defined by specific gene expression profiles with no BRAF signature. Pigment Cell Res 2006; 19: 290-302.
34. Smalley K S, Contractor R, Nguyen T K, et al. Identification of a novel subgroup of melanomas with KIT/cyclin-dependent kinase-4 overexpression. Cancer Res 2008; 68: 5743-52.
35. Schlauder S M, Steffensen T S, Morgan M, et al. Assessment of muscarinic and nicotinic acetylcholine receptor expression in primitive neuroectodermal tumor/ewing family of tumor and desmoplastic small round cell tumor: an immunohistochemical and Western blot study of tissue microarray and cell lines. Fetal Pediatr Pathol 2008; 27: 83-97.
36. Morse D L, Carroll D, Weberg L, Borgstrom M C, Ranger-Moore J, Gillies R J. Determining suitable internal standards for mRNA quantification of increasing cancer progression in human breast cells by real-time reverse transcriptase polymerase chain reaction. Anal Biochem 2005; 342: 69-77.
37. Xu L, Vagner J, Alleti R, et al. Synthesis and characterization of a Eu-DTPA-PEGO-MSH(4) derivative for evaluation of binding of multivalent molecules to melanocortin receptors. Bioorg Med Chem Lett 2010; 20: 2489-92.
38. Cheng Z, Xiong Z, Subbarayan M, Chen X, Gambhir S S. 64Cu-labeled alpha-melanocyte-stimulating hormone analog for microPET imaging of melanocortin 1 receptor expression. Bioconjug Chem 2007; 18: 765-72.
39. Shepherd B R, Chen H Y, Smith C M, Gruionu G, Williams S K, Hoying J B. Rapid perfusion and network remodeling in a microvascular construct after implantation. Arterioscler Thromb Vasc Biol 2004; 24: 898-904.
40. Baumann J B, Bagutti C, Siegrist W, Christen E, Zumsteg U, Eberle A N. MSH receptors and the response of human A375 melanoma cells to interleukin-1 beta. J Recept Signal Transduct Res 1997; 17: 199-210.
41. Palmer G M, Fontanella A N, Shan S, et al. In vivo optical molecular imaging and analysis in mice using dorsal window chamber models applied to hypoxia, vasculature and fluorescent reporters. Nat Protoc 2011; 6: 1355-66.
42. Di L, Kerns E H. Profiling drug-like properties in discovery research. Curr Opin Chem Biol 2003; 7: 402-8.
43. Fathi Z, Iben L G, Parker E M. Cloning, expression, and tissue distribution of a fifth melanocortin receptor subtype. Neurochem Res 1995; 20: 107-13.
44. Gong R. The renaissance of corticotropin therapy in proteinuric nephropathies. Nat Rev Nephrol 2012; 8: 122-8.
45. Bagutti C, Oestreicher M, Siegrist W, Oberholzer M, Eberle A N. alpha-MSH receptor autoradiography on mouse and human melanoma tissue sections and biopsies. J Recept Signal Transduct Res 1995; 15: 427-42.
46. Ghanem G E, Comunale G, Libert A, Vercammen-Grandjean A, Lejeune F J. Evidence for alpha-melanocyte-stimulating hormone (alpha-MSH) receptors on human malignant melanoma cells. Int J Cancer 1988; 41: 248-55.
47. Jiang J, Sharma S D, Fink J L, Hadley M E, Hruby V J. Melanotropic peptide receptors: membrane markers of human melanoma cells. Exp Dermatol 1996; 5: 325-33.
48. Stein W D, Litman T, Fojo T, Bates S E. A Serial Analysis of Gene Expression (SAGE) database analysis of chemosensitivity: comparing solid tumors with cell lines and comparing solid tumors from different tissue origins. Cancer Res 2004; 64: 2805-16.
49. Lopez M N, Pereda C, Ramirez M, et al. Melanocortin 1 receptor is expressed by uveal malignant melanoma and can be considered a new target for diagnosis and immunotherapy. Invest Ophthalmol Vis Sci 2007; 48: 1219-27.
50. Salazar-Onfray F, Lopez M, Lundqvist A, et al. Tissue distribution and differential expression of melanocortin 1 receptor, a malignant melanoma marker. Br J Cancer 2002; 87: 414-22.
51. Advances in amino acid mimetics and peptidomimetics. Greenwich, Conn.: JAI Press; 1997. p. v.
52. Bullok K E, Gammon S T, Violini S, et al. Permeation peptide conjugates for in vivo molecular imaging applications. Mol Imaging 2006; 5: 1-15.
53. Knight L C. Non-oncologic applications of radiolabeled peptides in nuclear medicine. Q J Nucl Med 2003; 47: 279-91.
54. Okarvi S M. Recent progress in fluorine-18 labelled peptide radiopharmaceuticals. Eur J Nucl Med 2001; 28: 929-38.
55. Okarvi S M. Peptide-based radiopharmaceuticals: future tools for diagnostic imaging of cancers and other diseases. Med Res Rev 2004; 24: 357-97.
56. Cheng Z, Zhang L, Graves E, et al. Small-animal PET of melanocortin 1 receptor expression using a 18F-labeled alpha-melanocyte-stimulating hormone analog. J Nucl Med 2007; 48: 987-94.
57. Adler M J, White C R, Jr. Amelanotic malignant melanoma. Semin Cutan Med Surg 1997; 16: 122-30.
58. Troyan S L, Kianzad V, Gibbs-Strauss S L, et al. The FLARE intraoperative near-infrared fluorescence imaging system: a first-in-human clinical trial in breast cancer sentinel lymph node mapping. Ann Surg Oncol 2009; 16: 2943-52.

Materials and Methods for Example 3

Online Methods

Synthesis of Gd-Tx.

Information on the synthesis of Gd-Tx, including mass spectral data, can be found in the Supporting Information.

Crystalization of Gd-Tx and Determination of Structure.

Crystals suitable for X-ray diffraction were obtained by dissolving Gd-Tx (2 mg, 2.26 μmol) in 1 mL methanol. Sodium nitrate (0.2 mg, 4 equiv.) was added and the solution was heated to reflux at 60° C. for 24 hours. At this point, 0.25 mL chloroform was added and the solution was placed in a vial and diethyl ether was allowed to slowly diffuse into the solution at 5° C. For full crystallographic data, please see Supporting Information. Further details of the structure may also be obtained from the Cambridge Crystallographic Data Centre by quoting CCDC number 859294.

Synthesis of Targeted Triblock Polymers.

IVECT™ triblock polymers with a terminal azide were obtained from Intezyne Technologies (Tampa, Fla.) and either NDP-α-MSH-lys-hexyne 2 or 1[40] (Scheme 1) were used as the MC1R-selective ligand. Standard click chemistry was conducted as previously published.[40]

Formulation and Stabilization of Gd-Tx Micelles.

For targeted formulations, 5-10% of the targeted polymer and 90-95% of the untargeted polymer were used, respectively. Gd-Tx (0.05-5% w/w), was dissolved in dimethylsulfoxide (DMSO, 380 μL). The triblock polymer (750 mg) was dissolved in water (150 mL) at a concentration of 5 mg/mL and stirred with slight heating until fully dissolved. After cooling to room temperature, the polymer solution was placed in a sheer mixer and the Gd-Tx solution was added. The resulting solution was then passed through a microfluidizer (Microfluidics M-110Y) at 23,000 PSI, filtered through a 0.22 μm Steriflip-GP Filter Unit (Millipore) and lyophilized.

For stabilized formulations, micelles were subject to an Fe(III)-mediated crosslinking reaction.[12] $FeCl_3$ was prepared at concentration of 1.35 g/mL in 20 mM Tris-Cl (pH 7.4). The targeted and untargeted micelles were then dissolved in the Fe(III)-tris solution at a concentration of 20 mg/mL and the solution was adjusted to pH 8 through the dropwise addition of 0.1-1 M aqueous NaOH. The crosslinking reaction was stirred for 12 hours. The contents of the reaction vessel were then lyophilized.

Cell Culture.

HCT116 cells overexpressing hMC1R were engineered in our lab. HCT116 cells were transfected with the pCMV6-Entry Vector (Origene; RC 203218) using the Fugene 6 transfection reagent (Roche; 1814-443). Transfected cells were grown in a selection media containing 0.4 mg/ml geneticin (Life Technologies; 11811-031) and tested for the hMC1R cell surface expression by saturation ligand binding assay.[23] Cells were maintained under standard conditions (37° C. and 5% $CO_2$) and were grown in Dulbecco's modified Eagle medium (DMEM) supplemented with 10% FBS and 5% penicillin/streptomycin. For HCT116/hMC1R cells, geneticin (G418S, 0.8%) was added to the media to ensure proper selection. hMC1R expression was verified through immunohistochemistry (IHC, see Supplemental Information).

Europium Binding Assays. Europium binding assays were conducted as previously published.[33,40]

In Vivo Murine Tumor Models.

All animal experiments were approved by institution review board guidelines on the care and use of animals in research. HCT116/hMC1R-expressing tumor models were studied in female SCID/beige mice obtained from Harlan Laboratories at 6-8 weeks of age. HCT116/hMC1R cells were injected at concentrations of $3\times10^6$-$10\times10^6$ cells per 0.1 mL of phosphate-buffered saline. Tumor volume measurements were made bi-weekly and calculated by multiplying the length by the width squared and dividing by two. Final volume measurements were determined through ROI analysis on the MRI.

MRI Imaging and Analysis.

All imaging was completed on a 7 Tesla, 30 cm horizontal bore Agilent magnetic resonance imaging spectrometer ASR310 (Agilent Life Sciences Technologies, Santa Clara, Calif. Detailed information on the MRI imaging and analysis, including imaging processing, can be found in the Supporting Information. Briefly, SCOUT images were acquired for slice selection for both in vitro and in vivo imaging. For in vitro phantom T1 studies, multiple TR SEMS (spin echo) imaging was performed to calculate T1 values. For in vivo imaging and quantification of tumor enhancement due to uptake of the micelles, T1 weighted spin echo multi slice (SEMS) images were acquired, and intensity histograms for right (R) and left (L) whole tumors, and R and L whole kidney and liver were prepared using the MATLAB program (Mathworks, Natick, Mass.) for each time point. This was done by drawing an ROI across all applicable slices. The mean intensity value for each time point was normalized to the mean intensity of the thigh muscle. A percent change value was then calculated by comparing each time point after injection to the normalized pre-injection intensity mean. The % change values for all tumors in a given group (n=3 for all groups) were averaged to obtain the "mean tumor % change" at time points from 1 to 48 h. Percent change values were also averaged for R and L kidney to obtain the "mean kidney % change" values.

Supporting Information for Example 3

Synthesis of Gd-Tx 6.

All chemicals were obtained from commercial sources (Fisher Scientific, Acros Chemicals, Sigma-Aldrich or Strem Chemicals) and used as supplied unless otherwise noted. All solvents were of reagent grade quality. Fisher silica gel (230-400 mesh, Grade 60 Å) and Sorbent Technologies alumina (neutral, standard activity I, 50-200 μm) were used for column chromatography. Thin layer chromatography (TLC) analyses were either performed on silica gel (aluminum backed, 200 μm or glass backed, 250 μm) or alumina neutral TLC plates (polyester backed, 200 μm), both obtained from Sorbent Technologies. Low- and high-resolution ESI mass spectra (MS) were obtained at the Mass Spectrometry Facility of the Department of Chemistry and Biochemistry at The University of Texas at Austin using a Thermo Finnigan LTQ instrument and a Qq FTICR (7 Tesla) instrument, respectively. HPLC spectra were taken on a Shimadzu High Performance Liquid Chromatograph (Fraction Collector Module FRC-10A, Auto Sampler SIL-20A, System Controller CBM-20A, UV/Vis Photodiode Array Detector SPD-M20A, Prominence). The tripyrrane dialdehyde species 5 (generally referred to as "TP-4") was provided by Pharmacyclics Inc. and synthesized as previously described.[1] The precursor 1,2-dimethoxy-4,5-dinitrobenzene 4 was synthesized as previously described.[2]

The gadolinium complex used in this study (Gd-Tx 6) was prepared as shown in Scheme 51. Briefly, compound 4 (1 g, 4.38 mmol) was dissolved in 10 mL methanol and placed in a hydrogenation flask. The solution was purged with nitrogen for 5 minutes and palladium on activated carbon (10%, 0.1 g) was added. The mixture was degassed and allowed to react with hydrogen gas at 100 psi with agitation for 18 hours, filtered under Schlenk conditions through a minimal pad of Celite, and added instantly to a solution of TP-4 5 (2.11 g, 4.38 mmol) in 15 mL methanol under nitrogen at 70° C. At this point, aqueous hydrochloric acid was added (2 mL, 0.5 M) and the deep red reaction mixture was stirred for 4 hours. Next, gadolinium acetate tetrahydrate (2.67 g, 6.57 mmol, 1.5 equiv) was added together with 3 ml triethylamine and the solution was stirred at 70° C. for 16 hours, during which time the solution gradually changed color from deep red to deep green. The solvent was removed in vacuo and the residue was then subjected to column chromatography (silica gel). To remove apolar impurities, the column was eluted first with a mixture of 95% $CH_2Cl_2$ and 5% MeOH. The product slowly starts to elute when a mixture of 60% $CH_2Cl_2$ and 40% MeOH is used as the eluent. The deep green fraction isolated using this eluent mixture was collected and the solvent was removed in vacuo to give 6 (Gd-Tx) as a deep green crystalline material (1.63 g, 42%). UV/Vis (MeOH, 25° C.): $\lambda_{max}$=470 (Soret-type band); 739 (Q-type band); Low Resolution MS (ESI in MeOH): 797.25 ($M^+$-2OAc+OMe), 825.42 ($M^+$-OAc). High Resolution MS (ESI in MeOH): calculated for $C_{38}H_{45}N_5O_6Gd^{+1}$=825.2611; found: 825.2621($C_{38}H_{45}N_5O_6Gd^{+1}$, $M^+$-OAc).

MRI Imaging and Analysis.

All imaging was completed on a 7 Tesla, 30 cm horizontal bore Agilent magnetic resonance imaging spectrometer ASR310 (Agilent Life Sciences Technologies, Santa Clara, Calif.). In vitro imaging of Gd-Tx micelle phantoms was completed using a SCOUT image for slice selection, and a multiple TR SEMS (spin echo) image was performed in order to calculate the $T_1$ values. The TR calculation sequence consisted of TR values of 20, 10.99, 6.03, 3.31, 1.82, 1.00, 0.55, 0.30, 0.17, 0.09 and 0.05 s; the TE was 8.62 ms, the data matrix was 128×128, 4 averages, 2 dummy scans, FOV was 80 mm×40 mm or 40 mm×90 mm and the slice thickness was 1-2 mm (depending on the phantom). The $T_1$ values were calculated using the VnmrJ software (Agilent Life Sciences Technologies, Santa Clara, Calif.), and values were verified using MATLAB (Mathworks, Natick, Mass.).

Once the tumors in the animals reached an average of ~500 $mm^3$, the animals were pair-matched by tumor size and sorted into four groups which would receive the following micelles: TG,XL; UT-XL; T-UXL; or UT-UXL. Each animal was imaged the day before micelle injection for "pre" images. The following morning, each animal was individually administered 12 μmol/kg Gd-Tx (as Gd-Tx micelles) dissolved in 200 uL saline, via tail vein injection, and the time of injection was noted. Follow-up MRI images were taken at 1 hr, 4 hr, 12 hr, 24 and 48 h after injection of the micelles.

All animals were sedated using isoflurane and remained under anesthesia for the duration of the imaging. Animals were kept at body temperature (~37° C.) using a warm air blower; the temperature of the air was adjusted to maintain the body temperature and was monitored using a fiber optic rectal probe. SCOUT images were taken to determine animal position within the magnet and setup the slices for the $T_1$ weighted spin echo multi slice (SEMS) images. The SEMS images were taken as coronal-90 images (read direction along the X-axis, phase-encode along the Z-axis), with data matrix of 128×128 and a FOV of 40 mm (read)×90 mm (phase); 15 one-mm thick slices were taken with a 0.5 mm gap between slices; the TR was 180 ms, and TE was 8.62 ms; there were 8 averages taken for each image, resulting in a total scan time of about 3 minutes per SEMS image.

Images were processed using MATLAB (Mathworks, Natick, Mass.) to draw regions of interest (ROI) in the tumors, kidney, liver and thigh muscle over multiple slices for each mouse at each time point. All intensities for each area of interest were averaged to determine a mean intensity. The mean intensity of each area was then normalized to the mean intensity of the thigh to generate a normalized intensity (NI):

$$NI = \frac{I_{tumor}}{I_{thigh}}$$

A percent change value was then calculated by comparing each normalized time point after injection to the normalized pre-injection intensity mean:

$$\% \text{ Change} = \frac{NI_{12h}}{NI_{pre}} \times 100$$

Since the right and left tumors are histologically equivalent (Figure S.4), the % change values for all tumors were averaged to obtain an "average tumor % change" at time points 1-24 h. Percent change values were also averaged for R and L kidney to obtain an "average kidney % change" at time points 1-24 h.

X-Ray Experimental for $(C_{36}H_{42}N_5O_4)Gd(NO_3)_2$—$CH_3OH$—$H_2O$ 6.

Crystals grew as dark green prisms by slow diffusion of diethyl ether into a solution of 6 dissolved in methanol/chloroform (4:1) and sodium nitrate (4 equiv.). The data crystal had approximate dimensions: 0.23×0.07×0.07 mm. The data were collected on a Nonius Kappa CCD diffractometer using a graphite monochromator with MoKa radiation ($\lambda$=0.71073 Å). A total of 384 frames of data were collected using w-scans with a scan range of 1.2° and a counting time of 144 seconds per frame. The data were collected at 153 K using an Oxford Cryostream low temperature device. Details of crystal data, data collection and structure refinement are listed in Table 7. Data reduction were performed using DENZO-SMN. The structure was solved by direct methods using SIR97[3] and refined by full-matrix least-squares on $F^2$ with anisotropic displacement parameters for the non-H atoms using SHELXL-97.[4] The hydrogen atoms were calculated in ideal positions with isotropic displacement parameters set to 1.2× Ueq of the attached atom (1.5× Ueq for methyl hydrogen atoms).

The function, $\Sigma w(|F_O|^2-|F_C|^2)^2$, was minimized, where $w=1/[(s(F_O))^2+(0.0313*P)^2+(3.8824*P)]$ and $P=(|F_O|^2+2|F_C|^2)/3$. $R_W(F^2)$ refined to 0.103, with R(F) equal to 0.0537 and a goodness of fit S=1.17. Definitions used for calculating $R(F), R_W(F^2)$ and the goodness of fit, S, are given below. * The data were checked for secondary extinction but no correction was necessary. Neutral atom scattering factors and values used to calculate the linear absorption coefficient are from the International Tables for X-ray Crystallography (1992).[5] All figures were generated using SHELXTL/PC.6 Tables of positional and thermal parameters, bond lengths and angles, torsion angles and figures are included in the tables below.

* $R_W(F^2)=\{Sw(|F_O|^2-|F|_C^2)^2/Sw(|F_O|)^4\}^{1/2}$ where w is the weight given each reflection. $R(F)=S(|F_O|-|F_C|)/S|F_O|$ for reflections with $F_O>4(s(F_O))$. $S=[Sw(|F_O|^2-|C_C|^2)^2/(n-p)]^{1/2}$, where n is the number of reflections and p is the number of refined parameters.

TABLE 7

Crystal data and structure refinement for 6.

| | |
|---|---|
| Empirical formula | C37 H48 Gd N7 O12 |
| Formula weight | 940.07 |
| Temperature | 123(2) K. |
| Wavelength | 0.71069 Å |
| Crystal system | Monoclinic |
| Space group | P21/c |
| Unit cell dimensions | a = 15.3250(10) Å  a = 90°. |
| | b = 11.5950(8) Å  b = 99.592(2)°. |
| | c = 21.5387(15) Å  g = 90°. |
| Volume | 3773.8(4) Å³ |
| Z | 4 |
| Density (calculated) | 1.655 Mg/m³ |
| Absorption coefficient | 1.832 mm⁻¹ |
| F(000) | 1916 |
| Crystal size | 0.23 × 0.07 × 0.07 mm |
| Theta range for data collection | 2.00 to 25.00°. |
| Index ranges | −18 <= h <= 18, −13 <= k <= 12, −25 <= l <= 25 |
| Reflections collected | 11918 |
| Independent reflections | 6623 [R(int) = 0.0816] |
| Completeness to theta = 25.00° | 99.9 % |
| Absorption correction | Semi-empirical from equivalents |
| Max. and min. transmission | 1.00 and 0.869 |
| Refinement method | Full-matrix least-squares on F² |
| Data/restraints/parameters | 6623/1/523 |
| Goodness-of-fit on F² | 1.171 |
| Final R indices [I > 2sigma(I)] | R1 = 0.0537, wR2 = 0.0838 |
| R indices (all data) | R1 = 0.1176, wR2 = 0.1031 |
| Largest diff. peak and hole | 1.759 and −0.791 e.Å⁻³ |

* $R_W(F^2) = \{Sw(|F_O|^2-|F|_C^2)^2/Sw(|F_O|)^4\}^{1/2}$ where w is the weight given each reflection. $R(F) = S(|F_O|-|F_C|)/S|F_O|$ for reflections with $F_O > 4(s(F_O))$.
$S = [Sw(|F_O|^2-|F_C|^2)^2/(n-p)]^{1/2}$, where n is the number of reflections and p is the number of refined parameters.

TABLE 8

Atomic coordinates (×10⁴) and equivalent isotropic displacement parameters (Å² × 10³) for 6. U(eq) is defined as one third of the trace of the orthogonalized $U^{ij}$ tensor.

| | x | y | z | U(eq) |
|---|---|---|---|---|
| Gd1 | 2938(1) | 2064(1) | 5736(1) | 23(1) |
| N1 | 2083(3) | 3925(4) | 5489(2) | 17(1) |
| N2 | 3053(3) | 2448(5) | 4665(2) | 24(1) |
| N3 | 3286(3) | 289(5) | 5126(2) | 22(1) |
| N4 | 2637(3) | 119(4) | 6196(2) | 19(1) |
| N5 | 1931(3) | 2166(5) | 6471(2) | 22(1) |
| O1 | 4487(3) | 6406(4) | 3226(2) | 45(1) |
| O2 | 4064(3) | −3804(4) | 5297(2) | 29(1) |
| O3 | 3469(3) | −3945(4) | 6334(2) | 26(1) |
| O4 | 1365(3) | 5187(4) | 9116(2) | 36(1) |
| O5 | 3875(3) | 3725(4) | 6020(2) | 40(1) |
| C1 | 1631(4) | 4533(6) | 5874(3) | 23(2) |
| C2 | 1404(4) | 5691(5) | 5629(3) | 22(2) |
| C3 | 1739(4) | 5767(5) | 5087(3) | 21(2) |
| C4 | 2168(4) | 4675(6) | 5001(3) | 22(2) |
| C5 | 2587(4) | 4440(5) | 4486(3) | 20(2) |
| C6 | 2986(4) | 3440(6) | 4317(3) | 23(2) |
| C7 | 3341(4) | 3225(6) | 3735(3) | 25(2) |
| C8 | 3587(4) | 2099(6) | 3745(3) | 26(2) |
| C9 | 3414(4) | 1636(6) | 4331(3) | 26(2) |
| C10 | 3525(4) | 491(6) | 4579(3) | 27(2) |
| C11 | 3361(4) | −784(6) | 5424(3) | 21(2) |
| C12 | 3739(4) | −1768(6) | 5191(3) | 27(2) |
| C13 | 3748(4) | −2802(6) | 5493(3) | 24(2) |
| C14 | 3413(4) | −2886(6) | 6075(3) | 21(1) |
| C15 | 3053(4) | −1936(6) | 6318(3) | 21(2) |
| C16 | 3009(4) | −874(6) | 5994(3) | 22(2) |
| C17 | 2212(4) | 152(5) | 6675(3) | 22(2) |
| C18 | 1851(4) | 1219(6) | 6826(3) | 23(2) |
| C19 | 1332(4) | 1490(6) | 7317(3) | 22(2) |
| C20 | 1135(4) | 2633(6) | 7253(3) | 22(2) |
| C21 | 1492(4) | 3037(6) | 6707(3) | 23(2) |
| C22 | 1381(4) | 4127(5) | 6433(3) | 24(2) |
| C23 | 886(4) | 6586(6) | 5915(3) | 26(2) |

TABLE 8-continued

Atomic coordinates (×10⁴) and equivalent isotropic displacement parameters ($Å^2 × 10^3$) for 6. U(eq) is defined as one third of the trace of the orthogonalized $U^{ij}$ tensor.

|  | x | y | z | U(eq) |
|---|---|---|---|---|
| C24 | −107(4) | 6433(6) | 5729(3) | 34(2) |
| C25 | 1670(4) | 6785(5) | 4640(3) | 24(2) |
| C26 | 921(4) | 6688(5) | 4084(3) | 28(2) |
| C27 | 3445(4) | 4109(6) | 3239(3) | 24(2) |
| C28 | 4400(5) | 4337(6) | 3187(3) | 33(2) |
| C29 | 4518(5) | 5430(6) | 2832(3) | 36(2) |
| C30 | 3970(6) | 1440(6) | 3255(3) | 44(2) |
| C31 | 4383(5) | −3745(6) | 4708(3) | 38(2) |
| C32 | 3192(4) | −4069(6) | 6939(3) | 27(2) |
| C33 | 1115(4) | 687(6) | 7810(3) | 31(2) |
| C34 | 643(5) | 3360(6) | 7661(3) | 32(2) |
| C35 | 1266(4) | 3917(6) | 8210(3) | 28(2) |
| C36 | 790(5) | 4700(6) | 8600(3) | 30(2) |
| O1A | 4559(3) | 1526(4) | 5890(2) | 43(1) |
| O2A | 3990(4) | 1671(5) | 6738(2) | 47(2) |
| O3A | 5357(4) | 1090(5) | 6795(3) | 69(2) |
| N1A | 4653(5) | 1426(5) | 6479(3) | 45(2) |
| O1B | 1570(4) | −1828(5) | 2746(3) | 58(2) |
| O2B | 2559(4) | −1697(5) | 3599(2) | 54(2) |
| O3B | 2650(4) | −3059(5) | 2915(2) | 54(2) |
| N1B | 2254(5) | −2175(6) | 3088(3) | 46(2) |
| O1C | 1533(3) | 1345(4) | 5107(2) | 30(1) |
| C1C | 696(5) | 1179(7) | 5306(3) | 50(2) |

TABLE 9

Bond lengths [Å] and angles [°] for 6.

| Gd1-N2 | 2.384(5) | O5-H1WA | 0.81 |
|---|---|---|---|
| Gd1-N5 | 2.391(5) | O5-H1WB | 0.81 |
| Gd1-O5 | 2.419(5) | C1-C22 | 1.406(9) |
| Gd1-O1C | 2.488(4) | C1-C2 | 1.463(9) |
| Gd1-O2A | 2.511(5) | C2-C3 | 1.356(8) |
| Gd1-O1A | 2.529(5) | C2-C23 | 1.498(8) |
| Gd1-N1 | 2.534(5) | C3-C4 | 1.452(9) |
| Gd1-N4 | 2.536(5) | C3-C25 | 1.515(8) |
| Gd1-N3 | 2.545(5) | C4-C5 | 1.397(9) |
| Gd1-N1A | 2.935(7) | C5-C6 | 1.387(9) |
| N1-C1 | 1.362(8) | C5-H5 | 0.95 |
| N1-C4 | 1.388(8) | C6-C7 | 1.471(9) |
| N2-C9 | 1.359(8) | C7-C8 | 1.358(9) |
| N2-C6 | 1.367(8) | C7-C27 | 1.507(9) |
| N3-C10 | 1.312(8) | C8-C9 | 1.435(8) |
| N3-C11 | 1.395(8) | C8-C30 | 1.499(9) |
| N4-C17 | 1.310(7) | C9-C10 | 1.431(9) |
| N4-C16 | 1.386(8) | C10-H10 | 0.95 |
| N5-C18 | 1.356(8) | C11-C12 | 1.410(8) |
| N5-C21 | 1.358(8) | C11-C16 | 1.424(8) |
| O1-C29 | 1.419(8) | C12-C13 | 1.363(9) |
| O1-H1 | 0.8400 | C12-H12 | 0.95 |
| O2-C13 | 1.352(8) | C13-C14 | 1.435(8) |
| O2-C31 | 1.435(7) | C14-C15 | 1.374(9) |
| O3-C14 | 1.346(7) | C15-C16 | 1.412(9) |
| O3-C32 | 1.443(7) | C15-H15 | 0.95 |
| O4-C36 | 1.415(7) | C17-C18 | 1.415(9) |
| O4-H4 | 0.84 | C17-H17 | 0.95 |
| C18-C19 | 1.459(8) |  |  |
| C19-C20 | 1.361(8) | C30-H30C | 0.98 |
| C19-C33 | 1.491(9) | C31-H31A | 0.98 |
| C20-C21 | 1.454(8) | C31-H31B | 0.98 |
| C20-C34 | 1.508(9) | C31-H31C | 0.98 |
| C21-C22 | 1.393(9) | C32-H32A | 0.98 |
| C22-H22 | 0.95 | C32-H32B | 0.98 |
| C23-C24 | 1.519(9) | C32-H32C | 0.98 |
| C23-H23A | 0.99 | C33-H33A | 0.98 |
| C23-H236 | 0.99 | C33-H33B | 0.98 |
| C24-H24A | 0.98 | C33-H33C | 0.98 |
| C24-H24B | 0.98 | C34-C35 | 1.535(9) |
| C24-H24C | 0.98 | C34-H34A | 0.99 |
| C25-C26 | 1.519(8) | C34-H34B | 0.99 |
| C25-H25A | 0.99 | C35-C36 | 1.505(9) |

TABLE 9-continued

Bond lengths [Å] and angles [°] for 6.

| C25-H25B | 0.99 | C35-H35B | 0.99 |
|---|---|---|---|
| C26-H26A | 0.98 | C36-H36A | 0.99 |
| C26-H26B | 0.98 | C36-H36B | 0.99 |
| C26-H26C | 0.98 | O1A-N1A | 1.257(8) |
| C27-C28 | 1.510(9) | O2A-N1A | 1.271(8) |
| C27-H27A | 0.99 | O3A-N1A | 1.239(7) |
| C27-H27B | 0.99 | O1B-N1B | 1.243(8) |
| C28-C29 | 1.506(9) | O2B-N1B | 1.250(8) |
| C28-H28A | 0.99 | O3B-N1B | 1.279(8) |
| C28-H28B | 0.99 | O1C-C1C | 1.430(8) |
| C29-H29A | 0.99 | O1C-H1OC | 0.80 |
| C29-H29B | 0.99 | C1C-H1C1 | 0.98 |
| C30-H30A | 0.98 | C1C-H1C2 | 0.98 |
| C30-H30B | 0.98 | C1C-H1C3 | 0.98 |
| N2-Gd1-N5 | 142.30(17) | N2-Gd1-O5 | 87.69(17) |
| N5-Gd1-O5 | 102.37(17) | O1A-Gd1-N3 | 65.33(16) |
| N2-Gd1-O1C | 74.53(16) | N1-Gd1-N3 | 136.53(15) |
| N5-Gd1-O1C | 77.36(15) | N4-Gd1-N3 | 63.23(16) |
| O5-Gd1-O1C | 145.86(15) | N2-Gd1-N1A | 111.7(2) |
| N2-Gd1-O2A | 136.46(18) | N5-Gd1-N1A | 105.6(2) |
| N5-Gd1-O2A | 80.37(17) | O5-Gd1-N1A | 67.83(16) |
| O5-Gd1-O2A | 69.99(16) | O1C-Gd1-N1A | 145.83(16) |
| O1C-Gd1-O2A | 141.28(16) | O2A-Gd1-N1A | 25.49(17) |
| N2-Gd1-O1A | 86.79(17) | O1A-Gd1-N1A | 25.21(17) |
| N5-Gd1-O1A | 130.79(17) | N1-Gd1-N1A | 135.54(16) |
| O5-Gd1-O1A | 68.56(16) | N4-Gd1-N1A | 76.57(17) |
| O1C-Gd1-O1A | 136.97(15) | N3-Gd1-N1A | 80.31(18) |
| O2A-Gd1-O1A | 50.67(17) | C1-N1-C4 | 104.9(5) |
| N2-Gd1-N1 | 75.92(16) | C1-N1-Gd1 | 127.6(4) |
| N5-Gd1-N1 | 74.26(16) | C4-N1-Gd1 | 125.6(4) |
| O5-Gd1-N1 | 68.89(15) | C9-N2-C6 | 107.0(5) |
| O1C-Gd1-N1 | 78.50(15) | C9-N2-Gd1 | 119.1(4) |
| O2A-Gd1-N1 | 124.78(17) | C6-N2-Gd1 | 132.6(4) |
| O1A-Gd1-N1 | 134.41(16) | C10-N3-C11 | 124.0(6) |
| N2-Gd1-N4 | 126.27(16) | C10-N3-Gd1 | 115.6(4) |
| N5-Gd1-N4 | 66.79(17) | C11-N3-Gd1 | 119.5(4) |
| O5-Gd1-N4 | 138.40(15) | C17-N4-C16 | 123.8(5) |
| O1C-Gd1-N4 | 73.58(15) | C17-N4-Gd1 | 115.4(4) |
| O2A-Gd1-N4 | 68.62(16) | C16-N4-Gd1 | 120.3(4) |
| O1A-Gd1-N4 | 88.16(17) | C18-N5-C21 | 107.1(5) |
| N1-Gd1-N4 | 135.87(16) | C18-N5-Gd1 | 117.6(4) |
| N2-Gd1-N3 | 66.22(17) | C21-N5-Gd1 | 134.4(4) |
| N5-Gd1-N3 | 126.54(17) | C29-O1-H1 | 109.5 |
| O5-Gd1-N3 | 127.43(16) | C13-O2-C31 | 115.3(5) |
| O1C-Gd1-N3 | 71.67(15) | C14-O3-C32 | 117.2(5) |
| O2A-Gd1-N3 | 97.85(18) | C36-O4-H4 | 109.5 |
| Gd1-O5-H1WA | 110.8 | N3-C10-H10 | 121.0 |
| Gd1-O5-H1WB | 130.8 | C9-C10-H10 | 121.0 |
| H1WA-O5-H1WB | 115.5 | N3-C11-C12 | 124.4(6) |
| N1-C1-C22 | 125.9(6) | N3-C11-C16 | 116.6(6) |
| N1-C1-C2 | 111.8(5) | C12-C11-C16 | 119.0(6) |
| C22-C1-C2 | 122.3(6) | C13-C12-C11 | 120.9(6) |
| C3-C2-C1 | 105.5(5) | C13-C12-H12 | 119.5 |
| C3-C2-C23 | 127.7(6) | C11-C12-H12 | 119.5 |
| C1-C2-C23 | 126.7(6) | O2-C13-C12 | 125.6(6) |
| C2-C3-C4 | 107.3(5) | O2-C13-C14 | 114.5(6) |
| C2-C3-C25 | 127.0(6) | C12-C13-C14 | 119.9(6) |
| C4-C3-C25 | 125.7(6) | O3-C14-C15 | 125.1(5) |
| N1-C4-C5 | 126.3(6) | O3-C14-C13 | 114.6(6) |
| N1-C4-C3 | 110.4(5) | C15-C14-C13 | 120.3(6) |
| C5-C4-C3 | 123.3(6) | C14-C15-C16 | 120.0(6) |
| C6-C5-C4 | 130.7(6) | C14-C15-H15 | 120.0 |
| C6-C5-H5 | 114.6 | C16-C15-H15 | 120.0 |
| C4-C5-H5 | 114.6 | N4-C16-C15 | 123.9(5) |
| N2-C6-C5 | 123.7(6) | N4-C16-C11 | 116.3(6) |
| N2-C6-C7 | 108.7(6) | C15-C16-C11 | 119.7(6) |
| C5-C6-C7 | 127.4(6) | N4-C17-C18 | 118.1(6) |
| C8-C7-C6 | 106.9(6) | N4-C17-H17 | 120.9 |
| C8-C7-C27 | 127.2(6) | C18-C17-H17 | 120.9 |
| C6-C7-C27 | 125.9(6) | N5-C18-C17 | 120.2(6) |
| C7-C8-C9 | 106.4(6) | N5-C18-C19 | 110.3(6) |
| C7-C8-C30 | 128.2(6) | C17-C18-C19 | 129.5(6) |
| C9-C8-C30 | 125.4(6) | C20-C19-C18 | 105.9(6) |
| N2-C9-C10 | 118.5(6) | C20-C19-C33 | 127.5(6) |
| N2-C9-C8 | 111.0(6) | C18-C19-C33 | 126.5(6) |
| C10-C9-C8 | 130.4(6) | C19-C20-C21 | 106.8(6) |
| N3-C10-C9 | 118.0(6) | C19-C20-C34 | 127.5(6) |
| C21-C20-C34 | 125.7(6) | C7-C27-C28 | 112.9(5) |

TABLE 9-continued

Bond lengths [Å] and angles [°] for 6.

| | | | |
|---|---|---|---|
| N5-C21-C22 | 123.3(6) | C7-C27-H27A | 109.0 |
| N5-C21-C20 | 109.9(6) | C28-C27-H27A | 109.0 |
| C22-C21-C20 | 126.8(6) | C7-C27-H27B | 109.0 |
| C21-C22-C1 | 129.5(6) | C28-C27-H27B | 109.0 |
| C21-C22-H22 | 115.3 | H27A-C27-H27B | 107.8 |
| C1-C22-H22 | 115.3 | C29-C28-C27 | 112.6(6) |
| C2-C23-C24 | 112.8(5) | C29-C28-H28A | 109.1 |
| C2-C23-H23A | 109.0 | C27-C28-H28A | 109.1 |
| C24-C23-H23A | 109.0 | C29-C28-H28B | 109.1 |
| C2-C23-H23B | 109.0 | C27-C28-H28B | 109.1 |
| C24-C23-H23B | 109.0 | H28A-C28-H28B | 107.8 |
| H23A-C23-H23B | 107.8 | O1-C29-C28 | 110.5(6) |
| C23-C24-H24A | 109.5 | O1-C29-H29A | 109.6 |
| C23-C24-H24B | 109.5 | C28-C29-H29A | 109.6 |
| H24A-C24-H24B | 109.5 | O1-C29-H29B | 109.6 |
| C23-C24-H24C | 109.5 | C28-C29-H29B | 109.6 |
| H24A-C24-H24C | 109.5 | H29A-C29-H29B | 108.1 |
| H24B-C24-H24C | 109.5 | C8-C30-H30A | 109.5 |
| C3-C25-C26 | 114.0(5) | C8-C30-H30B | 109.5 |
| C3-C25-H25A | 108.8 | H30A-C30-H30B | 109.5 |
| C26-C25-H25A | 108.8 | C8-C30-H30C | 109.5 |
| C3-C25-H25B | 108.8 | H30A-C30-H30C | 109.5 |
| C26-C25-H25B | 108.8 | H30B-C30-H30C | 109.5 |
| H25A-C25-H25B | 107.6 | O2-C31-H31A | 109.5 |
| C25-C26-H26A | 109.5 | O2-C31-H31B | 109.5 |
| C25-C26-H26B | 109.5 | H31A-C31-H31B | 109.5 |
| H26A-C26-H26B | 109.5 | O2-C31-H31C | 109.5 |
| C25-C26-H26C | 109.5 | H31A-C31-H31C | 109.5 |
| H26A-C26-H26C | 109.5 | H31B-C31-H31C | 109.5 |
| H26B-C26-H26C | 109.5 | O3-C32-H32A | 109.5 |
| O3-C32-H32A | 109.5 | C35-C36-H36A | 109.1 |
| H32A-C32-H32B | 109.5 | O4-C36-H36B | 109.1 |
| O3-C32-H32C | 109.5 | C35-C36-H36B | 109.1 |
| H32A-C32-H32C | 109.5 | H36A-C36-H36B | 107.8 |
| H32B-C32-H32C | 109.5 | N1A-O1A-Gd1 | 95.8(4) |
| C19-C33-H33A | 109.5 | N1A-O2A-Gd1 | 96.3(4) |
| C19-C33-H33B | 109.5 | O3A-N1A-O1A | 121.8(8) |
| H33A-C33-H33B | 109.5 | O3A-N1A-O2A | 121.0(7) |
| C19-C33-H33C | 109.5 | O1A-N1A-O2A | 117.2(6) |
| H33A-C33-H33C | 109.5 | O3A-N1A-Gd1 | 176.1(5) |
| H33B-C33-H33C | 109.5 | O1A-N1A-Gd1 | 59.0(4) |
| C20-C34-C35 | 112.1(6) | O2A-N1A-Gd1 | 58.3(3) |
| C20-C34-H34A | 109.2 | O1B-N1B-O2B | 122.2(7) |
| C35-C34-H34A | 109.2 | O1B-N1B-O3B | 118.7(7) |
| C20-C34-H34B | 109.2 | O2B-N1B-O3B | 119.1(7) |
| C35-C34-H34B | 109.2 | C1C-O1C-Gd1 | 128.3(4) |
| H34A-C34-H34B | 107.9 | C1C-O1C-H1OC | 103.3 |
| C36-C35-C34 | 112.8(6) | Gd1-O1C-H1OC | 115.7 |
| C36-C35-H35A | 109.0 | O1C-C1C-H1C1 | 109.5 |
| C34-C35-H35A | 109.0 | O1C-C1C-H1C2 | 109.5 |
| C36-C35-H35B | 109.0 | H1C1-C1C-H1C2 | 109.5 |
| C34-C35-H35B | 109.0 | O1C-C1C-H1C3 | 109.5 |
| H35A-C35-H35B | 107.8 | H1C1-C1C-H1C3 | 109.5 |
| O4-C36-C35 | 112.5(6) | H1C2-C1C-H1C3 | 109.5 |
| O4-C36-H36A | 109.1 | | |

TABLE 10

Anisotropic displacement parameters (Å$^2$ × 10$^3$) for 6. The anisotropic displacement factor exponent takes the form: $-2p^2[h^2 a^{*2} U^{11} + \ldots + 2 h k a^* b^* U^{12}]$.

| | U$^{11}$ | U$^{22}$ | U$^{33}$ | U$^{23}$ | U$^{13}$ | U$^{12}$ |
|---|---|---|---|---|---|---|
| Gd1 | 29(1) | 19(1) | 22(1) | 0(1) | 8(1) | 1(1) |
| N1 | 13(3) | 19(3) | 19(3) | −2(3) | 0(2) | 0(2) |
| N2 | 20(3) | 22(3) | 28(3) | 0(3) | 6(3) | 2(2) |
| N3 | 31(3) | 21(3) | 16(3) | 3(3) | 8(3) | 3(3) |
| N4 | 31(3) | 16(3) | 13(3) | −2(2) | 8(2) | 1(3) |
| N5 | 33(3) | 11(3) | 20(3) | 1(3) | 2(2) | 1(3) |
| O1 | 41(3) | 31(3) | 61(3) | −7(3) | 1(3) | −2(3) |
| O2 | 45(3) | 22(3) | 25(2) | 1(2) | 18(2) | 8(2) |
| O3 | 34(3) | 16(3) | 28(3) | 3(2) | 9(2) | 6(2) |
| O4 | 45(3) | 35(3) | 28(3) | −2(2) | 9(2) | −5(3) |
| O5 | 27(3) | 24(3) | 63(3) | 1(3) | −4(2) | 6(2) |
| C1 | 27(4) | 23(4) | 18(3) | −5(3) | 1(3) | −5(3) |
| C2 | 24(4) | 16(4) | 25(4) | −7(3) | 0(3) | 3(3) |
| C3 | 18(4) | 21(4) | 22(4) | 1(3) | 2(3) | 2(3) |
| C4 | 25(4) | 19(4) | 21(4) | 0(3) | −1(3) | −2(3) |
| C5 | 30(4) | 16(4) | 14(3) | 6(3) | −2(3) | −6(3) |
| C6 | 23(4) | 23(4) | 22(4) | −1(3) | 4(3) | −3(3) |
| C7 | 22(4) | 28(5) | 24(4) | −1(3) | 3(3) | −2(3) |
| C8 | 35(4) | 26(4) | 20(3) | 2(3) | 14(3) | −5(4) |
| C9 | 35(4) | 21(4) | 23(4) | 0(3) | 8(3) | −2(3) |
| C10 | 32(4) | 24(4) | 29(4) | −5(3) | 14(3) | 4(3) |
| C11 | 27(4) | 19(4) | 18(3) | −1(3) | 5(3) | −3(3) |
| C12 | 25(4) | 35(5) | 22(4) | −2(3) | 8(3) | 2(3) |
| C13 | 25(4) | 25(4) | 21(4) | −4(3) | 2(3) | 2(3) |
| C14 | 26(4) | 15(4) | 23(4) | 2(3) | 3(3) | −3(3) |
| C15 | 28(4) | 22(4) | 15(3) | 2(3) | 6(3) | 3(3) |
| C16 | 27(4) | 21(4) | 16(3) | −1(3) | 2(3) | 0(3) |
| C17 | 28(4) | 13(4) | 23(4) | 2(3) | −1(3) | −5(3) |
| C18 | 28(4) | 22(4) | 18(3) | 0(3) | 6(3) | 4(3) |
| C19 | 22(4) | 25(4) | 21(4) | −1(3) | 7(3) | −1(3) |
| C20 | 31(4) | 30(5) | 7(3) | −5(3) | 7(3) | 3(3) |
| C21 | 30(4) | 26(4) | 14(3) | −5(3) | 5(3) | −1(4) |
| C22 | 33(4) | 16(4) | 23(4) | −5(3) | 7(3) | 0(3) |
| C23 | 29(4) | 22(4) | 29(4) | 5(3) | 11(3) | 6(3) |
| C24 | 34(5) | 30(5) | 41(4) | 3(4) | 13(3) | 4(4) |
| C25 | 27(4) | 23(4) | 24(4) | 1(3) | 8(3) | 5(3) |
| C26 | 30(4) | 22(4) | 31(4) | 6(3) | 1(3) | 1(3) |
| C27 | 31(4) | 22(4) | 21(4) | 4(3) | 8(3) | 3(3) |
| C28 | 36(5) | 35(5) | 28(4) | 2(3) | 13(3) | 2(4) |
| C29 | 39(5) | 32(5) | 41(5) | −3(4) | 15(4) | −6(4) |

TABLE 10-continued

Anisotropic displacement parameters (Å² × 10³) for 6. The anisotropic displacement factor exponent takes the form: −2p²[h²a*²U¹¹ + . . . + 2 h k a* b* U¹²].

|  | U¹¹ | U²² | U³³ | U²³ | U¹³ | U¹² |
|---|---|---|---|---|---|---|
| C30 | 86(7) | 29(5) | 25(4) | 1(4) | 26(4) | 10(4) |
| C31 | 49(5) | 27(5) | 41(4) | −5(4) | 22(4) | 12(4) |
| C32 | 40(4) | 21(4) | 21(4) | 3(3) | 5(3) | 2(3) |
| C33 | 30(4) | 39(5) | 26(4) | 1(3) | 16(3) | 6(4) |
| C34 | 47(5) | 23(4) | 31(4) | 7(3) | 18(4) | −3(4) |
| C35 | 34(4) | 21(4) | 29(4) | −5(3) | 8(3) | 4(3) |
| C36 | 42(5) | 19(4) | 29(4) | −2(3) | 7(4) | 6(4) |
| O1A | 42(3) | 43(4) | 44(4) | −12(3) | 5(3) | 4(3) |
| O2A | 41(3) | 62(4) | 38(3) | 16(3) | 2(3) | −11(3) |
| O3A | 50(4) | 44(4) | 100(5) | 12(4) | −25(4) | 10(3) |
| N1A | 46(5) | 19(4) | 65(5) | 9(4) | −7(4) | −2(3) |
| O1B | 54(4) | 62(5) | 58(4) | 8(3) | 8(3) | 8(3) |
| O2B | 70(4) | 56(4) | 41(3) | −12(3) | 22(3) | −4(3) |
| O3B | 65(4) | 38(4) | 63(4) | −5(3) | 26(3) | 10(3) |
| N1B | 56(5) | 43(5) | 47(4) | 3(4) | 33(4) | −5(4) |
| O1C | 32(3) | 28(3) | 31(3) | −4(2) | 6(2) | 3(2) |
| C1C | 45(5) | 64(6) | 39(5) | −12(4) | −3(4) | 2(5) |

TABLE 11

Hydrogen coordinates (×10⁴) and isotropic displacement parameters (Å² × 10³) for 6.

|  | x | y | z | U(eq) |
|---|---|---|---|---|
| H1 | 3987 | 6718 | 3140 | 68 |
| H4 | 1800 | 5490 | 8988 | 54 |
| H1WA | 4334 | 3536 | 6246 | 59 |
| H1WB | 3757 | 4408 | 6021 | 59 |
| H5 | 2602 | 5069 | 4206 | 24 |
| H10 | 3764 | −104 | 4355 | 33 |
| H12 | 3992 | −1710 | 4818 | 32 |
| H15 | 2833 | −1995 | 6704 | 26 |
| H17 | 2149 | −521 | 6915 | 26 |
| H22 | 1095 | 4676 | 6658 | 28 |
| H23A | 1054 | 7360 | 5780 | 31 |
| H236 | 1044 | 6547 | 6379 | 31 |
| H24A | −269 | 6476 | 5270 | 51 |
| H246 | −413 | 7045 | 5923 | 51 |
| H24C | −281 | 5680 | 5876 | 51 |
| H25A | 2236 | 6863 | 4479 | 29 |
| H256 | 1585 | 7496 | 4878 | 29 |
| H26A | 1047 | 6059 | 3808 | 42 |
| H266 | 867 | 7414 | 3848 | 42 |
| H26C | 366 | 6530 | 4237 | 42 |
| H27A | 3167 | 4841 | 3341 | 29 |
| H276 | 3128 | 3839 | 2827 | 29 |
| H28A | 4753 | 4390 | 3615 | 39 |
| H28B | 4630 | 3679 | 2970 | 39 |
| H29A | 5094 | 5410 | 2682 | 44 |
| H29B | 4044 | 5489 | 2460 | 44 |
| H30A | 3858 | 1860 | 2855 | 67 |
| H30B | 3692 | 677 | 3200 | 67 |
| H30C | 4609 | 1351 | 3390 | 67 |
| H31A | 3929 | −3395 | 4389 | 56 |
| H31B | 4515 | −4525 | 4574 | 56 |
| H31C | 4922 | −3275 | 4758 | 56 |
| H32A | 3558 | −3575 | 7248 | 41 |
| H32B | 3259 | −4875 | 7076 | 41 |
| H32C | 2570 | −3841 | 6904 | 41 |
| H33A | 1497 | 854 | 8212 | 46 |
| H33B | 1210 | −110 | 7686 | 46 |
| H33C | 494 | 789 | 7857 | 46 |
| H34A | 207 | 2871 | 7830 | 39 |
| H34B | 313 | 3972 | 7400 | 39 |
| H35A | 1570 | 3302 | 8484 | 33 |
| H35B | 1724 | 4366 | 8041 | 33 |
| H36A | 501 | 5328 | 8330 | 36 |
| H36B | 322 | 4257 | 8759 | 36 |
| H1OC | 1576 | 791 | 4894 | 46 |

TABLE 11-continued

Hydrogen coordinates (×10⁴) and isotropic displacement parameters (Å² × 10³) for 6.

|  | x | y | z | U(eq) |
|---|---|---|---|---|
| H1C1 | 729 | 506 | 5585 | 76 |
| H1C2 | 239 | 1051 | 4937 | 76 |
| H1C3 | 548 | 1865 | 5533 | 76 |

TABLE 12

Torsion angles [°] for 6.

| | | | |
|---|---|---|---|
| N2-Gd1-N1-C1 | 177.5(5) | N4-Gd1-N2-C9 | −34.6(5) |
| N5-Gd1-N1-C1 | 20.8(5) | N3-Gd1-N2-C9 | −13.7(4) |
| O5-Gd1-N1-C1 | −89.5(5) | N1A-Gd1-N2-C9 | 54.4(5) |
| O1C-Gd1-N1-C1 | 100.8(5) | N5-Gd1-N2-C6 | 61.9(7) |
| O2A-Gd1-N1-C1 | −45.1(5) | O5-Gd1-N2-C6 | −45.4(6) |
| O1A-Gd1-N1-C1 | −111.6(5) | O1C-Gd1-N2-C6 | 105.1(6) |
| N4-Gd1-N1-C1 | 49.4(5) | O2A-Gd1-N2-C6 | −102.8(6) |
| N3-Gd1-N1-C1 | 147.8(4) | O1A-Gd1-N2-C6 | −114.1(6) |
| N1A-Gd1-N1-C1 | −75.7(6) | N1-Gd1-N2-C6 | 23.4(5) |
| N2-Gd1-N1-C4 | −20.2(4) | N4-Gd1-N2-C6 | 160.6(5) |
| N5-Gd1-N1-C4 | −176.9(5) | N3-Gd1-N2-C6 | −178.5(6) |
| O5-Gd1-N1-C4 | 72.8(5) | N1A-Gd1-N2-C6 | −110.4(6) |
| O1C-Gd1-N1-C4 | −96.9(5) | N2-Gd1-N3-C10 | 12.8(5) |
| O2A-Gd1-N1-C4 | 117.2(4) | N5-Gd1-N3-C10 | 151.4(4) |
| O1A-Gd1-N1-C4 | 50.7(5) | O5-Gd1-N3-C10 | −54.1(5) |
| N4-Gd1-N1-C4 | −148.3(5) | O1C-Gd1-N3-C10 | 93.5(5) |
| N3-Gd1-N1-C4 | −49.9(5) | O2A-Gd1-N3-C10 | −124.8(5) |
| N1A-Gd1-N1-C4 | 86.6(5) | O1A-Gd1-N3-C10 | −85.0(5) |
| N5-Gd1-N2-C9 | −133.3(4) | N1-Gd1-N3-C10 | 44.5(5) |
| O5-Gd1-N2-C9 | 119.4(5) | N4-Gd1-N3-C10 | 174.0(5) |
| O1C-Gd1-N2-C9 | −90.1(5) | N1A-Gd1-N3-C10 | −106.3(5) |
| O2A-Gd1-N2-C9 | 62.0(5) | N2-Gd1-N3-C11 | −177.9(5) |
| O1A-Gd1-N2-C9 | 50.7(5) | N5-Gd1-N3-C11 | −39.4(5) |
| N1-Gd1-N2-C9 | −171.8(5) | O5-Gd1-N3-C11 | 115.2(5) |
| O1C-Gd1-N3-C11 | −97.2(4) | O1C-Gd1-N5-C18 | 89.1(4) |
| O2A-Gd1-N3-C11 | 44.4(5) | O2A-Gd1-N5-C18 | −59.0(4) |
| O1A-Gd1-N3-C11 | 84.3(4) | O1A-Gd1-N5-C18 | −53.7(5) |
| N1-Gd1-N3-C11 | −146.3(4) | N1-Gd1-N5-C18 | 170.5(5) |
| N4-Gd1-N3-C11 | −16.8(4) | N4-Gd1-N5-C18 | 11.7(4) |
| N1A-Gd1-N3-C11 | 63.0(4) | N3-Gd1-N5-C18 | 33.6(5) |
| N2-Gd1-N4-C17 | −149.9(4) | N1A-Gd1-N5-C18 | −55.8(4) |
| N5-Gd1-N4-C17 | −11.1(4) | N2-Gd1-N5-C21 | −61.4(6) |
| O5-Gd1-N4-C17 | 71.4(5) | O5-Gd1-N5-C21 | 41.1(5) |
| O1C-Gd1-N4-C17 | −94.1(4) | O1C-Gd1-N5-C21 | −103.9(5) |
| O2A-Gd1-N4-C17 | 77.3(4) | O2A-Gd1-N5-C21 | 108.0(5) |
| O1A-Gd1-N4-C17 | 125.4(4) | O1A-Gd1-N5-C21 | 113.3(5) |
| N1-Gd1-N4-C17 | −41.1(5) | N1-Gd1-N5-C21 | −22.5(5) |

TABLE 12-continued

Torsion angles [°] for 6.

| | | | | |
|---|---|---|---|---|
| N3-Gd1-N4-C17 | −171.4(5) | N4-Gd1-N5-C21 | 178.7(6) |
| N1A-Gd1-N4-C17 | 102.8(4) | N3-Gd1-N5-C21 | −159.3(5) |
| N2-Gd1-N4-C16 | 38.2(5) | N1A-Gd1-N5-C21 | 111.2(5) |
| N5-Gd1-N4-C16 | 177.1(5) | C4-N1-C1-C22 | 179.6(6) |
| O5-Gd1-N4-C16 | −100.5(4) | Gd1-N1-C1-C22 | −15.2(9) |
| O1C-Gd1-N4-C16 | 94.1(4) | C4-N1-C1-C2 | 1.0(7) |
| O2A-Gd1-N4-C16 | −94.5(4) | Gd1-N1-C1-C2 | 166.2(4) |
| O1A-Gd1-N4-C16 | −46.5(4) | N1-C1-C2-C3 | −0.5(7) |
| N1-Gd1-N4-C16 | 147.0(4) | C22-C1-C2-C3 | −179.2(6) |
| N3-Gd1-N4-C16 | 16.7(4) | N1-C1-C2-C23 | 178.0(6) |
| N1A-Gd1-N4-C16 | −69.1(4) | C22-C1-C2-C23 | −0.7(10) |
| N2-Gd1-N5-C18 | 131.6(4) | C1-C2-C3-C4 | −0.2(7) |
| O5-Gd1-N5-C18 | −125.9(4) | C23-C2-C3-C4 | −178.6(6) |
| C1-C2-C3-C25 | 178.7(6) | C6-N2-C9-C10 | −177.5(6) |
| C23-C2-C3-C25 | 0.3(11) | Gd1-N2-C9-C10 | 14.2(8) |
| C1-N1-C4-C5 | 180.0(6) | C6-N2-C9-C8 | −0.3(7) |
| Gd1-N1-C4-C5 | 14.4(8) | Gd1-N2-C9-C8 | −168.6(4) |
| C1-N1-C4-C3 | −1.1(7) | C7-C8-C9-N2 | 1.3(8) |
| Gd1-N1-C4-C3 | −166.7(4) | C30-C8-C9-N2 | −178.9(6) |
| C2-C3-C4-N1 | 0.9(7) | C7-C8-C9-C10 | 178.1(7) |
| C25-C3-C4-N1 | −178.1(5) | C30-C8-C9-C10 | −2.2(12) |
| C2-C3-C4-C5 | 179.8(6) | C11-N3-C10-C9 | −179.7(6) |
| C25-C3-C4-C5 | 0.9(10) | Gd1-N3-C10-C9 | −11.0(8) |
| N1-C4-C5-C6 | 2.3(11) | N2-C9-C10-N3 | −1.3(9) |
| C3-C4-C5-C6 | −176.5(6) | C8-C9-C10-N3 | −177.8(6) |
| C9-N2-C6-C5 | 175.2(6) | C10-N3-C11-C12 | 3.2(10) |
| Gd1-N2-C6-C5 | −18.7(9) | Gd1-N3-C11-C12 | −165.1(5) |
| C9-N2-C6-C7 | −0.8(7) | C10-N3-C11-C16 | −175.5(6) |
| Gd1-N2-C6-C7 | 165.3(4) | Gd1-N3-C11-C16 | 16.2(7) |
| C4-C5-C6-N2 | −1.5(11) | N3-C11-C12-C13 | −176.6(6) |
| C4-C5-C6-C7 | 173.7(6) | C16-C11-C12-C13 | 2.0(9) |
| N2-C6-C7-C8 | 1.6(7) | C31-O2-C13-C12 | −2.3(9) |
| C5-C6-C7-C8 | −174.2(6) | C31-O2-C13-C14 | 178.6(5) |
| N2-C6-C7-C27 | −175.9(6) | C11-C12-C13-O2 | 177.4(6) |
| C5-C6-C7-C27 | 8.3(10) | C11-C12-C13-C14 | −3.5(9) |
| C6-C7-C8-C9 | −1.7(7) | C32-O3-C14-C15 | −5.1(9) |
| C27-C7-C8-C9 | 175.8(6) | C32-O3-C14-C13 | 176.4(5) |
| C6-C7-C8-C30 | 178.5(7) | O2-C13-C14-O3 | 0.2(8) |
| C27-C7-C8-C30 | −4.0(11) | C12-C13-C14-O3 | −179.0(5) |
| O2-C13-C14-C15 | −178.3(5) | C18-C19-C20-C21 | 3.0(7) |
| C12-C13-C14-C15 | 2.4(9) | C33-C19-C20-C21 | 179.5(6) |
| O3-C14-C15-C16 | −178.3(5) | C18-C19-C20-C34 | −177.2(6) |
| C13-C14-C15-C16 | 0.1(9) | C33-C19-C20-C34 | −0.7(11) |
| C17-N4-C16-C15 | −6.6(9) | C18-N5-C21-C22 | −175.6(6) |
| Gd1-N4-C16-C15 | 164.6(5) | Gd1-N5-C21-C22 | 16.5(9) |
| C17-N4-C16-C11 | 173.6(6) | C18-N5-C21-C20 | 1.8(7) |
| Gd1-N4-C16-C11 | −15.6(7) | Gd1-N5-C21-C20 | −166.2(4) |
| C14-C15-C16-N4 | 178.3(5) | C19-C20-C21-N5 | −3.1(7) |
| C14-C15-C16-C11 | −1.6(9) | C34-C20-C21-N5 | 177.1(6) |
| N3-C11-C16-N4 | −0.6(8) | C19-C20-C21-C22 | 174.1(6) |
| C12-C11-C16-N4 | −179.3(6) | C34-C20-C21-C22 | −5.7(10) |
| N3-C11-C16-C15 | 179.3(5) | N5-C21-C22-C1 | 3.9(11) |
| C12-C11-C16-C15 | 0.6(9) | C20-C21-C22-C1 | −173.0(6) |
| C16-N4-C17-C18 | −179.0(5) | N1-C1-C22-C21 | −3.1(11) |
| Gd1-N4-C17-C18 | 9.4(7) | C2-C1-C22-C21 | 175.4(6) |
| C21-N5-C18-C17 | 177.3(5) | C3-C2-C23-C24 | 94.0(8) |
| Gd1-N5-C18-C17 | −12.4(7) | C1-C2-C23-C24 | −84.1(7) |
| C21-N5-C18-C19 | 0.1(7) | C2-C3-C25-C26 | −96.7(8) |
| Gd1-N5-C18-C19 | 170.5(4) | C4-C3-C25-C26 | 82.0(8) |
| N4-C17-C18-N5 | 1.4(9) | C8-C7-C27-C28 | −62.7(9) |
| N4-C17-C18-C19 | 178.0(6) | C6-C7-C27-C28 | 114.3(7) |
| N5-C18-C19-C20 | −2.0(7) | C7-C27-C28-C29 | −164.1(6) |
| C17-C18-C19-C20 | −178.9(6) | C27-C28-C29-O1 | 78.7(7) |
| N5-C18-C19-C33 | −178.6(6) | C19-C20-C34-C35 | 90.3(8) |
| C17-C18-C19-C33 | 4.6(11) | C21-C20-C34-C35 | −89.9(8) |
| C20-C34-C35-C36 | 176.7(6) | O5-Gd1-N1A-O1A | −86.5(4) |
| C34-C35-C36-O4 | 178.4(5) | O1C-Gd1-N1A-O1A | 85.8(5) |
| N2-Gd1-O1A-N1A | 172.0(4) | O2A-Gd1-N1A-O1A | −176.3(7) |
| N5-Gd1-O1A-N1A | −4.8(5) | N1-Gd1-N1A-O1A | −100.4(4) |
| O5-Gd1-O1A-N1A | 83.2(4) | N4-Gd1-N1A-O1A | 115.4(5) |
| O1C-Gd1-O1A-N1A | −124.8(4) | N3-Gd1-N1A-O1A | 50.8(4) |
| O2A-Gd1-O1A-N1A | 2.1(4) | N2-Gd1-N1A-O2A | 167.7(4) |
| N1-Gd1-O1A-N1A | 105.3(4) | N5-Gd1-N1A-O2A | −7.5(4) |
| N4-Gd1-O1A-N1A | −61.5(4) | O5-Gd1-N1A-O2A | 89.8(4) |
| N3-Gd1-O1A-N1A | −122.7(4) | O1C-Gd1-N1A-O2A | −97.9(5) |
| N2-Gd1-O2A-N1A | −16.7(5) | O1A-Gd1-N1A-O2A | 176.3(7) |
| N5-Gd1-O2A-N1A | 172.4(4) | N1-Gd1-N1A-O2A | 75.8(5) |
| O5-Gd1-O2A-N1A | −80.2(4) | N4-Gd1-N1A-O2A | −68.3(4) |
| O1C-Gd1-O2A-N1A | 117.2(4) | N3-Gd1-N1A-O2A | −132.9(4) |
| O1A-Gd1-O2A-N1A | −2.0(4) | N2-Gd1-O1C-C1C | −156.7(6) |
| N1-Gd1-O2A-N1A | −124.2(4) | N5-Gd1-O1C-C1C | −2.1(6) |
| N4-Gd1-O2A-N1A | 104.0(4) | O5-Gd1-O1C-C1C | −95.5(6) |
| N3-Gd1-O2A-N1A | 46.8(4) | O2A-Gd1-O1C-C1C | 54.3(7) |
| Gd1-O1A-N1A-O3A | 175.5(6) | O1A-Gd1-O1C-C1C | 135.8(6) |
| Gd1-O1A-N1A-O2A | −3.6(6) | N1-Gd1-O1C-C1C | −78.3(6) |
| Gd1-O2A-N1A-O3A | −175.5(6) | N4-Gd1-O1C-C1C | 67.2(6) |
| Gd1-O2A-N1A-O1A | 3.6(6) | N3-Gd1-O1C-C1C | 133.8(6) |
| N2-Gd1-N1A-O1A | −8.6(4) | N1A-Gd1-O1C-C1C | 97.3(6) |
| N5-Gd1-N1A-O1A | 176.3(4) | | |

TABLE 13

Hydrogen bonds for 6 [Å and °].

| D-H...A | d(D-H) | d(H...A) | d(D...A) | <(DHA) |
|---|---|---|---|---|
| O1-H1...O3B#1 | 0.84 | 2.04 | 2.851(7) | 162 |
| O4-H4...O2B#2 | 0.84 | 2.08 | 2.887(7) | 160 |
| O1C-H1OC...O4#3 | 0.80 | 2.00 | 2.757(6) | 157 |
| O5-H1WA...O1#4 | 0.81 | 1.97 | 2.758(6) | 162 |
| O5-H1WB...O3#1 | 0.81 | 2.10 | 2.878(6) | 161 |

Symmetry transformations used to generate equivalent atoms:
1 x,y+1,z #2 x,−y+½,z+½ #3 x,−y+½,z−½
4 −x+1,−y+1,−z+1

REFERENCES (SUPPLEMENTAL INFORMATION FOR EXAMPLE 3)

1. Sessler J L, Mody T D, Hemmi G W, Lynch, V M. Synthesis and Structural Characterization of Lanthanide (III) Texaphyrins, Inorg. Chem. 1993, 32: 3175-3187.
2. Ehrlich, J.; Bogert, M. T., J. Org. Chem. 1947, 12: 522-534.
3. Otwinowski Z, Minor W. Methods in Enzymology: Academic Press; 1997. Altomare A, Burla M C, Camalli M, et al. SIR97: a new tool for crystal structure determination and refinement. J. Appl. Cryst 1999; 32:115-119.
4. Sheldrick G M. SHELXL97. In: Program for the Refinement of Crystal Structures. University of Göttingen, Germany; 1994. p. Program for the Refinement of Crystal Structures.
5. Wilson J C, editor. International Tables for X-ray Crystallography Boston: Kluwer Academic Press; 1992.
6. Sheldrick G M. SHELXTL/P C In. 5.03 ed. Madison, Wis., USA; 1994. p. Siemens Analytical X-ray Instruments, Inc.

Example 3—Development and In Vivo Quantitative Magnetic Resonance Imaging of Polymer Micelles Targeted to the Melanoma-Specific Marker MC1R Recent emphasis has been placed on the development of rationally-designed polymer-based micelle carriers for theragnostics. In this study, micelles were decorated with a specific ligand for the melanocortin 1 receptor (MC1R), which has been evaluated as a cell-surface marker for melanoma. The inventors describe the synthesis and characterization of a new gadolinium texaphyrin (Gd-Tx) chelate that was encapsulated in an IVECT™ micellar system, stabilized by crosslinking with Fe(III) and targeted to MC1R. The inventors have demonstrated that these stabilized Gd-Tx micelles are able to actively target MC1R expressing xenograft tumors in vitro and in vivo more effectively than control systems, including untargeted and/or uncrosslinked Gd-Tx micelles. Taken in concert, the findings reported herein provide support for the conclusion that appropriately designed micelles are able to deliver payloads to tumors expressing MC1R. Gd-Tx is a known redox active agent; therefore, this approach may see eventual use in the development of theragnostic agents.

Rationally-designed, polymer-based micelle carriers represent a promising approach to the delivery of therapeutic and/or diagnostic payloads. They offer many potential advantages as delivery agents and could serve to: (1) enhance the solubility of lipophilic drugs; (2) increase circulation times; and (3) lower the toxicity of the payload in question. Micelles with diameters between 20 and 200 nm are particularly attractive since particles of this size can escape renal clearance. This generally translates into longer circulation times and can lead to improved accumulation in tumor tissues as the result of an enhanced permeability and retention (EPR) effect.[1, 2] It has also been suggested that selective accumulation in tumors relative to normal tissues can be enhanced through the use of tumor-specific cell-surface targeting groups, and that binding events may be used to trigger release mechanisms. Such strategies are appealing since they could serve not only to enhance uptake in tumor relative to normal tissues, but also to reduce the toxicity in peripheral organs.[1-3]

Despite the advantages offered by micellar delivery systems, to date no micellar system has been described that achieves the full promise of targeting in vivo. Of additional concern is the fate of micelle delivery systems in biological media.[4] Though extensively studied in vitro, most published delivery systems lack adequate information on micelle integrity in vivo. Moreover, previously described micelle delivery systems have suffered from an inherent instability in vivo, generally undergoing collapse in the presence of serum lipids and proteins.[4] Micelles can be stabilized for in vivo use through crosslinking of individual acyl chains. To date numerous crosslinking reactions have been attempted, employing strategies that range from the use of disulfides[5, 6] and other redox-sensitive bonds[7] to temperature-[8] and pH-sensitive functional groups.[9-11] Here, the inventors describe a novel crosslinking procedure that relies on the pH sensitivity of metal-oxygen coordination bonds.[12, 31] This particular form of crosslinking is known to increase blood circulation times and result in a stable micelle delivery system that is able to selectively dissociate and release its contents in the acidic tumor microenvironments.[13]

There are a number of micelle-based delivery systems for drugs such as doxorubicin and paclitaxel currently in Phase I and Phase II clinical trials.[1, 2] These systems do provide for increased circulation times and larger area-under-the curve pharmacokinetics relative to the corresponding free drug.[2] Some systems now in preclinical study are also "passively targeted,"[6, 14, 15] meaning they lack any specific surface ligands and rely solely on EPR to deliver their payload.[5, 8, 16] A significant disadvantage with passive targeting of micelle delivery systems is an increased probability for nonspecific delivery and accumulation in clearance organs, such as liver and kidney, relative to tumor.[2, 17] Additionally, the significance of EPR in human cancers remains largely unproven and there is increasing evidence that EPR alone may not be enough to ensure the selective delivery of a payload.[17]

Most attempts at micelle targeting have come from the use of ligands such as $\alpha_v\beta_3$ (RGD), EGFR, or folate.[7, 18-23] Unfortunately, most of these targeted systems suffer from a high peripheral toxicity,[5, 7, 16, 19, 20] have only seen limited testing in vivo (e.g., in animal models lacking tumor xenografts[21, 22]), or have not yet quantitatively demonstrated selective tumor accumulation relative to peripheral organs.[7, 11, 18, 23, 24] It is also noteworthy, that various other targeted systems have been reported to provide little improvement in tumor uptake as compared to their untargeted controls.[7, 19, 20] Thus, there remains a need for more specific biological targeting agents, including those that rely on localization strategies that are not EPR dependent. This may be of particular relevance in clinical systems, where it has recently been proposed that human cancers have only a modest EPR, as compared to murine xenografts.[17]

One attractive target is the melanocortin 1 receptor (MC1R). Over 80% of malignant melanomas express high levels of this receptor.[25] Not surprisingly, the MC1R has been investigated as a target for delivery of imaging and therapeutic agents. Indeed, a number of MC1R ligands have been developed for this purpose.[26-28, 29] The best known of these, [Nle⁴,DPhe⁷]-α-MSH (NDP-α-MSH),[30] is considered the "gold standard" for in vitro assays due to its ease of synthesis, low cost and high MC1R affinity.[29, 31] However, NDP-α-MSH is not selective for MC1R and displays strong nanomolar binding affinities to other melanocortin receptor isoforms, e.g., MC4R and MC5R.[32-34] Such off-target binding is undesirable given the presence of these receptors in the kidney, brain and CNS.[35-39] Koikov et al. has reported the development of a ligand, 4-phenylbutyryl-His-DPhe-Arg-Trp-NH₂ (SEQ ID NO:6), with high selectivity and specificity for MC1R[28]. We have recently altered this ligand with an alkyne (4-phenylbutyryl-His-DPhe-Arg-Trp-Gly-Lys(hex-5-ynoyl)-NH₂ (SEQ ID NO:3); 1)[40] for click attachment to a micelle-forming triblock polymer. Moreover, we have demonstrated in vitro that micelles decorated with compound 1 retain the high binding affinity (2.9 nM $K_i$) of the free ligand and display improved target selectivity. In this prior work, the $K_i$ of targeted crosslinked (XL) micelles for MC1R was found be to four times lower than the corresponding targeted uncrosslinked (UXL) micelles while not binding to either of the undesired targets, MC4R or MC5R.[40] In this report we show how these micelles can be used to deliver a contrast-enhancing agent to MC1R-expressing tumor xenografts.

Texaphyrins are a series of expanded porphyrins that have attracted interest in the area of cancer research.[37, 41-44] Gadolinium complexes of texaphyrin (Gd-Tx) have been specifically evaluated in numerous clinical trials, including those for metastatic cancer to the brain, non-small cell lung cancer (NSCLC) and non-Hodgkin's lymphoma.[43] Due to its high electron-affinity[43], Gd-Tx is able to capture electrons from reducing metabolites and transfer them to endogenous oxygen, thereby triggering cell death via oxidative stress without modification of cellular DNA.[41, 44] Texaphyrins have been tested as radiation sensitizers in both animal and human trials.[40-43] Additionally, the incorporation of gadolinium into the texaphyrin macrocycle allows the tissue distribution of Gd-Tx to be studied non-invasively via standard magnetic resonance imaging (MRI) methods.[42, 44] The combined imaging and therapeutic features of Gd-Tx makes it attractive as a theragnostic agent. One way to realize this promise would be to enhance tumor localization through use of a targeted micelle. Here, we show that this can indeed be achieved through use of crosslinked systems conjugated to 1.

To develop micelles containing Gd-Tx, the inventors have taken advantage of a triblock polymer micelle system with enhanced stability (IVECT™) that was initially developed by Intezyne Technologies Inc. (Tampa, Fla.).[13, 40] This triblock polymer is composed of a hydrophobic encapsulation block, a responsive stabilizer block, and a hydrophilic masking block that contains an azide for functionalization via click chemistry. The main advantage of IVECT™ micelles over traditional micelles is the incorporation of the stabilization block, which allows the micelles to be crosslinked via a pH-sensitive Fe(III) metal coordination reaction.[12, 13, 40] They are also biodegradable and designed to release their payload in the acidic microenvironment of tumors.[13] As detailed below, this approach has allowed for the generation of a stabilized IVECT™ micelle system that incorporates Gd-Tx and which both penetrates into xenografted tumors with high selectively and clears from circulation without being retained in the kidney or liver. Tumor penetration, as inferred from MRI studies, was not observed with either untargeted or uncrosslinked micelles. On this basis, the inventors propose that the present approach provides for tumor-specific targeting that is superior to that provided by EPR alone.

Results

A. Gadolinium-Texaphyrin (Gd-Tx) Structure

Figure 39:
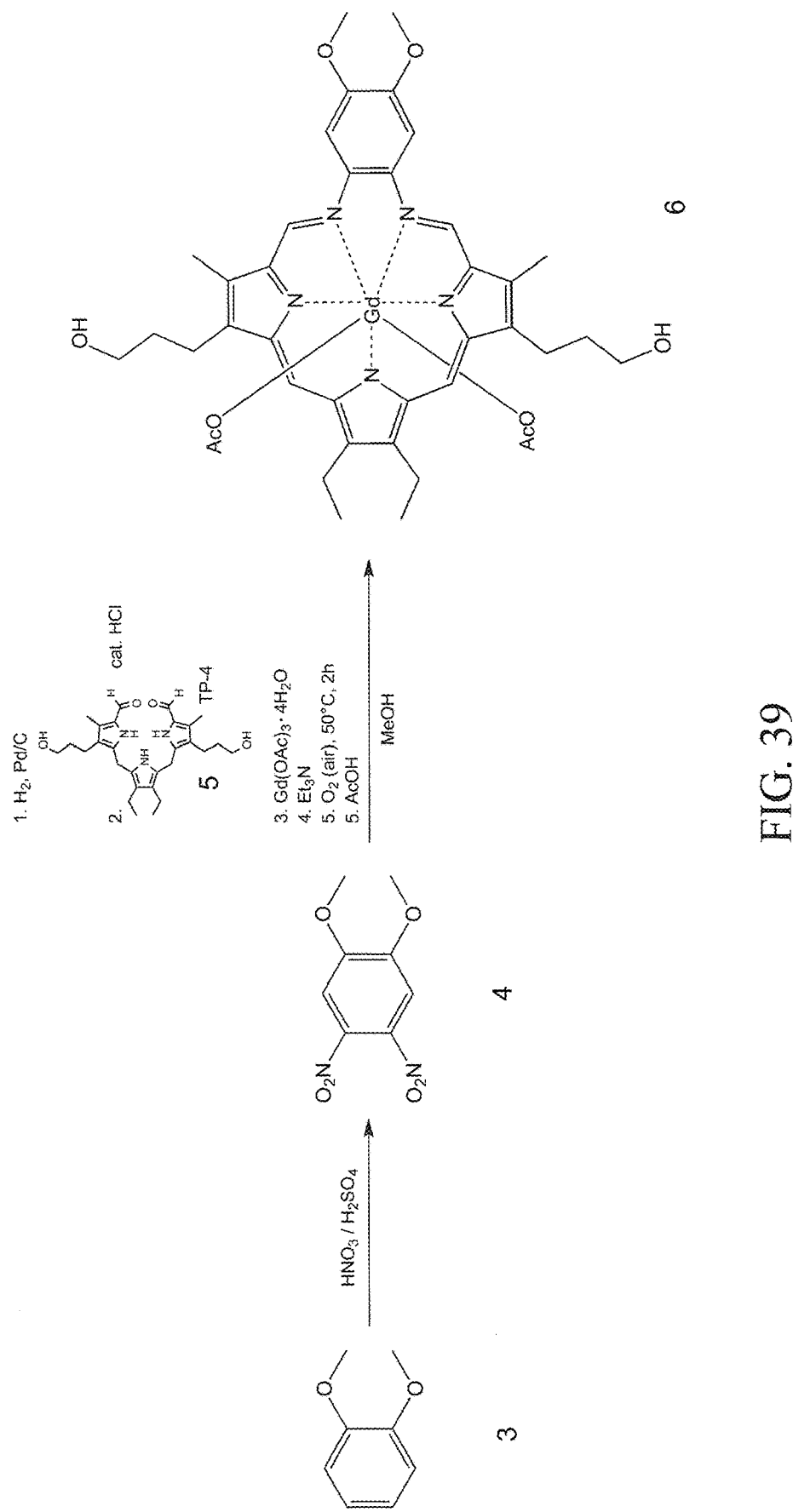
FIG. 39: Synthesis of Gd-Texaphyrin (Gd-Tx) 6.
Figure 40A:
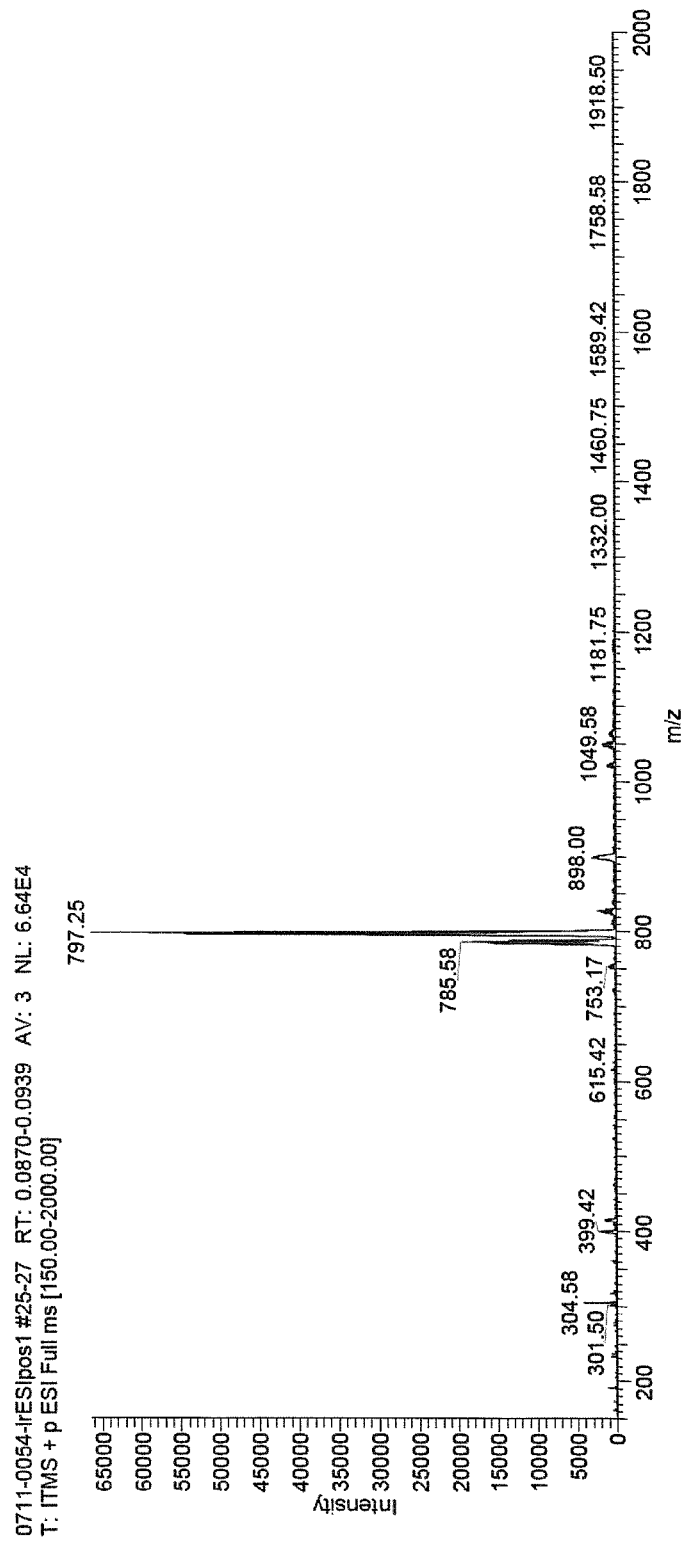
FIG. 40A-C: Low resolution ESI-MS spectrum for 6.
Figure 40B:
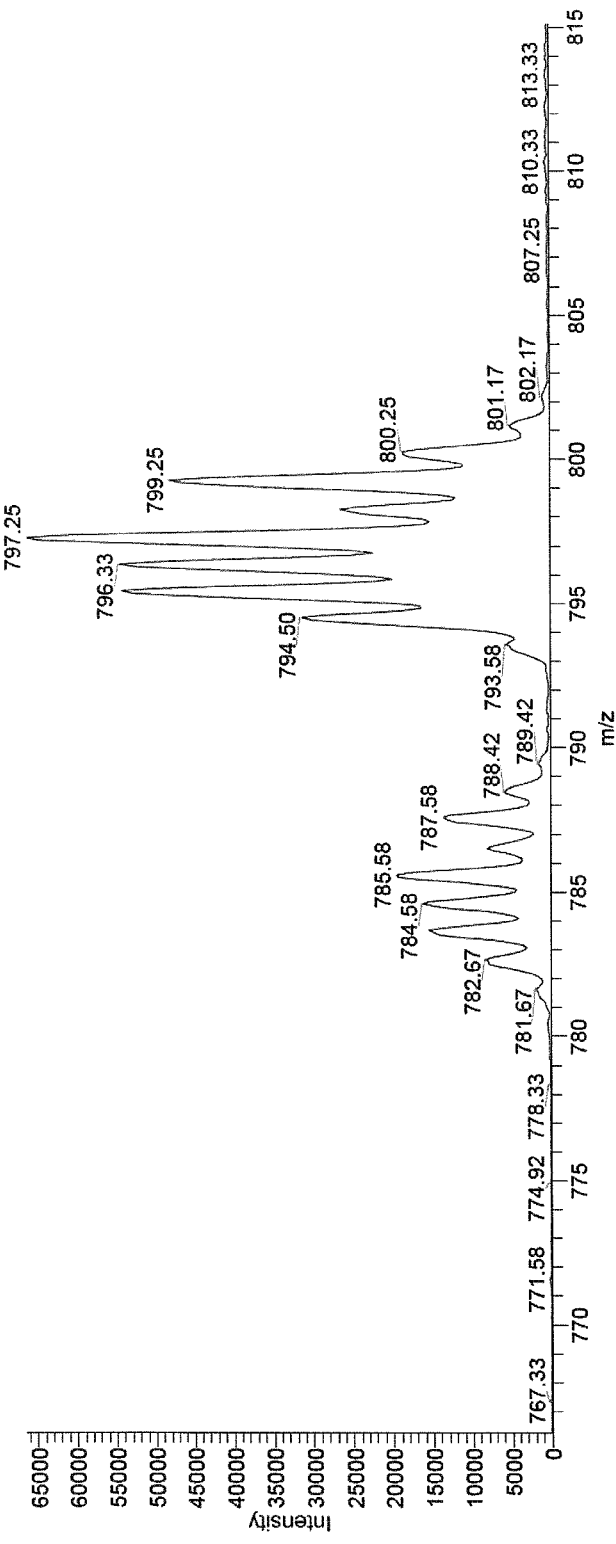
Figure 40C:
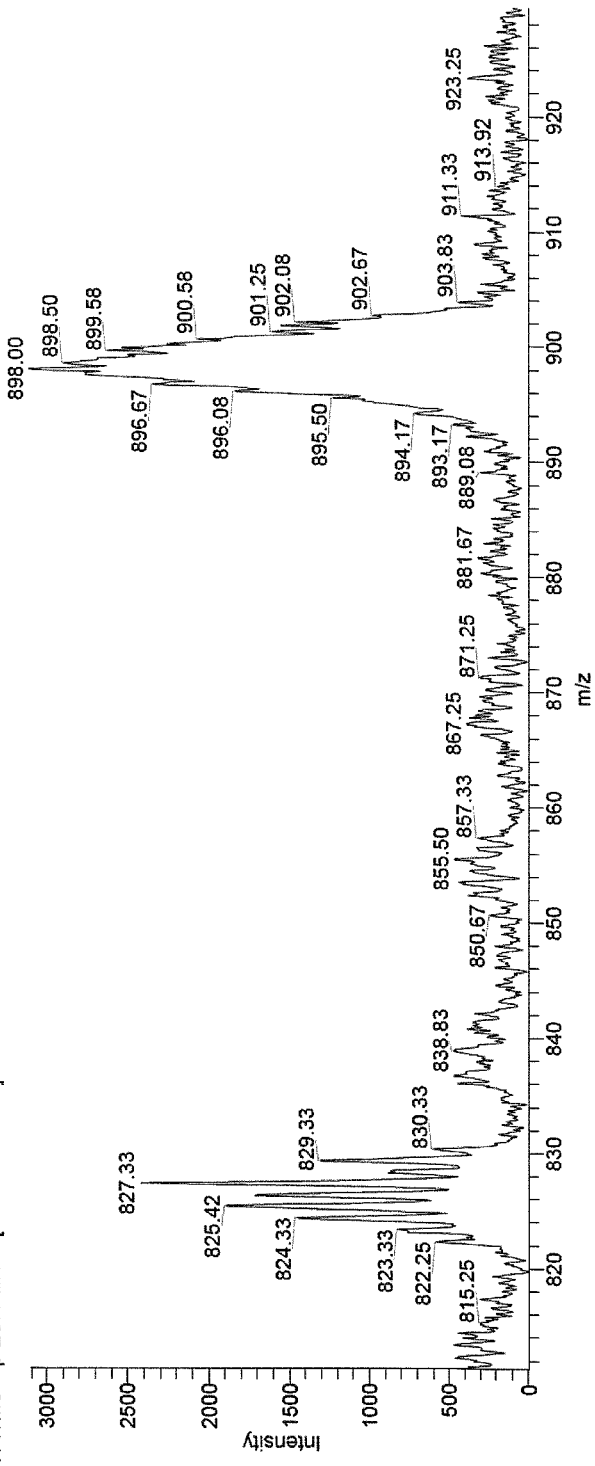
Figure 41:
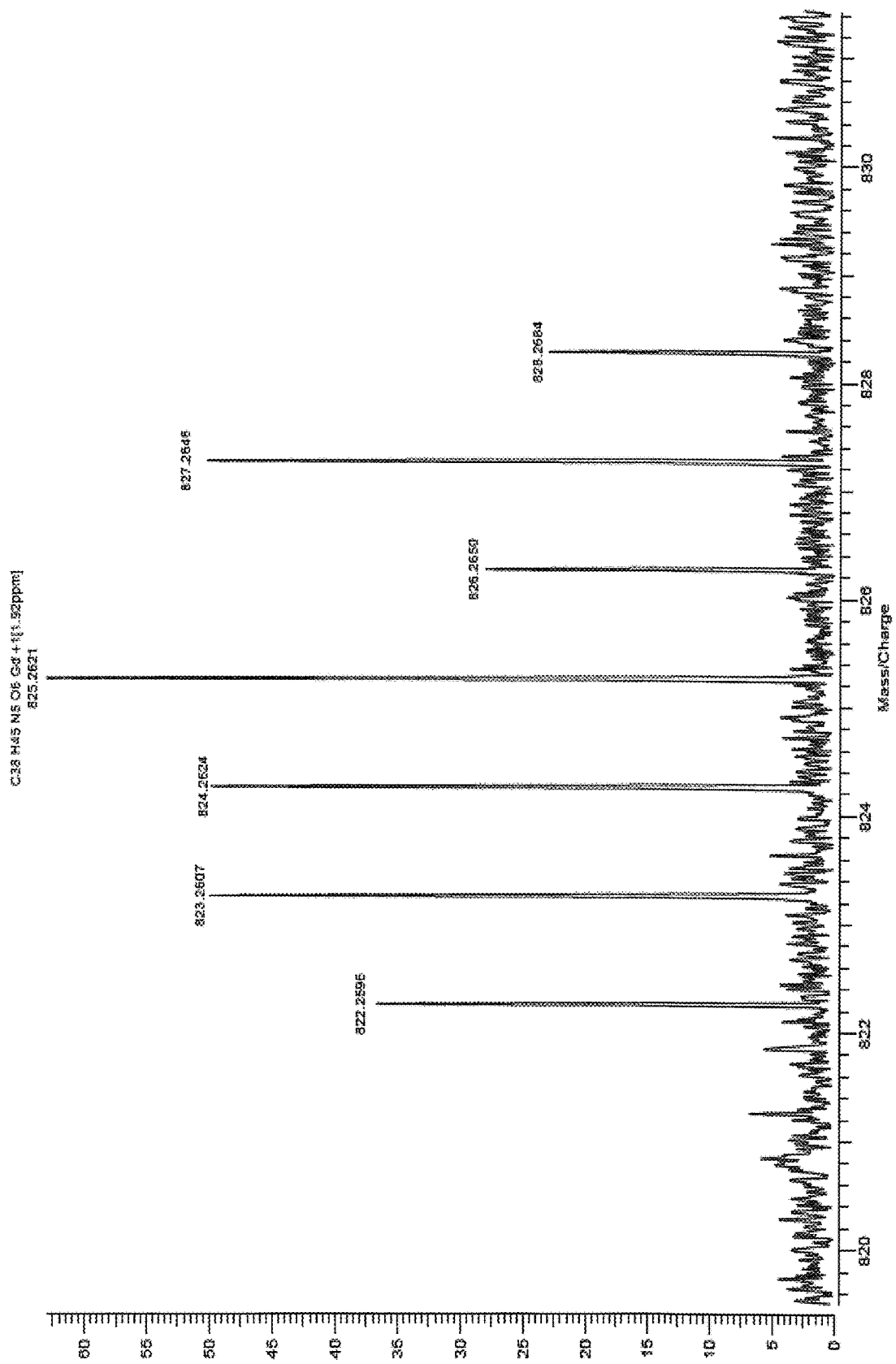
FIG. 41: High resolution ESI-MS spectrum for 6.
Figures 42A, 42B:
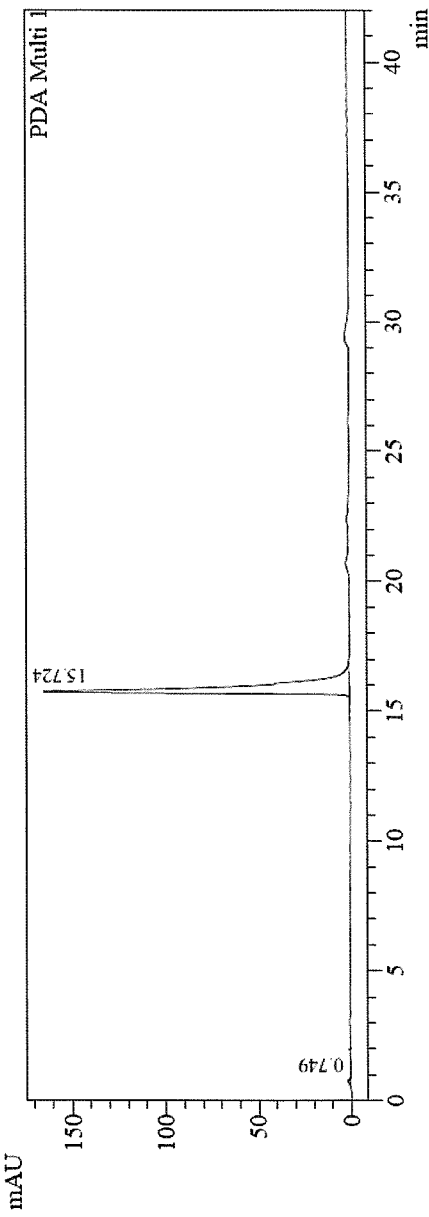

The Gd-Tx complex used in this study was prepared using a synthetic protocol similar to those published previously[45-47] (cf. FIG. 39). A single crystal X-ray diffraction analysis of the Gd-Tx complex confirmed the expected planar structure for the core macrocycle and revealed several ancillary ligand and solvent interactions (FIG. 34).

B. Physical Properties of the Gd-Tx Micelles

Figure 34:
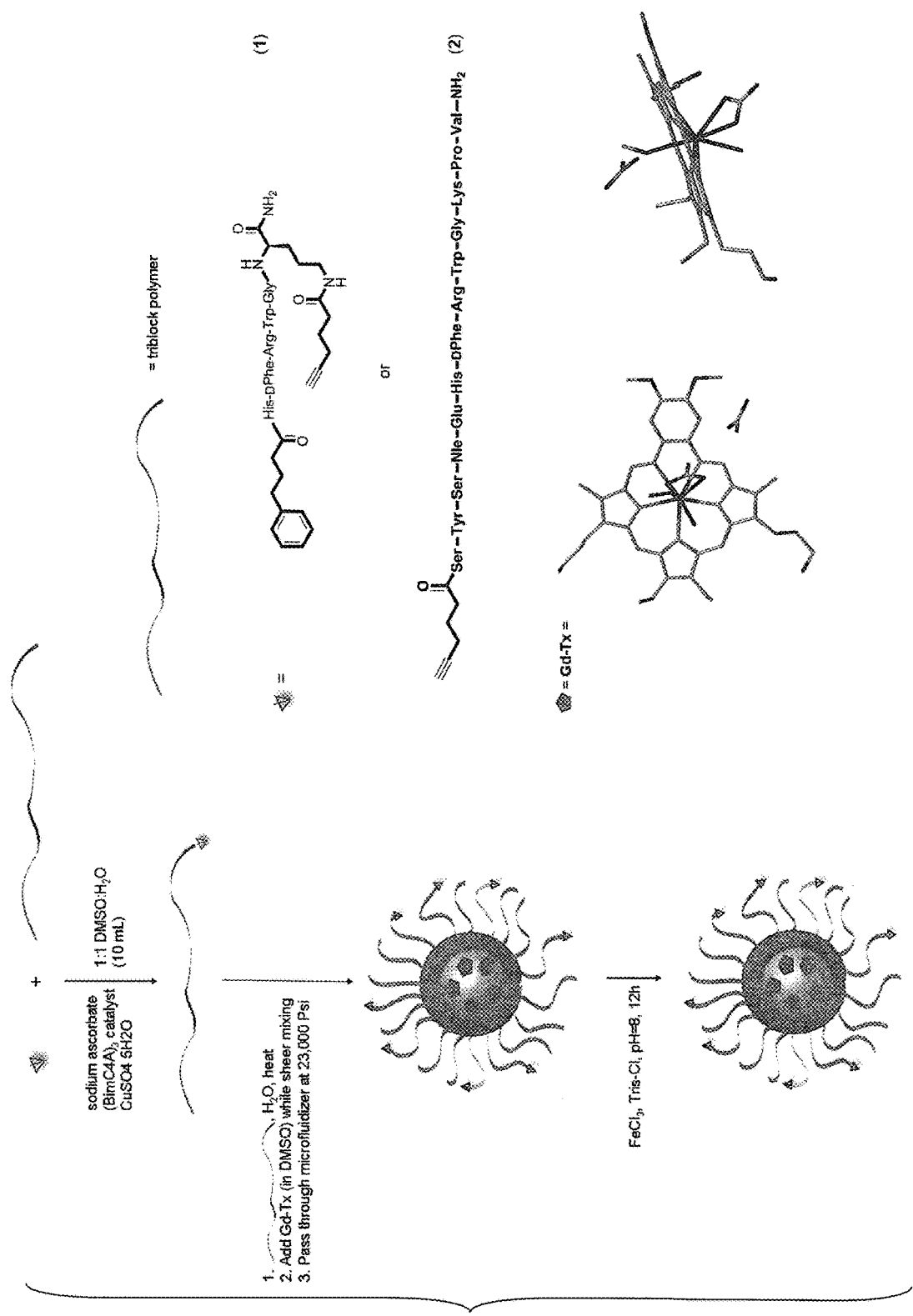
FIG. 34: Formulation of Gd-Tx micelles. Detailed information of the Gd-Tx crystal structure can be found in the Supporting Information.

The targeted Gd-Tx micelles were prepared using a novel optimized encapsulation strategy (FIG. 34). The average particle size was determined using standard dynamic light scattering (DLS) methods. The surface charge and gadolinium percent loading by weight were determined by zeta potential and elemental analyses, respectively (Table 6). These studies provided support for the notion that there are no differences in micelle size for the crosslinked (XL) and uncrosslinked (UXL) pairs, or for the targeted (T) and untargeted (UT) pairs. However, significant differences in micelle size were seen depending on the extent of Gd-weight loading. For example, micelles with 5% Gd-Tx (wt:wt) were significantly larger (169±40 nm) than those containing 0.5% (87±40 nm) (p≤0.01; vs. 5%) or 0.05% (84±24 nm) Gd-Tx (p≤0.01; vs. 5%). However, the size of the latter two micelle systems, both of which are characterized by relatively low Gd-Tx loading levels, were not significantly different. Attempts to create formulations with Gd-Tx weight loading percentages above 10% proved unsuccessful. Particle charges ranged from −0.33 to −29 mV as deduced from zeta potential analyses.

c. Gd-Tx Micelle Stability

Uncrosslinked Gd-Tx (20 mg/mL in PBS) micelles at 5% weight loading were dialyzed for 6 hours against PBS (pH 7.4). Elemental analyses (ICP-OES, Galbraith Labs) of the Gd-Tx micelles pre- and post-dialysis indicated that the uncrosslinked micelles retained 60% of the encapsulated Gd-Tx after dialysis.

D. Competitive Binding Assays

Time-resolved lanthanide fluorescence competitive binding assays[33, 40] were performed in an effort to optimize ligand loading for maximal avidity. In these assays, increasing concentrations of micelles were measured for their ability to competitively displace Eu-labeled NDP-α-MSH 2. The remaining Eu was then measured using time resolved fluorescence (TRF, see Methods). As gadolinium(III) cations can potentially interfere with the lanthanide-based TRF binding assays,[33] unloaded triblock polymer micelles (i.e., free of Gd-Tx) targeted with 2.5% to 30% ligand 2 by weight loading (see FIG. 34) were used. Micelles stabilized with Fe(III) crosslinking had the highest binding avidity at 5% ligand loading, as reflected in the lowest $K_i$ (1.49±0.12 nM $K_i$, n=4). It was also observed that XL micelles had significantly higher binding avidities at all ligand loading levels (p<0.001). In vitro assays were also conducted with ligand 1-targeted XL and UXL micelles at 10% ligand loading, as well as 1-targeted monomers (see FIG. 34).[40] The $K_i$ of the 1-targeted XL micelles (2.9±0.42 nM; n=4) was 4 times lower than the corresponding UXL micelles (12±2.6 nM; n=4).[40] Control assays with untargeted micelles (XL and UXL) and untargeted polymer revealed no detectable interaction with the receptor.

E. In Vitro MR Imaging

Figure 36:
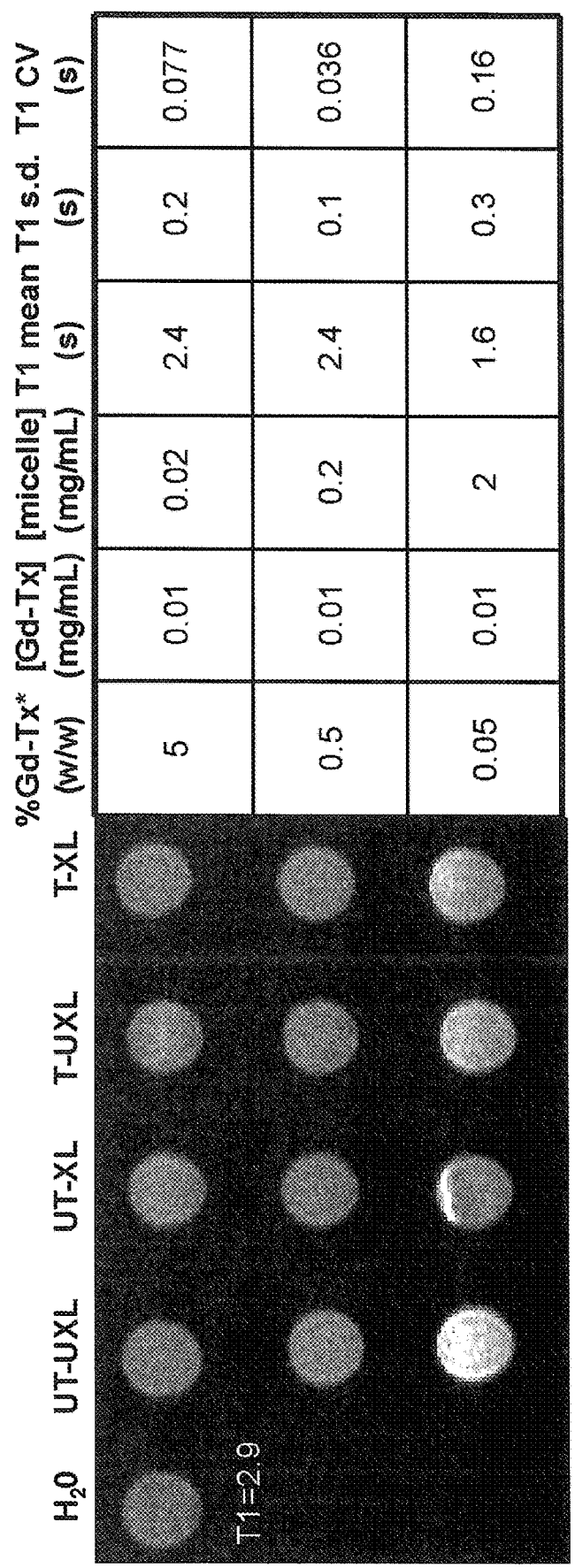
FIG. 36: Multiple TR SEMS (spin echo) images were acquired to calculate the T1 values of a Gd-Tx micelle MR phantom prepared with samples containing Gd-Tx at 0.01 mg/mL with varying weight loading percentages and micelle concentrations. T1 values from each row are presented as an average for simplicity. A table of the T1 values for each well is available in the Supplemental Information.
Figure 44:
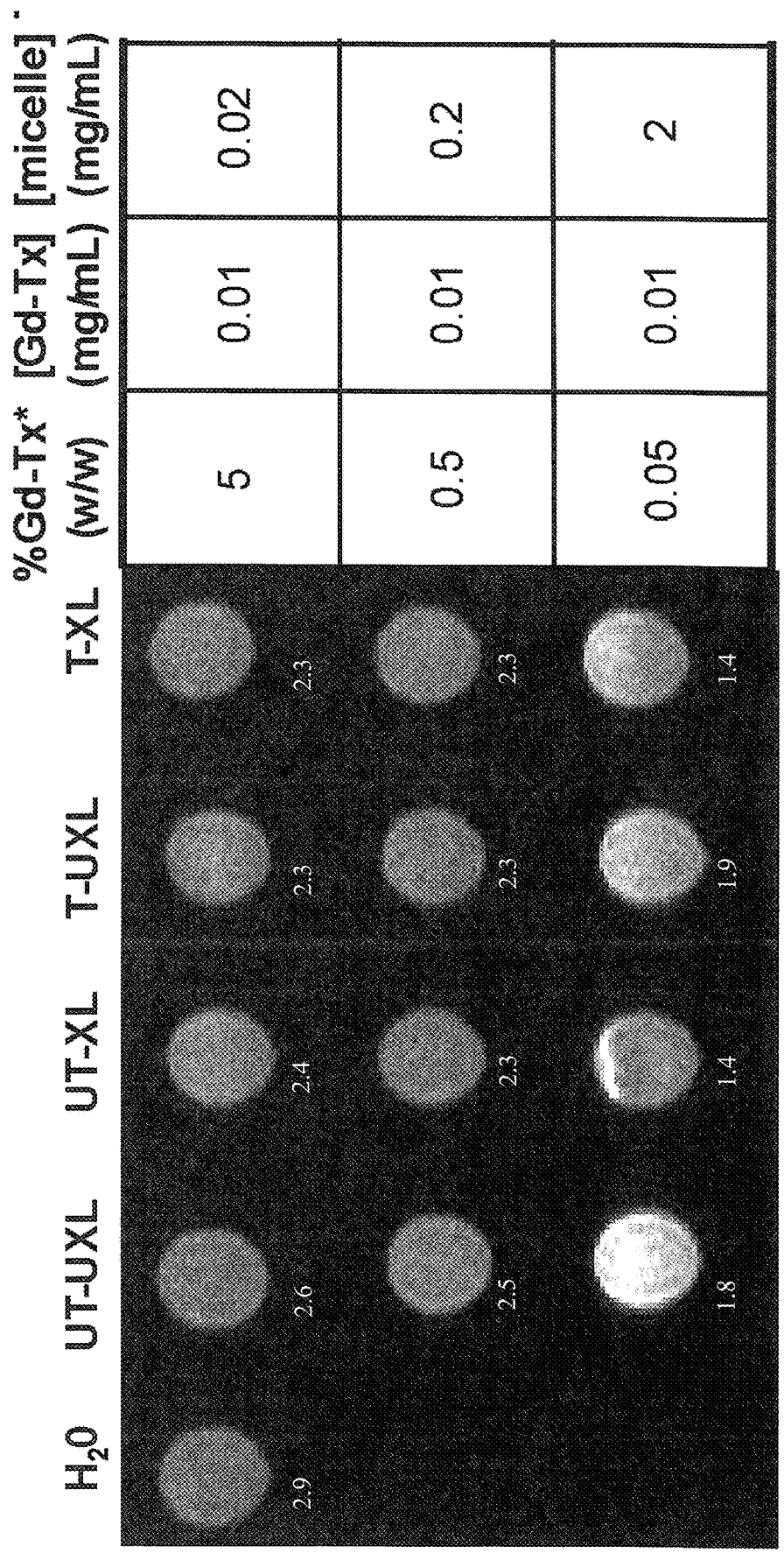
FIG. 44: Multiple TR SEMS (spin echo) images were acquired to calculate the T1 values of a Gd-Tx micelle MR phantom prepared with samples containing Gd-Tx at 0.01 mg/mL with varying weight loading percentages and micelle concentrations. Individual T1 values are located under each well.
Figure 45:
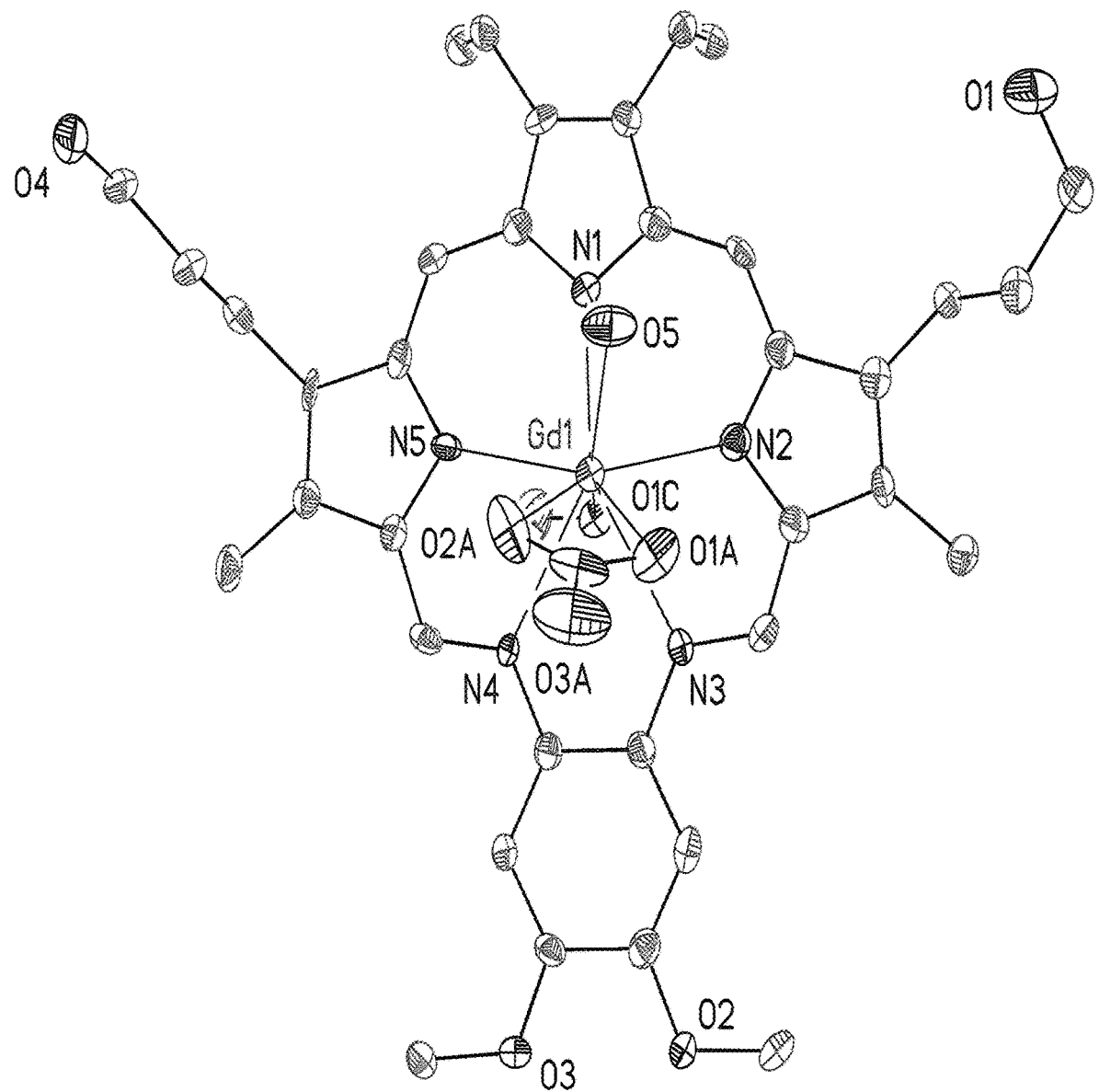
FIG. 45: View of the Gd-Tx complex 6 after showing a partial atom labeling scheme. Displacement ellipsoids are scaled to the 50% probability level. The hydrogen atoms were omitted for clarity.
Figure 46:
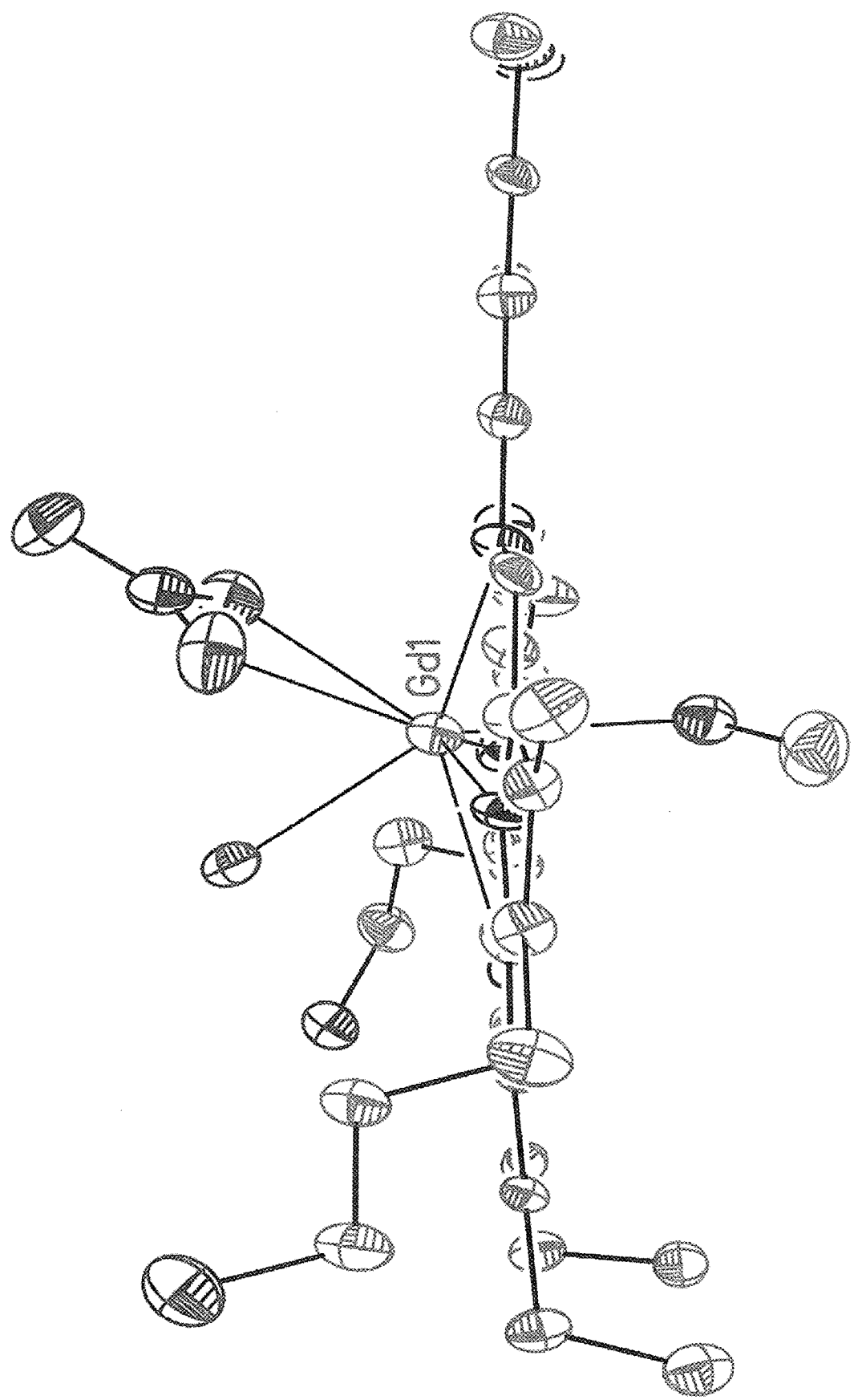
FIG. 46: Side view of the Gd complex 6 showing a partial atom labeling scheme. Displacement ellipsoids are scaled to the 50% probability level. The hydrogen atoms were omitted for clarity.

To determine the MRI relaxivity of Gd-Tx labeled micelles, phantoms were constructed in which each sample (T-XL, T-UXL, UT-XL, UT-UXL micelles) was prepared at the same Gd-Tx concentration (0.01 mg/mL) (FIG. 36). $T_1$ values were determined by progressive saturation relaxation measurements using an Agilent 7T small animal MRI spectrometer using a spin echo sequence, SEMS (see Methods) and $T_1$ values for each cohort of samples were averaged. There was no apparent $T_1$ effect attributable to the different micelle formulations, with coefficients of variation (CVs) ranging from 0.02 to 0.1 for each row of $T_1$ measurements. Individual $T_1$ values for each well are provided in the Supplemental Information (Supplemental FIG. 44). The phantom studies served to confirm the expectation that the observed $T_1$ values are positively correlated with Gd-Tx

TABLE 6

| Sample # | Stability* | Targeting** | % Gd-Tx Encap. (calculated) | % Gd-Tx Encap. (actual) | Charge (mV) | DLS Size (nm) |
|---|---|---|---|---|---|---|
| 1 | UXL | UT | 5.4 | 5.3 | −26.61 | 208.20 |
| 2 | UXL | T | 5.4 | 5.2 | −29.23 | 113.60 |
| 3 | XL | UT | 5.3 | 5.1 | −11.12 | 174.70 |
| 4 | XL | T | 5.2 | 5.0 | −13.73 | 179.40 |
| 5 | UXL | UT | 0.54 | 0.51 | −17.70 | 88.90 |
| 6 | UXL | T | 0.53 | 0.50 | −17.74 | 88.80 |
| 7 | XL | UT | 0.52 | 0.52 | −10.73 | 87.50 |
| 8 | XL | T | 0.51 | 0.51 | −9.49 | 82.50 |
| 9 | UXL | UT | 0.054 | 0.049 | −20.33 | 104.80 |
| 10 | UXL | T | 0.053 | 0.05 | −17.28 | 49.40 |
| 11 | XL | UT | 0.052 | 0.052 | −2.62 | 87.30 |
| 12 | XL | T | 0.051 | 0.051 | −0.33 | 93.50 |

*Micelles are stabilized with Fe(III) crosslinking (XL) reaction. UXL denotes uncrosslinked micelles.
**Micelles are targeted (T) with an MC1R-specific ligand. UT denotes untargeted micelles.

weight loading, with 0.05% encapsulated Gd-Tx providing the lowest mean $T_1$ value (1.6 s).

F. In Vivo MR Imaging

Figures 37A, 37B:
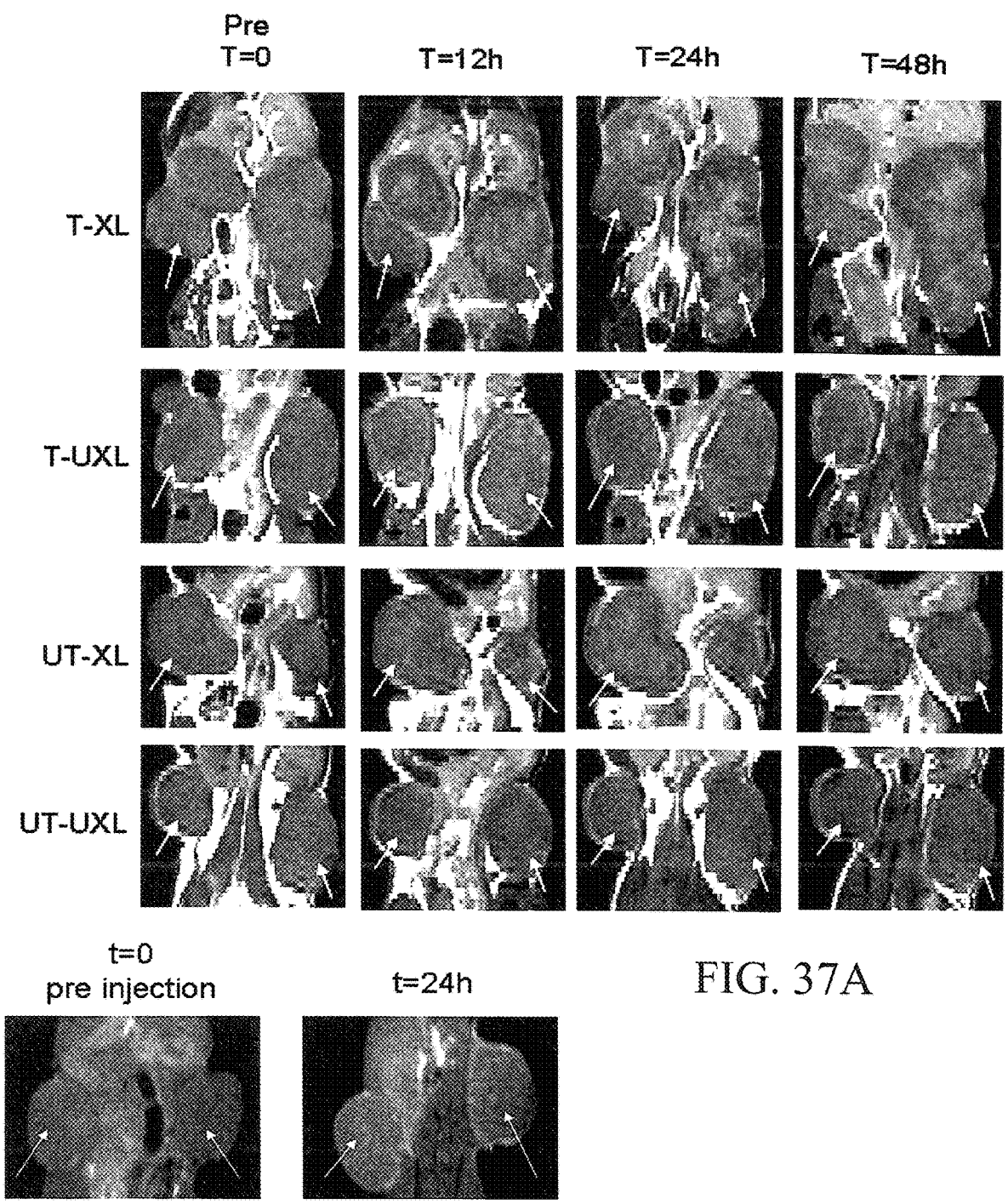
FIG. 37A-B: Coronal-90 T1 weighted spin echo multi slice (SEMS) images of mice treated with different Gd-Tx micelle formulations. A) Representative images from each group of mice treated with 0.5% Gd-Tx micelles at selected time points. White arrows denote location of tumors. B) Pre-injection and 24 h post-injection image of the 5% T-XL formulation loaded with 5% Gd-Tx (w/w).
Figure 43A:
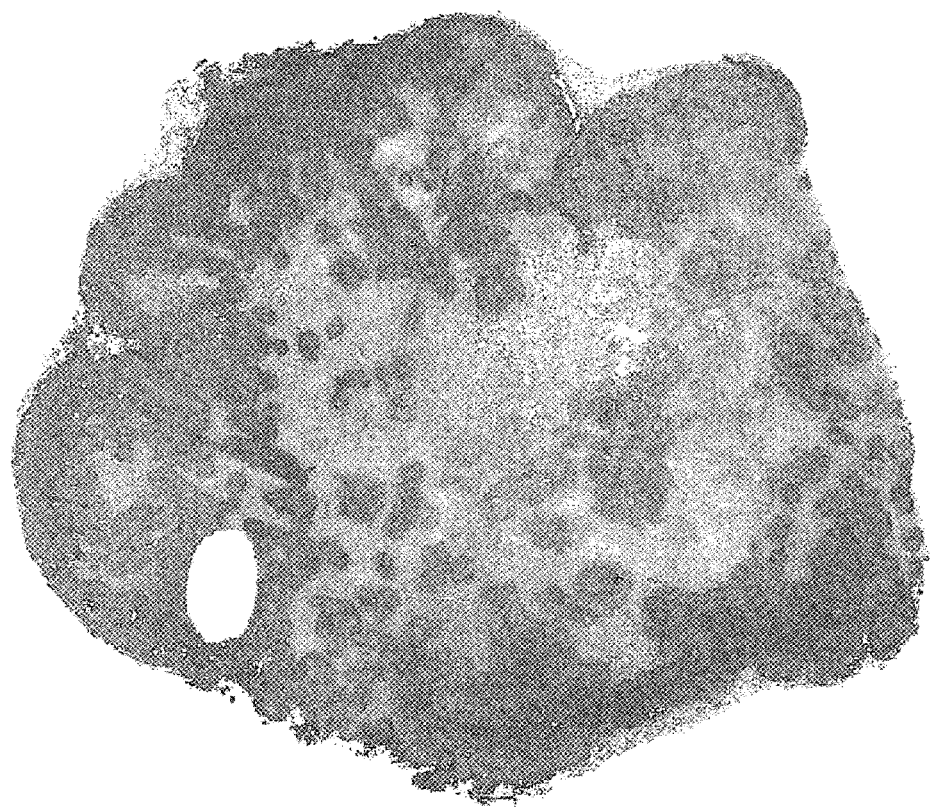
FIG. 43A-B: Xenograft tumor Expression of MC1R. In-vivo characterization of MC1R surface expression for HCT116/MC1R cells. (a-b) IHC staining of representative left (a) and right (b) tumors from a SCID mouse. Both were scored as 3 for MC1R by a Board Certified Pathologist.
Figure 43B:
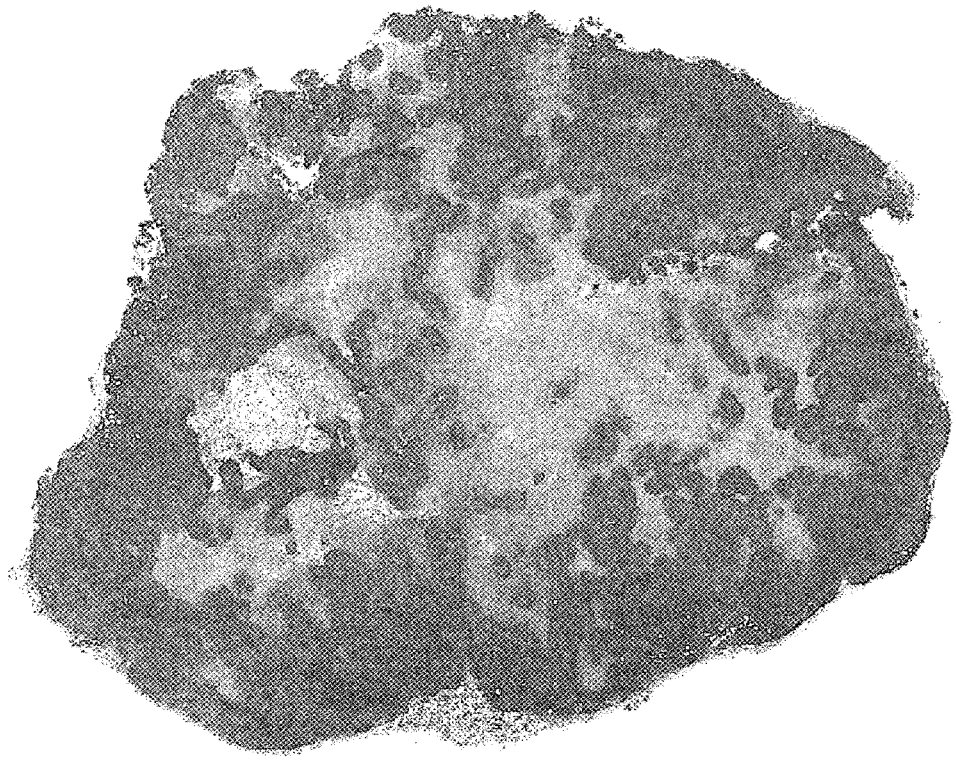

SCID mice with subcutaneous MC1R-expressing tumors were injected with 0.5% and 5% w/w Gd-Tx micelles (T-XL, T-UXL, UT-XL, UT-UXL) via tail vein at a dose of 12 μmol Gd-Tx/kg. Targeted micelles (T-UXL and T-XL) were formulated with 5% (w/w) of 2-targeted polymer. Using an Agilent 7T small animal MRI spectrometer, coronal $T_1$-weighted spin echo multi slice (SEMS) images were acquired of each animal prior to and 1, 4, 12, 24 and 48 h after injection of the micelles. Following imaging, MC1R expression was confirmed in each tumor by immunohistochemistry staining (FIGS. 43A-B). FIG. 37A shows representative images of the center slices of the tumors of animals injected with the different 0.5% Gd-Tx loaded micelles recorded at different time-points. FIG. 37B shows the pre-injection and 24 h post-injection image of the T-XL formulation loaded with 5% Gd-Tx (w/w).

To quantify enhancement due to tumor uptake of the micelles, intensity histograms for right (R) and left (L) whole tumors, kidneys and livers were prepared using a MATLAB program (Mathworks, Natick, Mass.) by drawing a region of interest (ROI) across all applicable slices for each time point. A mean intensity value was then calculated and normalized to thigh muscle (see Methods Section and Supporting Information for more details). FIGS. 38A-D show the tumor uptake and clearance data for each 0.5% Gd-Tx micelle group in tumor (FIG. 38A), kidneys (FIG. 38C) and liver (FIG. 38D). The T-XL micelle group is the only one to show significant contrast enhancement in the tumors (4b), with a peak accumulation occurring at 24 h (FIG. 48D). The 5% Gd-Tx loaded micelles did not show significant tumor enhancement at any time-point for any targeting or crosslinking formulation (FIG. 37B). The increased enhancement in the tumors of animals injected with the 0.5% Gd-Tx T-XL micelles can be visualized in the post-injection MR images (FIG. 37A, top row) relative to tumors in all other animals injected with the control formulation (UT-XL, T-UXL, UT-UXL). Again, no other micelle group displayed visible tumor uptake. The contrast enhancement for the T-XL micelles peaked in the kidneys at 4 h and steadily decreased thereafter, whereas enhancement in the liver peaked at 1 h.

To test whether the enhancement observed in the 0.5% Gd-Tx, T-XL tumors was statistically different from the other groups, a 1-way ANOVA analysis (Dunnett's Multiple Comparison Test) was carried out. While no significant difference was observed among the groups at 1 h, the T-XL group was statistically different from all other groups at 4 h to 48 h ($p<0.001$ for 4-24 h; $p<0.05$ at 48 h). Additional analyses using the Student's t-test revealed that there are no statistical differences among the control groups (UT-XL, T-UXL or UT-UXL) at any time point.

Figure 35:
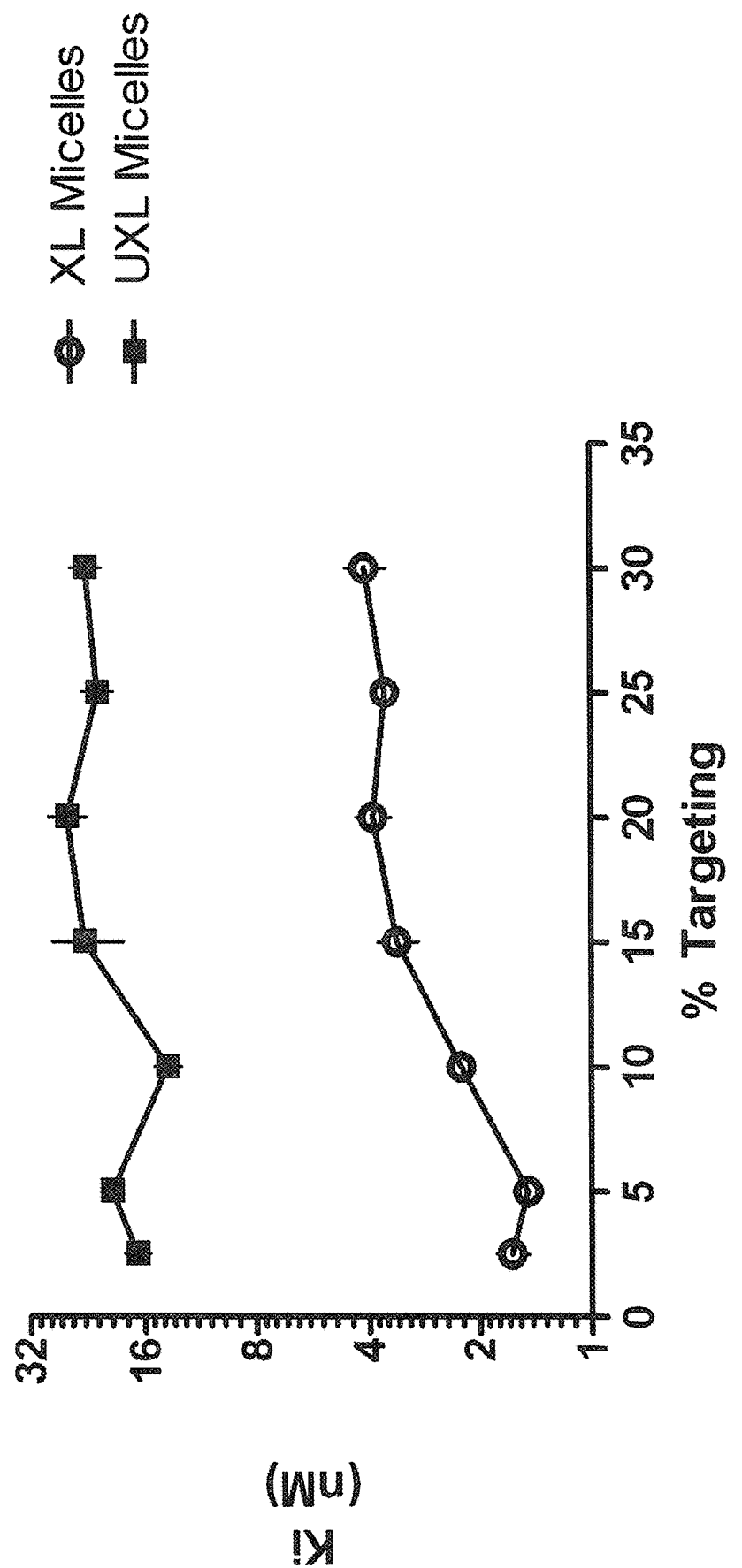
FIG. 35: Effect of % ligand 2 coverage on micelle binding avidity.

In vitro europium time-resolved fluorescence competition binding assays conducted with both 1- and 2-targeted micelles provide support for the central hypothesis underlying this study, namely that crosslinking provides stability to the micelle system and that the composition of the micelle can be modified to allow for targeting. NDP-α-MSH 2 was chosen as a model ligand for competition due to its relatively high affinity for MC1R (1.9 nM), and for the ease of synthesis that it provides.[29, 31] In the percent targeting optimization assays with an alkyne-functionalized NDP-α-MSH (2, FIG. 35), there was a clear difference between the binding affinities of the crosslinked (XL) and uncrosslinked (UXL) micelles. This finding is ascribed to the Fe(III) crosslinking, which serves to stabilize the micelles in biological media. In the absence of crosslinking, the micelles dissociate, in whole or in part, to free monomers, leading to a loss of structural integrity and the premature release of the payload (the encapsulated contrast agent in the present instance). A second advantage of crosslinking is that it leads to an operational increase in binding avidity, a result that may reflect a benefit of multivalent interactions. The 1-targeted (T) micelles of this study also exhibited a stronger avidity to the MC1R receptor when crosslinked (T-XL) as compared to their uncrosslinked counterpart (T-UXL), a finding we take as further support for the contention that i) crosslinking stabilizes micelles and ii) multiple ligands on the micelle surface provide for enhanced binding.

In vitro phantom experiments demonstrated that micelles with a lower percentage of Gd-Tx loading (w/w) produced shorter T1 values (FIG. 36). Moreover, in vivo experiments served to confirm that those with 5% Gd-Tx loading (w/w) provided no measurable contrast enhancement (relative to background) in tumor xenografts. At first blush, these observations appear counter-intuitive since higher contrast enhancement might be expected at higher gadolinium concentrations. However, gadolinium overloading, wherein encapsulated gadolinium is less accessible to water at higher concentrations due to "overcrowding" within the micelle, would give rise to a lower level of enhancement. The lack of differentiation in the $T_1$ values of the crosslinked and uncrosslinked micelles at lower loading levels is thought to result from overcrowding. However, overcrowding does not provide an explanation for the lack of differentiation between the crosslinked and uncrosslinked micelles at equal concentrations. We believe this result is best explained by a different effect, namely localization of the Gd-Tx complex within the stabilized (hydrophilic) block of the micelle, rather than within the core. This portion of the polymer is composed of poly(aspartic acid), to which Gd-Tx is known to coordinate,[48] and is expected to mask the differences is micelle stabilization.

Based on the results of the phantom experiment and the lack of significant in vivo tumor contrast enhancement in the case of the 5% (w/w) Gd-Tx micelles, the micelles with 0.5% Gd-Tx (w/w) micelle loading were chosen for the in vivo experiments. In accord with the design expectations, these in vivo experiments revealed improved MRI contrast enhancements upon administration of the Gd-Tx containing T-XL micelles, with maximal enhancement observed at 24 h. As can be seen by an inspection of FIGS. 37A-B and 38A-D, this enhancement was not seen with the other micelle systems, supporting the contention that the T-XL micelles provide good systems for effecting tumor localization and imaging.

The unique ability of the T-XL micelles to penetrate the tumor appears to result from a combination of the MC1R-specific targeting group and the enhanced stability provided by the Fe(III) crosslinking. If targeting alone were enough to produce effective tumor enhancement, we would also observe a substantial uptake in the case of the T-UXL micelles. Likewise, if crosslinking and EPR alone were enough to affect accumulation, we would observe an increased build-up in the UT-XL group. Finally, it is important to note that the enhancement observed in the T-XL group was not the result of free Gd-Tx (which is known to accumulate in tumors selectively[42, 43, 49, 50]). If this were the case, we would have observed enhanced uptake in all four micelle groups (i.e., UT-UXL, T-UXL and UT-UXL, in addition to the T-XL system). This was not seen. Thus, the in vivo data are consistent with the conclusion that the Gd-Tx containing T-XL micelles allow for functionally acceptable binding avidity, stability, tumor penetration and uptake. Presumably, the crosslinking reaction stabilizes the micelles after administration and during initial time points while they circulate throughout the bloodstream, while the targeting group allows the system to bind to, and be retained within, the tumor cells.

The present inventors have reported the development of a ligand specific to MC1R and have shown that the conjugation of this ligand to the IVECT™ micelle system does not result in a significant decrease in binding avidity.[40] In this Example, the inventors describe the synthesis, incorporation and characterization of a new gadolinium texaphyrin (Gd-Tx) that is characterized by a high inherent $T_1$ relaxivity. The inventors also detail its encapsulation within the IVECT™ system and the production of crosslinked micelles by reaction with Fe(III). Moreover, we have demonstrated that the targeted Gd-Tx micelles are selectively retained in target-expressing xenograft tumors in vivo. To the best of our knowledge, this is the first example of a targeted micelle that is capable of carrying a payload and which outperforms systems based on EPR in terms of tumor penetration, uptake and retention.

Advantages of the current system include the following: (1) the target, MC1R, is highly expressed in melanoma cells and not in healthy tissues, except for melanocytes; (2) high short term stability, and (3) an ability to accumulate in tumors, rather than various clearance organs. These attributes are reflected in the in vivo images that reveal uptake deep within the tumor with peak accumulation at 24 h. In contrast, peak kidney and liver accumulations were seen at 1-4 h. These differences are thought to reflect the benefits of targeting. However, biodegradation of the stabilized micelles may contribute to the effect; to the extent it occurs on short time scales (on the order of hours), it would allow for release of payload (Gd-Tx) within the tumor while concurrently clearing from circulation. While further investigations will be required to detail the full pharmokinetic profile of these new micelles, it is important to appreciate that from an operational perspective they constitute the first examples of systems that are capable of delivering a payload in a tumor selective fashion.

REFERENCES

1. Yokoyama M. Clinical Applications of Polymeric Micelle Carrier Systems in Chemotherapy and Image Diagnosis of Solid Tumors. J Exp Clin Med 2011; 3(4):151-158.
2. Oerlemans C, Bult W, Bos M, Storm G, Nijsen J F W, et al. Polymeric micelles in Anticancer Therapy: Targeting, Imaging, and Triggered Release. Pharm Res 2010; 27:2569-2589.
3. Kedar U, Phutane P, Shidhaye S, Kadam V. Advances in Polymeric Micelles for Drug Delivery and Tumor Targeting. Nanomedicine: Nanotechnology, Biology and Medicine 2010; 6:714-729.
4. Kim S, Shi Y, Kim J Y, K. P, Chen J-X. Overcoming the barriers in micellar drug delivery: loading efficiency, in vivo stability, and micelle-cell interaction. Expert Opin. Drug Deliv. 2010; 7(1):49-62.
5. Shiraishi K, Kawano K, Maitani Y, Yokoyama M. Polyion Complex Micele MRI Contrast Agents from Poly (ethylene glycol)-b-poly(L-lysine) Block Copolymers having Gd-DOTA; Preparations and their COntrol of T1 Relaxitivities and Blood Circulation Characteristics. J. Controlled Release 2010:1-8.
6. Li J, Huo M, Wang J, et al. Redox-sensitive micelles self-assembled from amphiphilic hyaluronic acid-deoxycholic acid conjugates for targeted intracellular delivery of paclitaxel. Biomaterials 2012; 33:2310-2320.
7. Lee H, Hoang B, Fonge H, Reilly R, Allen C. In-vivo Distribution of Polymeric Nanoparticles at the Whole Body, Tumor and Cellular Levels. Pharmaceutical Research 2010; 27(11):2343-2355.
8. Kim T, Chen Y, Mount C, Gambotz W, Li X, et al. Evaluation of Temperature-Sensitive, Indocyanine Green-Encapsulating Micelles for Noninvasive Near-Infrared Tumor Imaging. Pharm Res 2010; 27:1900-1913.
9. Jia Z, Wong L, Davis T P, Bulmus V. One-pot conversion of RAFT-generated multifunctional block copolymers of HPMA to doxorubicin conjugated acid- and reductant-sensitive crosslinked micelles. Biomacromolecules 2008; 9(11):3106-13.
10. Yang X, Grailer J J, Pilla S, Steebe D A, Gong S. Tumor-Targeting, pH-Responsive, and Stable Unimolecular Micelles as Drug Nanocarriers for Targeted Cancer Therapy. Bioconjugate Chem 2010; 21(3):496-504.
11. Li Y, Xio W, Xiao K, et al. Well-defined reversible boronate crosslinked nanocarriers for targeted drug delivery in response to acidic pH values and cis-diols. Angew. Chem. Int. Ed 2012; 51:1-7.
12. Cannan R K, Kibrick A. Complex Formation between Carboxylic Acids and Divalent Metal Cations. J. Am. Chem. Soc. 1938; 60:2314-2320.
13. Rios-Doria J, Carie A, Costich T, et al. A versatile polymer micelle drug delivery system for encapsulation and in vivo stabilization of hydrophobic anticancer drugs. J Drug Delivery 2011; in press:15 Oct. 2011.
14. Sun T-M, Du J-Z, Yao Y-D, et al. Simultaneous delivery of siRNA and paclitaxel via a "two-in-one" micelleplex promotes synergistic tumor suppression. ACS Nano 2011; 5(2):1483-1494.
15. Koo H, Huh M, Sun I-C, et al. In vivo targeted delivery of nanoparticles for theranosis. Accounts of Chemical Research 2011; 44(10):1018-1028.
16. Tang N, Dy G, Wang N, Liu C, Hang H, et al. Improving Penetration in Tumors with Nanoassemblies of Phospholipids and Doxorubicin. JNCI 2007; 99(13):1004-1015.
17. Chrastina A, Massey K A, Schnitzer J E. Overcoming in vivo barriers to targeted nanodelivery. Interdisciplinary Reviews: Nanomedicine and Nanobiotechnology 2011; 3(4):421-437.
18. Kessinger C, Khemtong C, Togao O, Takahashi M, Sumer B, et al. In-vivo angiogenesis imaging of solid tumors by avb3-targeted, dual-modality micellar nanoprobes. Experimental Biology and Medicine 2010; 235: 957-965.
19. Poon Z, Lee J, Huang S, Prevost R, Hammond P. Highly Stable, Ligand Clustered "Patchy" Micelle Nanocarriers for Systemic Tumor Targeting. Nanomedicine: Nanotechnology, Biology and medicine 2010:1-30.
20. Lee H, Fonge H, Hoang B, Reilly R, Allen C. The Effects of Particle Size and Molecular Targeting on the Intratumoral and Suncellular Distribution of Polymeric Nanoparticles. Molecular Pharmaceutics 2010; 7(4):1195-1208.
21. Hu J, Qian Y, Wang X, Liu W, Liu S. Drug-Loaded and Superparamagnetic Iron Oxide Nanoparticle Surface-Embedded Amphiphilic Block Copolymer Micelles for Integrated Chemotherapeutic Drug Delivery and M R Imaging. Langmuir 2012; epub ahead of print (DOI: 10.1021/1a203992q).
22. Liu T, Liu X, Qian Y, Hu X, Liu S. Multifunctional pH-Disintegrable micelle nanoparticles of asymmetrically functionalized beta-cyclodextrin-based star copolymer covalently conjugated with doxorubicin and DOTA-Gd moieties. Biomaterials 2012; 33:2521-2531.
23. Xiong X-B, Lavasanifar A. Traceable Multifunctional Micellar nanocarriers for Cancer-Targeted Co-delivery of MDR-1 siRNA and Doxorubicin. ACS Nano 2011; 5(6): 5202-5213.
24. Yang R, Meng F, Ma S, Huang F, Liu H, et al. Galactose-decorated cross-linked biodegradable poly9ethylene glycol)-b-poly(E-caprolactone) block copolymer micelles for enhanced hepatoma-targeting delivery of paclitaxel. Biomacromolecules 2011; 12:3047-3055.
25. Siegrist W, Solca F, Stutz S, et al. Characterization of receptors for alpha-melanocyte-stimulating hormone on human melanoma cells. Cancer Res 1989; 49(22):6352-8.
26. Cai M, Varga E V, Stankova M, et al. Cell signaling and trafficking of human melanocortin receptors in real time using two-photon fluorescence and confocal laser microscopy: differentiation of agonists and antagonists. Chem Biol Drug Des 2006; 68(4):183-93.
27. Mayorov A V, Han S Y, Cai M, Hammer M R, Trivedi D, et al. Effects of macrocycle size and rigidity on melanocortin receptor-1 and -5 selectivity in cyclic lactam alpha-melanocyte-stimulating hormone analogs. Chem Biol Drug Des 2006; 67(5):329-35.
28. Koikov L N, Ebetino F H, Solinsky M G, Cross-Doersen D, Knittel J J. Sub-nanomolar hMC1R agonists by end-capping of the melanocortin tetrapeptide His-D-Phe-Arg-Trp-NH(2). Bioorg Med Chem Lett 2003; 13(16):2647-50.
29. Chen J, Giblin M F, Wang N, Jurisson S S, Quinn T P. In vivo evaluation of 99mTc/188Re-labeled linear alpha-melanocyte stimulating hormone analogs for specific melanoma targeting. Nucl Med Biol 1999; 26(6):687-93.
30. Sawyer T, Sanfilippo P, Hruby V, et al. 4-Norleucine, 7-D-phenylalanine-alpha-melanocyte-stimulating hormone: a highly potent alpha-melanotropin with ultralong biological activity. Proc Natl Acad Sci USA 1980; 77(10): 5754-5758.
31. Chen J, Cheng Z, Hoffman T J, Jurisson S S, Quinn T P. Melanoma-targeting properties of (99m)technetium-labeled cyclic alpha-melanocyte-stimulating hormone peptide analogues. Cancer Res 2000; 60(20):5649-58.
32. Cai M, Mayorov A V, Cabello C, Stankova M, Trivedi D, et al. Novel 3D Pharmacophore of r-MSH/ç-MSH Hybrids Leads to Selective Human MC1R and MC3R Analogues. J. Med. Chem. 2005; 48(6):1839-1848.
33. Handl H L, Vagner J, Yamamura H I, Hruby V J, Gillies R J. Lanthanide-based time-resolved fluorescence of in cyto ligand-receptor interactions. Anal Biochem 2004; 330(2):242-50.
34. Yang Y, Hruby V J, Chen M, Crasto C, Cai M, et al. Novel Binding Motif of ACTH Analogues at the Melanocortin Receptors. Biochemistry 2009; 48:9775-9784.
35. Rodrigues A R, Pignatelli D, Almeida H, Gouveiaa A M. Melanocortin 5 receptor activates ERK1/2 through a PI3K-regulated signaling mechanism. Molecular and Cellular Endocrinology 2009; 303:74-81.
36. Webb T R, Clark A J L. Minireview: The Melanocortin 2 Receptor Accessory Proteins. Molecular Endocrinology 2009; 24(3):475-484.
37. VanderPloeg L H T, Martin W J, Howard A D, et al. A role for the melanocortin 4 receptor in sexual function. PNAS 2002; 99(17):11381-11386.
38. Hall J E, Silva A, Jussara M. do Carmo, et al. Obesity-induced Hypertension: Role of Sympathetic Nervous System, Leptin, and Melanocortins. J. Bio. Chem 2010; 28(23):17271-17276.
39. Jun D-J, Na K-Y, Kim W, et al. Melanocortins induce interleukin 6 gene expression and secretion through melanocortin receptors 2 and 5 in 3T3-L1 adipocytes. Journal of Molecular Endocrinology 2010; 44(225-236):225.
40. Barkey N M, Tafreshi N K, Josan J S, et al. Development of melanoma-targeted polymer micelles by conjugation of an MC1R specific ligand. J Med Chem 2011: accepted.
41. Young S W, Qing F, Harriman A, et al. Gadolinium(III) texaphyrin: A tumor selective radiation sensitizer that is detectable by Mitt Proc. Natl. Acad. Sci. USA 1996; 93:6610-6615.
42. Sessler J L, Miller R A. Texaphyrins. New Drugs with Diverse Clinical Applications in Radiation and Photodynamic Therapy. Biochem. Pharmacol. 2000; 59:733-739.
43. Viala J, Vanel D, Meingan P, Lartigau E, Carde P, et al. Phases IB and II Multidose Trial of Gadolinium Texaphyrin, a Radiation Sensitizer Detectable at MR Imaging: Preliminary Results in Brain Metastases. Radiology 1999; 212:755-759.
44. Sessler J L, Mody T D, Hemmi G W, Lynch V, Young S W, et al. Gadolinium(III) texaphyrin: a novel MRI contrast agent. J. Am. Chem. Soc. 1993; 115(22):10368-10369.
45. Ehrlich J, Bogert M T. Experiments in the veratrole and quinoxaline groups J. Org. Chem. 1947; 12(522-534).
46. Sessler J L, Hemmi G, Mody T D, Murai T, Burrell A, et al. Texaphyrins: Synthesis and Applications. Acc. Chem. Res. 1994; 27:43-50.
47. Sessler J L, Murai T, Lynch V, Cyr M. An "Expanded Porphyrin": The Synthesis and Structure of a New Aromatic Pentadentate Ligand. J Am Chem Soc 1988; 110 (16):5586-5588.
48. Magda D, Miles D, Gerasimchuk N, Lepp C, inventors; Pharmacyclics, Inc, assignee. Texaphyrin coordination compounds and uses thereof. United States. 2005.
49. Sessler J L, Krill V, Hoehner M C, Chin KOA, Davila R M. New texaphyrin-type expanded porphyrins. Pure & Appl. Chem 1996; 68(6):1291-1295.
50. Sessler J L, Mody T D, Hemmi G W, Lynch V M. Synthesis and Structural Characterization of lanthanide (III) texaphyrins. Inorg. Chem. 1993; 32:3175-3187.

We claim:

1. A method of treating melanoma in a human or non-human animal subject, comprising administering an MC1R-targeted agent to the subject, wherein the MC1R-targeted agent comprises a MC1R peptide ligand and a moiety, wherein the moiety comprises an anti-cancer agent, and wherein the MC1R peptide ligand and the moiety are covalently linked by a reaction product of a first functionality coupled to the MC1R peptide ligand and a complementary second functionality coupled to the moiety, wherein the MC1R peptide ligand comprises:

```
                                        (SEQ ID NO: 3)
4-phenylbutyryl-His-DPhe-Arg-Trp-Gly-Lys (hex-5-ynoyl)-NH₂;
or
                                        (SEQ ID NO: 4)
H-Lys(hex-5-ynoyl)-Tyr-Val-Nle-Gly-His-DNal(2')-

Arg-DTrp-Asp-Arg-Phe-Gly-NH₂;
or
                                        (SEQ ID NO: 5)
H-Lys(hex-5-ynoyl)Tyr-Val-Nle-Gly-His-DNal(2')-

Arg-DPhe-Asp-Arg-Phe-Gly-NH₂;
or
                                        (SEQ ID NO: 6)
4-phenylbutyryl-His-DPhe-Arg-Trp,
``` and
- a functional group coupled to the C-terminus of the MC1R peptide ligand.

2. The method of claim 1, wherein the MC1R peptide ligand comprises 4-phenylbutyryl-Hi s-DPhe-Arg-Trp-Gly-Lys(hex-5-ynoyl)-NH₂ (SEQ ID NO:3).

3. The method of claim 1, wherein the MC1R peptide ligand comprises H-Lys(hex-5-ynoyl)-Tyr-Val-Nle-Gly-His-DNal(2')-Arg-DTrp-Asp-Arg-Phe-Gly-NH₂ (SEQ ID NO:4).

4. The method of claim 1, wherein the MC1R peptide ligand comprises H-Lys(hex-5-ynoyl)Tyr-Val-Nle-Gly-His-DNal(2')-Arg-DPhe-Asp-Arg-Phe-Gly-NH₂ (SEQ ID NO:5).

5. The method of claim 1, wherein the MC1R peptide ligand comprises 4-phenylbutyryl-His-DPhe-Arg-Trp (SEQ ID NO:6).

6. The method of claim 1, wherein the subject is human.

7. The method of claim 1, wherein the subject is a non-human animal.

8. The method of claim 1, wherein the melanoma is metastatic melanoma.

9. The method of claim 1, wherein the anti-cancer agent kills melanoma cells or inhibits growth of melanoma cells.

10. The method of claim 1, wherein the anti-cancer agent is a chemotherapeutic agent.

11. The method of claim 1, wherein the anti-cancer agent is a cytotoxic agent.

12. The method of claim 1, wherein the anti-cancer agent is a taxane.

13. The method of claim 1, wherein the anti-cancer agent is one or more selected from among melphalan, ifosfamide, dacarbazine, paclitaxel, and vincristine.

14. The method of claim 1, wherein the MC1R-targeted agent is administered systemically.

15. The method of claim 1, wherein the MC1R-targeted agent is administered locally at a site of the melanoma.

16. The method of claim 1, wherein the MC1R-targeted agent is administered orally or intravenously.

17. The method of claim 1, wherein the MC1R-targeted agent is in a pharmaceutical composition comprising the MC1R-targeted agent and a pharmaceutically acceptable carrier, and wherein the pharmaceutical composition is administered to the subject.

18. The method of claim 17, wherein the pharmaceutical composition is administered by intratumoral injection.

* * * * *

SEQUENCE LISTING

<160> NUMBER OF SEQ ID NOS: 17

<210> SEQ ID NO 1
<211> LENGTH: 4
<212> TYPE: PRT
<213> ORGANISM: Artificial sequence
<220> FEATURE:
<223> OTHER INFORMATION: modified MC1R peptide ligand

```
<400> SEQUENCE: 1

His Phe Arg Trp
1

<210> SEQ ID NO 2
<211> LENGTH: 4
<212> TYPE: PRT
<213> ORGANISM: Artificial sequence
<220> FEATURE:
<223> OTHER INFORMATION: modified MC1R peptide ligand
<220> FEATURE:
<221> NAME/KEY: MISC_FEATURE
<222> LOCATION: (2)..(2)
<223> OTHER INFORMATION: D amino acid

<400> SEQUENCE: 2

His Phe Arg Trp
1

<210> SEQ ID NO 3
<211> LENGTH: 6
<212> TYPE: PRT
<213> ORGANISM: Artificial sequence
<220> FEATURE:
<223> OTHER INFORMATION: modified MC1R peptide ligand
<220> FEATURE:
<221> NAME/KEY: MISC_FEATURE
<222> LOCATION: (1)..(1)
<223> OTHER INFORMATION: 4-phenylbutyryl
<220> FEATURE:
<221> NAME/KEY: MISC_FEATURE
<222> LOCATION: (2)..(2)
<223> OTHER INFORMATION: D amino acid
<220> FEATURE:
<221> NAME/KEY: MISC_FEATURE
<222> LOCATION: (6)..(6)
<223> OTHER INFORMATION: hex-5-ynoyl

<400> SEQUENCE: 3

His Phe Arg Trp Gly Lys
1               5

<210> SEQ ID NO 4
<211> LENGTH: 13
<212> TYPE: PRT
<213> ORGANISM: Artificial sequence
<220> FEATURE:
<223> OTHER INFORMATION: modified MC1R peptide ligand
<220> FEATURE:
<221> NAME/KEY: MISC_FEATURE
<222> LOCATION: (1)..(1)
<223> OTHER INFORMATION: hex-5-ynoyl
<220> FEATURE:
<221> NAME/KEY: MISC_FEATURE
<222> LOCATION: (4)..(4)
<223> OTHER INFORMATION: Norleucine
<220> FEATURE:
<221> NAME/KEY: MISC_FEATURE
<222> LOCATION: (7)..(7)
<223> OTHER INFORMATION: DNal(2')
<220> FEATURE:
<221> NAME/KEY: MISC_FEATURE
<222> LOCATION: (9)..(9)
<223> OTHER INFORMATION: D amino acid

<400> SEQUENCE: 4

Lys Tyr Val Leu Gly His Xaa Arg Trp Asp Arg Phe Gly
1               5                   10

<210> SEQ ID NO 5
<211> LENGTH: 13
```

```
<212> TYPE: PRT
<213> ORGANISM: Artificial sequence
<220> FEATURE:
<223> OTHER INFORMATION: modified MC1R peptide ligand
<220> FEATURE:
<221> NAME/KEY: MISC_FEATURE
<222> LOCATION: (1)..(1)
<223> OTHER INFORMATION: hex-5-ynoyl
<220> FEATURE:
<221> NAME/KEY: MISC_FEATURE
<222> LOCATION: (4)..(4)
<223> OTHER INFORMATION: Norleucine
<220> FEATURE:
<221> NAME/KEY: MISC_FEATURE
<222> LOCATION: (7)..(7)
<223> OTHER INFORMATION: DNal(2')
<220> FEATURE:
<221> NAME/KEY: MISC_FEATURE
<222> LOCATION: (9)..(9)
<223> OTHER INFORMATION: D amino acid

<400> SEQUENCE: 5

Lys Tyr Val Leu Gly His Xaa Arg Phe Asp Arg Phe Gly
1               5                  10

<210> SEQ ID NO 6
<211> LENGTH: 4
<212> TYPE: PRT
<213> ORGANISM: Artificial sequence
<220> FEATURE:
<223> OTHER INFORMATION: modified MC1R peptide ligand
<220> FEATURE:
<221> NAME/KEY: MISC_FEATURE
<222> LOCATION: (1)..(1)
<223> OTHER INFORMATION: 4-phenylbutyryl
<220> FEATURE:
<221> NAME/KEY: MISC_FEATURE
<222> LOCATION: (2)..(2)
<223> OTHER INFORMATION: D amino acid

<400> SEQUENCE: 6

His Phe Arg Trp
1

<210> SEQ ID NO 7
<211> LENGTH: 4
<212> TYPE: PRT
<213> ORGANISM: Artificial sequence
<220> FEATURE:
<223> OTHER INFORMATION: MC1R-selective ligand
<220> FEATURE:
<221> NAME/KEY: MISC_FEATURE
<222> LOCATION: (1)..(1)
<223> OTHER INFORMATION: Ac-Homophenylalanine
<220> FEATURE:
<221> NAME/KEY: MISC_FEATURE
<222> LOCATION: (2)..(2)
<223> OTHER INFORMATION: D amino acid

<400> SEQUENCE: 7

His Phe Arg Trp
1

<210> SEQ ID NO 8
<211> LENGTH: 4
<212> TYPE: PRT
<213> ORGANISM: Artificial sequence
<220> FEATURE:
<223> OTHER INFORMATION: MC1R-selective ligand
<220> FEATURE:
<221> NAME/KEY: MISC_FEATURE
<222> LOCATION: (1)..(1)
<223> OTHER INFORMATION: 4-hydroxycinnamoyl
```

```
<220> FEATURE:
<221> NAME/KEY: MISC_FEATURE
<222> LOCATION: (2)..(2)
<223> OTHER INFORMATION: D amino acid

<400> SEQUENCE: 8

His Phe Arg Trp
1

<210> SEQ ID NO 9
<211> LENGTH: 12
<212> TYPE: PRT
<213> ORGANISM: Artificial sequence
<220> FEATURE:
<223> OTHER INFORMATION: MC1R-selective ligand
<220> FEATURE:
<221> NAME/KEY: MISC_FEATURE
<222> LOCATION: (3)..(3)
<223> OTHER INFORMATION: Norleucine
<220> FEATURE:
<221> NAME/KEY: MISC_FEATURE
<222> LOCATION: (6)..(6)
<223> OTHER INFORMATION: DNal(2')
<220> FEATURE:
<221> NAME/KEY: MISC_FEATURE
<222> LOCATION: (8)..(8)
<223> OTHER INFORMATION: D amino acid

<400> SEQUENCE: 9

Tyr Val Leu Gly His Xaa Arg Trp Asp Arg Phe Gly
1               5                   10

<210> SEQ ID NO 10
<211> LENGTH: 12
<212> TYPE: PRT
<213> ORGANISM: Artificial sequence
<220> FEATURE:
<223> OTHER INFORMATION: MC1R-selective ligand
<220> FEATURE:
<221> NAME/KEY: MISC_FEATURE
<222> LOCATION: (3)..(3)
<223> OTHER INFORMATION: Norleucine
<220> FEATURE:
<221> NAME/KEY: MISC_FEATURE
<222> LOCATION: (6)..(6)
<223> OTHER INFORMATION: DNal(2')
<220> FEATURE:
<221> NAME/KEY: MISC_FEATURE
<222> LOCATION: (8)..(8)
<223> OTHER INFORMATION: D amino acid

<400> SEQUENCE: 10

Tyr Val Leu Gly His Xaa Arg Phe Asp Arg Phe Gly
1               5                   10

<210> SEQ ID NO 11
<211> LENGTH: 12
<212> TYPE: PRT
<213> ORGANISM: Artificial sequence
<220> FEATURE:
<223> OTHER INFORMATION: MC1R-selective ligand
<220> FEATURE:
<221> NAME/KEY: MISC_FEATURE
<222> LOCATION: (3)..(3)
<223> OTHER INFORMATION: Norleucine
<220> FEATURE:
<221> NAME/KEY: MISC_FEATURE
<222> LOCATION: (6)..(6)
<223> OTHER INFORMATION: D amino acid
<220> FEATURE:
<221> NAME/KEY: MISC_FEATURE
<222> LOCATION: (8)..(8)
<223> OTHER INFORMATION: DNal(2')
```

<400> SEQUENCE: 11

Tyr Val Leu Gly His Phe Arg Xaa Asp Arg Phe Gly
1               5                   10

<210> SEQ ID NO 12
<211> LENGTH: 23
<212> TYPE: DNA
<213> ORGANISM: Artificial sequence
<220> FEATURE:
<223> OTHER INFORMATION: MC1R specific primer (forward)

<400> SEQUENCE: 12
aatgtcattg acgtgatcac ctg                                              23

<210> SEQ ID NO 13
<211> LENGTH: 22
<212> TYPE: DNA
<213> ORGANISM: Artificial sequence
<220> FEATURE:
<223> OTHER INFORMATION: MC1R specific primer (reverse)

<400> SEQUENCE: 13
gcagtgcgta gaagatggag at                                               22

<210> SEQ ID NO 14
<211> LENGTH: 6
<212> TYPE: PRT
<213> ORGANISM: Artificial sequence
<220> FEATURE:
<223> OTHER INFORMATION: MC1R-selective ligand
<220> FEATURE:
<221> NAME/KEY: MISC_FEATURE
<222> LOCATION: (1)..(1)
<223> OTHER INFORMATION: 4-phenylbutyryl
<220> FEATURE:
<221> NAME/KEY: MISC_FEATURE
<222> LOCATION: (2)..(2)
<223> OTHER INFORMATION: D amino acid
<220> FEATURE:
<221> NAME/KEY: MISC_FEATURE
<222> LOCATION: (6)..(6)
<223> OTHER INFORMATION: Mpr-IR800CW

<400> SEQUENCE: 14

His Phe Arg Trp Gly Lys
1               5

<210> SEQ ID NO 15
<211> LENGTH: 12
<212> TYPE: PRT
<213> ORGANISM: Artificial sequence
<220> FEATURE:
<223> OTHER INFORMATION: MC1R peptide ligand
<220> FEATURE:
<221> NAME/KEY: MISC_FEATURE
<222> LOCATION: (4)..(4)
<223> OTHER INFORMATION: Norleucine
<220> FEATURE:
<221> NAME/KEY: MISC_FEATURE
<222> LOCATION: (7)..(7)
<223> OTHER INFORMATION: D amino acid

<400> SEQUENCE: 15

Ser Tyr Ser Leu Glu His Phe Arg Trp Gly Lys Pro
1               5                   10

<210> SEQ ID NO 16
<211> LENGTH: 5

```
<212> TYPE: PRT
<213> ORGANISM: Artificial sequence
<220> FEATURE:
<223> OTHER INFORMATION: MC1R peptide ligand
<220> FEATURE:
<221> NAME/KEY: MISC_FEATURE
<222> LOCATION: (2)..(2)
<223> OTHER INFORMATION: D amino acid

<400> SEQUENCE: 16

His Phe Arg Trp Gly
1               5

<210> SEQ ID NO 17
<211> LENGTH: 13
<212> TYPE: PRT
<213> ORGANISM: Artificial sequence
<220> FEATURE:
<223> OTHER INFORMATION: MC1R peptide ligand
<220> FEATURE:
<221> NAME/KEY: MISC_FEATURE
<222> LOCATION: (4)..(4)
<223> OTHER INFORMATION: Norleucine
<220> FEATURE:
<221> NAME/KEY: MISC_FEATURE
<222> LOCATION: (7)..(7)
<223> OTHER INFORMATION: D amino acid

<400> SEQUENCE: 17

Ser Tyr Ser Leu Glu His Phe Arg Trp Gly Lys Pro Val
1               5                   10
```